(12) United States Patent
Hasuoka

(10) Patent No.: US 8,420,694 B2
(45) Date of Patent: *Apr. 16, 2013

(54) PYRROLIDIN-2-ONE DERIVATIVES AS ANDROGEN RECEPTOR MODULATOR

(75) Inventor: Atsushi Hasuoka, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 418 days.

This patent is subject to a terminal disclaimer.

(21) Appl. No.: 12/672,516

(22) PCT Filed: Aug. 6, 2008

(86) PCT No.: PCT/JP2008/064500
§ 371 (c)(1),
(2), (4) Date: Feb. 7, 2010

(87) PCT Pub. No.: WO2009/020234
PCT Pub. Date: Feb. 12, 2009

(65) Prior Publication Data
US 2011/0098336 A1    Apr. 28, 2011

(30) Foreign Application Priority Data

Aug. 7, 2007 (JP) ................. 2007-205966
Nov. 19, 2007 (JP) ................. 2007-299658

(51) Int. Cl.
A61K 31/40 (2006.01)
C07D 207/00 (2006.01)
(52) U.S. Cl.
USPC ............ 514/425; 514/424; 548/543; 548/544
(58) Field of Classification Search .......... 548/543, 548/544; 514/424, 425
See application file for complete search history.

(56) References Cited

U.S. PATENT DOCUMENTS

| 5,338,860 | A | 8/1994 | Baasner et al. |
| 2004/0083559 | A1 | 5/2004 | Sabelle et al. |
| 2005/0101657 | A1 | 5/2005 | Furuya et al. |
| 2006/0106067 | A1 | 5/2006 | Shiraishi et al. |
| 2009/0042857 | A1 | 2/2009 | Yamaoka et al. |
| 2009/0042967 | A1 | 2/2009 | Hasuoka |
| 2009/0203694 | A1 | 8/2009 | Hurley et al. |
| 2010/0087506 | A1 | 4/2010 | Hasuoka et al. |
| 2010/0152236 | A1 | 6/2010 | Yamamoto et al. |

FOREIGN PATENT DOCUMENTS

| JP | S46-041305 | 12/1971 |
| JP | H05-262727 | 10/1993 |
| JP | 2002-088073 | 3/2002 |
| JP | 2003-252854 | 9/2003 |
| RU | 2006144863 | 5/2005 |
| WO | WO-01/47905 | 7/2001 |
| WO | WO-02-45669 | 6/2002 |
| WO | WO-03/049675 | 6/2003 |
| WO | WO-03/106401 | 12/2003 |
| WO | WO-2004-016576 | 2/2004 |
| WO | WO-2004/035736 | 4/2004 |
| WO | WO-2005/077935 | 8/2005 |
| WO | WO-2005/090282 | 9/2005 |
| WO | WO-2005/108351 | 11/2005 |
| WO | WO-2005-115361 | 12/2005 |
| WO | WO-2005/120483 | 12/2005 |
| WO | WO-2006-076317 | 7/2006 |
| WO | WO-2006-117677 | 11/2006 |
| WO | WO-2006-124447 | 11/2006 |
| WO | WO-2007-015567 | 2/2007 |
| WO | WO-2007-097289 | 8/2007 |
| WO | WO-2008-011072 | 1/2008 |
| WO | WO 2008/014311 | 1/2008 |
| WO | WO-2008-066117 | 6/2008 |

OTHER PUBLICATIONS

Testa "Prodrug Research: Futile or fertile?" Biochemical Pharmacology, 2004, vol. 68, pp. 2097-2106.*
International Search Report dated Feb. 26, 2009, in corresponding PCT Patent Application No. PCT/JP2008/064500.
Written Opinion dated Feb. 26, 2009, in corresponding PCT Patent Application No. PCT/JP2008/064500.
Georgian Search Report dated Sep. 22, 2011, in corresponding Georgian patent application No. AP 2008 011715 (including English translation).
GE-2006 3984.
GE-2009 4851.
GE-2007 4191.
GE-2008 4361.
GE-2008 4434.
GE-2004 3384.
Oudeyer et al, "Yb(OTf)$_3$-Catalyzed Vinylogous Mannich Reaction of Trialkylsilyloxyfuran", Heterocycles, 65(4), pp. 823-841 (2005).
Kunz et al., "91. Bildung von 4-, 5- und 6gliedrigen Heterocyclen durch ambidoselektive Ringschlusse von Enolat-Ionen", Helvetica Chimica Acta, 62(3), pp. 872-881 (1979).

(Continued)

*Primary Examiner* — Shengjun Wang
(74) *Attorney, Agent, or Firm* — Edwards Wildman Palmer LLP; David G. Conlin; Mark D. Russett

(57) ABSTRACT

A compound represented by the formula (I'):

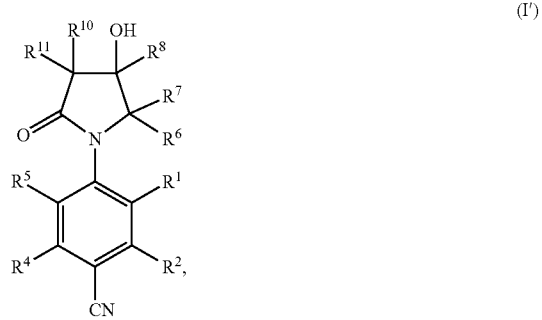

or a salt thereof, has a superior androgen modulating action, wherein $R^1$, $R^2$, $R4$ to $R^8$, $R^{10}$ and $R^{11}$ are defined in the claim.

8 Claims, No Drawings

OTHER PUBLICATIONS

Schmierer et al., "Cyclisierung von *N*-Acylalanin- und *N*-Acylglycinestern", Liebigs Ann. Chem., (5), pp. 1095-1098 (1985).

Sapi et al., "Simple and Condensed β-Lactams. Part 32. Base- and Acid-Catalyzed Ring Expansions of 3-Substituted 4-Acetylazetidin-2-Ones and Related Compounds", Collect. Czech. Chem. Commun., 64(2), pp. 190-202 (1999).

Liao et al., "A concise enantioselective synthesis of iminosugar derivatives", Chem. Commun., (6), pp. 674-676 (2006).

Notice of Reasons for Refusal mailed Feb. 19, 2013, in corresponding Japanese Patent Application No. 504096/2010 (with English translation).

* cited by examiner

PYRROLIDIN-2-ONE DERIVATIVES AS ANDROGEN RECEPTOR MODULATOR

CROSS-REFERENCE TO RELATED APPLICATIONS

This application is the national stage application pursuant to 35 U.S.C. §371 of PCT application PCT/JP2008/064500, filed Aug. 6, 2008, which claims priority to Japanese Patent Application No. 2007-299658, filed Nov. 19, 2007 and Japanese Patent Application No. 2007-205966, filed Aug. 7, 2007. The contents of these applications are incorporated herein by reference in their entirety.

TECHNICAL FIELD

The present invention relates to a cyclic amine compound useful as an androgen receptor modulator and the like.

BACKGROUND OF THE INVENTION

Androgen is synthesized in the testis and adrenal cortex, bound to an androgen receptor in a target organ, and shows various physiological activities. Chemically, any natural androgen belongs to C19 steroid. The major androgen among them is testosterone mainly synthesized in the testis, uptaken in a target cell and shows strong physiological activity. In female, adrenal cortex is a major androgen supply source.

Androgen is involved in the growth and function maintenance of genital organ (prostate, vesicular gland, epididymis, vas deferens etc.), sex differentiation in the embryonic stage, spermatozoon formation, expression of secondary sexual characteristics (induction of masculinization, for example, muscle-skeleton, voice, fat distribution etc., and the like), promotion of protein elaboration in muscle and the like, bone metabolism and the like. Therefore, shortage of androgen due to testis dysfunction, castration and the like results in insufficient actions mentioned above, thus leading to various diseases and degraded QOL (quality of life). To deal with the situation, an androgen replacement therapy is generally employed. Besides testosterone, synthetic androgen showing different balance of androgenic action has been studied and put to practical use in clinical situations.

On the other hand, when androgen is involved in the progression of pathology, an androgen deprivation therapy is employed. For example, in androgen dependent prostate cancer, castration and administration of GnRH agonist decrease testosterone and increase a treatment effect.

For androgen replacement therapy, testosterone and synthetic androgen are generally used. However, they have a steroid skeleton, which places much burden on the liver or shows other steroid hormone action. Therefore, an androgen receptor modulator (particularly agonist) having a non-steroidal skeleton is considered to be useful for the improvement of pathology caused by insufficient androgen action (hypogonadism, male climacteric disorder and the like) and pathology expected to show improvement by the action of androgen (osteoporosis and the like).

It is known that a naphthalene derivative having a pyrrolidine ring has a superior androgen receptor modulator action (WO 2004/16576). However, this reference does not disclose a pyrrolidinobenzene derivative having a substituent at the 3-position of pyrrolidine ring.

While a benzene derivative having a pyrrolidine ring, is which shows an anti-androgen action (JP 2002-88073 A and WO 2005/090282), and a benzene derivative having a pyrrolidine ring, which is used for osteoporosis and the like (WO 2005/108351) are known, a compound having a substituent at the 3-position of a pyrrolidine ring is not disclosed.

DISCLOSURE OF THE INVENTION

Problems to be Solved by the Invention

The present invention aims to provide a compound having a more superior androgen receptor modulating action.

Means of Solving the Problems

The present inventors have conducted intensive studies in view of the aforementioned problems and found that a cyclic aminobenzene compound represented by the formula (I) unexpectedly has a superior androgen receptor modulating action, which resulted in the completion of the present invention.

Accordingly, the present invention relates to
[1] a compound represented by the formula (I)

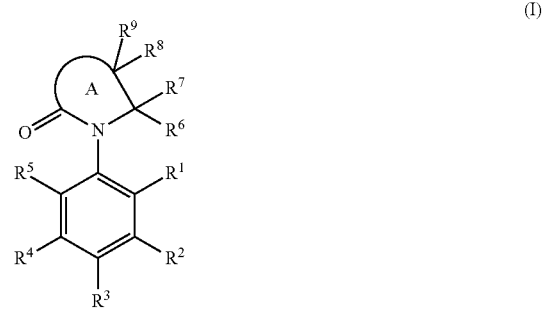

wherein
$R^1$ is a hydrogen atom, a halogen atom, a group via a carbon atom, a group via a nitrogen atom, a group via an oxygen atom or a group via a sulfur atom;
$R^2$ is a hydrogen atom, a halogen atom, a group via a carbon atom, a group via a nitrogen atom, a group via an oxygen atom or a group via a sulfur atom;
$R^3$ is an electron-withdrawing group;
$R^4$ is a hydrogen atom, a halogen atom, a group via a carbon atom, a group via a nitrogen atom, a group via an oxygen atom or a group via a sulfur atom;
$R^5$ is a hydrogen atom, a halogen atom, a group via a carbon atom, a group via a nitrogen atom, a group via an oxygen atom or a group via a sulfur atom;
$R^6$ is a hydrogen atom, a halogen atom, a group via a carbon atom, a group via a nitrogen atom, a group via an oxygen atom or a group via a sulfur atom;
$R^7$ is an alkyl group optionally having substituent(s) or an aralkyl group optionally having substituent(s);
$R^8$ is a hydrogen atom, an alkyl group optionally having substituent(s), an alkenyl group optionally having substituent(s) or a cycloalkyl group optionally having substituent(s);
$R^9$ is a group via an oxygen atom; and
Ring A is a 5- or 6-membered ring optionally further having substituent(s) (in this case, Ring A may be a 5- or 6-membered ring forming a spiro bond with $C_{3-6}$ cycloalkane), or a salt thereof;
[2] the compound of the above-mentioned [1], wherein Ring A is a pyrrolidine ring optionally further having substituent(s) or a piperidine ring optionally further having substituent(s) (the pyrrolidine ring and piperidine ring optionally form a spiro bond with $C_{3-6}$ cycloalkane);

[3] the compound of the above-mentioned [1], wherein
$R^1$ is a hydrogen atom, a halogen atom or a lower alkyl group optionally having substituent(s);
$R^2$ is a halogen atom, a lower alkyl group optionally having substituent(s) or a lower alkoxy group optionally having substituent(s);
$R^3$ is a cyano group;
$R^4$ is a hydrogen atom or a halogen atom;
$R^5$ is a hydrogen atom;
$R^6$ is a hydrogen atom;
$R^7$ is a lower alkyl group optionally having substituent(s) or an aralkyl group optionally having substituent(s);
$R^8$ is a hydrogen atom, a lower alkyl group optionally having substituent(s) or a $C_{3-6}$ cycloalkyl group optionally having substituent(s);
$R^9$ is a hydroxy group; and
Ring A is a 5-membered ring (pyrrolidine ring) which optionally has 1 or 2 substituents selected from a halogen atom, a lower alkyl group optionally having a hydroxy group, a lower alkenyl group and an aralkyl group, or a 5-membered ring (pyrrolidine ring) forming a spiro bond with $C_{3-6}$ cycloalkane;

[4] the compound of the above-mentioned [1], wherein the formula (I) is the formula (I')

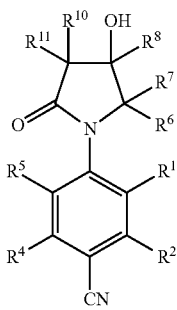

(I')

wherein
$R^1$ is a hydrogen atom, a halogen atom or a lower alkyl group optionally having substituent(s);
$R^2$ is a halogen atom, a lower alkyl group optionally having halogen atom(s) or a lower alkoxy group optionally having halogen atom(s);
$R^4$ is a hydrogen atom or a halogen atom;
$R^5$ and $R^6$ are each a hydrogen atom;
$R^7$ is a lower alkyl group optionally having substituent(s) or an aralkyl group optionally having substituent(s);
$R^8$ is a hydrogen atom, a lower alkyl group optionally having substituent(s) or a $C_{3-6}$ cycloalkyl group optionally having substituent(s); and
$R^{10}$ and $R^{11}$ are the same or different and each is a hydrogen atom, a halogen atom, a lower alkyl group optionally having a hydroxy group, a lower alkenyl group or an aralkyl group; in this case, $R^{10}$ and $R^{11}$ may form $C_{3-6}$ cycloalkane together with the adjacent carbon atom;

[5] the compound of the above-mentioned [4], wherein $R^1$ is a hydrogen atom, a halogen atom or a lower alkyl group;
$R^2$ is a halogen atom, a lower alkyl group optionally having halogen atom(s) or a lower alkoxy group optionally having halogen atom(s);
$R^7$ is a lower alkyl group optionally having substituent(s) selected from a hydroxy group, a lower alkoxy group and a $C_{3-6}$ cycloalkyl group, or an aralkyl group optionally having substituent(s) selected from a halogen atom and a cyano group;
$R^8$ is a hydrogen atom, a lower alkyl group or a $C_{3-6}$ cycloalkyl group; and
$R^{10}$ and $R^{11}$ are the same or different and each is a hydrogen atom, a halogen atom, a lower alkyl group, a lower alkenyl group, an aralkyl group, or a lower alkyl group substituted by a hydroxyl group (in this case, $R^{10}$ and $R^{11}$ optionally form cyclopropane together with the adjacent carbon atom);

[6] 4-[(2S,3S)-2-ethyl-3-hydroxy-5-oxopyrrolidin-1-yl]-2-(trifluoromethyl)benzonitrile, or a salt thereof;
[7] 2-chloro-4-[(4S,5S)-4-hydroxy-5-methyl-2-oxopyrrolidin-1-yl]benzonitrile, or a salt thereof;
[8] 4-[(4R,5S)-5-ethyl-3,3-difluoro-4-hydroxy-2-oxopyrrolidin-1-yl]-2-methoxybenzonitrile, or a salt thereof;
[9] 2-chloro-4-[(2S,3S,4S)-2-ethyl-3-hydroxy-4-methyl-5-oxopyrrolidin-1-yl]benzonitrile, or a salt thereof;
[10] 2-chloro-4-[(4R,5S)-5-ethyl-3,3-difluoro-4-hydroxy-2-oxopyrrolidin-1-yl]benzonitrile, or a salt thereof;
[11] 4-[(2S,3S)-2-ethyl-3-hydroxy-5-oxopyrrolidin-1-yl]-2-(trifluoromethyl)benzonitrile;
[12] 2-chloro-4-[(4S,5S)-4-hydroxy-5-methyl-2-oxopyrrolidin-1-yl]benzonitrile;
[13] 4-[(4R,5S)-5-ethyl-3,3-difluoro-4-hydroxy-2-oxopyrrolidin-1-yl]-2-methoxybenzonitrile;
[14] 2-chloro-4-[(2S,3S,4S)-2-ethyl-3-hydroxy-4-methyl-5-oxopyrrolidin-1-yl]benzonitrile;
[15] 2-chloro-4-[(4R,5S)-5-ethyl-3,3-difluoro-4-hydroxy-2-oxopyrrolidin-1-yl]benzonitrile;
[16] a prodrug of the compound of the above-mentioned [1];
[17] a pharmaceutical agent comprising the compound of the above-mentioned [1] or a prodrug thereof;
[18] the pharmaceutical agent of the above-mentioned [17], which is an androgen receptor modulator;
[19] the pharmaceutical agent of the above-mentioned [17], which is an androgen receptor agonist;
[20] the pharmaceutical agent of the above-mentioned [17], which is a tissue-selective androgen receptor modulator;
[21] the pharmaceutical agent of the above-mentioned [17], which is an agent for the prophylaxis or treatment of hypogonadism, male climacteric disorder, frailty, cachexia or osteoporosis;
[22] the pharmaceutical agent of the above-mentioned [17], which is a frailty suppressant, a muscle strength enhancer, a muscle increasing agent, a cachexia suppressant, a body weight decrease suppressant, an agent for the prophylaxis or treatment of prostate hypertrophy, amyotrophy or muscle loss caused by a disease or an agent for reducing the prostate weight;
[23] a method for the prophylaxis or treatment of hypogonadism, male climacteric disorder, frailty, cachexia or osteoporosis in a mammal, which comprises administering an effective amount of the compound of the above-mentioned [1] or a prodrug thereof;
[24] use of the compound of the above-mentioned [1] or a prodrug thereof for the production of an agent for the prophylaxis or treatment of hypogonadism, male climacteric disorder, frailty, cachexia or osteoporosis; and the like.

The definitions of the substituents of compound (I) are explained below.

Examples of the "halogen atom" for $R^1$, $R^2$, $R^4$, $R^5$ or $R^6$ include a fluorine atom, a chlorine atom, a bromine atom and an iodine atom.

Examples of the "group via a carbon atom" for $R^1$, $R^2$, $R^4$, $R^5$ or $R^6$ include cyano, a hydrocarbon group optionally having substituent(s), acyl, optionally esterified carboxyl, imidoyl optionally having substituent(s), amidino optionally having substituent(s), carbamoyl optionally having substituent(s), thiocarbamoyl optionally having substituent(s), a heterocyclic group via a carbon atom, which optionally has substituent(s) and the like.

Examples of the above-mentioned "hydrocarbon group optionally having substituent(s)" include alkyl optionally having substituent(s), alkenyl optionally having substituent(s), alkynyl optionally having substituent(s), cycloalkyl optionally having substituent(s), aryl optionally having substituent(s), aralkyl optionally having substituent(s) and the like.

Examples of the "alkyl" of the above-mentioned "alkyl optionally having substituent(s)" include lower alkyl (e.g., methyl, ethyl, propyl, isopropyl, butyl, isobutyl, sec-butyl, tert-butyl, pentyl, hexyl etc.) and the like. The lower alkyl is alkyl having a carbon number of 1 to 6.

Examples of the substituent that the above-mentioned "alkyl optionally having substituent(s)" may have include
(i) a halogen atom (e.g., fluorine atom, chlorine atom, bromine atom and iodine atom),
(ii) $C_{1-6}$ alkoxy (e.g., methoxy, ethoxy, propoxy, isopropoxy, butoxy, isobutoxy, sec-butoxy, tert-butoxy etc.),
(iii) $C_{2-6}$ alkenyl (e.g., vinyl, allyl etc.),
(iv) $C_{2-6}$ alkynyl (e.g., ethynyl, propargyl etc.),
(v) amino,
(vi) mono-$C_{1-6}$ alkylamino (e.g., methylamino, ethylamino, propylamino etc.),
(vii) di-$C_{1-6}$ alkylamino (e.g., dimethylamino, diethylamino, dipropylamino etc.),
(viii) mono-$C_{1-6}$ alkyl-carbonylamino (e.g., acetylamino, ethylcarbonylamino etc.),
(ix) di($C_{1-6}$ alkyl-carbonyl)amino (e.g., di(acetyl)amino, di(ethylcarbonyl)amino, di(propylcarbonyl)amino etc.),
(x) hydroxy,
(xi) cyano,
(xii) amidino,
(xiii) carboxyl,
(xiv) $C_{1-6}$ alkoxy-carbonyl (e.g., methoxycarbonyl, ethoxycarbonyl, propoxycarbonyl etc.),
(xv) carbamoyl,
(xvi) mono-$C_{1-6}$ alkyl-carbamoyl (e.g., methylcarbamoyl, ethylcarbamoyl etc.)
(xvii) alkyl-carbamoyl (e.g., dimethylcarbamoyl, diethylcarbamoyl etc.),
(xviii) cyclic aminocarbonyl (e.g., 1-azetinylcarbonyl, piperidinocarbonyl, morpholinocarbonyl etc.),
(xix) ureido,
(xx) $C_{1-6}$ alkyl-ureido (e.g., methylureido, ethylureido etc.),
(xxi) $C_{3-6}$ cycloalkyl (e.g., cyclopropyl etc.) and the like, and 1 to 3 substituents may be present at substitutable position(s).

Examples of the "alkenyl" of the above-mentioned "alkenyl optionally having substituent(s)" include lower alkenyl (e.g., vinyl, allyl, 2-methylprop-2-en-1-yl etc.) and the like. The lower alkenyl is alkenyl having a carbon number of 2 to 6.

Examples of the substituent that the above-mentioned "alkenyl optionally having substituent(s)" may have include those similar to the substituents that the above-mentioned "alkyl optionally having substituent(s)" may have, lower alkyl (e.g., methyl, ethyl, propyl, isopropyl, butyl, isobutyl, sec-butyl, tert-butyl, pentyl, hexyl etc.) and the like, and 1 to 3 substituents may be present at substitutable position(s).

Examples of the "alkynyl" of the above-mentioned "alkynyl optionally having substituent(s)" include lower alkynyl (e.g., ethynyl, propargyl etc.) and the like. The lower alkynyl is alkynyl having a carbon number of 2 to 6.

Examples of the substituent that the above-mentioned "alkynyl optionally having substituent(s)" may have include those similar to the substituents that the above-mentioned "alkenyl optionally having substituent(s)" may have and the like, and 1 to 3 substituents may be present at substitutable position(s).

Examples of the "cycloalkyl" of the above-mentioned "cycloalkyl optionally having substituent(s)" include $C_{3-8}$ cycloalkyl (e.g., cyclopropyl, cyclobutyl, cyclopentyl, cyclohexyl, cycloheptyl, cyclooctyl etc.) and the like.

Examples of the substituent which the above-mentioned "cycloalkyl optionally having substituent(s)" may have include those similar to the substituent which the above-mentioned "alkenyl optionally having substituent(s)" may have and the like, and 1 to 3 substituents may be present at substitutable position(s).

Examples of the "aryl" of the above-mentioned "optionally having substituent(s) aryl" include $C_{6-14}$ aryl (e.g., phenyl, naphthyl, anthryl etc.) and the like.

Examples of the substituent that the above-mentioned "aryl optionally having substituent(s)" may have include those similar to the substituents that the above-mentioned "alkenyl optionally having substituent(s)" may have and the like, and 1 to 3 substituents may be present at substitutable position(s).

Examples of the "aralkyl" of the above-mentioned "aralkyl optionally having substituent(s)" include $C_{7-34}$ aralkyl (e.g., benzyl, phenylethyl, naphthylmethyl etc.) and the like.

Examples of the substituent that the above-mentioned "aralkyl optionally having substituent(s)" may have include those similar to the substituents that the above-mentioned "alkenyl optionally having substituent(s)" may have and the like, and 1 to 3 substituents may be present at substitutable position(s).

Examples of the above-mentioned "acyl" include a group formed by binding the above-mentioned "hydrocarbon group optionally having substituent(s)" with carbonyl.

Examples of the above-mentioned "optionally esterified carboxyl" include carboxyl optionally esterified by the above-mentioned "hydrocarbon group optionally having substituent(s)".

Examples of the above-mentioned "imidoyl optionally having substituent(s)" include imidoyl optionally having 1 or 2 from the above-mentioned "hydrocarbon group optionally having substituent(s)".

Examples of the above-mentioned "amidino optionally having substituent(s)" include amidino optionally having 1 to 3 from the above-mentioned "hydrocarbon group optionally having substituent(s)".

Examples of the above-mentioned "carbamoyl optionally having substituent(s)" include carbamoyl optionally having 1 or 2 from the above-mentioned "hydrocarbon group optionally having substituent(s)".

Examples of the above-mentioned "thiocarbamoyl optionally having substituent(s)" include thiocarbamoyl optionally having 1 or 2 from the above-mentioned "hydrocarbon group optionally having substituent(s)".

As the "heterocyclic group via a carbon atom" of the above-mentioned "heterocyclic group via a carbon atom, which optionally has substituent(s)", an aromatic heterocyclic group or a saturated or unsaturated non-aromatic heterocyclic group (aliphatic heterocyclic group), each containing, as a ring-constituting atom (ring atom) besides carbon atoms, at least one, preferably 1 to 4, more preferably 1 or 2, hetero atoms of 1 to 3 kinds (preferably 1 or 2 kinds) selected from an oxygen atom, a sulfur atom, a nitrogen atom and the like, and having a bond at a carbon atom, and the like are used.

As the "aromatic heterocyclic group", for example, a 5- or 6-membered monocyclic aromatic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like and, for example, a 8- to 12-membered condensed polycyclic aromatic heterocyclic group such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like, and the like are used.

As the "non-aromatic heterocyclic group", for example, a 3- to 8-membered (preferably 5- or 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like, and the like, or a non-aromatic heterocyclic group wherein the double bond of the aforementioned monocyclic aromatic heterocyclic group or condensed polycyclic aromatic heterocyclic group is partly or entirely saturated such as 1,2,3,4-tetrahydroquinolyl, 1,2,3,4-tetrahydroisoquinolyl and the like, and the like are used.

Examples of the substituent that the above-mentioned "heterocyclic group via a carbon atom, which optionally has substituent(s)" may have include those similar to the substituents that the above-mentioned "alkenyl group optionally having substituent(s)" may have and the like, and 1 to 3 substituents may be present at substitutable position(s).

Examples of the "group via a nitrogen atom" for $R^1$, $R^2$, $R^4$, $R^5$ or $R^6$ include (i) amino, (ii) amino mono-substituted by the above-mentioned "group via a carbon atom" and (iii) amino di-substituted by the above-mentioned "group via a carbon atom" and $C_{1-6}$ alkyl (e.g., methyl, ethyl, propyl etc.) and the like.

Examples of the "group via an oxygen atom" for $R^1$, $R^2$, $R^4$, $R^5$, $R^6$ or $R^9$ include hydroxyl optionally substituted by the above-mentioned "group via a carbon atom" and the like.

Examples of the "group via a sulfur atom" for $R^1$, $R^2$, $R^4$, $R^5$ or $R^6$ include thiol optionally substituted by the above-mentioned "group via a carbon atom" and the like. The thiol may be oxidized.

The "electron-withdrawing group" for $R^3$ generally means a group having a tendency to attract an electron from others based on hydrogen in a molecule, and is not particularly limited as long as it is used in organic chemistry. For example, cyano, nitro, halogen atom (e.g., fluorine atom, chlorine atom, bromine atom, iodine atom), acyl (similar to the above-mentioned "acyl"), optionally esterified carboxyl (similar to the above-mentioned "optionally esterified carboxyl"), optionally substituted carbamoyl (similar to the above-mentioned "optionally substituted carbamoyl") or alkyl substituted by 1 to 5 halogen atoms (e.g., fluoromethyl, chloromethyl, difluoromethyl, dichloromethyl, trifluoromethyl, trichloromethyl etc.) and the like can be mentioned.

Examples of the "alkyl group optionally having substituent(s)" for $R^7$ or $R^8$ include those similar to the above-mentioned "alkyl optionally having substituent(s)".

Examples of the "aralkyl group optionally having substituent(s)" for $R^7$ include those similar to the above-mentioned "aralkyl optionally having substituent(s)".

Examples of the "alkenyl group optionally having substituent(s)" for $R^8$ include those similar to the above-mentioned "alkenyl optionally having substituent(s)".

Examples of the "cycloalkyl group optionally having substituent(s)" for $R^8$ include those similar to the above-mentioned "cycloalkyl optionally having substituent(s)".

Ring A is a 5- or 6-membered ring optionally having substituent(s) besides $R^6$ to $R^9$. Examples of Ring A include a pyrrolidine ring and a piperidine ring.

Examples of the substituent that Ring A may further have include those similar to the substituents that the above-mentioned "alkenyl optionally having substituent(s)" may have, lower, alkyl having hydroxy (e.g., hydroxymethyl, 1-hydroxy-1-methylethyl etc.), lower alkenyl (e.g., vinyl, allyl, 2-methylprop-2-en-1-yl etc.), $C_{6-14}$ aryl (e.g., phenyl, naphthyl, anthryl etc.), $C_{7-14}$ aralkyl (e.g., benzyl, phenylethyl, naphthylmethyl etc.) and the like, and 1 to 3 substituents may be present at substitutable position(s). In addition, Ring A optionally forms a spiro bond with $C_{3-6}$ cycloalkane (e.g., cyclopropane, cyclobutane, cyclohexane).

Preferred as $R^1$ is a hydrogen atom, a halogen atom or a lower alkyl group optionally having substituent(s). Of these, (i) a hydrogen atom, (ii) a halogen atom or (iii) a lower alkyl group is preferable. Particularly, (i) a hydrogen atom, (ii) a fluorine atom or (iii) methyl is preferable.

Preferred as $R^2$ is a halogen atom, a lower alkyl group optionally having substituent(s) or a lower alkoxy group optionally having substituent(s). Of these, a halogen atom, a lower alkyl group optionally having halogen atom(s) or a lower alkoxy group optionally having halogen atom(s) is preferable. Particularly, a fluorine atom, a chlorine atom, methyl optionally having fluorine atom(s) (e.g., trifluoromethyl etc.) or methoxy is preferable.

Preferred as $R^3$ is a cyano group.

Preferred as $R^4$ is a hydrogen atom or a halogen atom. Of these, a hydrogen atom or a fluorine atom is preferable.

Preferred as $R^5$ is a hydrogen atom.

Preferred as $R^6$ is a hydrogen atom.

Preferred as $R^7$ is a lower alkyl group optionally having substituent(s) or an aralkyl group optionally having substituent(s). Of these, a lower alkyl group optionally having substituent(s) selected from a lower alkoxy group, a hydroxy group and a $C_{3-6}$ cycloalkyl group, or an aralkyl group optionally having substituent(s) selected from a halogen atom and a cyano group is preferable. Particularly, (1) methyl optionally having substituent(s) selected from methoxy, hydroxy and cyclopropyl, (2) ethyl, (3) n-propyl, (4) isopropyl, (5) isobutyl, or (6) benzyl optionally having substituent(s) selected from a fluorine atom and cyano is preferable.

Preferred as $R^8$ is a hydrogen atom, a lower alkyl group optionally having substituent(s) or a $C_{3-6}$ cycloalkyl group optionally having substituent(s). Of these, a hydrogen atom, a lower alkyl group or a $C_{3-6}$ cycloalkyl group is preferable. Particularly, a hydrogen atom, methyl or cyclopropyl is preferable.

Preferred as $R^9$ is a hydroxy group.

Preferred as Ring A is a 5-membered ring (pyrrolidine ring) which optionally further has, besides $R^6$ to $R^9$, 1 or 2 substituents selected from a halogen atom, a lower alkyl group optionally has a hydroxy group, a lower alkenyl group and an aralkyl group, or a 5-membered ring (pyrrolidine ring) forming a spiro bond with $C_{3-6}$ cycloalkane. Of these, a 5-membered ring (pyrrolidine ring) which optionally has, besides $R^6$ to $R^9$, 1 or 2 substituents selected from a fluorine atom, methyl, ethyl, 1-hydroxy-1-methylethyl, isobutyl, 2-methylprop-2-en-1-yl and benzyl or a 5-membered ring (pyrrolidine ring) forming a spiro bond with cyclopropane is preferable.

Preferred as compound (I) is a compound wherein $R^1$ is a hydrogen atom, a halogen atom or a lower alkyl group optionally having substituent(s);

$R^2$ is a halogen atom, a lower alkyl group optionally having substituent(s) or a lower alkoxy group optionally having substituent(s);

$R^3$ is a cyano group;

$R^4$ is a hydrogen atom or a halogen atom;

$R^5$ is a hydrogen atom;

$R^6$ is a hydrogen atom;

$R^7$ is a lower alkyl group optionally having substituent(s) or an aralkyl group optionally having substituent(s);

$R^8$ is a hydrogen atom, a lower alkyl group optionally having substituent(s) or a $C_{3-6}$ cycloalkyl group optionally having substituent(s);

$R^9$ is a hydroxy group; and

Ring A is a 5-membered ring (pyrrolidine ring) which optionally has 1 or 2 substituents selected from a halogen atom, a lower alkyl group optionally having a hydroxy group, a lower alkenyl group and an aralkyl group, or a 5-membered ring (pyrrolidine ring) forming a spiro bond with $C_{3-6}$ cycloalkane.

Particularly, preferred is a compound wherein $R^1$ is (i) a hydrogen atom, (ii) a halogen atom or (iii) a lower alkyl group;

$R^2$ is a halogen atom, a lower alkyl group optionally having halogen atom(s) or a lower alkoxy group optionally having halogen atom(s);

$R^3$ is a cyano group;

$R^4$ is a hydrogen atom or a halogen atom;

$R^5$ is a hydrogen atom;

$R^6$ is a hydrogen atom;

$R^7$ is a lower alkyl group optionally having substituent(s) or an aralkyl group optionally having substituent(s);

$R^8$ is a hydrogen atom, a lower alkyl group or a $C_{3-6}$ cycloalkyl group;

$R^9$ is a hydroxy group; and

Ring A is preferably a 5-membered ring (pyrrolidine ring) which further optionally has, besides $R^6$ to $R^9$, 1 or 2 substituents selected from a halogen atom, a lower alkyl group optionally having a hydroxy group, a lower alkenyl group and an aralkyl group, or a 5-membered ring (pyrrolidine ring) forming a spiro bond with cyclopropane.

Furthermore, preferred is a compound of the formula (I')

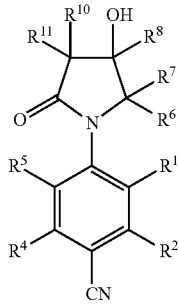

(I')

wherein $R^1$ is a hydrogen atom, a halogen atom or a lower alkyl group optionally having substituent(s);

$R^2$ is a halogen atom, a lower alkyl group optionally having halogen atom(s) or a lower alkoxy group optionally having halogen atom(s);

$R^4$ is a hydrogen atom or a halogen atom;

$R^5$ and $R^6$ are each a hydrogen atom;

$R^7$ is a lower alkyl group optionally having substituent(s) or an aralkyl group optionally having substituent(s);

$R^8$ is a hydrogen atom, a lower alkyl group optionally having substituent(s) or a $C_{3-6}$ cycloalkyl group optionally having substituent(s); and $R^{10}$ and $R^{11}$ are the same or different and each is a hydrogen atom, a halogen atom, a lower alkyl group optionally having a hydroxy group, a lower alkenyl group or an aralkyl group; wherein $R^{10}$ and $R^{11}$ may form $C_{3-6}$ cycloalkane together with the adjacent carbon atom.

Preferred as compound (I') is a compound wherein $R^1$ is a hydrogen atom, a halogen atom (e.g., fluorine atom) or a lower alkyl group (e.g., methyl);

$R^2$ is a halogen atom (e.g., fluorine atom, chlorine atom), a lower alkyl group optionally having halogen atom(s) (e.g., trifluoromethyl) or a lower alkoxy group optionally having halogen atom(s) (e.g., methoxy);

$R^7$ is a lower alkyl group (e.g., methyl, ethyl, n-propyl, isopropyl, isobutyl) optionally having substituent(s) selected from a hydroxy group, a lower alkoxy group (e.g., methoxy) and a $C_{3-6}$ cycloalkyl group (e.g., cyclopropyl), or an aralkyl group (e.g., benzyl) optionally having substituent(s) selected from a halogen atom (e.g., fluorine atom) and a cyano group;

$R^8$ is a hydrogen atom, a lower alkyl group (e.g., methyl) or a $C_{3-6}$ cycloalkyl group (e.g., cyclopropyl); and $R^{10}$ and $R^{11}$ are the same or different and each is a hydrogen atom, a halogen atom (e.g., fluorine atom), a lower alkyl group (e.g., methyl, ethyl, isobutyl), a lower alkenyl group (e.g., 2-methylprop-2-en-1-yl etc.), an aralkyl group (e.g., benzyl), a lower alkyl group substituted by a hydroxy group (e.g., 1-hydroxy-1-methylethyl) (in this case, $R^{10}$ and $R^{11}$ may form cyclopropane together with the adjacent carbon atom).

Preferred as compound (I) are more specifically the compounds described in the below-mentioned Examples 1 to 84 and salts thereof.

The production methods of the compound (I) are described in the following. Compound (I) can be produced by a general organic synthesis method, or according to a known synthetic method (e.g., WO 2004-016576).

Compound (I) can be produced, for example, by reacting a compound represented by the formula (II)

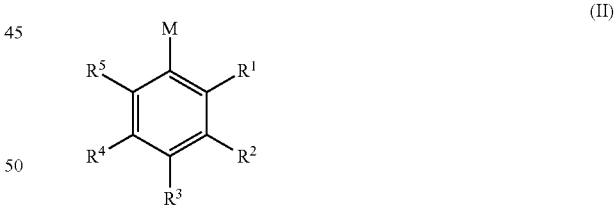

(II)

wherein M is a leaving group, and the other symbols are as defined above, with a compound represented by the formula (III)

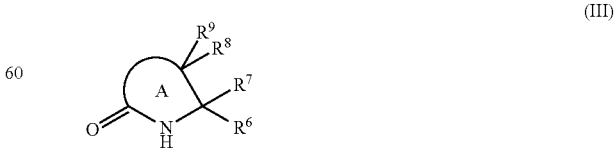

(III)

wherein each symbol is as defined above, in the presence of a palladium catalyst and a suitable ligand, and removing a protecting group when it is present.

Compounds (II) and (III) to be used as starting materials can be synthesized according to a known method or a method analogous thereto, for example, according to the methods shown in the Reference Examples below.

The above-mentioned compounds (II) and (III) also include salts thereof, and as such salts, those similar to the salts of compound (I) and the like are used. In addition, the groups in compounds (II) and (III) may be protected by protecting groups used in general organic syntheses and, when desired, the protecting groups can be removed after reaction, according to known methods.

As the "leaving group" for M, for example, a halogen such as chlorine, bromine, iodine and the like, trifluoromethanesulfonyloxy and the like can be used.

The compound (III) is generally used in an amount of 1 to 3 mol per 1 mol of compound (II). The reaction also proceeds smoothly by, where necessary, adding a base such as lithium carbonate, potassium carbonate, sodium carbonate, cesium carbonate, sodium hydrogen carbonate, sodium hydroxide, sodium tert-butoxide, potassium tert-butoxide, triethylamine and the like.

As the palladium catalyst, palladium (II) acetate, tris(dibenzylideneacetone)dipalladium(0) and the like can be used. Of these, tris(dibenzylideneacetone)dipalladium(0) is preferable.

As the ligand to be used for the reaction, tris(ortho-tolyl)phosphine, BINAP, 1,1'-bis(diphenylphosphino)ferrocene, 4,5-bis(diphenylphosphino)-9,9-dimethylxanthene and the like can be used. Of these, 4,5-bis(diphenylphosphino)-9,9-dimethylxanthene is preferable.

The reaction can be performed in an inert solvent, for example, tetrahydrofuran, diethyl ether, 1,2-dimethoxyethane, 1,4-dioxane, toluene, benzene, xylene, N,N-dimethylformamide (DMF) etc., or a mixed solvent thereof. The reaction can be performed in a temperature range of about 0° C. to 180° C. The reaction time is not particularly limited but it is generally 0.1 hr to 100 hr, preferably 0.5 hr to 72 hr.

Moreover, one or more substituents on Ring A in compound (I) can be converted to other substituents. For example, it is possible to reduce a carbonyl group to alcohol, lead alcohol to olefin by dehydration, or alkylate alcohol to ether according to a method known per se.

When compound (I) is a compound represented by the formula (I')

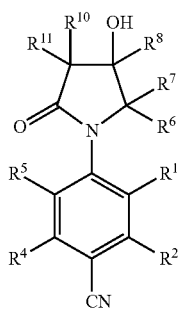

(I')

wherein each symbol is as defined above, compound (I') can be produced, for example, according to any of the following synthetic methods 1 to 3, or a synthetic method analogous thereto.

Compounds (IV) to (XVI) in synthetic methods 1 to 3 also include salts thereof, and as such salts, those similar to the salts of compound (I) and the like are used. In addition, the groups in compounds (IV) to (XVI) may be protected by protecting groups generally used for organic syntheses and, when desired, the protecting groups can be removed after reaction, according to known methods.

A simplified representation of reaction method 1 is shown below.

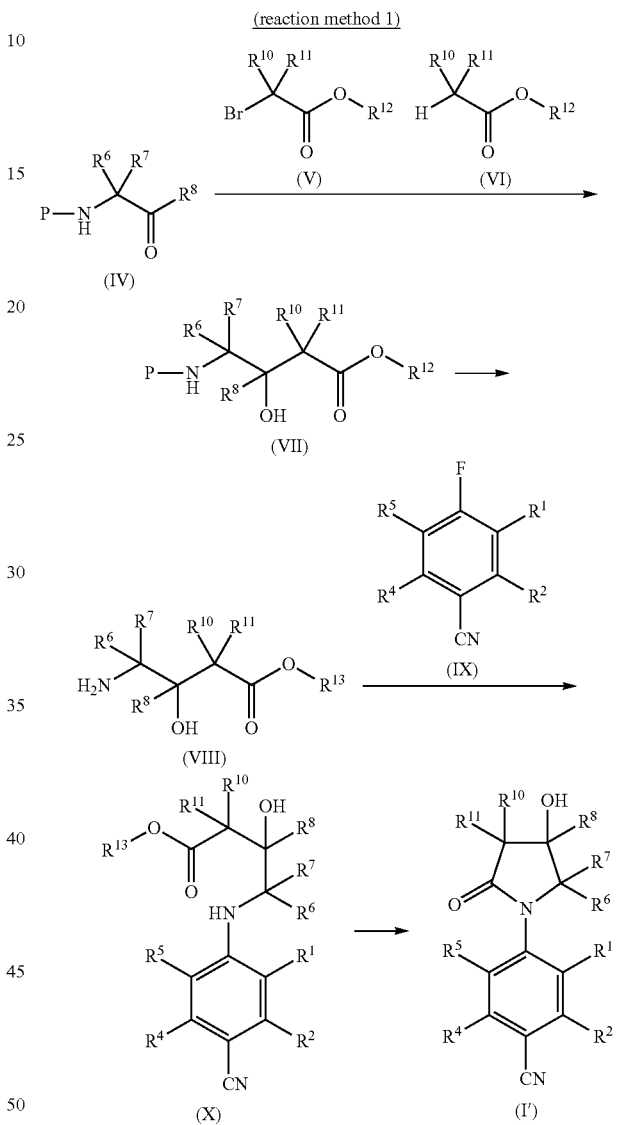

Compound (VII) wherein each symbol is as defined above can be synthesized according to a known synthetic method (e.g., J. R. Luly, et al., J. Org. Chem., 52, 1487-1492 (1987), A. Wyslouch., et al., Tetrahedron Asymmetry, 3, 1401-1410 (1992), S. Steurer, et al., Eur. J. Org. Chem., 1551-1560 (1999), D. Schirlin, et al., Tetrahedron, 52, 305-318 (1996)) or a method analogous thereto.

Compound (VII) can be produced by reacting compound (IV), wherein $R^6$ to $R^8$ are as defined above, and P is an amino-protecting group, with compound (V) or compound (VI) wherein $R^{10}$ and $R^{11}$ are as defined above, and $R^{12}$ is lower alkyl such as tert-butyl and the like.

As the amino-protecting group for P, the protecting groups described in Theodora W. Greene, Peter G. M. Wuts, Protective Groups in Organic Synthesis third edition, pages 494-

653. Among those described, a benzyloxycarbonyl group (Z group) or a tert-butoxycarbonyl group (Boc group) is preferable.

When compound (V) is used, a reaction can be carried out according to the conditions of a known Reformatsky reaction (e.g., Org. React., 22, 423 (1975); Synthesis, 571 (1989)).

Compound (V) is generally used in 1 to 3 mol per 1 mol of compound (IV).

Compound (VII) can be produced by reacting compound (IV) with a Reformatsky reagent prepared from compound (V) and generally 1 to 3 mol of zinc per 1 mol of compound (V).

For preparation of a Reformatsky reagent, the copresence of generally 0.1 to 1 mol of trimethylsilyl chloride or copper (I) chloride per 1 mol of compound (V) is effective.

The reaction can be carried out in an inert solvent, such as tetrahydrofuran, diethyl ether, 1,2-dimethoxyethane, 1,4-dioxane, toluene, benzene, xylene and the like, and a mixed solvent thereof. The reaction is carried out within a temperature range of from about −40° C. to 100° C. While the reaction time is not particularly limited, it is generally 0.1 hr to 100 hr, preferably 0.5 hr to 72 hr.

When compound (VI) is used, compound (VII) can be produced by reacting compound (VI) with a base such as lithium diisopropylamide and the like and then reacting the resulting compound with compound (IV).

As the base, lithium hexamethyldisilazide, sodium hexamethyldisilazide, potassium hexamethyldisilazide and the like can be used in addition to lithium diisopropylamide. The amount thereof to be used is generally 1 to 5 mol per 1 mol of compound (VI).

The reaction can be carried out in an inert solvent, such as tetrahydrofuran, diethyl ether, 1,2-dimethoxyethane, 1,4-dioxane, toluene, benzene, xylene and the like, and a mixed solvent thereof. The reaction is carried out within a temperature range of about −40° C. to 100° C., preferably −40° C. to 25° C. While the reaction time is not particularly limited, it is generally 0.1 hr to 100 hr, preferably 0.5 hr to 72 hr.

Compound (VIII) wherein $R^6$ to $R^{11}$ are as defined above, and $R^{13}$ is a hydrogen atom, lower alkyl such as tert-butyl and the like can be produced by removing an amino-protecting group P from compound (VII) according to the method described in, for example, Theodora W. Greene, Peter G. M. Wuts, Protective Groups in Organic Synthesis third edition, pages 494 to 653 or a method analogous thereto.

The purity can be improved by recrystallizing a salt of compound (VIII) with an inorganic or organic acid. As the salt with an inorganic acid, a salt with hydrochloric acid, hydrobromic acid, nitric acid, sulfuric acid, phosphoric acid and the like is used. As the salt with an organic acid, a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like is used.

Compound (X) wherein each symbol is as defined above can be produced by reacting compound (VIII) with compound (IX).

Compound (IX) is generally used in 1 to 3 mol per 1 mol of compound (VIII). The reaction can also be carried out smoothly by adding, where necessary, a base such as lithium carbonate, potassium carbonate, sodium carbonate, cesium carbonate, sodium hydrogen carbonate, sodium hydroxide, sodium tert-butoxide, potassium tert-butoxide, triethylamine, diisopropylamine and the like in 1 to 3 mol per 1 mol of compound (IX).

The reaction can be carried out in an inert solvent, such as tetrahydrofuran, diethyl ether, 1,2-dimethoxyethane, 1,4-dioxane, toluene, benzene, xylene, dimethylformamide, dimethyl sulfoxide and the like, and a mixed solvent thereof. The reaction is carried out within a temperature range of about −40° C. to 120° C., preferably 25° C. to 100° C. While the reaction time is not particularly limited, it is generally 0.1 hr to 100 hr, preferably 0.5 hr to 72 hr.

Compound (I') wherein each symbol is as defined above can be produced by a cyclization reaction of compound (X).

The reaction can be carried out in an inert solvent, such as tetrahydrofuran, diethyl ether, 1,2-dimethoxyethane, 1,4-dioxane, toluene, benzene, xylene, dimethylformamide, dimethyl sulfoxide, acetic acid, trifluoroacetic acid and the like, and a mixed solvent thereof. The reaction is carried out within a temperature range of about 0° C. to 120° C., preferably 25° C. to 80° C. While the reaction time is not particularly limited, it is generally 0.1 hr to 100 hr, preferably 0.5 hr to 72 hr.

The reaction can be carried out smoothly by adding, where necessary, a base such as lithium carbonate, potassium carbonate, sodium carbonate, cesium carbonate, sodium hydrogen carbonate, sodium hydroxide, sodium tert-butoxide, potassium tert-butoxide, triethylamine, diisopropylamine and the like, acetic acid, trifluoroacetic acid, sulfuric acid and the like in generally 1 to 3 mol per 1 mol of compound (X).

A simplified representation of reaction method 2 is shown below.

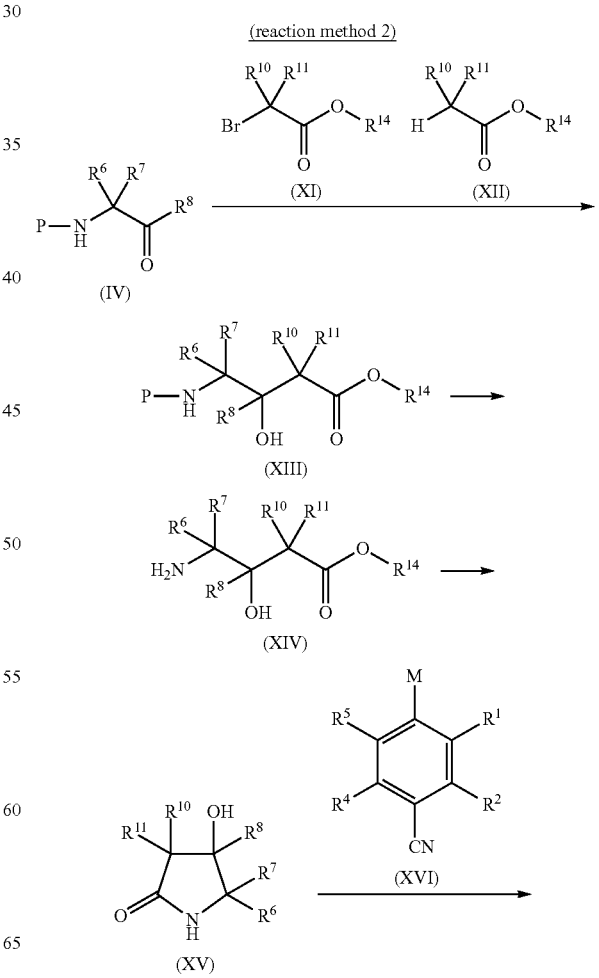

-continued

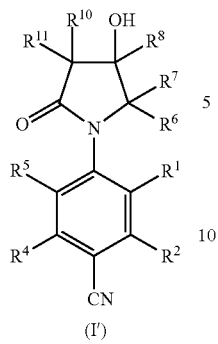

(I')

Compound (XIII) wherein $R^8$ to $R^{11}$ are as defined above, and $R^{14}$ is lower alkyl such as methyl, ethyl, propyl and the like, or aralkyl such as benzyl and the like can be produced by reacting compound (IV) wherein each symbol is as defined above with compound (XI) or compound (XII) wherein each symbol is as defined above under the same conditions as for the production method of compound (VII).

Compound (XIV) wherein each symbol is as defined above can be produced from compound (XIII) in the same manner as in the production method of compound (VIII).

Compound (XV) wherein each symbol is as defined above can be produced by a cyclization reaction of compound (XIV).

The reaction can be carried out in an inert solvent, such as tetrahydrofuran, diethyl ether, 1,2-dimethoxyethane, 1,4-dioxane, toluene, benzene, xylene, dimethylformamide, dimethyl sulfoxide and the like, and a mixed solvent thereof. The reaction is carried out within a temperature range of about 0° C. to 120° C., preferably 25° C. to 80° C. While the reaction time is not particularly limited, it is generally 0.1 hr to 100 hr, preferably 0.5 hr to 72 hr.

The reaction can also be carried out smoothly by adding, where necessary, a base such as lithium carbonate, potassium carbonate, sodium carbonate, cesium carbonate, sodium hydrogen carbonate, sodium hydroxide, sodium tert-butoxide, potassium tert-butoxide, triethylamine, diisopropylamine and the like in 1 to 3 mol per 1 mol of compound (XIV).

Compound (I') can be produced by reacting'compound (XV) with compound (XVI) wherein each symbol is as defined above under the same conditions as for the production method of compound (I) from compound (II) and compound (III).

A simplified representation of reaction method 3 is shown below.

(reaction method 3)

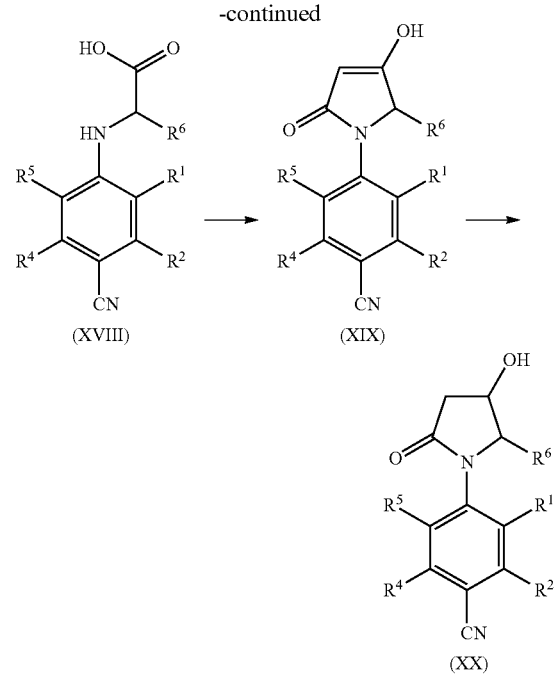

Compound (XX) wherein each symbol is as defined above, which is compound (I') wherein $R^7$ to $R^{11}$ are hydrogen atoms can be produced from amino acid (XVII) wherein each symbol is as defined above by the following method.

Compound (XVIII) can be produced by a condensation reaction of amino acid (XVII) and compound (IX) wherein each symbol is as defined above.

The reaction can be carried out using compound (IX) generally in 1-3 mol per 1 mol of compound (XVII) in an inert solvent, such as tetrahydrofuran, diethyl ether, 1,2-dimethoxyethane, 1,4-dioxane, toluene, benzene, xylene, dimethylformamide, dimethyl sulfoxide and the like, and a mixed solvent thereof. The reaction is carried out within a temperature range of about 0° C. to 120° C., preferably 25° C. to 100° C. While the reaction time is not particularly limited, it is generally 0.1 hr to 100 hr, preferably 0.5 hr to 72 hr.

The reaction can also be carried out smoothly by adding, where necessary, a base such as lithium carbonate, potassium carbonate, sodium carbonate, cesium carbonate, sodium hydrogen carbonate, sodium hydroxide, sodium tert-butoxide, potassium tert-butoxide; triethylamine, diisopropylamine and the like in 1 to 3 mol per 1 mol of compound (XVII).

Compound (XIX) can be produced by reacting compound (XVIII) with N,N'-carbonyldiimidazole and the like to give an active ester, and reacting the ester with Meldrum's acid.

In addition to N,N'-carbonyldiimidazole, dicyclohexylcarbodiimide, diisopropylcarbodiimide, aqueous carbodiimide (e.g., 1-ethyl-3-(3-dimethylaminopropyl)carbodiimide hydrochloride) and isopropyl chloroformate can be used. Particularly, N,N'carbonyldiimidazole is preferable.

Where necessary, the reaction can be carried out smoothly by adding, where necessary, 1-hydroxybenzotriazole, 4-(N,N-dimethylamino)pyridine and the like.

The reaction can be carried out using a condensation agent and Meldrum's acid each generally in 1-3 mol per 1 mol of compound (XVIII) in an inert solvent, such as tetrahydrofuran, diethyl ether, 1,2-dimethoxyethane, ethyl acetate, 1,4-dioxane, toluene, benzene, xylene, dimethylformamide, dimethyl sulfoxide and a mixed solvent thereof. The reaction is carried out within a temperature range of about 0° C. to 120° C., preferably 25° C. to 80° C.

While the reaction time is not particularly limited, it is generally 0.1 hr to 100 hr, preferably 0.5 hr to 72 hr.

Compound (XX) can be produced by reducing compound (XIX).

As the reducing agent, sodium borohydride, lithium borohydride, diisobutylaluminum hydride and the like can be used, with preference given to sodium borohydride. Using the reducing agent in 1 to 5 mol per 1 mol of compound (XIX), the reaction can be carried out in an inert solvent, such as tetrahydrofuran, diethyl ether, 1,2-dimethoxyethane, 1,4-dioxane, toluene, benzene, xylene and a mixed solvent thereof. The reaction is carried out within a temperature range of about 0° C. to 100° C., preferably 0° C. to 50° C. While the reaction time is not particularly limited, it is generally 0.1 hr to 100 hr, preferably 0.5 hr to 72 hr.

Thus-obtained compound (I) can be isolated and purified by a separation means known per se, such as concentration, concentration under reduced pressure, solvent extraction, liquid conversion, salting out, crystallization, recrystallization, phase transfer, chromatography and the like.

When compound (I) is obtained as a free form, it can be converted to a desired salt by a method known per se or a modification thereof; conversely, when compound (I) is obtained as a salt, it can be converted to a free form or other desired salt by a method known per se or a modification thereof.

The compound (I) may be a hydrate or a non-hydrate.

When compound (I) is obtained as a mixture of optically active forms, they can be separated to the object optically active forms by an optical resolution means known per se.

Compound (I) may be labeled with an isotope (e.g., $^2$H, $^3$H, $^{14}$C etc.) and the like.

A prodrug of the compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc. A prodrug of compound (I) may be a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, 1990, Published by HIROKAWA SHOTEN.

The compound (including prodrug) of the present invention may form a salt. A salt of the compound is not particularly limited as long as it does not inhibit the reaction. For example, a salt with inorganic base, an ammonium salt, a salt with organic base, a salt with inorganic acid, a salt with organic acid, a salt with amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like.

The compound (I) of the present invention or a salt thereof or a prodrug thereof (hereinafter sometimes to be abbreviated as the compound of the present invention) has an androgen receptor modulating action, particularly an androgen receptor agonistic action, and can be used for the prophylaxis or treatment of diseases in mammals, for which administration of an androgen receptor agonist is effective. The diseases for which administration of an androgen receptor agonist is effective include hypogonadism, osteoporosis, hormone resistant cancer (particularly LHRH agonist resistant cancer), climacteric disorder (particularly male climacteric disorder), frailty, cachexia, anemia, arteriosclerosis, Alzheimer's disease, erectile dysfunction, depression, wasting disease, hypertriglyceridemia (hyperlipidemia) and the like. Particularly, it is used for the prophylaxis or treatment of hypogonadism, male climacteric disorder, frailty, cachexia or osteoporosis.

The compound of the present invention has a tissue-selective androgen receptor modulating action and shows, for example, an antagonistic action on the prostate and an agonistic action on the muscle. Specifically, the compound of the present invention shows an action to not increase the weight of the prostate at a dose that increases the weight of the muscle (e.g., levator ani muscle and the like). More specifically, it increases the prostate weight by about 10% or less (preferably 0% or less) at a dose that increases the levator ani muscle weight by about 20% or more (preferably about 20% to about 50%). Here, referring to the "increase in the prostate weight of 0% or less", an increase of 0% means that the prostate weight does not increase or decrease, and an increase of less than 0% means that the prostate weight decreases by the absolute value thereof. Accordingly, the compound of the present invention can be used as a pharmaceutical agent shown below.

(1) A frailty suppressant.

(2) A muscle strength enhancer or muscle increasing agent (providing effects of no bedridden aged patients, shortened rehabilitation period and the like).

(3) A suppressant of cachexia caused by, for example, AIDS, cancer and the like.
(4) A body weight decrease suppressant.
(5) An agent for the prophylaxis or treatment of prostate hypertrophy (that decreases the prostate weight).
(6) An agent for the prophylaxis or treatment of amyotrophy.
(7) An agent for reducing prostate weight.
(8) An agent for the prophylaxis or treatment of muscle loss caused by diseases (e.g., muscular dystrophy, muscular atrophy, X-linkage spinal cord medulla oblongata muscular atrophy (SBMA), cachexia, malnutrition, Hansen's disease, diabetes, renal disease, COPD (chronic obstructive pulmonary diseases), cancer, terminal renal failure, sarcopenia (loss of muscle due to advancing age), emphysema, osteomalacia, HIV infection, AIDS, cardiomyopathy and the like).
(9) A suppressant of loss of muscle strength in postmenopausal female.
(10) A suppressant of bone mineral density of postmenopausal female.
(11) A suppressant of hot flash (e.g., glow, sweating and the like) in postmenopausal female.
(12) An agent for reducing the side effects of LHRH modulators such as LHRH agonists (leuprorelin, goserelin, buserelin, nafarelin, triptorelin, gonadorelin and the like), LHRH antagonists (ganirelix, cetrorelix, antarelix, abarelix, sufugolix and the like) and the like.
(13) A suppressant of loss of muscle strength after administration of a pharmaceutical agent such as an LHRH modulator and the like.
(14) A suppressant of decreased bone mineral density after administration of a pharmaceutical agent such as an LHRH modulator and the like.
(15) A suppressant of hot flash (e.g., glow, sweating and the like) after administration of a pharmaceutical agent such as an LHRH modulator and the like.

In addition, the compound of the present invention shows effect as a frailty suppressant, a muscle strength enhancer or a muscle increasing agent while using as an agent for the prophylaxis or treatment of prostate hypertrophy or an agent for reducing the weight of the prostate. Accordingly, it is expected to shorten the period of rehabilitation without leaving aged inpatients bedridden. Without the side effect of increasing the weight of the prostate, it is expected to provide an agent for the prophylaxis or treatment of prostate cancer in patients with high possibility of prostate cancer. Without the side effect of virilization, moreover, it can be applied to female, and is expected to provide a suppressant of loss of muscle strength or bone mineral density loss in postmenopausal female, or a suppressant of hot flash (glow, sweating etc.) in postmenopausal female. Furthermore, it also is expected as an agent for reducing the side effects of LHRH agonists (leuprorelin, goserelin, buserelin, nafarelin, triptorelin, gonadorelin and the like), and LHRH antagonists (ganirelix, cetrorelix, antarelix, abarelix, sufugolix and the like), a suppressant of loss of muscle strength or bone mineral density loss after administration of these pharmaceutical agents, or a suppressant of hot flash (glow, sweating and the like) after administration of these pharmaceutical agents.

The compound of the present invention achieves growth inhibition and cell death by conversely placing an excessive stimulation on cancer that has acquired resistance to a hormone treatment by being hypersensitive to androgen. Thus, it can be used as an agent for the prophylaxis or treatment of, from various cancers, breast cancer, prostate cancer, endometrial cancer, cancer of the uterine cervix, ovarian cancer, urinary bladder cancer, thyroid cancer, bone tumor and penile cancer, that acquired hormone resistance, and is particularly useful as an agent for the prophylaxis or treatment of prostate cancer.

As hormone resistant cancer, for example, LHRH derivative resistant cancer, preferably LHRH agonist resistant cancer can be mentioned.

The compound of the present invention shows low toxicity and can be used as a pharmaceutical agent as it is, or as a pharmaceutical composition in admixture with a commonly known pharmaceutically acceptable carrier etc. in mammals (e.g., humans, horses, bovines, dogs, cats, rats, mice, rabbits, pigs, monkeys, and the like).

In addition to the compound of the present invention, said pharmaceutical composition may contain other active ingredients, e.g., the following hormonal therapeutic agents, anticancer agent (e.g., chemotherapeutic agents, immunotherapeutic agents, or pharmaceutical agents inhibiting the action of cell growth factors or cell growth factor receptors), antiemetic and the like.

As a pharmaceutical agent for mammals such as humans, the compound of the present invention can be administered orally in the form of, for example, tablets, capsules (including soft capsules and microcapsules), powders, granules and the like, or parenterally in the form of injections, suppositories, pellets and the like. Examples of the "parenteral administration route" include intravenous, intramuscular, subcutaneous, intra-tissue, intranasal, intradermal, instillation, intracerebral, intrarectal, intravaginal, intraperitoneal, intratumoral, juxtaposition of tumor and administration directly to the lesion.

The dose of the compound of the present invention varies depending on the route of administration, symptoms, etc. For example, when it is administered orally as an anticancer agent to a patient (body weight 40 to 80 kg) with breast cancer or prostate cancer, its dose is, for example, 0.1 to 200 mg/kg body weight per day, preferably 1 to 100 mg/kg body weight per day, and more preferably 1 to 50 mg/kg body weight per day. This amount may be administered once or in 2 to 3 divided portions daily.

The compound of the present invention can be orally or parenterally administered in the form of a solid dosage form such as tablet, capsule, granule, powder and the like; or a liquid preparation such as syrup, injection and the like, by admixing with a pharmaceutically acceptable carrier.

As a pharmaceutically acceptable carrier, various organic or inorganic carrier substances conventionally used as preparation materials can be used. For example, excipient, lubricant, binder and disintegrant for solid preparations, solvent, solubilizing agents, suspending agent, isotonicity agent, buffer and soothing agent for liquid preparations and the like can be mentioned. Where necessary, preparation additives such as preservatives, antioxidants, colorants, sweetening agents and the like can be used.

Preferable examples of the excipient include lactose, sucrose, D-mannitol, starch, crystalline cellulose, light anhydrous silicic acid and the like.

Preferable examples of the lubricant include magnesium stearate, calcium stearate, talc, colloidal silica and the like.

Preferable examples of the binder include crystalline cellulose, sucrose, D-mannitol, dextrin, hydroxypropylcellulose, hydroxypropylmethylcellulose, polyvinylpyrrolidone and the like.

Preferable examples of the disintegrant include starch, carboxymethylcellulose, calcium carboxymethylcellulose, croscarmellose sodium, sodium carboxymethyl starch and the like.

Preferable examples of the solvent include water for injection, alcohol, propylene glycol, macrogol, sesame oil, corn oil and the like.

Preferable examples of the solubilizing agents include polyethylene glycol, propylene glycol, D-mannitol, benzyl benzoate, ethanol, trisaminomethane, cholesterol, triethanolamine, sodium carbonate, sodium citrate and the like.

Preferable examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; and the like.

Preferable examples of the isotonicity agent include sodium chloride, glycerol, D-mannitol and the like.

Preferable examples of the buffer include buffers such as phosphate, acetate, carbonate, citrate and the like; and the like.

Preferable examples of the soothing agent include benzyl alcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbic acid and the like.

A pharmaceutical composition can be produced according to a conventional method by adding the compound of the present invention generally in a proportion of 0.1 to 95% (w/w) relative to the total amount of the preparation, though subject to change depending on the dosage form, administration method, carrier and the like.

In addition, a combination of (1) administration of an effective amount of a compound of the present invention and (2) 1 to 3 selected from the group consisting of (i) administration of an effective amount of other anticancer agents, (ii) administration of an effective amount of other hormonal therapeutic agents and (iii) non-drug therapy can prevent and/or treat cancer more effectively. As the non-drug therapy, for example, surgery, hypertensive chemical therapy using angiotensin II and the like, radiotherapy, gene therapy, thermotherapy, cryotherapy, laser cauterization, and the like are used, and two or more of these may be combined.

For example, the compound of the present invention can be used in combination with other hormonal therapeutic agents, other anti-cancer agents (e.g., chemotherapeutic agent, immunotherapeutic agent (including vaccine), antibody, gene therapy drugs, pharmaceutical agents inhibiting the action of cell growth factors and receptors thereof, pharmaceutical agents inhibiting angiogenesis), antiemetics and the like (hereinafter to be abbreviated as concomitant drug).

While the compound of the present invention exhibits excellent anticancer action even when used as a simple agent, its effect can be still more enhanced or QOL of patients can be improved by using it in combination with one or more of the concomitant drug(s) mentioned above (multi-agent co-administration).

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, dienogest, asoprisnil, allylestrenol, gestrinone, nomegestrol, tadenan, mepartricin, raloxifene, ormeloxifene, levormeloxifene, anti-estrogen (e.g., tamoxifen citrate, toremifene citrate etc.), ER down-regulator (for example, fulvestrant etc.), human postmenopausal gonadotropin, follitropin, pill preparation, mepitiostane, testrolactone, aminoglutethimide, LH-RH derivative (e.g., LH-RH agonist (e.g., goserelin acetate, buserelin, leuprorelin etc.), LH-RH antagonist), droloxifene, epitiostanol, ethinylestradiol sulfonate, aromatase inhibitor (e.g., fadrozole hydrochloride, anastrozole, letrozole, exemestane, vorozole, formestane etc.), anti-androgens (e.g., flutamide, bicalutamide, nilutamide etc.), 5α-reductase inhibitor (e.g., finasteride, dutasteride, epristeride etc.), corticosteroid (e.g., dexamethasone, prednisolone, betamethasone, triamcinolone etc.), androgen synthesis inhibitor (e.g., abiraterone etc.), retinoid and drugs that retard retinoid metabolism (e.g., liarozole etc.) and the like. Preferred is LH-RH derivative.

Examples of the "chemotherapeutic agents" include alkylating agent, metabolic antagonist, antitumor antibiotics, plant-derived antitumor agent, other chemotherapeutic agents and the like.

Examples of the "alkylating agent" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, and the like.

Examples of the "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emitefur etc.), aminopterine, leucovorin calcium, tabloid, butocin, folinate calcium, levofolinate calcium, cladribine, emitefur, fludarabine, gemcitabine, hydroxycarbamide, pentostatin, piritrexim, idoxuridine, mitoguazone, thiazophrine, ambamustine and the like.

Examples of the "antitumor antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride and the like.

Examples of the "plant-derived antitumor agent" include etoposide, etoposide phosphate, vinblastine sulfate, vincristine sulfate, vindesine sulfate, teniposide, paclitaxel, docetaxel, DJ-927, vinorelbine, irinotecan, topotecan and the like.

Examples of the "other chemotherapeutic agents" include sobuzoxane and the like.

Examples of the "immunotherapeutic agent (BRM)" include picibanil, krestin, schizophyllan, lentinan, ubenimex, interferon, interleukin, macrophage colony stimulating factor, granulocyte colony stimulating factor, erythropoietin, lymphotoxin, *Corynebacterium parvum*, levamisole, polysaccharide K, procodazole and the like. As the vaccine, BCG vaccine, PROVENGE, Onyvax-P, PROSTVAC-VF, GVAX, DCVax-Prostate, SAPOIMMUNE, VPM-4-001 and the like are used.

Examples of the "antibody" include an antibody to EpiCAM, an antibody to PSCA, and an antibody to PSMA.

The "growth factor" in said "pharmaceutical agents inhibiting the action of cell growth factors or cell growth factor receptors" may be any as long as it promotes cell proliferation, which is normally peptide having a molecular weight of not more than 20,000 that is capable of exhibiting its activity at low concentrations by binding to a receptor. Examples thereof include (1) EGF (epidermal growth factor) or substances possessing substantially the same activity as it [e.g., EGF, heregulin TGF-α, HB-EGF etc.], (2) insulin or substances possessing substantially the same activity as it [e.g., insulin, IGF (insulin-like growth factor)-1, IGF-2, and the like], (3) FGF (fibroblast growth factor) or substance possessing substantially the same activity as it [e.g., acidic FGF, basic FGF, KGF (keratinocyte growth factor), FGF-10, and the like], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial cell growth factor), and the like], and the like.

Examples of the "growth factor receptors" include any receptors capable of binding to the aforementioned cell growth factors, such as EGF receptor, HER2, HER3 and HER4 belonging to the same family as that of EGF receptor, insulin receptor, IGF receptor, FGF receptor-1, FGF receptor-2, and the like.

Examples of the "pharmaceutical agents inhibiting the action of cell growth factors and receptors thereof" include trastuzumab (Herceptin (trademark); HER2 antibody), imatinib mesylate, ZD1839, cetuximab, gefitinib, erlotinib and the like.

Examples of the "pharmaceutical agents inhibiting angiogenesis" include antibodies to VEGF (e.g., bevacizumab), antibodies to VEGF receptors, VEGF receptor kinase inhibitors (e.g., SU11248 etc.), PDGF receptor kinase inhibitors, Tie2 kinase inhibitors, thalidomide and the like.

In addition to the aforementioned drugs, L-asparaginase, aceglatone, procarbazine hydrochloride, protoporphyrin-cobalt complex salt, mercuric hematoporphyrin-sodium, differentiation inducer (e.g., retinoid, vitamin D etc.), α-blocker (e.g., tamsulosin hydrochloride, naftopidil, urapidil, alfuzosin, terazosin, prazosin, silodosin etc.) serine/threonine kinase inhibitor, endothelin receptor antagonist (e.g., atrasentan etc.), proteasome inhibitor (e.g., bortezomib etc.), Hsp90 inhibitor (e.g., 17-AAG etc.), spironolactone, minoxidil, 11α-hydroxyprogesterone, and bone resorption inhibitory metastasis suppressing agent (e.g., zoledronic acid, alendronic acid, pamidronic acid, etidronic acid, ibandronic acid, clodronic acid) can also be used.

As the "antiemetic", gastric motility enhancers such as $5$-$HT_3$ antagonist such as ondansetron, tropisetron hydrochloride, azasetron, ramosetron, grahisetron, dolasetron mesylate, palonosetron and the like, $5$-$HT_4$ antagonists such as domperidone, mosapride, metoclopramide and the like, and the like; gastrointestinal tract motility regulators such as trimebutine and the like; phenothiazine pharmaceutical agents such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like can be used.

As the aforementioned LH-RH derivative, an LH-RH derivative or a salt thereof effective for hormone dependent disease, particularly sex hormone dependent disease such as sex hormone dependent cancer (e.g., prostate cancer, uterine cancer, breast cancer, pituitary gland tumor, liver cancer and the like), prostate hypertrophy, endometriosis, hysteromyoma, precocious puberty, dysmenorrhea, amenorrhea, premenstrual syndrome, polycystic ovary syndrome and the like and contraception (or infertility when rebound effect after cessation of the drug is used) are used. In addition, an LH-RH derivative or a salt thereof effective for benignant or malignant tumor, which is sex hormone independent but LH-RH sensitive, and the like is also used.

Specific examples of the LH-RH derivative or a salt thereof include peptides described in Treatment with GnRH analogs: Controversies and perspectives (The Parthenon Publishing Group Ltd., published in 1996), JP-A-3-503165, JP-A-3-101695, JP-A-7-97334, JP-A-8-259460 and the like.

Examples of the LH-RH derivative include an LH-RH agonist and an LH-RH antagonist. As the LH-RH antagonist, for example, physiologically active peptide represented by the formula X-D2Nal-D4ClPhe-D3Pal-Ser-A-B-Leu-C-Pro-DAlaNH$_2$ wherein X is N(4H$_2$-furoyl)Gly or NAc, A is a residue selected from NMeTyr, Tyr, Aph(Atz) and NMeAph (Atz), B is a residue selected from DLys(Nic), DCit, DLys (AzaglyNic), DLys(AzaglyFur), DhArg(Et$_2$), DAph(Atz) and DhCi, and C is Lys(Nisp), Arg or hArg(Et$_2$), or a salt thereof and the like are used, particularly preferably abarelix, ganirelix, cetrorelix, 5-(N-benzyl-N-methylaminomethyl)-1-(2,6-difluorobenzyl)-6-[4-(3-methoxyureido)phenyl]-3-phenylthieno[2,3-d]pyrimidin-2,4(1H,3H)-dione, 5-(N-benzyl-N-methylaminomethyl)-1-(2,6-difluorobenzyl)-6-[4-(3-ethylureido)phenyl]-3-phenylthieno[2,3-d]pyrimidin-2,4 (1H,3H)-dione, 5-(N-benzyl-N-methylaminomethyl)-1-(2, 6-difluorobenzyl)-6-[4-(3-ethylureido)phenyl]-3-phenylthieno[2,3-d]pyrimidin-2,4(1H,3H)-dione hydrochloride and the like are used.

As the LH-RH agonist, for example, physiologically active peptides represented by the formula 5-oxo-Pro-His-Trp-Ser-Tyr-Y-Leu-Arg-Pro-Z wherein Y is a residue selected from DLeu, DAla, DTrp, DSer(tBu), D2Nal and DHis(ImBzl), and Z is NH—C$_2$H$_5$ or Gly-NH$_2$, or a salt thereof and the like are used. For example, they are goserelin acetate, buserelin and the like. Particularly, peptide wherein Y is DLeu and Z is NH—C$_2$H$_5$ (i.e., peptide A represented by 5-oxo-Pro-His-Trp-Ser-Tyr-DLeu-Leu-Arg-Pro-NH—C$_2$H$_5$; leuprorelin) or a salt thereof (e.g., acetate) is preferable.

When the amino acid, peptide, protecting group and the like of the polypeptide described in the present specification are indicated using abbreviations, they are based on the abbreviations according to the IUPAC-IUB Commission on Biochemical Nomenclature or conventional abbreviations in the field. When an optical isomer due to amino acid is present, it means an L form unless otherwise specified.

Examples of the abbreviations are as follows.
Abu: aminobutyric acid
Aibu: 2-aminobutyric acid
Ala: alanine
Arg: arginine
Gly: glycine
His: histidine
Ile: isoleucine
Leu: leucine
Met: methionine
Nle: norleucine
Nval: norvaline
Phe: phenylalanine
Phg: phenylglycine
Pro: proline
(Pyr)Glu: pyroglutamic acid
Ser: serine
Thr: threonine
Trp: tryptophan Tyr: tyrosine
Val: valine
D2Nal: D-3-(2-naphthyl)alanine residue
DSer(tBu): O-tert-butyl-D-serine
DHis(ImBzl): $N^{im}$-benzyl-D-histidine
PAM: phenylacetamidomethyl
Boc: t-butyloxycarbonyl
Fmoc: 9-fluorenylmethyloxycarbonyl
Cl—Z: 2-chloro-benzyloxycarbonyl
Br—Z: 2-bromo-benzyloxycarbonyl
Bzl: benzyl
$Cl_2$-Bzl: 2,6-dichlorobenzyl
Tos: p-toluenesulfonyl
HONb: N-hydroxy-5-norbornane-2,3-dicarboxyimide
HOBt: 1-hydroxybenzotriazole
HOOBt: 3-hydroxy-3,4-dihydro-4-oxo-1,2,3-benzotriazine
MeBzl: 4-methylbenzyl
Bom: benzyloxymethyl
Bum: t-butoxy methyl
Trt: trityl
DNP: dinitrophenyl
DCC: N,N'-dicyclohexylcarbodiimide Of the aforementioned drugs, preferable concomitant drugs are an LH-RH agonist (e.g., goserelin acetate, buserelin, leuprorelin etc.) and the like.

When using the compound of the present invention and a concomitant drug in combination, the administration time of the compound of the present invention and the concomitant drug is is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the compound of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like. In the following, these administration modes are collectively abbreviated as the concomitant drug of the present invention.

The concomitant drug of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, vein, and the like). An injection can be administered intravenously, intramuscularly, subcutaneously, into the organ, intranasally, intradermally, by instillation, intracerebrally, intrarectally, vaginally and intraperitoneally, intratumorally, proximally to the tumor and the like, or directly to the lesion.

As a pharmacologically acceptable carrier which may be used for producing the concomitant drug of the present invention, those similar to the aforementioned pharmacologically acceptable carriers that can be used for the pharmaceutical composition of the present invention can be used.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually is from about 0.01 to 100% by weight, preferably from about 0.1 to 50% by weight, further preferably from about 0.5 to 20% by weight, based on the entire preparation.

The content of the concomitant drug in the combination agent of the present invention differs depending on the form of a preparation, and usually is from about 0.01 to 100% by weight, preferably from about 0.1 to 50% by weight, further preferably from about 0.5 to 20% by weight, based on the entire preparation.

The content of additives such as carrier and the like in the combination agent of the present invention differs depending on the form of a preparation, and usually from about 1 to 99.99% by weight, preferably from about 10 to 90% by weight, based on the entire preparation.

In the case when the compound of the present invention and the concomitant drug are separately prepared respectively, the same contents may be adopted.

These preparations can be produced by a method known per se usually used in a preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH regulator (e.g., hydrochloric acid, sodium hydroxide and the like), a preservative (e.g., ethyl parahydroxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and prepared into an oily injection, whereby an injection is afforded.

To produce a preparation for oral administration, an excipient (e.g., lactose, sucrose, starch and the like), a disintegrating agent (e.g., starch, calcium carbonate and the like), a binder (e.g., starch, gum Arabic, carboxymethylcellulose, polyvinylpyrrolidone, hydroxpropylcellulose and the like), a lubricant (e.g., talc, magnesium stearate, polyethylene glycol 6000 and the like) and the like, for example, can be added to the compound of the present invention or the concomitant drug, according to a method known per se, and the mixture can be compression-molded, then if desirable, the molder product can be coated by a method known per se for the purpose of masking of taste, enteric property or durability, to obtain a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid•acrylic acid copolymer, manufactured by Rohm, DE), pigment (e.g., iron oxide red, titanium dioxide, etc.) and the like can be used. The preparation for oral administration may be any of a immediate-release preparation and a sustained release preparation.

For example, to give a suppository, the compound of the present invention and the concomitant drug can be made into an oily or aqueous solid, semisolid or liquid suppository according to a method known per se. As the oily substrate to be used for the aforementioned composition, for example, glycerides of higher fatty acids [e.g., cacao butter, Witepsols (manufactured by Dynamit Nobel, Germany), etc.], medium chain fatty acid [e.g., Miglyols (manufactured by Dynamit Nobel, Germany), etc.], or vegetable oils (e.g., sesame oil, soybean oil, cotton seed oil and the like), and the like are listed. Further, as the aqueous substrate, for example, polyethylene glycols, propylene glycol are listed, and as the aqueous gel substrate, for example, natural gums, cellulose derivatives, vinyl polymers, acrylic acid polymers and the like are listed.

As the above-mentioned sustained release preparation, sustained release microcapsules and the like are used.

The sustained release microcapsule can be produced by a method known per se and, for example, a sustained-release preparation such as the one shown in the following [2] is preferably formed and administered.

The compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be specifically described in the following.

[1] Injection and Preparation Thereof.

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic acid salts such as tromethamol and the like, etc. are used.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

Into this injection, additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl parahydroxybenzoate, benzoic acid and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection is advantageously heated, alternatively, for example, filter sterilization, high pressure heat sterilization and the like can be conducted in the same manner as for a usual injection, to provide an injection.

It is advantageous that an aqueous solution for injection be subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof A sustained release preparation is preferable, which is obtained, if desirable, by coating a nucleus containing the compound of the present invention or the concomitant drug with a film agent such as a water-insoluble substance, swellable polymer and the like. For example, a sustained release preparation for oral administration of once administration per day is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylates, polymethacrylamides, aminoalkyl methacrylate copolymers, poly(methacrylic anhydride), glycidyl methacrylate copolymers, particularly, acrylic acid-based polymers such as Eudoragit (Rohm Pharma) such as Eudoragit RS-100, RL-100, RS-30D, RL-30D, RL-PO, RS-PO (ethyl acrylate/methyl methacrylate/trimethylammoniumethyl methacrylate chloride copolymer), Eudoragit NE-30D (methyl methacrylate/ethyl acrylate copolymer), and the like, hydrogenated oils such as hydrogenated castor oil (e.g., Lubri wax (Freund Corporation) and the like) and the like, waxes such as carnauba wax, glycerin fatty acid ester, paraffin and the like, polyglycerin fatty esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (last two are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to 40% (w/w), further preferably from about 5 to 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the average particle size thereof is preferably from about 150 to about 2000 µm, further preferably, from about 500 to about 1400 µm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and coagulation inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned, for example, a rolling granulation method in which a drug or a mixture of a drug with an excipient, lubricant and the like are added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the average particle size thereof is preferably from about 100 µm to about 1500 µm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and is preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be performed by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). Oral agents and parenteral agents such as an injection and the like are used, and oral agents are preferable.

The immediate-release preparation, usually, may contain, in addition to an active component drug, also carriers, additives and excipients conventionally used in the production field (hereinafter, sometimes abbreviated as excipient). The preparation excipient to be used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95%, preferably from about 1 to about 60% based on the total amount of the immediate-release preparation.

When the immediate-release preparation is an oral solid preparation, it usually contains, in addition to the above-mentioned components, also an integrating agent. As this integrating agent, for example, carboxymethylcellulose calcium (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (manufactured by Shin-Etsu Chemical Co., Ltd.), carboxymethylstarch (manufactured by Matsutani Kagaku K.K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by adsorbing water in contact with water, causing swelling, or making a channel between an effective ingredient constituting the nucleus and an excipient, can be used. These disintegrating agents can be used alone or in combination of two or more. The amount of the disintegrating agent to be used is appropriately selected depending on the kind and blending amount of a drug to be used, design of releasing property, and the like, and for example, from about 0.05 to about 30 w/w %, preferably from about 0.5 to about 15 w/w %, based on the total amount of the quick releasing agent.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into preparations or made into preparations appropriately together with preparation excipients and the like, separately, by an ordinary method, then, may be administered simultaneously or may be administered in combination at any administration interval, or they may be themselves made into one oral preparation (e.g., granule, fine particle, tablet, capsule and the like) or made into one oral preparation appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased bioavailability, β-cyclodextrin or β-cyclodextrin derivatives (e.g., hydroxypropyl-β-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, guar gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, aqueous starch, polyacrylic acids (e.g., Carbomer), polymethacylic acid, polyvinyl alcohol, polyethylene glycol, polyvinylpyrrolidone, polycarbophil, ascorbate palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

As the preferable intraoral quick disintegrating agent, there are used solid quick scattering dosage form composed of a network body comprising the compound of the present invention or the concomitant drug, and an aqueous or water-diffusible carrier which is inert to the compound of the present invention or concomitant drug. This network body is obtained by sublimating a solvent from the solid composition constituted of a solution prepared by dissolving the compound of the present invention or the concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include animal proteins or vegetable proteins such as gelatins, dextrins, soybean, wheat and psyllium seed protein and the like; rubber substances such as gum Arabic, guar gum, agar, xanthane gum and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one prostate cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dosage as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal and this is usually administered once to 4-times in division a day.

In administration of a combination agent of the present invention, it may be permissible that the compound of the present invention is administered after the first administration of the concomitant drugs or vice versa, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the pharmaceutical composition or the concomitant drug of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the pharmaceutical composition of the present invention or the concomitant drug of the present invention before and after an operation and the like, or before and after a treatment combining two or three kinds thereof, effects of prevention of resistance expression, elongation of Disease-Free Survival, suppression of cancer metastasis or recurrence, apothanasia and the like can be obtained.

In addition, a treatment with the pharmaceutical composition of the present invention or the concomitant drug of the present invention can be combined with a supporting therapy [(i) administration of antibiotic (e.g., β-lactam such as pansporin and the like, macrolides such as clarithromycin and the like etc.) for complication with various infectious diseases, (ii) administration of high-calory infusion, amino acid preparation or general vitamin preparation for malnutrition improvement, (iii) administration of morphine for pain mitigation, (iv) administration of pharmaceutical agent for reducing side effects such as nausea, vomiting, anorexia, diarrhea, leucopenia, thrombocytopenia, hemoglobin concentration decrease, hair loss, hepatopathy, renopathy, DIC, fever and the like, and (v) administration of pharmaceutical agent for suppressing multiple drug resistance of cancer etc.].

Specific examples of a pharmaceutical agent for such object, e.g., "antiemetic", include gastric motility enhancers such as 5-HT$_3$ antagonists (e.g., ondansetron, tropisetron hydrochloride, azasetron, ramosetron, granisetron, dolasetron mesylate, palonosetron and the like); NK1 receptor antagonists (e.g., sendide, CP-99994, CP-100263, CP-122721-1, CP-96345, FK224, RPR100893, NKP608, aprepitant (EMEND (trademark)) and the like; 5-HT$_4$ antagonists (e.g., domperidone, mosapride, metoclopramide and the like), and the like; gastrointestinal tract motility regulators such as trimebutine and the like; phenothiazine pharmaceutical agents such as prochlorperazine maleate, promethazine, thiethylperazine and the like; tranquilizers such as haloperidol, chlorpromazine phenolphthalinate, diazepam, droperidol and the like; steroids such as dexamethasone, prednisolone, betamethasone, triamcinolone and the like; as well as dimethylhydrin acid, diphenhydramine, hyoscine, hyoscine hydrobromide, tetrabenazine and the like.

Preferably, the pharmaceutical composition of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administration of the pharmaceutical composition of the present invention or the combination agent of the present invention before the surgery, etc., for example, it can be administered once about 30 min to 24 hr before the surgery, etc., or in 1 to 3 cycles about 3 to 6 months before the surgery, etc. In this way, the surgery, etc. can be conducted easily because, for example, a cancer tissue can be reduced by administering the pharmaceutical composition of the present invention or the combination agent of the present invention before the surgery, and the like.

As a period for administration of the pharmaceutical composition of the present invention or the combination agent of the present invention after the surgery and the like, for example, it can be administered repeatedly about 30 min to 24 hr after the surgery, and the like in a unit of several weeks to 3 months. In this way, the effect of the surgery and the like can be enhanced by administering the pharmaceutical composition of the present invention or the combination agent of the present invention after the surgery and the like.

EXAMPLES

The present invention is explained in detail in the following by referring to Reference Examples, Examples, Preparation Examples and Experimental Examples, which are not to be construed as limitative.

The elution in column chromatography in Reference Examples and Examples was performed under observation by TLC (thin-layer chromatography). In the TLC observation, Kieselgel 60F$_{254}$ plate (Merck) was used as a TLC plate, the solvent used as an elution solvent in the column chromatography was used as a developing solvent, and the means of detection used was an UV detector. As silica gel for column, Kieselgel 60F$_{254}$ (70-230 mesh) manufactured by Merck again or Purif-Pack (SI 60 μm), Purif-Pack (NH 60 μm) manufactured by MORITEX was used. NMR spectra are shown by proton NMR with tetramethylsilane as the internal standard, using VARIAN Gemini-200 (200 MHz type spectrometer), VARIAN Mercury-300 (300 MHz) or JMTCO400/54 (400 MHz type) (JEOL Ltd.); δ values are expressed in ppm. The reaction using a microwave reaction apparatus was performed using Emrys Optimizer manufactured by Biotage. The infrared absorption spectrum (IR) was measured using Paragon 1000 manufactured by PerkinElmer. The melting point was measured using MPA100 type melting point measurement apparatus, Optimelt, manufactured by Stanford Research System.

The abbreviations used in Reference Examples and Examples mean the following.
s: singlet
br: broad
brs: broad singlet
d: doublet
t: triplet
q: quartet
dd: double doublet
ddd: double double doublet
dt: double triplet
dq: double quartet
m: multiplet
J: coupling constant
Hz: hertz
THF: tetrahydrofuran
DMSO: dimethyl sulfoxide
DMF: N,N-dimethylformamide Reference Example 1

1-bromo-3-fluoro-4-iodo-2-methylbenzene

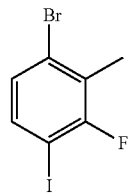

A solution of diisopropylamine (6.06 mL) in THF (100 mL) was cooled to −78° C., n-butyllithium-hexane (24.9 mL, 1.6 mol/L) was added dropwise and, after the completion of the dropwise addition, the mixture was stirred at −78° C. for 1 hr. Subsequently, a solution of 4-bromo-2-fluoro-1-iodobenzene (10.0 g) in THF (50 mL) was added dropwise, and the mixture was further stirred at −78° C. for 1 hr. Methyl iodide (2.90 mL) was added dropwise at −78° C. and the mixture was further stirred at −78° C. for 2 hr, and the mixture was warmed to room temperature. Water was added to the reaction mixture, and the mixture was extracted with ethyl acetate. The extract was washed with saturated brine, dried over anhydrous magnesium sulfate, and concentrated under reduced pressure to give the title compound as a brown oil (yield: 10.5 g, yield: 100%).
$^1$H-NMR (CDCl$_3$) δ: 2.37 (3H, d, J=2.6 Hz), 7.10 (1H, dd, J=8.5, 1.1 Hz), 7.39-7.46 (1H, m).

Reference Example 2

4-bromo-2-fluoro-3-methylbenzonitrile

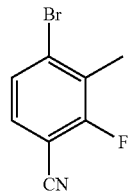

To a solution of 1-bromo-3-fluoro-4-iodo-2-methylbenzene (2.00 g) in DMF (15 mL) were added zinc cyanide (336 mg) and tetrakis(triphenylphosphine)palladium(0) (367 mg), and the mixture was stirred under an argon atmosphere at 100° C. for 5.5 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography to give the title compound as a colorless solid (yield: 1.21 g, 89%).

$^1$H-NMR (CDCl$_3$) δ: 2.39 (3H, d, J=2.6 Hz), 7.29-7.36 (1H, m), 7.44-7.50 (1H, m).

Reference Example 3

4-[(2S,3S)-3-(tert-butyldimethylsilyloxy)-2-methyl-5-oxopyrrolidin-1-yl]-2-fluoro-3-methylbenzonitrile

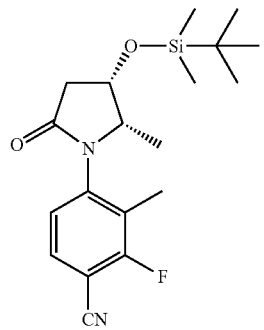 [SMILES: Cc1c(N2C(=O)C[C@H](O[Si](C)(C)C(C)(C)C)[C@@H]2C)ccc(C#N)c1F]

To a solution of 4-bromo-2-fluoro-3-methylbenzonitrile (1.10 g), (4S,5S)-4-(tert-butyldimethylsilyloxy)-5-methylpyrrolidin-2-one (1.18 g), cesium carbonate (2.51 g), tris(dibenzylideneacetone)dipalladium(0) (235 mg) and 4,5-bis(diphenylphosphino)-9,9-dimethylxanthene (297 mg) in dioxane (30 mL) was stirred under an argon atmosphere at 80° C. for 8 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography to give the title compound as a colorless solid (yield: 347 mg, 19%).

$^1$H-NMR (CDCl$_3$) δ: 0.11 (6H, d, J=7.2 Hz), 0.91 (9H, s), 1.04 (3H, d, J=6.4 Hz), 2.19 (3H, d, J=2.3 Hz), 2.50 (1H, dd, J=16.8, 2.4 Hz), 2.78 (1H, dd, J=16.8, 5.4 Hz), 4.09-4.22 (1H, m), 4.44-4.50 (1H, m), 6.96 (1H, d, J=8.7 Hz), 7.45-7.53 (1H, m).

Reference Example 4

Ethyl 4-{[(benzyloxy)carbonyl]amino}-2,2-dimethyl-3-oxopentanoate

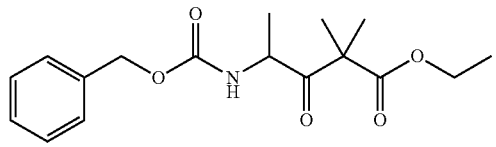 [SMILES: CCOC(=O)C(C)(C)C(=O)C(C)NC(=O)OCc1ccccc1]

A solution of ethyl (4S)-4-{[(benzyloxy)carbonyl]amino}-3-oxopentanoate (13.8 g) synthesized according to the method described in Tetrahedron Letters, vol. 41, pages 3979-3982, 2000, methyl iodide (8.79 mL) and potassium carbonate (13.01 g) in acetone (200 mL) was stirred under reflux overnight. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography to give the title compound as a colorless oil (yield: 11.82 g, 78%).

$^1$H-NMR (CDCl$_3$) δ: 1.22 (3H, t, J=7.2 Hz), 1.31 (3H, d, J=6.8 Hz), 1.41 (3H, s), 1.43 (3H, s), 4.06-4.22 (2H, m), 4.74 (1H, dd, J=8.5, 7.2 Hz), 5.02-5.17 (2H, m), 5.23-5.37 (1H, m), 7.28-7.46 (5H, m).

Reference Example 5

3,3,5-trimethylpyrrolidine-2,4-dione

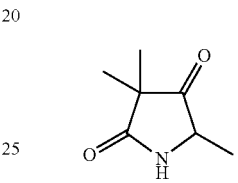

To a solution of ethyl 4-{[(benzyloxy)carbonyl]amino}-2,2-dimethyl-3-oxopentanoate (10.5 g) in methanol (150 mL) was added 10% palladium carbon (containing 50% water, 5.0 g), and the mixture was stirred under a hydrogen atmosphere overnight. The reaction mixture was filtered, and the filtrate was concentrated under reduced pressure. The obtained solid was washed with hexane to give the title compound as a colorless solid (yield: 4.00 g, 87%).

$^1$H-NMR (CDCl$_3$) δ: 1.26 (3H, s), 1.27 (3H, s), 1.40 (3H, d, J=6.8 Hz), 4.08 (1H, q, J=6.9 Hz), 6.07 (1H, brs).

Reference Example 6

2-chloro-4-(3,3,5-trimethyl-2,4-dioxopyrrolidin-1-yl)benzonitrile

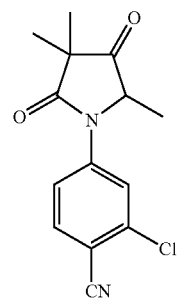 [SMILES: CC1C(=O)C(C)(C)C(=O)N1c1ccc(C#N)c(Cl)c1]

Using 4-bromo-2-chlorobenzonitrile (199 mg), 3,3,5-trimethylpyrrolidine-2,4-dione (100 mg), cesium carbonate (346 mg), tris(dibenzylideneacetone)dipalladium(0) (65 mg) and 4,5-bis(diphenylphosphino)-9,9-dimethylxanthene (82 mg), and in the same manner as in Reference Example 3, the title compound was obtained as a colorless solid (yield: 135 mg, 69%).

$^1$H-NMR (CDCl$_3$) δ: 1.35 (3H, s), 1.40 (3H, s), 1.46 (3H, d, J=6.8 Hz), 4.61 (1H, q, J=6.9 Hz), 7.55 (1H, dd, J=8.6, 2.1 Hz), 7.72 (1H, d, J=8.5 Hz), 7.87 (1H, d, J=2.1 Hz).

Reference Example 7

4-amino-2-methoxybenzonitrile

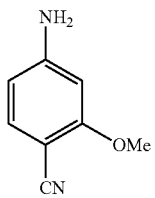

2-Methoxy-4-nitrobenzonitrile (5.0 g) and iron powder (7.84 g) were suspended in ethanol (150 mL), and concentrated hydrochloric acid (35 mL) was added dropwise at room temperature. The reaction mixture was stirred at room temperature for 3 hr, neutralized with sodium hydrogen carbonate, and extracted with ethyl acetate. The extract was washed with saturated brine, dried over anhydrous magnesium sulfate, and concentrated under reduced pressure. The residue was purified by silica gel column chromatography, and the obtained solid was washed with hexane to give the title compound as a red-brown solid (yield: 3.05 g, 73%).

$^1$H-NMR (CDCl$_3$) δ: 3.86 (3H, s), 4.15 (2H, brs), 6.16 (1H, d, J=2.1 Hz), 6.22 (1H, dd, J=8.3, 2.1 Hz), 7.30 (1H, d, J=8.3 Hz).

Reference Example 8

4-iodo-2-methoxybenzonitrile

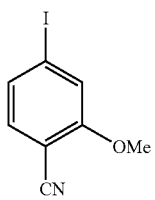

To a suspension of copper iodide (4.63 g) in acetonitrile (50 mL) was added tert-butyl nitrite (3.61 mL) at room temperature, a solution of 4-amino-2-methoxybenzonitrile (3.00 g) in acetonitrile (30 mL) was added dropwise thereto at 65° C. and, after the completion of the dropwise addition, the mixture was further stirred at 65° C. for 2 hr. The reaction mixture was added to aqueous sodium thiosulfate solution, and the mixture was extracted with ethyl acetate. The extract was washed with saturated brine, dried over anhydrous magnesium sulfate, and concentrated under reduced pressure. The residue was purified by silica gel column chromatography, and the obtained solid was washed with diisopropyl ether to give the title compound as a yellow solid (yield: 2.56 g, 49%).

$^1$H-NMR (CDCl$_3$) δ: 3.93 (3H, s), 7.24 (1H, d, J=8.1 Hz), 7.33 (1H, d, J=1.1 Hz), 7.39 (1H, dd, J=8.1, 1.1 Hz).

Reference Example 9

2-methoxy-4-(3,3,5-trimethyl-2,4-dioxopyrrolidin-1-yl)benzonitrile

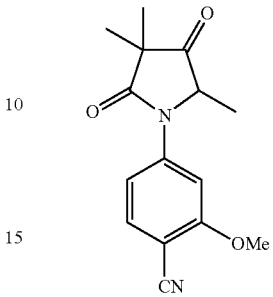

Using 4-iodo-2-methoxybenzonitrile (835 mg), 3,3,5-trimethylpyrrolidine-2,4-dione (350 mg), cesium carbonate (1.21 g), tris(dibenzylideneacetone)dipalladium(0) (227 mg) and 4,5-bis(diphenylphosphino)-9,9-dimethylxanthene (287 mg), and in the same manner as in Reference Example 3, the title compound was obtained as a colorless solid (yield: 330 mg, 49%).

$^1$H-NMR (CDCl$_3$) δ: 1.35 (3H, s), 1.40 (3H, s), 1.46 (3H, d, J=6.8 Hz), 3.97 (3H, s), 4.62 (1H, q, J=6.9 Hz), 6.88 (1H, dd, J=8.5, 2.1 Hz), 7.60 (1H, d, J=8.5 Hz), 7.66 (1H, d, J=2.1 Hz).

Reference Example 10

4-iodo-2-(trifluoromethyl)benzonitrile

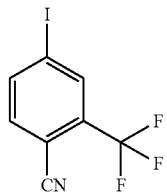 [SMILES: N#Cc1ccc(I)cc1C(F)(F)F]

Using copper iodide (6.14 g), tert-butyl nitrite (4.79 mL) and 4-amino-2-(trifluoromethyl)benzonitrile (5.00 g), and in the same manner as in Reference Example 8, the title compound was obtained as a pale-yellow solid (yield: 4.40 g, 55%).

$^1$H-NMR (CDCl$_3$) δ: 7.54 (1H, d, J=8.1 Hz), 8.06 (1H, dd, J=8.1, 1.1 Hz), 8.14 (1H, s).

Reference Example 11

2-(trifluoromethyl)-4-(3,3,5-trimethyl-2,4-dioxopyrrolidin-1-yl)benzonitrile

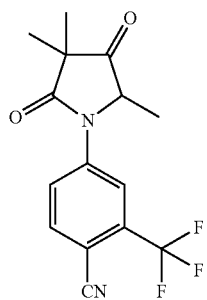 [SMILES: CC1C(=O)C(C)(C)C(=O)N1c1ccc(C#N)c(C(F)(F)F)c1]

Using 4-iodo-2-(trifluoromethyl)benzonitrile (957 mg), 3,3,5-trimethylpyrrolidine-2,4-dione (350 mg), cesium carbonate (1.21 g), tris(dibenzylideneacetone)dipalladium(0) (227 mg) and 4,5-bis(diphenylphosphino)-9,9-dimethylxanthene (287 mg), and in the same manner as in Reference Example 3, the title compound was obtained as a colorless solid (yield: 452 mg, 59%).

$^1$H-NMR (CDCl$_3$) δ: 1.36 (3H, s), 1.42 (3H, s), 1.48 (3H, d, J=7.0 Hz), 4.68 (1H, q, J=6.8 Hz), 7.86 (1H, dd, J=8.7, 1.5 Hz), 7.91 (1H, d, J=8.7 Hz), 8.12 (1H, d, J=1.5 Hz).

Reference Example 12

2,6-difluoro-4-(3,3,5-trimethyl-2,4-dioxopyrrolidin-1-yl)benzonitrile

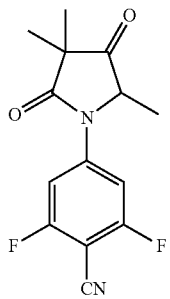 [SMILES: CC1C(=O)C(C)(C)C(=O)N1c1cc(F)c(C#N)c(F)c1]

Using 4-bromo-2,6-difluorobenzonitrile (502 mg), 3,3,5-trimethylpyrrolidine-2,4-dione (250 mg), cesium carbonate (866 mg), tris(dibenzylideneacetone)dipalladium(0) (162 mg) and 4,5-bis(diphenylphosphino)-9,9-dimethylxanthene (205 mg), and in the same manner as in Reference Example 3, the title compound was obtained as a colorless solid (yield: 305 mg, 62%).

$^1$H-NMR (CDCl$_3$) δ: 1.35 (3H, s), 1.40 (3H, s), 1.50 (3H, d, J=7.0 Hz), 4.54 (1H, q, J=7.0 Hz), 7.38-7.45 (2H, m).

Reference Example 13

2-chloro-3-methyl-4-(3,3,5-trimethyl-2,4-dioxopyrrolidin-1-yl)benzonitrile

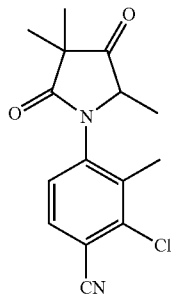 [SMILES: Cc1c(N2C(=O)C(C)(C)C(=O)C2C)ccc(C#N)c1Cl]

Using 2-chloro-4-iodo-3-methylbenzonitrile (894 mg) synthesized from 4-amino-2-chloro-3-methylbenzonitrile in the same method as in Reference Example 8, 3,3,5-trimethylpyrrolidine-2,4-dione (350 mg), cesium carbonate (1.21 g), tris(dibenzylideneacetone)dipalladium(0) (227 mg) and 4,5-bis(diphenylphosphino)-9,9-dimethylxanthene (287 mg), and in the same manner as in Reference Example 3, the title compound was obtained as a colorless solid (yield: 46 mg, 6%).

$^1$H-NMR (CDCl$_3$) δ: 1.30 (3H, d, J=6.8 Hz), 1.38 (3H, brs), 1.40 (3H, s), 2.31 (3H, s), 4.15-4.58 (1H, m), 7.21 (1H, d, J=8.3 Hz), 7.63 (1H, d, J=8.3 Hz).

Reference Example 14

5-ethyl-3,3-dimethylpyrrolidine-2,4-dione

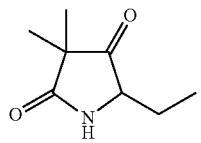

Using ethyl 4-{[(benzyloxy)carbonyl]amino}-3-oxohexanoate, and in the same manner as in Reference Example 4 and Reference Example 5, the title compound was obtained as a colorless solid.

$^1$H-NMR (CDCl$_3$) δ: 0.97 (3H, t, J=7.5 Hz), 1.23 (3H, s), 1.26 (3H, s), 1.63-1.94 (2H, m), 3.98 (1H, dd, J=6.6, 5.1 Hz), 6.28 (1H, brs).

Reference Example 15

2-chloro-4-(5-ethyl-3,3-dimethyl-2,4-dioxopyrrolidin-1-yl)benzonitrile

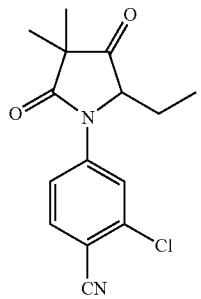 [SMILES: CCC1C(=O)C(C)(C)C(=O)N1c1ccc(C#N)c(Cl)c1]

Using 4-bromo-2-chlorobenzonitrile (219 mg), 5-ethyl-3,3-dimethylpyrrolidine-2,4-dione (120 mg), cesium carbonate (378 mg), tris(dibenzylideneacetone)dipalladium(0) (71 mg) and 4,5-bis(diphenylphosphino)-9,9-dimethylxanthene (89 mg), and in the same manner as in Reference Example 3, the title compound was obtained as a colorless solid (yield: 147 mg, 65%).

$^1$H-NMR (CDCl$_3$) δ: 0.76 (3H, t, J=7.5 Hz), 1.34 (3H, s), 1.36 (3H, s), 1.77-1.91 (1H, m), 1.99-2.14 (1H, m), 4.62-4.66 (1H, m), 7.55 (1H, dd, J=8.5, 2.1 Hz), 7.73 (1H, d, J=8.5 Hz), 7.84 (1H, d, J=2.1 Hz).

Reference Example 16

4-(5-ethyl-3,3-dimethyl-2,4-dioxopyrrolidin-1-yl)-2-methoxybenzonitrile

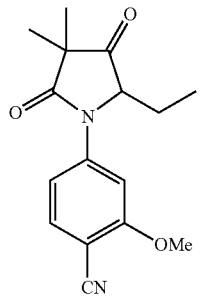 [SMILES: CCC1C(=O)C(C)(C)C(=O)N1c1ccc(C#N)c(OC)c1]

Using 4-iodo-2-methoxybenzonitrile (459 mg), 5-ethyl-3,3-dimethylpyrrolidine-2,4-dione (250 mg), cesium carbonate (787 mg), tris(dibenzylideneacetone)dipalladium(0) (148 mg) and 4,5-bis(diphenylphosphino)-9,9-dimethylxanthene (186 mg), and in the same manner as in Reference Example 3, the title compound was obtained as a colorless solid (yield: 300 mg, 65%).

¹H-NMR (CDCl₃) δ: 0.78 (3H, t, J=7.5 Hz), 1.34 (3H, s), 1.36 (3H, s), 1.79-1.95 (1H, m), 1.97-2.13 (1H, m), 3.97 (3H, s), 4.63-4.68 (1H, m), 6.90 (1H, dd, J=8.5, 1.9 Hz), 7.57-7.62 (2H, m).

Reference Example 17

4-(5-ethyl-3,3-dimethyl-2,4-dioxopyrrolidin-1-yl)-2-(trifluoromethyl)benzonitrile

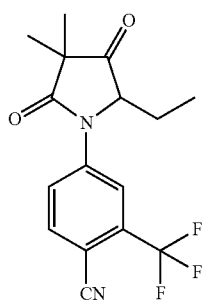 [SMILES: CCC1C(=O)C(C)(C)C(=O)N1c1ccc(C#N)c(C(F)(F)F)c1]

Using 4-iodo-2-(trifluoromethyl)benzonitrile (526 mg), 5-ethyl-3,3-dimethylpyrrolidine-2,4-dione (250 mg), cesium carbonate (787 mg), tris(dibenzylideneacetone)dipalladium (0) (148 mg) and 4,5-bis(diphenylphosphino)-9,9-dimethylxanthene (186 mg), and in the same manner as in Reference Example 3, the title compound was obtained as a pale-yellow oil (yield: 298 mg, 57%).

¹H-NMR (CDCl₃) δ: 0.77 (3H, t, J=7.4 Hz), 1.36 (3H, s), 1.38 (3H, s), 1.77-1.93 (1H, m), 2.02-2.17 (1H, m), 4.71 (1H, dd, J=6.1, 2.7 Hz), 7.86 (1H, dd, J=8.4, 1.9 Hz), 7.91 (1H, d, J=8.4 Hz), 8.08 (1H, d, J=1.9 Hz).

Reference Example 18

2-chloro-4-(5-ethyl-3,3-dimethyl-2,4-dioxopyrrolidin-1-yl)-3-methylbenzonitrile

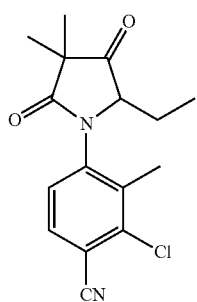 [SMILES: CCC1C(=O)C(C)(C)C(=O)N1c1ccc(C#N)c(Cl)c1C]

A solution of 2-chloro-4-iodo-3-methylbenzonitrile (983 mg), 5-ethyl-3,3-dimethylpyrrolidine-2,4-dione (550 mg), cesium carbonate (1.73 g), tris(dibenzylideneacetone)dipalladium(0) (325 mg) and 4,5-bis(diphenylphosphino)-9,9-dimethylxanthene (615 mg) in dioxane was reacted in a microwave reactor at 120° C. for 5 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography and recrystallized from THF/hexane to give the title compound as a colorless solid (yield: 294 mg, 27%).

¹H-NMR (CDCl₃) δ: 0.78-0.95 (3H, m), 1.31-1.42 (6H, m), 1.49-1.95 (2H, m), 2.32 (3H, s), 4.18-4.57 (1H, m), 7.15-7.39 (1H, m), 7.62 (1H, d, J=8.1 Hz).

Reference Example 19 ethyl 4-{[(benzyloxy)carbonyl]amino}-2,2-dimethyl-3-hydroxypentanoate

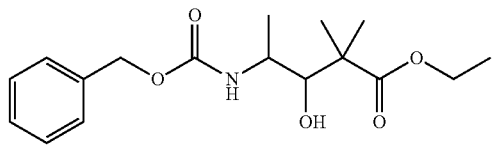 [SMILES: CCOC(=O)C(C)(C)C(O)C(C)NC(=O)OCc1ccccc1]

To a solution of ethyl 4-{[(benzyloxy)carbonyl]amino}-2,2-dimethyl-3-oxopentanoate (5.76 g) in methanol (100 mL) was added sodium borohydride (940 mg) at 0° C., and the mixture was stirred at room temperature for 17 hr. Saturated aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/3) to give the title compound as a colorless solid (yield: 4.26 g, 74%).

¹H-NMR (CDCl₃) δ: 1.01 (3H, d, J=6.8 Hz), 1.12-1.40 (10H, m), 3.39-3.64 (1H, m), 3.76-4.24 (3H, m), 4.85-5.33 (3H, m), 7.22-7.42 (5H, m).

Reference Example 20 ethyl 4-{[(benzyloxy)carbonyl]amino}-2,2-dimethyl-3-(tert-butyldimethylsilyloxy)pentanoate

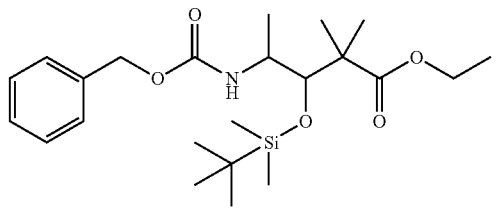 [SMILES: CCOC(=O)C(C)(C)C(O[Si](C)(C)C(C)(C)C)C(C)NC(=O)OCc1ccccc1]

To a solution of ethyl 4-{[(benzyloxy)carbonyl]amino}-2,2-dimethyl-3-hydroxypentanoate (5.7 g) and 2,6-lutidine (2.27 mL) in THF (80 mL) was added under ice-cooling tert-butyldimethylsilyl trifluoromethanesulfonate (3.44 mL) and, after warming to room temperature, the mixture was stirred for 17 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→32/1) to give the title compound as a colorless oil (yield: 5.42 g, 70%).

¹H-NMR (CDCl₃) δ: 0.03-0.20 (6H, m), 0.88-0.95 (9H, m), 1.06-1.33 (12H, m), 3.73-4.19 (4H, m), 4.55-5.22 (3H, m), 7.26-7.41 (5H, m).

Reference Example 21

(4RS,5SR)-4-(tert-butyldimethylsilyloxy)-3,3,5-trimethylpyrrolidin-2-one

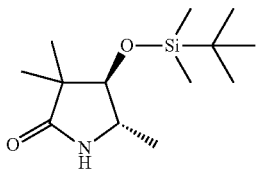 [SMILES: C[C@@H]1NC(=O)C(C)(C)[C@H]1O[Si](C)(C)C(C)(C)C]

To a solution of ethyl 4-{([(benzyloxy)carbonyl]amino}-2,2-dimethyl-3-(tert-butyldimethylsilyloxy)pentanoate (2.73 g) in methanol (13 mL) was added 10% palladium carbon (containing 50% water, 170 mg), and the mixture was stirred at room temperature for 3 hr under a hydrogen atmosphere and filtered. The filtrate was concentrated under reduced pressure, and the residue was dissolved in ethanol (20 mL). A 20% solution (4 mL) of sodium ethoxide-ethanol was added thereto, and the mixture was refluxed for 2 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/2) to give the title compound (yield: 700 mg, 44%) and (4RS,5RS)-4-(tert-butyldimethylsilyloxy)-3,3,5-trimethylpyrrolidin-2-one (yield: 380 mg, 24%), each as an oil.

(4RS,5SR)-4-(tert-butyldimethylsilyloxy)-3,3,5-trimethylpyrrolidin-2-one $^1$H-NMR (CDCl$_3$) δ: 0.09 (6H, s), 0.90 (9H, s), 1.06 (3H, s), 1.15 (3H, s), 1.25 (3H, d, J=6.2 Hz), 3.31-3.44 (1H, m), 3.55 (1H, d, J=6.8 Hz), 5.17-5.42 (1H, m).

(4RS,5RS)-4-(tert-butyldimethylsilyloxy)-3,3,5-trimethylpyrrolidin-2-one $^1$H-NMR (CDCl$_3$) δ: 0.07 (3H, s), 0.08 (3H, s), 0.92 (9H, s), 1.12 (3H, s), 1.15 (3H, s), 1.18 (3H, d, J=6.8 Hz), 3.69-3.82 (1H, m), 4.00 (1H, d, J=6.4 Hz), 6.04-6.48 (1H, m).

Reference Example 22 rac-2-chloro-4-[(4R,5S)-4-(tert-butyldimethylsilyloxy)-3,3,5-trimethyl-2-oxopyrrolidin-1-yl]benzonitrile

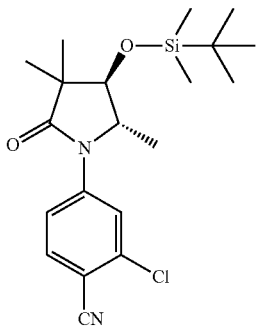 [SMILES: C[C@H]1[C@H](O[Si](C)(C)C(C)(C)C)C(C)(C)C(=O)N1c1ccc(C#N)c(Cl)c1]

Using (4RS,5SR)-4-(tert-butyldimethylsilyloxy)-3,3,5-trimethylpyrrolidin-2-one (105.9 mg), 4-bromo-2-chlorobenzonitrile (89 mg), cesium carbonate (200 mg), tris(dibenzylideneacetone)dipalladium(0) (20 mg) and 4,5-bis (diphenylphosphino)-9,9-dimethylxanthene (25 mg), and in the same manner as in Reference Example 3, the title compound was obtained as a colorless solid (yield: 121 mg, 75%).

$^1$H-NMR (CDCl$_3$) δ: 0.13-0.16 (6H, m), 1.12 (9H, s), 1.12 (3H, s), 1.28 (3H, s), 1.31 (3H, d, J=6.1 Hz), 3.72 (1H, d, J=6.1 Hz), 3.90 (1H, t, J=6.1 Hz), 7.39 (1H, dd, J=8.7, 2.1 Hz), 7.59-7.71 (2H, m).

Reference Example 23 rac-2-chloro-4-[(4R,5R)-4-(tert-butyldimethylsilyloxy)-3,3,5-trimethyl-2-oxopyrrolidin-1-yl]benzonitrile

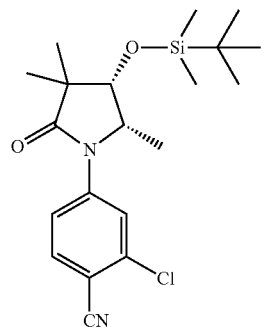 [SMILES: C[C@H]1[C@@H](O[Si](C)(C)C(C)(C)C)C(C)(C)C(=O)N1c1ccc(C#N)c(Cl)c1]

Using (4RS,5RS)-4-(tert-butyldimethylsilyloxy)-3,3,5-trimethylpyrrolidin-2-one (380 mg), 4-bromo-2-chlorobenzonitrile (320 mg), cesium carbonate (722 mg), tris(dibenzylideneacetone)dipalladium(0) (68 mg) and 4,5-bis (diphenylphosphino)-9,9-dimethylxanthene (85 mg), and in the same manner as in Reference Example 3, the title compound was obtained as a colorless solid (yield: 400 mg, 69%).

$^1$H-NMR (CDCl$_3$) δ: 0.13 (3H, s), 0.14 (3H, s), 0.95 (9H, s), 1.21-1.22 (6H, m), 1.28 (3H, d, J=6.6 Hz), 4.18 (1H, d, J=7.4 Hz), 4.25-4.37 (1H, m), 7.55-7.68 (2H, m), 7.89 (1H, d, J=1.9 Hz).

Reference Example 24

(4S,5S)-4-(tert-butyldimethylsilyloxy)-5-methylpyrrolidin-2-one

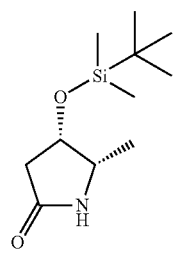

A solution of (4S,5S)-4-hydroxy-5-methylpyrrolidin-2-one (3.0 g) in THF (50 mL) was cooled to 0° C., 2,6-lutidine (4.55 mL) and tert-butyldimethylsilyl trifluoromethanesulfonate (6.6 mL) were added thereto and, after warming to room temperature, the mixture was stirred at room temperature for 18 hr. Water was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent: hexane/ethyl acetate=9/1→1/2) to give the title compound as a colorless solid (yield: 4.54 g, 76%).

$^1$H-NMR (CDCl$_3$) δ: 0.07 (6H, s), 0.90 (9H, s), 1.17 (3H, d, J=6.3 Hz), 2.27 (1H, dd, J=16.5, 4.2 Hz), 2.52 (1H, dd, J=16.5, 9.3 Hz), 3.70-3.80 (1H, m), 4.37-4.45 (1H, m), 6.00 (1H, br).

Reference Example 25

2-chloro-4-[(4S,5S)-4-(tert-butyldimethylsilyloxy)-5-methyl-2-oxopyrrolidin-1-yl]benzonitrile

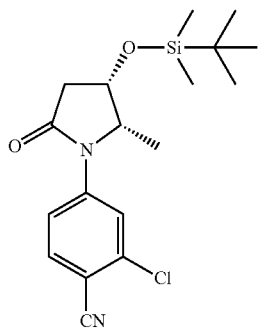 [SMILES: C[C@H]1[C@@H](O[Si](C)(C)C(C)(C)C)CC(=O)N1c1ccc(C#N)c(Cl)c1]

Using (4S,5S)-4-(tert-butyldimethylsilyloxy)-5-methylpyrrolidin-2-one (1.06 g), 4-bromo-2-chlorobenzonitrile (1.0 g), cesium carbonate (2.25 g), tris(dibenzylideneacetone)dipalladium(0) (210 mg) and 4,5-bis(diphenylphosphino)-9,9-dimethylxanthene (399 mg), and in the same manner as in Reference Example 3, the title compound was obtained as a colorless solid (yield: 1.2 g, 71%).

$^1$H-NMR (CDCl$_3$) δ: 0.12 (6H, s), 0.92-0.93 (9H, m), 1.26 (3H, d, J=6.3 Hz), 2.58-2.80 (2H, m), 4.27-4.36 (1H, m), 4.50-4.60 (1H, m), 7.55 (1H, dd, J=8.7, 2.1 Hz), 7.64 (1H, d, J=8.7 Hz), 7.81 (1H, d, J=2.1 Hz).

Reference Example 26

2-chloro-4-[(4S,5S)-4-(tert-butyldimethylsilyloxy)-5-methyl-2-oxopyrrolidin-1-yl]-3-methylbenzonitrile

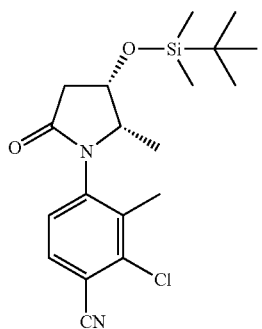 [SMILES: Cc1c(N2C(=O)C[C@H](O[Si](C)(C)C(C)(C)C)[C@@H]2C)ccc(C#N)c1Cl]

Using (4S,5S)-4-(tert-butyldimethylsilyloxy)-5-methylpyrrolidin-2-one (495 mg), 4-bromo-2-chloro-3-methylbenzonitrile (500 mg), cesium carbonate (1.05 g), tris(dibenzylideneacetone)dipalladium(0) (99 mg) and 4,5-bis(diphenylphosphino)-9,9-dimethylxanthene (124 mg), and in the same manner as in Reference Example 3, the title compound was obtained as a colorless solid (yield: 505 mg, 74%).

$^1$H-NMR (CDCl$_3$) δ: 0.10-0.13 (6H, m), 0.92 (9H, s), 1.03 (3H, d, J=6.3 Hz), 2.31 (3H, s), 2.49 (1H, dd, J=16.8, 2.1 Hz), 2.77 (1H, dd, J=16.8, 5.1 Hz), 4.00-4.30 (1H, m), 4.40-4.55 (1H, m), 7.07 (1H, d, J=8.1 Hz), 7.55 (1H, d, J=8.1 Hz).

Reference Example 27

Ethyl 4-[(tert-butoxycarbonyl)amino]-2,4,5-trideoxy-2,2-difluoro-L-threo-pentonate

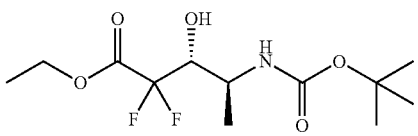 [SMILES: CCOC(=O)C(F)(F)[C@H](O)[C@H](C)NC(=O)OC(C)(C)C]

tert-Butyl [(1S)-1-methyl-2-oxoethyl]carbamate (7.21 g) and ethyl bromodifluoroacetate (25.1 g) were dissolved in THF (65 mL), and the solution was added dropwise to a suspension of zinc powder (25.1 g) in THF (14 mL) at room temperature over 30 min. The suspension was heated under reflux for 30 min and cooled to 0° C. A 1 mol/L aqueous hydrochloric acid solution (200 mL) was added, and the mixture was extracted with ethyl acetate (100 mL). The extracted organic layer was washed with water (100 mL) and saturated brine (100 mL), dried over anhydrous magnesium sulfate, and concentrated under reduced pressure. The residue was purified by silica gel column chromatography (eluent: ethyl acetate/hexane=1/10→3/10) to give the title compound as a pale-yellow oil (yield: 5.45 g, 44%).

$^1$H-NMR (CDCl$_3$) δ: 1.33 (3H, d, J=7.2 Hz), 1.36 (3H, t, J=7.1 Hz), 1.44 (9H, s), 3.83-4.07 (2H, m), 4.35 (2H, q, J=7.1 Hz), 4.80 (1H, brs).

Reference Example 28

(4R,5S)-3,3-difluoro-4-hydroxy-5-methylpyrrolidin-2-one

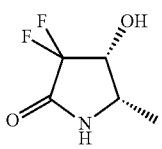

Ethyl 4-[(tert-butoxycarbonyl)amino]-2,4,5-trideoxy-2,2-difluoro-L-threo-pentonate (5.45 g) was dissolved in a 4 mol/L solution (100 mL) of hydrogen chloride/ethyl acetate, and the mixture was stirred at room temperature for 1.5 hr. The reaction solution was concentrated under reduced pressure, THF (200 mL) and diisopropylethylamine (9.9 mL) were added thereto, and the mixture was heated under reflux for 3 hr. The reaction solution was concentrated under reduced pressure and water (50 mL) was added to the residue. The mixture was extracted with ethyl acetate (100 mL×5) and ethyl acetate/THF=2/1 (100 mL×3). The extract was dried over anhydrous magnesium sulfate and concentrated under reduced pressure. The residue was washed with diisopropyl ether to give the title compound as a white powder (yield: 1.55 g, 46%).

$^1$H-NMR (CD$_3$SOCD$_3$) δ: 1.07 (3H, d, J=6.4 Hz), 3.56-3.85 (1H, m), 4.10-4.40 (1H, m), 6.12 (1H, d, J=5.9 Hz), 8.86 (1H, brs).

IR(KBr): 3470, 3250, 1721, 1598 cm$^{-1}$.

mp: 139-142° C.

Reference Example 29

Ethyl 4-{[(benzyloxy)carbonyl]amino-}-2,2,5-trimethyl-3-oxohexanoate

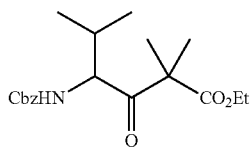 [SMILES: CCOC(=O)C(C)(C)C(=O)C(NC(=O)OCc1ccccc1)C(C)C]

To a solution of N-[(benzyloxy)carbonyl]-L-valine (25.0 g) in dry THF (100 mL) was added 1,1'-carbonylbis-1H-imidazole (19.4 g) at 0° C. in small portions, and the mixture was stirred at room temperature overnight (solution 1). To a solution of diisopropylamine (30.2 g) in dry THF (330 ml) was added dropwise a 1.6 mol/L n-butyllithium-hexane solution (186.5 mL) under an argon atmosphere at −78° C. and the mixture was stirred for 30 min, and a solution of ethyl acetate (29.2 mL) in dry THF (100 mL) was added dropwise thereto. The mixture was stirred at −78° C. for 30 min and solution 1 was added dropwise and, after the completion of the dropwise addition, the mixture was further stirred at −78° C. for 1 hr. Acetic acid (25 mL) was added to the reaction mixture, and the mixture was warmed to room temperature. Water was added and the mixture was extracted with ethyl acetate. The extract was washed with saturated brine, dried over magnesium sulfate, and concentrated under reduced pressure. The obtained residue was purified by silica gel column chromatography (eluent: hexane-ethyl acetate=50:1→1:1) to give ethyl 4-{[benzyloxy)carbonyl]amino}-5-methyl-3-oxohexanoate as a colorless oil (yield: 24.0 g, 75%). To a solution (150 mL) of ethyl 4-{[(benzyloxy)carbonyl]amino}-5-methyl-3-oxohexanoate (12.0 g) in acetone were added potassium carbonate (10.3 g) and iodomethane (7.0 mL), and the mixture was refluxed overnight. After allowing to room temperature, water was added and the mixture was extracted with ethyl acetate. The extract was washed with saturated brine, dried over magnesium sulfate, and concentrated under reduced pressure. The obtained residue was purified by silica gel column chromatography (eluent: hexane-ethyl acetate=50:1→1:1) to give the title compound as a colorless oil (yield: 7.35 g, 56%).

$^1$H-NMR (CDCl$_3$) δ: 0.78 (3H, d, J=6.8 Hz), 0.96 (3H, d, J=6.8 Hz), 1.22 (3H, t, J=7.1 Hz), 1.41 (3H, s), 1.43 (3H, s), 2.09-2.22 (1H, m), 4.04-4.22 (2H, m), 4.66 (1H, dd, J=9.8, 4.0 Hz), 5.07-5.23 (3H, m), 7.30-7.39 (5H, m).

Reference Example 30

5-isopropyl-3,3-dimethylpyrrolidine-2,4-dione

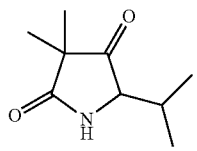

To a solution of ethyl 4-{[(benzyloxy)carbonyl]amino}-2,2,5-trimethyl-3-oxohexanoate (7.2 g) in methanol (80 mL) was added 10% palladium carbon (containing 50% water, 3.0 g), and the mixture was stirred under a hydrogen atmosphere overnight. The reaction mixture was filtered, and the filtrate was concentrated under reduced pressure. The obtained solid was washed with hexane to give the title compound as a colorless solid (yield: 2.64 g, 76%).

$^1$H NMR (CDCl$_3$) δ: 0.90 (3H, d, J=6.8 Hz), 1.04 (3H, d, J=7.0 Hz), 1.21 (3H, s), 1.25 (3H, s), 2.10-2.27 (1H, m), 3.91 (1H, d, J=4.3 Hz), 6.50 (1H, brs).

Reference Example 31

2-chloro-4-(5-isopropyl-3,3-dimethyl-2,4-dioxopyrrolidin-1-yl)benzonitrile

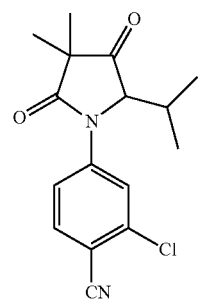 [SMILES: CC(C)C1C(=O)C(C)(C)C(=O)N1c1ccc(C#N)c(Cl)c1]

Using 5-isopropyl-3,3-dimethylpyrrolidine-2,4-dione (400 mg), 4-bromo-2-chlorobenzonitrile (614 mg), cesium carbonate (1.16 g), tris(dibenzylideneacetone)dipalladium (0) (216 mg) and 4,5-bis(diphenylphosphino)-9,9-dimethylxanthene (410 mg), and in the same manner as in Reference Example 3, the title compound was obtained as colorless crystals (yield: 343 mg, 48%).

$^1$H-NMR (CDCl$_3$) δ: 0.79 (3H, d, J=7.0 Hz), 1.21 (3H, d, J=7.2 Hz), 1.32 (3H, s), 1.33 (3H, s), 2.09-2.2.4 (1H, m), 4.51 (1H, d, J=3.2 Hz), 7.46-7.51 (1H, m), 7.70-7.75 (1H, m), 7.78-7.81 (1H, m).

mp: 116-117° C.

Reference Example 32

Ethyl 4-{[(benzyloxy)carbonyl]amino}-2,2,6-trimethyl-3-oxoheptanoate

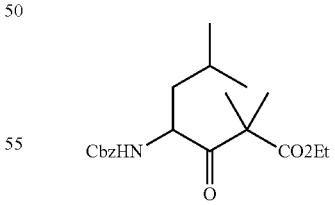

Using N-[(benzyloxy)carbonyl]-L-leucine, and in the same manner as in Reference Example 29, the title compound was obtained as a colorless oil.

$^1$H-NMR (CDCl$_3$) δ: 0.91 (3H, d, J=6.8 Hz), 0.96 (3H, d, J=6.6 Hz), 1.22 (3H, t, J=7.2 Hz), 1.26-1.38 (2H, m), 1.41 (3H, s), 1.43 (3H, s), 1.62-1.77 (1H, m), 4.07-4.24 (2H, m), 4.74 (1H, td, J=10.0, 3.7 Hz), 5.01-5.19 (3H, m), 7.28-7.42 (5H, m).

Reference Example 33

5-isobutyl-3,3-dimethylpyrrolidine-2,4-dione

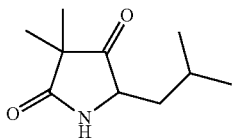

Using ethyl 4-{([(benzyloxy)carbonyl]amino}-2,2,6-trimethyl-3-oxoheptanoate (5.0 g), and in the same manner as in Reference Example 30, the title compound was obtained as a colorless solid (yield: 2.21 g, 87%).

$^1$H-NMR (CDCl$_3$) δ: 0.97 (6H, t, J=6.2 Hz), 1.25 (3H, s), 1.26 (3H, s), 1.34-1.54 (1H, m), 1.67-1.83 (2H, m), 4.01 (1H, dd, J=9.8, 3.6 Hz), 6.31 (1H, brs).

Reference Example 34

2-chloro-4-(5-isobutyl-3,3-dimethyl-2,4-dioxopyrrolidin-1-yl)benzonitrile

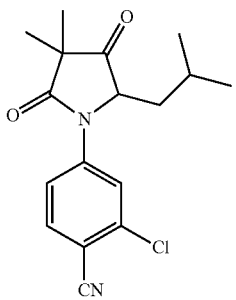 [SMILES: CC(C)CC1C(=O)C(C)(C)C(=O)N1c1ccc(C#N)c(Cl)c1]

Using 5-isobutyl-3,3-dimethylpyrrolidine-2,4-dione (500 mg), 4-bromo-2-chlorobenzonitrile (709 mg), cesium carbonate (1.33 g), tris(dibenzylideneacetone)dipalladium(0) (125 mg) and 4,5-bis(diphenylphosphino)-9,9-dimethylxanthene (237 mg), and in the same manner as in Reference Example 3, the title compound was obtained as a colorless oil (yield: 744 mg, 86%).

$^1$H-NMR (CDCl$_3$) δ: 0.85 (3H, d, J=6.6 Hz), 0.96 (3H, d, J=6.4 Hz), 1.33 (3H, s), 1.40 (3H, s), 1.58-1.91 (3H, m), 4.54-4.60 (1H, m), 7.53 (1H, dd, J=8.6, 2.1 Hz), 7.72 (1H, d, J=8.6 Hz), 7.84 (1H, d, J=2.1 Hz).

Reference Example 35

3,3-diethyl-5-methylpyrrolidine-2,4-dione

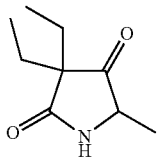

To a solution of ethyl 4-{[benzyloxy)carbonyl]amino}-3-oxopentanoate (3.0 g) in acetone (50 mL) were added potassium carbonate (2.83 g) and iodoethane (2.45 mL), and the mixture was refluxed overnight. After allowing to room temperature, potassium carbonate (2.83 g) and iodoethane (2.45 mL) were added, and the mixture was refluxed for 1 day. After allowing to room temperature, water was added and the mixture was extracted with ethyl acetate. The extract was washed with saturated brine, dried over magnesium sulfate, and concentrated under reduced pressure. The obtained residue was purified by silica gel column chromatography (eluent: hexane-ethyl acetate=20:1→3:2) to give ethyl 4-{[(benzyloxy) carbonyl]amino}-2,2-diethyl-3-oxopentanoate as a colorless oil (yield: 1.91 g, 53%). To a solution of ethyl 4-{[(benzyloxy)carbonyl]amino}-2,2-diethyl-3-oxopentanoate (1.91 g) in methanol (15 mL) was added 10% palladium carbon (containing 50% water, 1.0 g), and the mixture was stirred under a hydrogen atmosphere overnight. The reaction mixture was filtered, and the filtrate was concentrated under reduced pressure to give the title compound as a colorless solid (yield: 920 mg, 99%).

$^1$H-NMR (CDCl$_3$) δ: 0.80 (3H, t, J=7.5 Hz), 0.86 (3H, t, J=7.6 Hz), 1.34 (3H, d, J=6.8 Hz), 1.68-1.80 (4H, m), 3.88 (1H, q, J=7.0 Hz), 6.23 (1H, brs).

Reference Example 36

2-chloro-4-(3,3-diethyl-5-methyl-2,4-dioxopyrrolidin-1-yl)benzonitrile

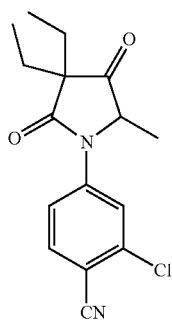 [SMILES: CCC1(CC)C(=O)C(C)N(c2ccc(C#N)c(Cl)c2)C1=O]

Using 3,3-diethyl-5-methylpyrrolidine-2,4-dione (150 mg), 4-bromo-2-chlorobenzonitrile (230 mg), cesium carbonate (433 mg), tris(dibenzylideneacetone)dipalladium(0) (40.6 mg) and 4,5-bis(diphenylphosphino)-9,9-dimethylxanthene (76.9 mg), and in the same manner as in Reference Example 3, the title compound was obtained as colorless crystals (yield: 101 mg, 37%).

$^1$H-NMR (CDCl$_3$) δ: 0.81-0.92 (6H, m), 1.40 (3H, d, J=7.0 Hz), 1.77-1.93 (4H, m), 4.42 (1H, q, J=6.9 Hz), 7.54 (1H, dd, J=8.6, 2.1 Hz), 7.73 (1H, d, J=8.6 Hz), 7.84 (1H, d, J=2.1 Hz).
mp: 93.5-94.5° C.

Reference Example 37

Ethyl (4S)-4-{[(benzyloxy)carbonyl]amino}-5-tert-butoxy-3-oxopentanoate

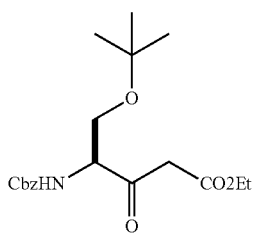 [SMILES: CCOC(=O)CC(=O)[C@H](COC(C)(C)C)NC(=O)OCc1ccccc1]

To a solution of N-[(benzyloxy)carbonyl]-O-(tert-butyl)-L-serine (25.0 g) in dry THF (100 mL) was added 1,1'-carbonylbis-1H-imidazole (16.5 g) at 0° C. by small portions, and the mixture was stirred at room temperature overnight (solution 1). To a solution of diisopropylamine (25.7 g) in dry THF (330 mL) was added dropwise a 1.6 mol/L n-butyllithium-hexane solution (158.7 mL) under an argon atmosphere at −78° C. The mixture was stirred at −78° C. for 30 min, and a solution of ethyl acetate (24.8 mL) in dry THF (100 mL) was added dropwise. After the completion of the dropwise addition, the mixture was stirred for 30 min, and solution 1 was added dropwise. The mixture was stirred at −78° C. for 1 hr, and acetic acid (25 mL) was added to the reaction mixture. After warming to room temperature, water was added and the mixture was extracted with ethyl acetate. The extract was washed with saturated brine, dried over magnesium sulfate, and concentrated under reduced pressure. The obtained residue was purified by silica gel column chromatography (eluent: hexane-ethyl acetate=50:1→1:1) to give the title compound as a colorless oil (yield: 19.2 g, 62%).

$^1$H-NMR (CDCl$_3$) δ: 1.14 (9H, s), 1.26 (3H, t, J=7.1 Hz), 3.48-3.63 (3H, m), 3.85 (1H, dd, J=9.3, 3.4 Hz), 4.18 (2H, q, J=7.1 Hz), 4.48-4.55 (1H, m), 5.12 (2H, s), 5.70 (1H, d, J=7.6 Hz), 7.30-7.40 (5H, m).

Reference Example 38

Ethyl 4-{[(benzyloxy)carbonyl]amino}-5-tert-butoxy-2,2-dimethyl-3-oxopentanoate

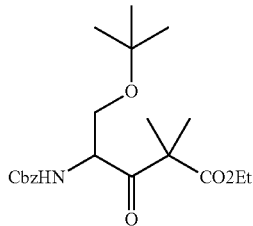 [SMILES: CCOC(=O)C(C)(C)C(=O)C(COC(C)(C)C)NC(=O)OCc1ccccc1]

To a solution of ethyl (4S)-4-{[(benzyloxy)carbonyl]amino}-5-tert-butoxy-3-oxopentanoate (9.0 g) in acetone (120 mL) were added potassium carbonate (6.81 g) and iodomethane (4.6 mL), and the mixture was refluxed overnight. After allowing to room temperature, water was added and the mixture was extracted with ethyl acetate. The extract was washed with saturated brine, dried over magnesium sulfate, and concentrated under reduced pressure. The obtained residue was purified by silica gel column chromatography (eluent: hexane-ethyl acetate=50:1→1:1) to give the title compound as a colorless oil (yield: 8.83 g, 91%).

$^1$H-NMR (CDCl$_3$) δ: 1.11 (9H, s), 1.20 (3H, t, J=7.1 Hz), 1.39 (3H, s), 1.40 (3H, s), 3.46 (1H, dd, J=8.8, 5.1 Hz), 3.71 (1H, dd, J=8.8, 3.7 Hz), 3.98-4.18 (2H, m), 4.71-4.81 (1H, m), 5.10 (2H, s), 5.42 (1H, d, J=9.1 Hz), 7.28-7.39 (5H, m).

Reference Example 39

5-(tert-butoxymethyl)-3,3-dimethylpyrrolidine-2,4-dione

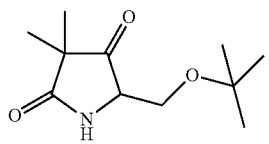

To a solution of ethyl 4-{[(benzyloxy)carbonyl]amino}-5-tert-butoxy-2,2-dimethyl-3-oxopentanoate (8.7 g) in methanol (100 mL) was added 10% palladium carbon (containing 50% water, 4.0 g), and the mixture was stirred overnight under a hydrogen atmosphere. The reaction mixture was filtered, and the filtrate was concentrated under reduced pressure. The obtained solid was washed with hexane to give the title compound as colorless to crystals (yield: 3.81 g, 81%).

$^1$H-NMR (CDCl$_3$) δ: 1.15 (9H, s), 1.24 (3H, s), 1.25 (3H, s), 3.50-3.64 (2H, m), 4.07-4.12 (1H, m), 6.04 (1H, brs).

Reference Example 40

4-[5-(tert-butoxymethyl)-3,3-dimethyl-2,4-dioxopyrrolidin-1-yl]2-chlorobenzonitrile

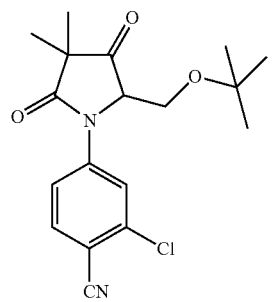 [SMILES: CC(C)(C)OCC1C(=O)C(C)(C)C(=O)N1c1ccc(C#N)c(Cl)c1]

Using 5-(tert-butoxymethyl)-3,3-dimethylpyrrolidine-2,4-dione (1.20 g), 4-bromo-2-chlorobenzonitrile (1.46 g), cesium carbonate (2.75 g), tris(dibenzylideneacetone)dipalladium(0) (258 mg) and 4,5-bis(diphenylphosphino)-9,9-dimethylxanthene (488 mg), and in the same manner as in Reference Example 3, the title compound was obtained as colorless crystals (yield: 1.59 g, 81%).

$^1$H-NMR (CDCl$_3$) δ: 0.98 (9H, s), 1.32 (3H, s), 1.37 (3H, s), 3.55 (1H, dd, J=9.7, 2.5 Hz), 3.76 (1H, dd, J=9.7, 1.8 Hz), 4.55-4.58 (1H, m), 7.56 (1H, dd, J=8.5, 2.0 Hz), 7.71 (1H, d, J=8.5 Hz), 7.84 (1H, d, J=2.0 Hz).

mp: 124-125° C.

Reference Example 41

2-chloro-4-[5-(hydroxymethyl)-3,3-dimethyl-2,4-dioxopyrrolidin-1-yl]benzonitrile

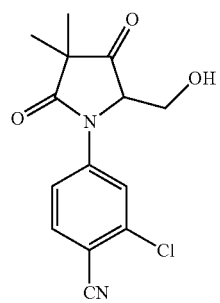 [SMILES: CC1(C)C(=O)C(CO)N(c2ccc(C#N)c(Cl)c2)C1=O]

To 4-[5-(tert-butoxy methyl)-3,3-dimethyl-2,4-dioxopyrrolidin-1-yl]-2-chlorobenzonitrile (900 mg) was added trifluoroacetic acid (10 mL) at 0° C., and the mixture was stirred at room temperature for 1 hr. The reaction mixture was cooled to 0° C., and neutralized with saturated sodium hydrogen carbonate solution. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane-ethyl acetate=4:1→1:4), and recrystallized from hexane-ethyl acetate to give the title compound as colorless crystals (yield: 655 mg, 87%).

¹H-NMR (CDCl₃) δ: 1.35 (3H, s), 1.39 (3H, s), 1.75 (1H, t, J=4.9 Hz), 3.84-3.95 (1H, m), 4.06-4.17 (1H, m), 4.59 (1H, t, J=2.2 Hz), 7.57 (1H, dd, J=8.5, 2.1 Hz), 7.73 (1H, d, J=8.5 Hz), 7.88 (1H, d, J=2.1 Hz).

mp: 150-152° C.

Reference Example 42

2-fluoro-3-methyl-4-(3,3,5-trimethyl-2,4-dioxopyrrolidin-1-yl)benzonitrile

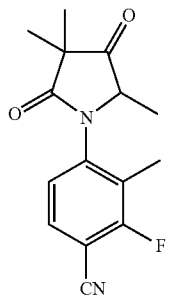 [SMILES: Cc1c(N2C(=O)C(C)(C)C(=O)C2C)ccc(C#N)c1F]

Using 3,3,5-trimethylpyrrolidine-2,4-dione (400 mg), 4-bromo-2-fluoro-3-methylbenzonitrile (667 mg), cesium carbonate (1.39 g), tris(dibenzylideneacetone)dipalladium (0) (130 mg) and 4,5-bis(diphenylphosphino)-9,9-dimethylxanthene (246 mg), and in the same manner as in Reference Example 18, the title compound was obtained as colorless crystals (yield: 137 mg, 18%).

¹H-NMR (CDCl₃) δ: 1.30 (3H, d, J=6.8 Hz), 1.38 (3H, s), 1.40 (3H, s), 2.19 (3H, d, J=2.5 Hz), 4.43 (1H, brs), 7.09 (1H, d, J=8.3 Hz), 7.52-7.61 (1H, m).

Reference Example 43

Ethyl (4S)-4-{[(benzyloxy)carbonyl]amino}-5-methoxy-3-oxopentanoate

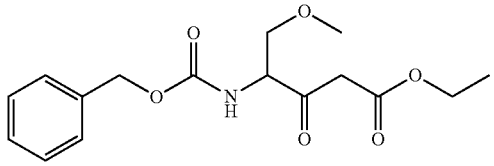 [SMILES: CCOC(=O)CC(=O)C(COC)NC(=O)OCc1ccccc1]

Using N-[(benzyloxy)carbonyl]-O-methylserine, and in the same manner as in Reference Example 37, the title compound was obtained as a colorless oil (yield: 11.1 g, 50%).

¹H-NMR (CDCl₃) δ: 1.27 (3H, t, J=7.1 Hz), 3.33 (3H, s), 3.51-3.66 (3H, m), 3.87 (1H, dd, J=9.8, 3.6 Hz), 4.19 (2H, q, J=7.1 Hz), 4.51-4.63 (1H, m), 5.13 (2H, s), 5.72 (1H, d, J=7.4 Hz), 7.29-7.43 (5H, m).

Reference Example 44

Ethyl 4-{[(benzyloxy)carbonyl]amino}-5-methoxy-2,2-dimethyl-3-oxopentanoate

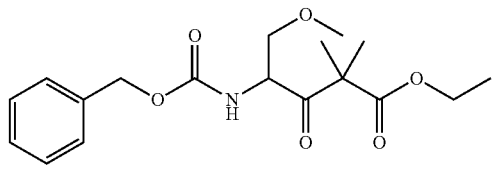 [SMILES: CCOC(=O)C(C)(C)C(=O)C(COC)NC(=O)OCc1ccccc1]

Using ethyl 4-{[(benzyloxy)carbonyl]amino}-5-methoxy-3-oxopentanoate (11.0 g), potassium carbonate (9.40 g) and iodomethane (14.5 g, 6.4 mL), and in the same manner as in Reference Example 38, the title compound was obtained as a colorless oil (yield: 10.5 g, 88%).

¹H-NMR (CDCl₃) δ: 1.22 (3H, t, J=7.1 Hz), 1.40 (3H, s), 1.41 (3H, s), 3.29 (3H, s), 3.51 (1H, dd, J=9.7, 4.6 Hz), 3.68-3.78 (1H, m), 4.02-4.21 (2H, m), 4.77-4.87 (1H, m), 5.11 (2H, s), 5.46 (1H, d, J=9.1 Hz), 7.29-7.38 (5H, m).

Reference Example 45

5-(methoxymethyl)-3,3-dimethylpyrrolidine-2,4-dione

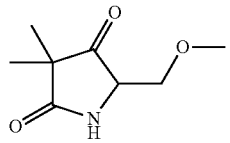

To a solution of 4-{[(benzyloxy)carbonyl]amino}-5-methoxy-2,2-dimethyl-3-oxopentanoate (10.2 g) in methanol (100 mL) was added 10% palladium carbon (containing 50% water, 3.1 g), and the mixture was stirred overnight under a hydrogen atmosphere. Palladium carbon was filtered off, and the filtrate was concentrated under reduced pressure. The obtained solid was washed with hexane to give the title compound as colorless crystals (yield: 4.16 g, 84%).

¹H-NMR (CDCl₃) δ: 1.23 (3H, s), 1.26 (3H, s), 3.35 (3H, s), 3.52-3.67 (2H, m), 4.12-4.16 (1H, m), 6.51 (1H, brs).

Reference Example 46

2-chloro-4-[5-(methoxymethyl)-3,3-dimethyl-2,4-dioxopyrrolidin-1-yl]benzonitrile

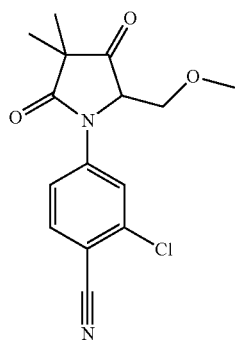 [SMILES: COCC1C(=O)C(C)(C)C(=O)N1c1ccc(C#N)c(Cl)c1]

Using 5-(methoxymethyl)-3,3-dimethylpyrrolidine-2,4-dione (700 mg), 4-bromo-2-chlorobenzonitrile (1.06 g), cesium carbonate (2.00 g), tris(dibenzylideneacetone)dipalladium(0) (187 mg) and 4,5-bis(diphenylphosphino)-9,9- dimethylxanthene (355 mg), and in the same manner as in Reference Example 3, the title compound was obtained as colorless crystals (yield: 219 mg, 17%).

$^1$H-NMR (CDCl$_3$) δ: 1.33 (3H, s), 1.36 (3H, s), 3.21 (3H, s), 3.60 (1H, d, J=10.2 Hz), 3.78 (1H, d, J=10.2 Hz), 4.54-4.58 (1H, m), 7.55 (1H, d, J=8.5 Hz), 7.72 (1H, d, J=8.3 Hz), 7.85 (1H, s).

mp: 98-99° C.

Reference Example 47

Benzyl (2S,3S)-3-hydroxy-2-methylpyrrolidine-1-carboxylate

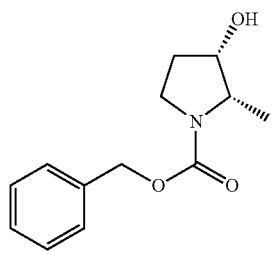 [SMILES: C[C@H]1[C@@H](O)CCN1C(=O)OCc1ccccc1]

To a suspension of (4S,5S)-4-hydroxy-5-methylpyrrolidin-2-one (10.45 g) in dry THF (418 mL) was added dropwise Red-Al (104.9 g: 363 mmol: 70% toluene solution) under ice-cooling and a nitrogen stream. The mixture was stirred at room temperature for 20 min, and further refluxed for 3 hr. The reaction mixture was ice-cooled again, and sodium carbonate decahydrate (41.6 g) was added under a nitrogen stream. The mixture was stirred at room temperature overnight, insoluble materials were filtered through celite and washed with THF. The filtrate and washing were combined and concentrated under reduced pressure to give (2S,3S)-3-hydroxy-2-methylpyrrolidine. Without further purification, this compound was diluted with DMSO to give 0.9 mol/L-DMSO solution. A solution (170 mL) of (2S,3S)-3-hydroxy-2-methylpyrrolidine in 0.9 mol/L-DMSO was diluted with water (200 mL), sodium hydrogen carbonate (24.6 g) and benzyl chloroformate (15 mL) were added, and the mixture was stirred at room temperature for 18 hr. Water was added to the reaction mixture, and the mixture was extracted with ethyl acetate. The extract was washed with saturated brine, dried over anhydrous sodium sulfate, and concentrated under reduced pressure to give the title compound as a pale-yellow oil (yield: 20.64 g, 84%).

$^1$H-NMR (CDCl$_3$) δ: 1.10-1.30 (3H, br), 1.60-2.20 (3H, m), 3.40-4.40 (5H, m), 7.20-7.40 (5H, m).

Reference Example 48

Benzyl (2S)-2-methyl-3-oxopyrrolidine-1-carboxylate

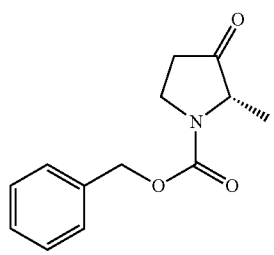 [SMILES: C[C@H]1C(=O)CCN1C(=O)OCc1ccccc1]

To a solution of benzyl (2S,3S)-3-hydroxy-2-methylpyrrolidine-1-carboxylate (20.5 g) in acetonitrile (150 mL) were added powdery molecular sieves 4 A (25 g) and 4-methylmorpholine-N-oxide (20.4 g). After cooling to 0° C., tetra-n-propylammonium perruthenate (3.0 g) was added, and the mixture was stirred at 0° C. for 1 hr, and at room temperature for 18 hr. The reaction mixture was concentrated under reduced pressure, and the residue was suspended in ethyl acetate. Insoluble materials were filtered through Hyflo Super-Cel. The filtrate was concentrated under reduced pressure, and the residue was purified by silica gel column chromatography (eluent: hexane/ethyl acetate=9/1→2/1) to give the title compound as a colorless oil (yield: 18.0 g, 89%).

$^1$H-NMR (CDCl$_3$) δ: 1.34 (3H, d, J=6.6 Hz), 2.50-2.70 (2H, m), 3.60-3.75 (1H, m), 3.90-4.10 (2H, m), 5.15 (1H, d, J=12.3 Hz), 5.20 (1H, d, J=12.3 Hz), 7.30-7.40 (5H, m).

Reference Example 49

Benzyl (2S,3S)-3-hydroxy-2,3-dimethylpyrrolidine-1-carboxylate

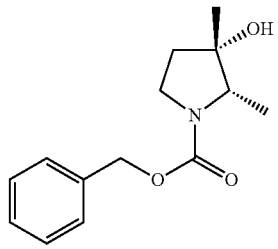 [SMILES: C[C@@H]1N(C(=O)OCc2ccccc2)CC[C@]1(C)O]

A suspension of cerium chloride (47 g) in THF (300 mL) was cooled to −78° C., methylmagnesium bromide-diethyl ether solution (56 mL, 3 mol/L) was added dropwise while adjusting the solution temperature to −70° C. or below. After the completion of the dropwise addition, the mixture was stirred at −78° C. for 30 min, a solution of benzyl (2S)-2-methyl-3-oxopyrrolidine-1-carboxylate (18 g) in THF (60 mL) was added dropwise while adjusting the solution temperature to −70° C. or below. The reaction mixture was warmed to 0° C. over 2 hr, ethyl acetate (1 L) was added, and insoluble materials were filtered off. The filtrate was partitioned with water, and the organic layer was washed with saturated brine, dried over anhydrous sodium sulfate, and concentrated under reduced pressure. The residue was purified by silica gel column chromatography (eluent: hexane/ethyl acetate=9/1→1/1) to give the title compound as a colorless oil (yield: 16.2 g, 84%).

$^1$H-NMR (CDCl$_3$) δ: 1.10-1.35 (3H, br), 1.34 (3H, s), 1.47 (1H, s), 1.75-1.90 (1H, m), 1.91-2.00 (1H, m), 3.49 (2H, t, J=7.2 Hz), 3.55-3.65 (1H, m), 5.05-5.20 (2H, m), 7.20-7.40 (5H, m).

Reference Example 50

(2S,3S)-2,3-dimethylpyrrolidin-3-ol 0.5 oxalic acid salt

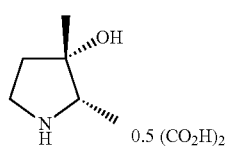

To a solution of benzyl (2S,3S)-3-hydroxy-2,3-dimethylpyrrolidine-1-carboxylate (16.1 g) in methanol (200 mL) was added 50% water containing −10% Pd/C (0.4 g), and the mixture was vigorously stirred under a hydrogen atmosphere.

The catalyst was filtered off, oxalic acid (2.90 g) was added to the filtrate, and the mixture was concentrated under reduced pressure. The residual solid was suspended in ethyl acetate, and filtered to give the title compound as a colorless solid (yield: 9.09 g, 88%).

$^1$H-NMR (DMSO-d$_6$) δ: 1.05 (3H, d, J=6.6 Hz), 1.18 (3H, s), 1.74-1.86 (2H, m), 2.80-2.95 (2H, m), 2.98-3.10 (1H, m), 4.00-5.20 (3H, m).

Reference Example 51 tert-Butyl (2S,3S)-3-hydroxy-2,3-dimethylpyrrolidine-1-carboxylate

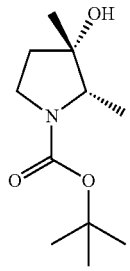

To a solution of (2S,3S)-2,3-dimethylpyrrolidine-3-ol 0.5 oxalic acid salt (3.31 g) in THF (50 mL) were successively added 1 mol/L aqueous sodium hydroxide solution (40 mL) and a solution of di-tert-butyl dicarbonate (5.42 g) in THF (10 mL). The mixture was stirred at room temperature for 20 hr, water (50 mL) was added to the reaction mixture, and the mixture was extracted with ethyl acetate twice. The extract was washed with saturated brine, dried over anhydrous magnesium sulfate, and concentrated under reduced pressure. The residue was purified by silica gel column chromatography (eluent: ethyl acetate/hexane=1/10→4/10) to give the title compound as a white powder (yield: 3.21 g, 72%)

$^1$H-NMR (CDCl$_3$) δ: 1.21 (3H, d, J=6.4 Hz), 1.33 (3H, s), 1.46 (9H, s), 1.66 (1H, s), 1.73-1.85 (1H, m), 1.86-1.98 (1H, m), 3.40 (2H, dd, J=7.2, 6.7 Hz), 3.46-3.57 (1H, m).

mp: 109-112° C.

Reference Example 52 tert-Butyl (2S,3S)-3-hydroxy-2,3-dimethyl-5-oxo-pyrrolidine-1-carboxylate

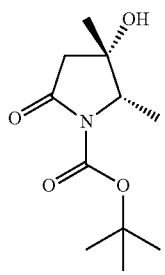 [SMILES: C[C@@H]1N(C(=O)OC(C)(C)C)C(=O)C[C@]1(C)O]

To a solution of tert-butyl (2S,3S)-3-hydroxy-2,3-dimethylpyrrolidine-1-carboxylate (3.05 g) in ethyl acetate (45 mL) were successively added water (68 mL), ruthenium dioxide monohydrate (566 mg) and sodium periodate (4.57 g) at room temperature. The mixture was stirred at room temperature for 40 hr, the organic layer and the aqueous layer were separated, and the aqueous layer was extracted with ethyl acetate. The obtained organic layers were mixed, isopropanol (0.7 mL) was added, and the mixture was stirred at room temperature for 5 min. The reaction solution was dried over anhydrous magnesium sulfate, and concentrated under reduced pressure. The residue was purified by silica gel column chromatography (eluent: ethyl acetate/hexane=1/10→4/10) to give the title compound as a white powder (yield: 1.11 g, 34%).

$^1$H-NMR (CDCl$_3$) δ: 1.34 (3H, d, J=6.4 Hz), 1.46 (3H, s), 1.54 (9H, s), 1.72 (1H, s), 2.47 (1H, d, J=17.0 Hz), 2.73 (1H, d, J=17.0 Hz), 3.91 (1H, q, J=6.4 Hz).

mp: 122-125° C.

Reference Example 53

(4S,5S)-4-hydroxy-4,5-dimethylpyrrolidin-2-one

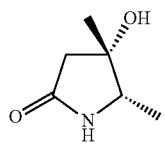

tert-Butyl (2S,3S)-3-hydroxy-2,3-dimethyl-5-oxo-pyrrolidine-1-carboxylate (1.00 g) was dissolved in hydrogen chloride-ethyl acetate solution (10 mL, 4 mol/L), and the mixture was stirred at room temperature for 14 hr. The reaction solution was concentrated under reduced pressure, and recrystallized from isopropanol/n-hexane to give the title compound (309 mg, 55%) as colorless crystals. Furthermore, the filtrate was concentrated under reduced pressure. The residue was purified by silica gel column chromatography (eluent: ethyl acetate→methanol/ethyl acetate=1/10), and the obtained solid was crystallized from diisopropyl ether to give the title compound (220 mg, 39%) as a white powder.

$^1$H-NMR (DMSO-d$_6$) δ: 1.00 (3H, d, J=6.4 Hz), 1.20 (3H, s), 2.06 (1H, d, J=16.2 Hz), 2.23 (1H, d, J=16.2 Hz), 3.33 (1H, q, J=6.4 Hz), 4.70 (1H, brs), 7.48 (1H, brs).

mp: 169-173° C.

Reference Example 54 rac-4-((4R,5S)-4-(tert-butyldimethylsilyloxy)-3,3,5-trimethyl-2-oxopyrrolidin-1-yl)-2-chloro-3-methyl-benzonitrile

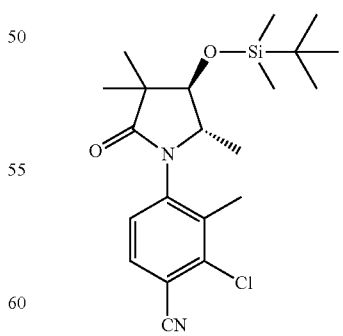

Using (4RS,5SR)-4-(tert-butyldimethylsilyloxy)-3,3,5-trimethylpyrrolidin-2-one (200 mg), 2-chloro-4-iodo-3-methylbenzonitrile (250 mg), cesium carbonate (380 mg), tris(dibenzylideneacetone)dipalladium(0) (36 mg) and 4,5-bis(diphenylphosphino)-9,9-dimethylxanthene (45 mg), and in the same manner as in Reference Example 3, the title compound was obtained as a pale-yellow oil (yield: 103 mg, yield: 33.7%).

$^1$H-NMR (CDCl$_3$) δ: 0.13 (3H, s), 0.15 (3H, s), 0.94 (9H, s), 1.04-1.36 (9H, m), 2.26 (3H, s), 3.60-3.91 (2H, m), 7.01-7.17 (1H, m), 7.50-7.60 (1H, m).

Reference Example 55

Ethyl 1-[2-(dibenzylamino)propanoyl]cyclopropanecarboxylate

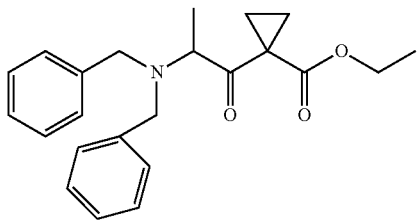 [SMILES: CCOC(=O)C1(C(=O)C(C)N(Cc2ccccc2)Cc2ccccc2)CC1]

A solution of ethyl (4S)-4-(dibenzylamino)-3-oxopentanoate (500 mg) synthesized according to the method described in Journal of Organic Chemistry, vol. 62, pp. 2292-2297 (1997), 1,2-dibromoethane (0.19 mL) and potassium carbonate (405 mg) in acetone (15 mL), was stirred under reflux overnight. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→2/1) to give the title compound as a colorless oil (yield: 231.4 mg, 43.0%).

$^1$H-NMR (CDCl$_3$) δ: 1.01 (3H, t, J=7.2 Hz), 1.07-1.19 (2H, m), 1.20 (3H, d, J=6.8 Hz), 1.58-1.73 (2H, m), 3.56 (2H, d, J=14.0 Hz), 3.61 (2H, d, J=14.0 Hz), 3.72 (1H, 10.8, 7.2 Hz), 3.96 (1H, dq, J=10.8, 7.2 Hz), 4.40 (1H, q, J=6.8 Hz), 7.19-7.27 (2H, m), 7.27-7.39 (8H, m).

Reference Example 56

Ethyl 1-[(1RS,2RS)-2-(dibenzylamino)-1-hydroxypropyl]cyclopropanecarboxylate

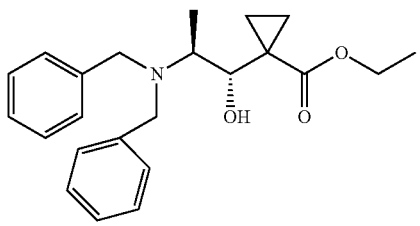 [SMILES: CCOC(=O)C1([C@H](O)[C@H](C)N(Cc2ccccc2)Cc2ccccc2)CC1]

A solution of ethyl 1-[2-(dibenzylamino)propanoyl]cyclopropanecarboxylate (1.31 g) in methanol (60 mL) was cooled to 0° C., 90% sodium borohydride (350 mg) was added, and the mixture was stirred at room temperature for 17 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→1/1) to give the title compound as a colorless oil (yield: 1.31 g, 99%).

$^1$H-NMR (CDCl$_3$) δ: 0.53-0.66 (1H, m), 0.95-1.09 (2H, m), 1.05 (3H, d, J=6.7 Hz), 1.06 (3H, t, J=7.1 Hz), 1.14-1.22 (1H, m), 3.03 (1H, dq, J=9.6, 6.7 Hz), 3.33 (2H, d, J=13.2 Hz), 3.60 (1H, d, J=9.6 Hz), 3.83 (2H, d, J=13.2 Hz), 3.96 (1H, q, J=7.1 Hz), 3.97 (1H, q, J=7.1 Hz), 4.20 (1H, brs), 7.17-7.38 (10H, m).

Reference Example 57

Ethyl 1-[(1RS,2RS)-1-(tert-butyldimethylsilyloxy)-2-(dibenzylamino)propyl]cyclopropanecarboxylate

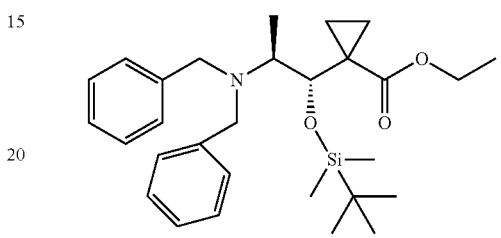

A solution of ethyl 1-[(1RS,2RS)-2-(dibenzylamino)-1-hydroxypropyl]cyclopropanecarboxylate (1.30 g) in THF (15 mL) was cooled to 0° C., tert-butyl(dimethyl)silyl trifluoromethanesulfonate (0.98 mL) and 2,6-dimethylpyridine (0.621 mL) were added, and the mixture was stirred at room temperature for 17 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→4/1) to give the title compound as a colorless oil (yield: 1.30 g, 76%).

$^1$H-NMR (CDCl$_3$) δ: 0.04 (3H, s), 0.11 (3H, s), 0.81-1.36 (4H, m), 0.88 (9H, s), 1.03 (3H, t, J=7.1 Hz), 1.11 (3H, d, J=7.0 Hz), 3.19 (1H, dd, J=6.9, 4.4 Hz), 3.40 (2H, d, J=14.0 Hz), 3.80 (2H, q, J=7.1 Hz), 4.02 (2H, d, J=14.0 Hz), 4.06-4.17 (1H, m), 7.10-7.42 (10H, m).

Reference Example 58

(6RS,7RS)-7-(tert-butyldimethylsilyloxy)-6-methyl-5-azaspiro[2.4]heptan-4-one

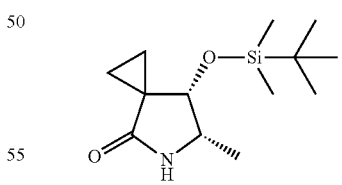

To a solution of ethyl 1-[(1RS,2RS)-1-(tert-butyldimethylsilyloxy)-2-(dibenzylamino)propyl]cyclopropanecarboxylate (1.36 g) in methanol (16 mL) was added 10% palladium hydroxide-carbon (containing 50% water, 280 mg), and the mixture was stirred at room temperature for 18 hr under a hydrogen atmosphere. The reaction mixture was filtered. The filtrate was concentrated under reduced pressure and the residue was purified by silica gel column chromatography (eluent: hexane/ethyl acetate=10/1→1/4) to give the title compound as a colorless solid (yield: 164 mg, yield: 22.8%).

¹H-NMR (CDCl₃) δ: 0.02 (3H, s), 0.05 (3H, s), 0.61-0.71 (1H, m), 0.85-1.21 (3H, m), 0.90 (9H, s), 1.17 (3H, d, J=6.6 Hz), 3.75-3.88 (1H, m), 4.43 (1H, d, J=6.8 Hz), 5.45 (1H, brs).

Reference Example 59 rac-4-((6R,7R)-7-(tert-butyldimethylsilyloxy)-6-methyl-4-oxo-5-azaspiro[2.4]hept-5-yl)-2-chlorobenzonitrile

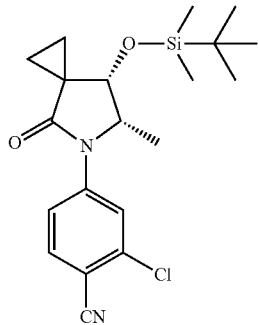 [SMILES: C[C@H]1[C@@H](O[Si](C)(C)C(C)(C)C)C2(CC2)C(=O)N1c1ccc(C#N)c(Cl)c1]

Using (6RS,7RS)-7-(tert-butyldimethylsilyloxy)-6-methyl-5-azaspiro[2.4]heptan-4-one (162 mg), 4-bromo-2-chlorobenzonitrile (157 mg), cesium carbonate (310 mg), tris(dibenzylideneacetone)dipalladium(0) (30 mg) and 4,5-bis(diphenylphosphino)-9,9-dimethylxanthene (75 mg), and in the same manner as in Reference Example 3, the title compound was obtained as a colorless solid (yield: 140 mg, 56%).

¹H-NMR (CDCl₃) δ: 0.07 (3H, s), 0.12 (3H, s), 0.67-0.79 (1H, m), 0.88-1.37 (3H, m), 0.93 (9H, s), 1.30 (3H, d, J=6.4 Hz), 4.29-4.41 (1H, m), 4.59 (1H, d, J=7.2 Hz), 7.01-8.04 (3H, m).

Reference Example 60 ethyl (4S)-4-{[(benzyloxy)carbonyl]amino}-2,2-dimethyl-3-oxopentanoate

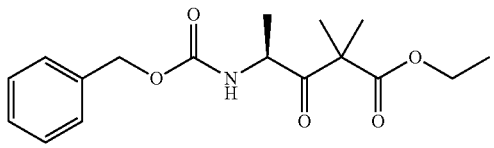 [SMILES: CCOC(=O)C(C)(C)C(=O)[C@H](C)NC(=O)OCc1ccccc1]

A solution of diisopropylamine (0.665 mL) in THF (25 mL) was cooled to −78° C., and n-butyllithium-hexane solution (2.93 mL, 1.6 mol/L) was added dropwise. After the completion of the dropwise addition, the mixture was stirred at −78° C. for 1 hr. Subsequently, ethyl 2-methylpropanoate (0.675 mL) was added dropwise, and the mixture was further stirred at −78° C. for 1 hr. A solution of benzyl (4S)-4-methyl-2,5-dioxo-1,3-oxazolidine-3-carboxylate (900 mg) in THF (5.0 mL) was added dropwise at −78° C., and the mixture was further stirred at −78° C. for 20 min. Acetic acid (2.0 mL) was added to the reaction mixture and, after warming to room temperature, water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→1/1) to give the title compound as a colorless oil (yield: 905 mg, yield: 78.0%).

¹H-NMR (CDCl₃) δ: 1.22 (3H, t, J=7.2 Hz), 1.31 (3H, d, J=6.8 Hz), 1.41 (3H, s), 1.43 (3Hs), 4.06-4.22 (2H, m), 4.74 (1H, dd, J=8.5, 7.2 Hz), 5.02-5.17 (2H, m), 5.23-5.37 (1H, m), 7.28-7.46 (5H, m).

Reference Example 61

(4S,5S)-4-(tert-butyldimethylsilyloxy)-3,3,5-trimethylpyrrolidin-2-one

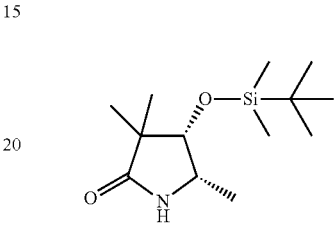

A solution of ethyl (4S)-4-{[(benzyloxy)carbonyl]amino}-2,2-dimethyl-3-oxopentanoate (905 mg) in methanol (30 mL) was cooled to 0° C., 90% sodium borohydride (180 mg) was added, and the mixture was stirred at 0° C. for 2 hr. Saturated aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/3) to give ethyl (4S)-4-{([(benzyloxy)carbonyl]amino}-2,2-dimethyl-3-hydroxypentanoate as is a colorless oil (yield: 720 mg, 79%).

A solution of ethyl (4S)-4-{[(benzyloxy)carbonyl]amino}-2,2-dimethyl-3-hydroxypentanoate (720 mg) in THF (20 mL) was cooled to 0° C., tert-butyl(dimethyl)silyl trifluoromethanesulfonate (0.589 mL) and 2,6-dimethylpyridine (0.390 mL) were added, and the mixture was stirred at room temperature for 3 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→1/1) to give ethyl (4S)-4-{([(benzyloxy)carbonyl]amino}-3-(tert-butyldimethylsilyloxy)-2,2-dimethylpentanoate as a colorless oil (yield: 0.916 g, 94%).

To a solution of ethyl (4S)-4-{([(benzyloxy)carbonyl]amino}-3-(tert-butyldimethylsilyloxy)-2,2-dimethylpentanoate (0.916 g) in methanol (20 mL) was added 10% palladium carbon (containing 50% water, 89 mg), and the mixture was stirred at room temperature for 16 hr under a hydrogen atmosphere and filtered. The filtrate was concentrated under reduced pressure, and the residue was dissolved in THF (15 mL). Diisopropylethylamine (1.5 mL) was added, and the mixture was fluxed for 3 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/3) to give the title compound (yield: 161.8 mg, yield: 30.1%) and (4R,5S)-4-(tert-butyldimethylsilyloxy)-3,3,5-trimethylpyrrolidin-2-one (yield: 289 mg, yield: 53.7%), each as a colorless solid.

¹H-NMR (CDCl₃) δ: 0.07 (6H, s), 0.90 (9H, s), 1.17 (3H, d, J=6.3 Hz), 2.27 (1H, dd, J=16.5, 4.2 Hz), 2.25 (1H, dd, J=16.5, 9.3 Hz), 3.70-3.80 (1H, m), 4.37-4.45 (1H, m), 6.00 (1H, brs).

(4R,5S)-4-(tert-butyldimethylsilyloxy)-3,3,5-trimethylpyrrolidin-2-one

¹H-NMR (CDCl₃) δ: 0.09 (6H, s), 0.90 (9H, s), 1.06 (3H, s), 1.15 (3H, s), 1.25 (3H, d, J=6.2 Hz), 3.31-3.44 (1H, m), 3.55 (1H, d, J=6.8 Hz), 5.17-5.42 (1H, m).

Reference Example 62

4-((4S,5S)-4-(tert-butyldimethylsilyloxy)-3,3,5-trimethyl-2-oxopyrrolidin-1-yl)-2-(trifluoromethyl)benzonitrile

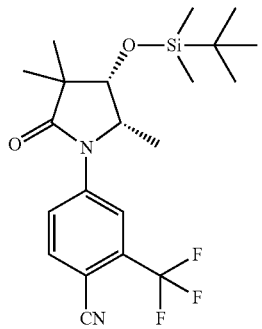 [SMILES: C[C@H]1[C@@H](O[Si](C)(C)C(C)(C)C)C(C)(C)C(=O)N1c1ccc(C#N)c(C(F)(F)F)c1]

Using (4S,5S)-4-(tert-butyldimethylsilyloxy)-3,3,5-trimethylpyrrolidin-2-one (161.8 mg), 4-iodo-2-(trifluoromethyl)benzonitrile (205 mg), cesium carbonate (307 mg), tris(dibenzylideneacetone)dipalladium(0) (30 mg) and 4,5-bis(diphenylphosphino)-9,9-dimethylxanthene (73 mg), and in the same manner as in Reference Example 3, the title compound was obtained as a colorless solid (yield: 232.2 mg, yield: 87%).
¹H-NMR (CDCl₃) δ: 0.14 (3H, s), 0.15 (3H, s), 0.96 (9H, s), 1.23 (3H, s), 1.24 (3H, s), 1.30 (3H, d, J=6.6 Hz), 4.20 (1H, d, J=7.4 Hz), 4.30-4.44 (1H, m), 7.77-7.93 (2H, m), 8.16 (1H, d, J=2.1 Hz).

Reference Example 63

4-[(4R,5S)-4-(tert-butyldimethylsilyloxy)-3,3,5-trimethyl-2-oxopyrrolidin-1-yl]-2-(trifluoromethyl)benzonitrile

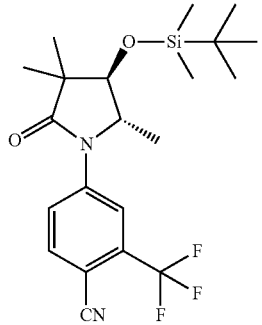 [SMILES: C[C@H]1[C@H](O[Si](C)(C)C(C)(C)C)C(C)(C)C(=O)N1c1ccc(C#N)c(C(F)(F)F)c1]

Using (4R,5S)-4-(tert-butyldimethylsilyloxy)-3,3,5-trimethylpyrrolidin-2-one (266.6 mg), 4-iodo-2-(trifluoromethyl)benzonitrile (340 mg), cesium carbonate (505 mg), tris(dibenzylideneacetone)dipalladium(0) (47 mg) and 4,5-bis(diphenylphosphino)-9,9-dimethylxanthene (120 mg), and in the same manner as in Reference Example 3, the title compound was obtained as a colorless oil (yield: 391.7 mg, yield: 89%).
¹H-NMR (CDCl₃) δ: 0.15 (6H, s), 0.95 (9H, s), 1.13 (3H, s), 1.30 (3H, s), 1.31 (3H, d, J=6.2 Hz), 3.75 (1H, d, J=6.2 Hz), 3.89-4.02 (1H, m), 7.58-7.74 (1H, m), 7.80-7.93 (2H, m).

Reference Example 64

4-[(2S,3S)-3-(tert-butyldimethylsilyloxy)-2-methyl-5-oxopyrrolidin-1-yl]-2-(trifluoromethyl)benzonitrile

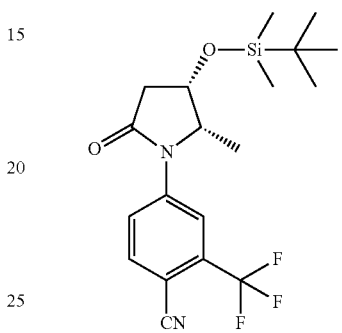

Using (4S,5S)-4-(tert-butyldimethylsilyloxy)-5-methylpyrrolidin-2-one (5.00 g), 4-iodo-2-(trifluoromethyl)benzonitrile (6.80 g), cesium carbonate (10.65 g), tris(dibenzylideneacetone)dipalladium(0) (1.00 g) and 4,5-bis(diphenylphosphino)-9,9-dimethylxanthene (2.52 g), and in the same manner as in Reference Example 3, the title compound was obtained as a colorless solid (yield: 5.617 g, yield: 64.7%).
¹H-NMR (CDCl₃) δ: 0.13 (6H, s), 0.93 (9H, s), 1.28 (3H, d, J=6.4 Hz), 2.65 (1H, dd, J=17.0, 7.0 Hz), 2.76 (1H, dd, J=17.0, 7.0 Hz), 4.30-4.44 (1H, m), 4.57 (1H, q, J=7.0 Hz), 7.82 (1H, d, J=8.7 Hz), 7.89 (1H, dd, J=8.7, 2.1 Hz, 1H), 8.04 (1H, d, J=2.1 Hz).

Reference Example 65 tert-butyl 1-((2S)-2-{[(benzyloxy)carbonyl]amino}propanoyl)cyclopropanecarboxylate

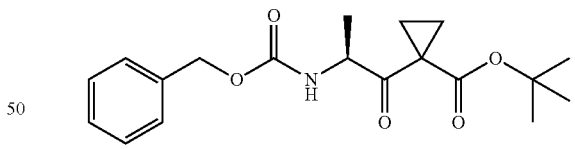

A solution of diisopropylamine (0.740 mL) in THF (25 mL) was cooled to −78° C., n-butyllithium-hexane solution (3.26 mL, 1.6 mol/L) was added dropwise and, after the completion of the dropwise addition, the mixture was stirred at −78° C. for 1 hr. Subsequently, a solution of tert-butyl cyclopropanecarboxylate (0.800 g) in THF (5 mL) was added dropwise, and the mixture was further stirred at −78° C. for 30 min. A solution of benzyl (4S)-4-methyl-2,5-dioxo-1,3-oxazolidine-3-carboxylate (1.00 g) in THF (10 mL) was added dropwise at −78° C. over 10 min, and the mixture was further stirred at −78° C. for 30 min. Acetic acid (2.0 mL) was added to the reaction mixture and, after warming to room temperature, water was added, and the mixture was extracted with ethyl acetate. The extract was washed with saturated brine; dried over anhydrous magnesium sulfate, and concentrated under reduced pressure. The residue was purified by silica gel column chromatography (eluent: hexane/ethyl acetate=50/1→1/1) to give the title compound as a colorless oil (yield: 401 mg, 29%).

¹H-NMR (CDCl₃) δ: 1.10-1.54 (2H, m), 1.41 (3H, d, J=7.0 Hz), 1.49 (9H, s), 1.54-1.78 (2H, m), 5.11 (2H, s), 5.16-5.33 (1H, m), 5.46-5.62 (1H, m), 7.27-7.43 (5H, m).

Reference Example 66 tert-butyl 1-((2S)-2-{[(benzyloxy)carbonyl]amino}-1-hydroxypropyl)cyclopropanecarboxylate

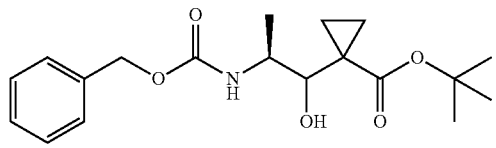 [SMILES: C[C@H](NC(=O)OCc1ccccc1)C(O)C1(C(=O)OC(C)(C)C)CC1]

A solution of tert-butyl 1-((2S)-2-{[(benzyloxy)carbonyl]amino}propanoyl)cyclopropanecarboxylate (1.66 g) in methanol (25 mL) was cooled to 0° C., 90% sodium borohydride (305 mg) was added, and the mixture was stirred at 0° C. for 30 min. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/1) to give the title compound as a colorless oil (yield: 1.58 g, 94%).

¹H-NMR (CDCl₃) δ: 0.68-1.35 (7H, m), 1.44 (9H, s), 2.87-3.05 (1H, m), 3.53-4.20 (2H, m), 4.91-5.17 (3H, m), 7.29-7.40 (5H, m).

Reference Example 67 tert-butyl 1-((2S)-2-{[(benzyloxy)carbonyl]amino}-1-(tert-butyldimethylsilyloxy)propyl)cyclopropanecarboxylate

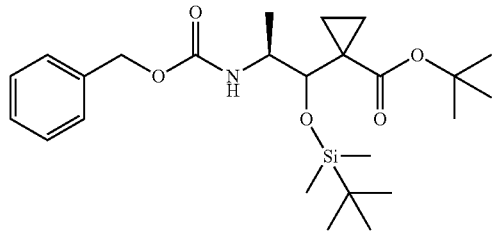 [SMILES: C[C@H](NC(=O)OCc1ccccc1)C(O[Si](C)(C)C(C)(C)C)C1(C(=O)OC(C)(C)C)CC1]

A solution of tert-butyl 1-((2S)-2-{[(benzyloxy)carbonyl]amino}-1-hydroxypropyl)cyclopropanecarboxylate (1.58 g) in THF (15 mL) was cooled to 0° C., tert-butyl(dimethyl)silyl trifluoromethanesulfonate (1.56 mL) and 2,6-dimethylpyridine (1.05 mL) were added, and the mixture was stirred at room temperature for 16 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→1/1) to give the title compound as a colorless oil (yield: 1.57 g, 75%).

¹H-NMR (CDCl₃) δ: 0.03-0.14 (6H, m), 0.78-1.29 (7H, m), 0.88 (9H, s), 1.41 (9H, s), 3.83-4.28 (3H, s), 3.84-4.99 (2H, m), 7.28-7.41 (5H, m).

Reference Example 68

(6S)-7-(tert-butyldimethylsilyloxy)-6-methyl-5-azaspiro[2.4]heptan-4-one

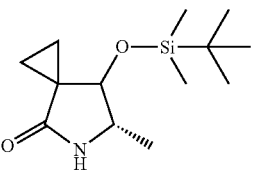 [SMILES: C[C@@H]1NC(=O)C2(CC2)C1O[Si](C)(C)C(C)(C)C]

To a solution of tert-butyl 1-((2S)-2-{[(benzyloxy)carbonyl]amino}-1-(tert-butyldimethylsilyloxy)propyl)cyclopropanecarboxylate (693.9 mg) in methanol (8 mL) was added 10% palladium carbon (containing 50% water, 80 mg), and the mixture was stirred at room temperature for 3 hr under a hydrogen atmosphere and filtered. The filtrate was concentrated under reduced pressure, and the residue was dissolved in methanol (10 mL). Sodium methoxide (404 mg) was added and the mixture was refluxed for 4 hr. A saturated aqueous ammonium chloride solution was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/3) to give the title compound as a colorless solid (yield: 200.8 mg, yield: 60%).

¹H-NMR (CDCl₃) δ: 0.00-0.09 (6H, m), 0.57-1.38 (4H, m), 0.86-0.92 (9H, m), 1.26-1.33 (3H, m), 3.47-4.49 (2H, m), 5.66-5.95 (1H, m).

Reference Example 69

4-[(6S,7S)-7-(tert-butyldimethylsilyloxy)-6-methyl-4-oxo-5-azaspiro[2.4]hept-5-yl]-2-chlorobenzonitrile

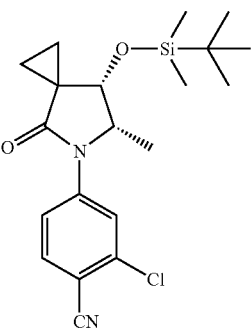 [SMILES: C[C@H]1[C@@H](O[Si](C)(C)C(C)(C)C)C2(CC2)C(=O)N1c1ccc(C#N)c(Cl)c1]

Using (6S)-7-(tert-butyldimethylsilyloxy)-6-methyl-5-azaspiro[2.4]heptan-4-one (200.8 mg), 4-bromo-2-chlorobenzonitrile (194.3 mg), cesium carbonate (384 mg), tris(dibenzylideneacetone)dipalladium(0) (36 mg) and 4,5-bis(diphenylphosphino)-9,9-dimethylxanthene (91 mg), and in the same manner as in Reference Example 3, the title compound (yield: 68.4 mg, yield: 22.2%) and 4-[(6S,7R)-7-(tert-butyldimethylsilyloxy)-6-methyl-4-oxo-5-azaspiro[2.4]hept-5-yl]-2-chlorobenzonitrile (yield: 161 mg, yield: 52.4%) were obtained each as a colorless solid.

4-[(6S,7S)-7-(tert-butyldimethylsilyloxy)-6-methyl-4-oxo-5-azaspiro[2.4]hept-5-yl]-2-chlorobenzonitrile;

¹H-NMR (CDCl₃) δ: 0.07 (3H, s), 0.12 (3H, s), 0.67-0.79 (1H, m), 0.88-1.37 (3H, m), 0.93 (9H, s), 1.30 (3H, d, J=6.4Hz), 4.29-4.41 (1H, m), 4.59 (1H, d, J=7.2 Hz), 7.01-8.04 (3H, m).

4-[(6S,7R)-7-(tert-butyldimethylsilyloxy)-6-methyl-4-oxo-5-azaspiro[2.4]hept-5-yl]-2-chlorobenzonitrile ¹H-NMR (CDCl₃) δ: 0.06 (3H, s), 0.10 (3H, s), 0.89 (9H, s), 0.97-1.17 (2H, m), 1.21-1.42 (2H, m), 1.36 (3H, d, J=6.6 Hz), 3.79-3.82 (1H, m), 4.06-4.19 (1H, m), 7.54-7.69 (2H, m), 7.91-7.95 (1H, m).
mp: 169-172° C.

Reference Example 70

2-chloro-4-[(6S)-6-methyl-4,7-dioxo-5-azaspiro[2.4]hept-5-yl]benzonitrile

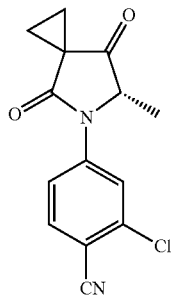 [SMILES: C[C@H]1C(=O)C2(CC2)C(=O)N1c1ccc(C#N)c(Cl)c1]

A solution of oxalyl chloride (0.050 mL) in methylene chloride (2.0 mL) was cooled to −60° C., dimethyl sulfoxide (0.062 mL) was added dropwise, and the mixture was stirred at the same temperature for 30 min. A solution of 2-chloro-4-[(6S,7R)-7-hydroxy-6-methyl-4-oxo-5-azaspiro[2.4]hept-5-yl]benzonitrile (40.1 mg) in methylene chloride (2.5 mL) was added dropwise to the reaction mixture, and the mixture was stirred at −40° C. for 1 hr. Triethylamine (0.202 mL) was added, and the mixture was stirred at 0° C. for 30 min. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/1) to give the title compound as a pale-yellow oil (yield: 35 mg, 88%).
¹H-NMR (CDCl₃) δ: 1.50 (3H, d, J=6.8 Hz), 1.78-1.96 (4H, m), 4.68 (1H, q, J=6.9 Hz), 7.57 (1H, dd, J=8.6, 2.1 Hz), 7.72 (1H, d, J=8.6 Hz), 7.90 (1H, d, J=2.1 Hz).
mp: 169-172° C.

Reference Example 71

4-[(6S,7R)-7-(tert-butyldimethylsilyloxy)-6-methyl-4-oxo-5-azaspiro[2.4]hept-5-yl]-2-(trifluoromethyl)benzonitrile

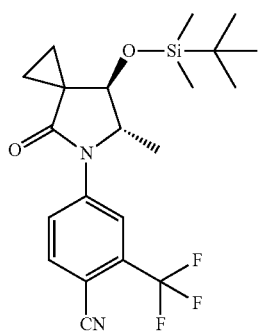 [SMILES: C[C@H]1[C@H](O[Si](C)(C)C(C)(C)C)C2(CC2)C(=O)N1c1ccc(C#N)c(C(F)(F)F)c1]

Using (6S)-7-(tert-butyldimethylsilyloxy)-6-methyl-5-azaspiro[2.4]heptan-4-one (720.5 mg), 4-iodo-2-trifluoromethylbenzonitrile (921.3 mg), cesium carbonate (1.38 g), tris(dibenzylideneacetone)dipalladium(0) (129 mg) and 4,5-bis(diphenylphosphino)-9,9-dimethylxanthene (326 mg), and in the same manner as in Reference Example 3, the title compound (yield: 670 mg, yield 56%) and 4-[(6S,7S)-7-(tert-butyldimethylsilyloxy)-6-methyl-4-oxo-5-azaspiro[2.4]hept-5-yl]-2-(trifluoromethyl)benzonitrile (yield: 309 mg, 26%) were obtained each as a colorless solid.

4-[(6S,7R)-7-(tert-butyldimethylsilyloxy)-6-methyl-4-oxo-5-azaspiro[2.4]hept-5-yl]-2-(trifluoromethyl)benzonitrile ¹H-NMR (CDCl₃) δ: 0.06 (3H, s), 0.10 (3H, s), 0.90 (9H, s), 0.99-1.18 (2H, m), 1.21-1.33 (1H, m), 1.31-1.44 (1H, m), 1.37 (3H, d, J=6.4 Hz), 3.79-3.86 (1H, m), 4.09-4.25 (1H, m), 7.79-7.86 (2H, m), 8.23 (1H, s).

4-[(6S,7S)-7-(tert-butyldimethylsilyloxy)-6-methyl-4-oxo-5-azaspiro[2.4]hept-5-yl]-2-(trifluoromethyl)benzonitrile ¹H-NMR (CDCl₃) δ: 0.08 (3H, s), 0.13 (3H, s), 0.69-0.81 (1H, m), 0.93 (9H, s), 0.93-1.09 (1H, m), 1.18-1.41 (2H, m), 1.32 (3H, d, J=6.4 Hz), 4.43-4.46 (1H, m), 4.61 (1H, d, J=7.2 Hz), 7.80 (1H, d, J=8.7 Hz), 7.95 (1H, dd, J=8.7, 2.3 Hz), 8.25 (1H, d, J=2.3 Hz).

Reference Example 72

4-[(6S,7R)-7-(tert-butyldimethylsilyloxy)-6-methyl-4-oxo-5-azaspiro[2.4]hept-5-yl]-2-methoxybenzonitrile

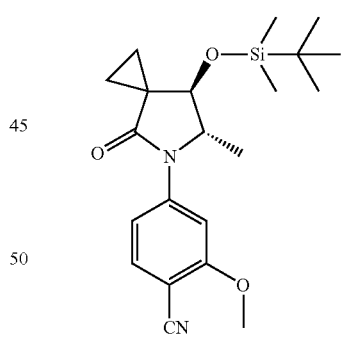

Using (6S)-7-(tert-butyldimethylsilyloxy)-6-methyl-5-azaspiro[2.4]heptan-4-one (762.2 mg), 4-bromo-2-methoxybenzonitrile (724 mg), cesium carbonate (1.46 g), tris(dibenzylideneacetone)dipalladium(0) (136.6 mg) and 4,5-bis(diphenylphosphino)-9,9-dimethylxanthene (345.3 mg), and in the same manner as in Reference Example 3, the title compound was obtained as a colorless solid (yield: 760 mg, 66%).
¹H-NMR (CDCl₃) δ: 0.06 (3H, s), 0.09 (3H, s), 0.90 (9H, s), 0.96-1.14 (2H, m), 1.19-1.38 (2H, m), 1.36 (3H, d, J=6.6 Hz), 3.80 (1H, d, J=1.9 Hz), 3.93 (3H, s), 4.11-4.21 (1H, m), 6.80 (1H, dd, J=8.5, 1.9 Hz), 7.53 (1H, d, J=8.5 Hz), 7.92 (1H, d, J=1.9 Hz).

Reference Example 73

(4S)-4-ethyl-1,3-oxazolidine-2,5-dione

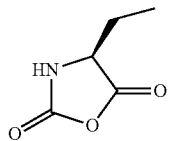

To a suspension of (2S)-2-aminobutanoic acid (10 g) and activated carbon (116 mg) in tetrahydrofuran (50 mL) was added dropwise a solution of triphosgene (10.07 g) in tetrahydrofuran (50 mL) at room temperature, and the mixture was stirred at 50° C. for 2 hr. The same experimental process was performed twice, in each of which insoluble materials were filtered off with celite, and the filtrates were combined and concentrated under reduced pressure. The residue was washed with hexane to give the title compound as a solid (yield: 22.39 g, 89%).

$^1$H-NMR (CDCl$_3$) δ: 1.06 (3H, t, J=7.5 Hz), 1.81-2.03 (2H, m), 4.29-4.38 (1H, m), 5.79 (1H, brs).

Reference Example 74

Benzyl (4S)-4-ethyl-2,5-dioxo-1,3-oxazolidine-3-carboxylate

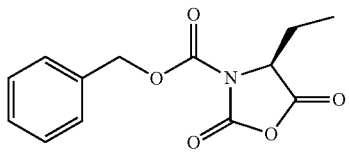 [SMILES: CC[C@H]1C(=O)OC(=O)N1C(=O)OCc1ccccc1]

A solution of (4S)-4-ethyl-1,3-oxazolidine-2,5-dione (69.57 g) and benzyl chloroformate (101.1 g) in tetrahydrofuran (800 mL) was cooled to 0° C., N-methylmorpholine (81.74 g) was added dropwise, and the mixture was stirred at 0° C. for 2 hr. A 4 mol/L hydrogen chloride-ethyl acetate solution (86.9 mL) was added dropwise at 0° C. to the reaction mixture, and the precipitated morpholine hydrochloride was filtered off with celite. The filtrate was concentrated under reduced pressure to give the title compound as a pale-yellow oil (yield: 91.58 g, 52%).

$^1$H-NMR (CDCl$_3$) δ: 0.95 (3H, t, J=7.5 Hz), 1.75-2.35 (2H, m), 4.74 (1H, dd, J=6.0, 3.2 Hz), 5.27-5.44 (2H, m), 7.28-7.49 (5H, m).

Reference Example 75 tert-butyl 1-((2S)-2-{([(benzyloxy)carbonyl]amino}butanoyl)cyclopropanecarboxylate

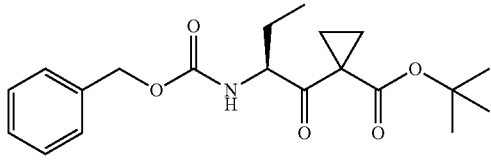 [SMILES: CC[C@H](NC(=O)OCc1ccccc1)C(=O)C1(C(=O)OC(C)(C)C)CC1]

A solution of diisopropylamine (3.76 mL) in tetrahydrofuran (50 mL) was cooled to −78° C., n-butyllithium-hexane solution (16.56 mL, 1.6 mol/L) was added dropwise and, after the completion of the dropwise addition, the mixture was stirred at −78° C. for 1 hr. Subsequently, a solution of tert-butyl cyclopropanecarboxylate (3.77 g) in tetrahydrofuran (10 mL) was added dropwise, and the mixture was further stirred at −78° C. for 30 min. A solution of benzyl (4S)-4-ethyl-2,5-dioxo-1,3-oxazolidine-3-carboxylate (3.49 g) in tetrahydrofuran (50 mL) was added dropwise at −78° C. for 30 min and the mixture was stirred at −78° C. for 30 min. Acetic acid was added to the reaction mixture at −78° C., water was added and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→2/1) to give the title compound as a colorless oil (yield: 1.16 g, 24%).

$^1$H-NMR (CDCl$_3$) δ: 0.89 (3H, t, J=7.6 Hz), 1.04-1.79 (6H, m), 1.50 (9H, s), 5.07-5.17 (2H, m), 5.25-5.38 (1H, m), 5.42-5.52 (1H, m), 7.29-7.40 (5H, m).

Reference Example 76 tert-butyl 1-((2S)-2-{[[(benzyloxy)carbonyl]amino}-1-(tert-butyldimethylsilyloxy) butyl)cyclopropanecarboxylate

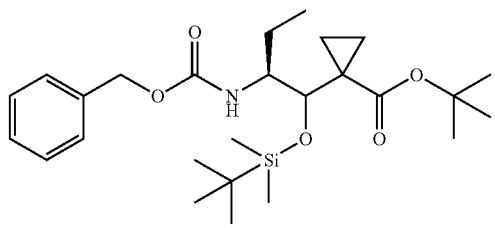 [SMILES: CC[C@H](NC(=O)OCc1ccccc1)C(O[Si](C)(C)C(C)(C)C)C1(C(=O)OC(C)(C)C)CC1]

To a solution of tert-butyl 1-((2S)-2-{([(benzyloxy)carbonyl]amino}butanoyl)cyclopropanecarboxylate (1.16 g) in methanol (25 mL) was added sodium borohydride (180 mg) at 0° C., and the mixture was stirred at 0° C. for 30 min. Aqueous ammonium chloride was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/1) to give tert-butyl 1-((2S)-2-{([(benzyloxy)carbonyl]amino}-1-hydroxybutyl)cyclopropanecarboxylate as a colorless oil (yield: 914.8 mg, yield: 78%).

To a solution of tert-butyl 1-((2S)-2-{[(benzyloxy)carbonyl]amino}-1-hydroxybutyl)cyclopropanecarboxylate (914.8 mg) and 2,6-lutidine (0.632 mL) in tetrahydrofuran (20 mL) was added under ice-cooling tert-butyldimethylsilane trifluoromethanesulfonate (0.934 mL) and, after warming to room temperature, the mixture was stirred for 1 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→2/1) to give the title compound as a colorless oil (yield: 1.18 g, 98%).

$^1$H-NMR (CDCl$_3$) δ: 0.03-0.10 (6H, m), 0.77-1.48 (9H, m), 0.81-0.92 (9H, m), 1.36-1.47 (9H, m), 3.61-3.77 (1H, m), 4.19-4.28 (1H, m), 4.71-4.84 (1H, m), 5.03-5.18 (2H, m), 7.13-7.41 (5H, m).

Reference Example 77

(6S)-7-(tert-butyldimethylsilyloxy)-6-ethyl-5-aza-spiro[2.4]heptan-4-one

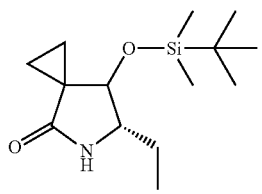 [SMILES: CC[C@@H]1NC(=O)C2(CC2)C1O[Si](C)(C)C(C)(C)C]

To a solution of tert-butyl 1-((2S)-2-{[(benzyloxy)carbonyl]amino}-1-(tert-butyldimethylsilyloxy)butyl)cyclopropanecarboxylate (1.18 g) in methanol (20 mL) was added 10% palladium carbon (150 mg), and the mixture was stirred at room temperature for 18 hr under a hydrogen atmosphere and filtered. The filtrate was concentrated under reduced pressure and the residue was dissolved in methanol (20 mL). Sodium methoxide (230 mg) was added and the mixture was refluxed for 2.5 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/2) to give the title compound as a colorless oil (yield: 397.8 mg, 60%).

$^1$H-NMR (CDCl$_3$) δ: 0.00-0.07 (6H, m), 0.59-1.29 (7H, m), 0.87-0.92 (9H, m), 1.40-1.57 (1H, m), 1.60-1.81 (1H, m), 3.34-3.66 (1H, m), 3.84-3.90 (1H, m), 5.51-5.73 (1H, m).

Reference Example 78

4-[(6S,7R)-7-(tert-butyldimethylsilyloxy)-6-ethyl-4-oxo-5-azaspiro[2.4]hept-5-yl]-2-(trifluoromethyl)benzonitrile

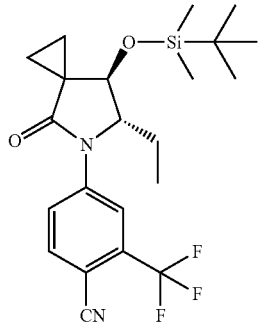 [SMILES: CC[C@H]1[C@H](O[Si](C)(C)C(C)(C)C)C2(CC2)C(=O)N1c1ccc(C#N)c(C(F)(F)F)c1]

Using (6S)-7-(tert-butyldimethylsilyloxy)-6-ethyl-5-azaspiro[2.4]heptan-4-one (397.8 mg), 4-iodo-2-trifluoromethylbenzonitrile (482 mg), cesium carbonate (721 mg), tris(dibenzylideneacetone)dipalladium(0) (68 mg) and 4,5-bis(diphenylphosphino)-9,9-dimethylxanthene (171 mg), and in the same manner as in Reference Example 3, the title compound was obtained as a colorless solid (yield: 433.7 mg, yield: 67%).

$^1$H-NMR (CDCl$_3$) δ: 0.07 (3H, s), 0.11 (3H, s), 0.90 (9H, s), 0.96 (3H, t, J=7.6 Hz), 1.02-1.17 (2H, m), 1.30-1.38 (2H, m), 1.65-1.83 (2H, m), 3.83-3.91 (1H, m), 4.05-4.16 (1H, m), 7.80-7.86 (2H, m), 8.28 (1H, s).

Reference Example 79

(4S,5S)-1-(3-chloro-4-iodophenyl)-3,3-difluoro-4-hydroxy-5-methylpyrrolidin-2-one

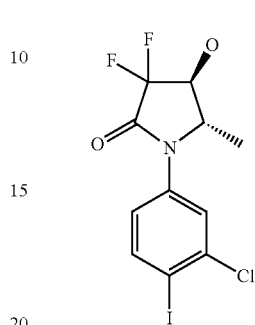

To a solution of (4S,5S)-1-(3-chlorophenyl)-3,3-difluoro-4-hydroxy-5-methylpyrrolidin-2-one (110.5 mg) and N-iodosuccinimide (130 mg) in acetic acid (3 mL) was added dropwise conc. sulfuric acid (3 drops), and the mixture was stirred at room temperature for 18 hr. The reaction mixture was concentrated, water was added and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/2) to give the title compound as a pale-yellow oil (yield: 113 mg, 69%).

$^1$H-NMR (CDCl$_3$) δ: 1.38 (3H, dd, J=6.5, 1.2 Hz), 2.38 (1H, brs), 4.05-4.23 (2H, m), 7.14 (1H, dd, J=8.7, 2.5 Hz), 7.64 (1H, d, J=2.5 Hz), 7.90 (1H, d, J=8.7 Hz).

Reference Example 80

4-[(4R,5S)-4-(tert-butyldimethylsilyloxy)-3,3,5-trimethyl-2-oxopyrrolidin-1-yl]-2-(trifluoromethyl)benzonitrile

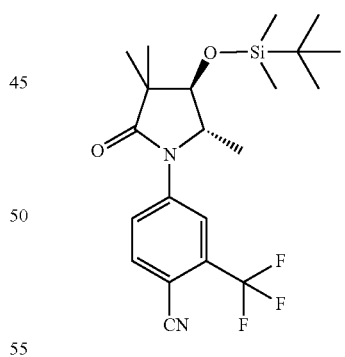

Using (4R,5S)-4-(tert-butyldimethylsilyloxy)-3,3,5-trimethylpyrrolidin-2-one (266.6 mg), 4-iodo-2-trifluoromethylbenzonitrile (340 mg), cesium carbonate (505 mg), tris(dibenzylideneacetone)dipalladium(0) (47 mg) and 4,5-bis(diphenylphosphino)-9,9-dimethyxanthene (120 mg), and in the same manner as in Reference Example 3, the title compound was obtained as a pale-yellow oil (yield: 391.7 mg, yield: 89%).

$^1$H-NMR (CDCl$_3$) δ: 0.15 (3H, s), 0.15 (3H, s), 0.95 (9H, s), 1.13 (3H, s), 1.30 (3H, s), 1.31 (3H, d, J=6.2 Hz), 3.75 (1H, d, J=6.2 Hz), 3.89-4.02 (1H, m), 7.58-7.74 (1H, m), 7.80-7.93 (2H, m).

Reference Example 81

(4R,5S)-4-(tert-butyldimethylsilyloxy)-5-ethylpyrrolidin-2-one

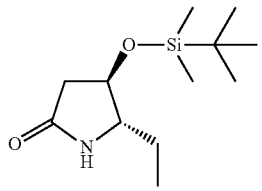 [SMILES: CC[C@@H]1NC(=O)C[C@H]1O[Si](C)(C)C(C)(C)C]

A solution of diisopropylamine (74.5 mL) in tetrahydrofuran (1 L) was cooled to −78° C., n-butyllithium-hexane solution (329 mL, 1.6 mol/L) was added dropwise, and the mixture was stirred for 1 hr. Ethyl acetate (51.6 mL) was added dropwise and the mixture was stirred at −78° C. for 1 hr. Then, a solution of benzyl [(1S)-1-(1H-imidazol-1-ylcarbonyl)propyl]carbamate prepared from (2S)-2-{[(benzyloxy)carbonyl]amino}butanoic acid (50 g) and N,N'-carbonyldiimidazole (39.5 g) in tetrahydrofuran (300 mL) was added dropwise at −78° C. After stirring at −78° C. for 1 hr, acetic acid was added to the reaction mixture. Water was added and the mixture was extracted with ethyl acetate. The extract was dried over anhydrous magnesium sulfate and concentrated under reduced pressure. The residue was purified by silica gel column chromatography (eluent: hexane/ethyl acetate=1/0→2/1) to give ethyl (4S)-4-{[(benzyloxy)carbonyl]amino}-3-oxohexanoate as a colorless oil (yield: 36.7 g, 57%).

To a solution of ethyl (4S)-4-{[(benzyloxy)carbonyl]amino}-3-oxohexanoate (70.68 g) in methanol (500 mL) was added sodium borohydride (9.66 g) at −78° C., and the mixture was stirred at −78° C. for 1 hr and at room temperature for 1 hr. Saturated aqueous ammonium chloride was added to the reaction mixture, and the mixture was extracted with ethyl acetate. The extract was dried over anhydrous magnesium sulfate and concentrated under reduced pressure. The residue was purified by silica gel column chromatography (eluent: ethyl acetate) to give ethyl (4S)-4-{[benzyloxy)carbonyl]amino}-3-hydroxyhexanoate (yield: 63.2 g, 89%) as a colorless solid.

To a solution of ethyl (4S)-4-{[(benzyloxy)carbonyl]amino}-3-hydroxyhexanoate (63.2 g) and 2,6-lutidine (47.6 mL) in tetrahydrofuran (800 mL) was added tert-butyldimethylsilane trifluoromethanesulfonate (70 mL) under ice-cooling and, after warming to room temperature, and the mixture was stirred for 1 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate-1/0→1/1) to give ethyl (4S)-4-{[(benzyloxy)carbonyl]amino}-3-(tert-butyldimethylsilyloxy)hexanoate as a colorless oil (yield: 64.0 g, 74%).

To a solution of ethyl (4S)-4-{([(benzyloxy)carbonyl]amino}-3-(tert-butyldimethylsilyloxy)hexanoate (64.0 g) in methanol (500 mL) was added 10% palladium carbon (containing 50% water, 6.5 g), and the mixture was stirred at room temperature for 3.5 hr under a hydrogen atmosphere and filtered. Sodium methoxide (13.6 g) was added to the filtrate, and the mixture was stirred at room temperature for 2 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate-20/1→1/4) to give the title compound (yield: 21.6 g, 59%) and (4S,5S)-4-(tert-butyldimethylsilyloxy)-5-ethylpyrrolidin-2-one (yield: 4.64 g, 13%) as a colorless solid and a colorless oil, respectively.

(4R,5S)-4-(tert-butyldimethylsilyloxy)-5-ethylpyrrolidin-2-one $^1$H-NMR (CDCl$_3$) δ: 0.07 (3H, s), 0.08 (3H, s), 0.88 (9H, s), 0.96 (3H, t, J=7.5 Hz), 1.33-1.54 (1H, m), 1.54-1.71 (1H, m), 2.26 (1H, dd, J=16.9, 4.6 Hz), 2.60 (1H, dd, J=16.9, 6.9 Hz), 3.30-3.41 (1H, m), 4.05-4.18 (1H, m), 5.71 (1H, brs).

(4S,5S)-4-(tert-butyldimethylsilyloxy)-5-ethylpyrrolidin-2-one $^1$H-NMR (CDCl$_3$) δ: 0.068 (3H, s), 0.070 (3H, s), 0.89 (9H, s), 0.95 (3H, t, J=7.5 Hz), 1.43-1.76 (2H, m), 2.26 (1H, dd, J=16.9, 4.2 Hz), 2.51 (1H, dd, J=16.7, 6.3 Hz), 3.43-3.56 (1H, m), 4.39-4.50 (1H, m), 5.94 (1H, brs).

Reference Example 82

4-[(2S,3R)-3-(tert-butyldimethylsilyloxy)-2-ethyl-5-oxopyrrolidin-1-yl]-2-chlorobenzonitrile

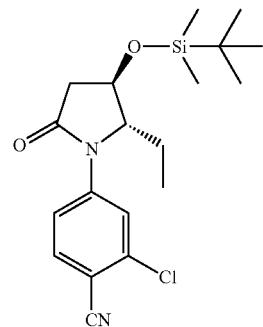 [SMILES: CC[C@H]1[C@H](O[Si](C)(C)C(C)(C)C)CC(=O)N1c1ccc(C#N)c(Cl)c1]

Using (4R,5S)-4-(tert-butyldimethylsilyloxy)-5-ethylpyrrolidin-2-one (320 mg), 4-bromo-2-chlorobenzonitrile (325 mg), cesium carbonate (643 mg), tris(dibenzylideneacetone)dipalladium(0) (60 mg) and 4,5-bis(diphenylphosphino)-9,9-dimethylxanthene (152 mg), and in the same manner as in Reference Example 3, the title compound was obtained as a colorless solid (yield: 366 mg, 73%).

$^1$H-NMR (CDCl$_3$) δ: 0.11 (3H, s), 0.12 (3H, s), 0.89 (9H, s), 0.97 (3H, t, J=7.5 Hz), 1.42-1.58 (1H, m), 1.65-1.79 (1H, m), 2.48 (1H, dd, J=17.6, 1.3 Hz), 2.91 (1H, dd, J=17.6, 5.9 Hz), 3.97 (1H, dd, J=9.3, 2.1 Hz), 4.21-4.28 (1H, m), 7.56 (1H, dd, J=8.7, 1.9 Hz), 7.65 (1H, d, J=8.7 Hz), 7.90 (1H, d, J=1.9 Hz).

Reference Example 83

4-[(2S,3S)-3-(tert-butyldimethylsilyloxy)-2-ethyl-5-oxopyrrolidin-1-yl]-2-chlorobenzonitrile

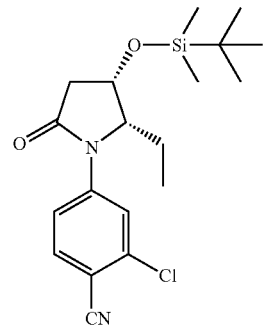 [SMILES: CC[C@H]1[C@@H](O[Si](C)(C)C(C)(C)C)CC(=O)N1c1ccc(C#N)c(Cl)c1]

Using (4S,5S)-4-(tert-butyldimethylsilyloxy)-5-ethylpyrrolidin-2-one (470 mg), 4-bromo-2-chlorobenzonitrile (477 mg), cesium carbonate (944 mg), tris(dibenzylideneacetone)dipalladium(0) (88.5 mg) and 4,5-bis(diphenylphosphino)-9,9-dimethylxanthene (224 mg), and in the same manner as in Reference Example 3, the title compound was obtained as a colorless solid (yield: 550 mg, 75%).

¹H-NMR (CDCl₃) δ: 0.13 (3H, s), 0.13 (3H, s), 0.92 (9H, s), 0.96 (3H, t, J=7.6 Hz), 1.60-1.77 (1H, m), 1.76-1.92 (1H, m), 2.63 (1H, dd, J=17.0, 6.8 Hz), 2.73 (1H, dd, J=17.0, 6.8 Hz), 4.09-4.22 (1H, m), 4.63 (1H, q, J=6.8 Hz), 7.49 (1H, dd, J=8.5, 2.1 Hz), 7.65 (1H, d, J=8.5 Hz), 7.76 (1H, d, J=2.1 Hz).

Reference Example 84

4-[(2S,3R)-3-(tert-butyldimethylsilyloxy)-2-ethyl-5-oxopyrrolidin-1-yl]-2-(trifluoromethyl)benzonitrile

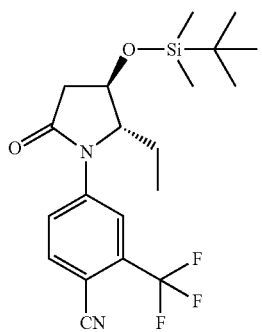 [SMILES: CC[C@H]1[C@H](O[Si](C)(C)C(C)(C)C)CC(=O)N1c1ccc(C#N)c(C(F)(F)F)c1]

Using (4R,5S)-4-(tert-butyldimethylsilyloxy)-5-ethylpyrrolidin-2-one (1.00 g), 4-iodo-2-trifluoromethylbenzonitrile (1.46 g), cesium carbonate (2.08 g), tris(dibenzylideneacetone)dipalladium(0) (193 mg) and 4,5-bis(diphenylphosphino)-9,9-dimethylxanthene (490 mg), and in the same manner as in Reference Example 3, the title compound was obtained as a colorless solid (yield: 1.32 g, 78%).

¹H-NMR (CDCl₃) δ: 0.12 (3H, s), 0.13 (3H, s), 0.89 (9H, s), 0.98 (3H, t, J=7.5 Hz), 1.42-1.61 (1H, m), 1.64-1.80 (1H, m), 2.50 (1H, dd, J=17.6, 1.5 Hz), 2.94 (1H, dd, J=17.6, 5.9 Hz), 3.97-4.07 (1H, m), 4.23-4.31 (1H, m), 7.77-7.92 (2H, m), 8.14 (1H, d, J=2.1 Hz).

Reference Example 85

4-[(2S,3R)-3-(tert-butyldimethylsilyloxy)-2-ethyl-5-oxopyrrolidin-1-yl]-2-methoxybenzonitrile

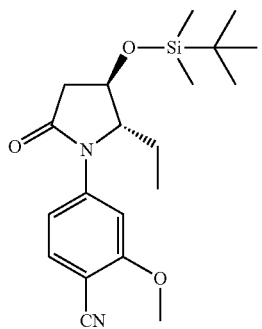 [SMILES: CC[C@H]1[C@H](O[Si](C)(C)C(C)(C)C)CC(=O)N1c1ccc(C#N)c(OC)c1]

Using (4R,5S)-4-(tert-butyldimethylsilyloxy)-5-ethylpyrrolidin-2-one (1.00 g), 4-bromo-2-methoxybenzonitrile (1.00 g), cesium carbonate (2.08 g), tris(dibenzylideneacetone)dipalladium(0) (193 mg) and 4,5-bis(diphenylphosphino)-9,9-dimethylxanthene (490 mg), and in the same manner as in Reference Example 3, the title compound was obtained as a colorless solid (yield: 1.04 g, 65%).

¹H-NMR (CDCl₃) δ: 0.11 (3H, s), 0.12 (3H, s), 0.89 (9H, s), 0.96 (3H, t, J=7.6 Hz), 1.39-1.55 (1H, m), 1.63-1.83 (1H, m), 2.48 (1H, dd, J=17.4, 1.5 Hz), 2.91 (1H, dd, J=17.4, 5.9 Hz), 3.94 (3H, s), 3.94-4.03 (1H, m), 4.19-4.28 (1H, m), 6.82 (1H, dd, J=8.5, 1.9 Hz), 7.53 (1H, d, J=8.5 Hz), 7.78 (1H, d, J=1.9 Hz).

Reference Example 86

4-[(2S,3R)-3-(tert-butyldimethylsilyloxy)-2-ethyl-5-oxopyrrolidin-1-yl]-2-chloro-3-methylbenzonitrile

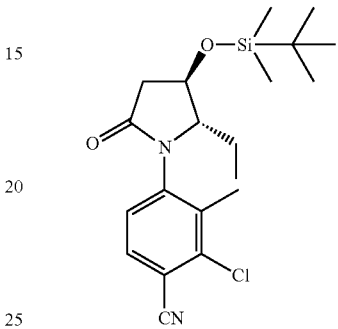

Using (4R,5S)-4-(tert-butyldimethylsilyloxy)-5-ethylpyrrolidin-2-one (1.00 g), 2-chloro-4-iodo-3-methylbenzonitrile (1.31 g), cesium carbonate (2.08 g), tris(dibenzylideneacetone)dipalladium(0) (193 mg) and 4,5-bis(diphenylphosphino)-9,9-dimethylxanthene (490 mg), and in the same manner as in Reference Example 3, the title compound was obtained as a colorless solid (yield: 650 mg, 39%).

¹H-NMR (CDCl₃) δ: 0.13 (3H, s), 0.13 (3H, s), 0.89-0.94 (3H, m), 0.92 (9H, s), 1.33-1.51 (1H, m), 1.51-1.67 (1H, m), 2.34 (3H, s), 2.44 (1H, dd, J=17.3, 2.1 Hz), 2.85 (1H, dd, J=17.3, 5.8 Hz), 3.59-3.76 (1H, m), 4.26 (1H, m), 7.15 (1H, d, J=8.1 Hz), 7.57 (1H, d, J=8.1 Hz).

Reference Example 87

4-[(2S,3S)-3-(tert-butyldimethylsilyloxy)-2-ethyl-5-oxopyrrolidin-1-yl]-2-chloro-3-methylbenzonitrile

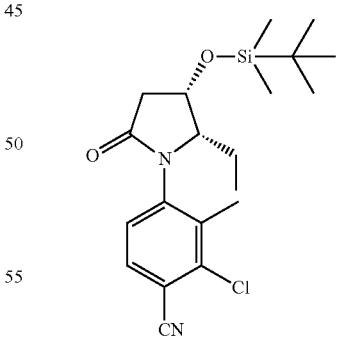

Using (4S,5S)-4-(tert-butyldimethylsilyloxy)-5-ethylpyrrolidin-2-one (1.00 g), 2-chloro-4-iodo-3-methylbenzonitrile (1.31 g), cesium carbonate (2.08 g), tris(dibenzylideneacetone)dipalladium(0) (193 mg) and 4,5-bis(diphenylphosphino)-9,9-dimethylxanthene (490 mg), and in the same manner as in Reference Example 3, the title compound was obtained as a colorless solid (yield: 134.5 mg, yield: 8%).

¹H-NMR (CDCl₃) δ: 0.12 (3H, s), 0.15 (3H, s), 0.85 (3H, t, J=7.4 Hz), 0.91 (9H, s), 1.49-1.76 (2H, m), 2.31 (3H, s), 2.45-2.56 (1H, m), 2.74 (1H, dd, J=16.8, 4.9 Hz), 3.83-3.97 (1H, m), 4.51-4.59 (1H, m), 6.99-7.16 (1H, m), 7.55 (1H, d, J=8.3 Hz).

Reference Example 88

4-[(2S,3S)-3-(tert-butyldimethylsilyloxy)-2-ethyl-5-oxopyrrolidin-1-yl]-2-(trifluoromethyl)benzonitrile

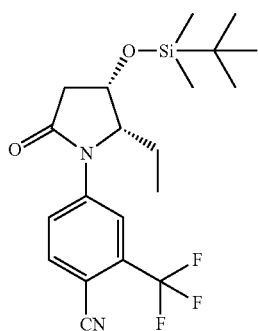 [SMILES: CC[C@H]1[C@@H](O[Si](C)(C)C(C)(C)C)CC(=O)N1c1ccc(C#N)c(C(F)(F)F)c1]

A suspension of (4S,5S)-4-(tert-butyldimethylsilyloxy)-5-ethylpyrrolidin-2-one (6.00 g), 4-iodo-2-trifluoromethylbenzonitrile (8.42 g), cesium carbonate (12.05 g), tris(dibenzylideneacetone)dipalladium(0) (1.13 g) and 4,5-bis(diphenylphosphino)-9,9-dimethylxanthene (2.14 g) in toluene (70 mL) was stirred at 80° C. for 18 hr. Water and ethyl acetate were added to the reaction mixture and insuluble material was filtered off. The filtrate was extracted with ethyl acetate. The extract was dried over anhydrous magnesium sulfate and concentrated under reduced pressure. The residue was purified by silica gel column chromatography (eluent: hexane/ethyl acetate=50/1→1/2) to give the title compound as a pale-yellow solid (yield: 7.76 g, 76%).
$^1$H-NMR (CDCl$_3$) δ: 0.14 (3H, s), 0.14 (3H, s), 0-0.93 (9H, s), 0.96 (3H, t, J=7.5 Hz), 1.60-1.78 (1H, m), 1.77-1.94 (1H, m), 2.66 (1H, dd, J=17.0, 6.8 Hz), 2.76 (1H, dd, J=17.0, 7.2 Hz), 4.16-4.26 (1H, m), 4.66 (1H, q, J=6.9 Hz), 7.81-7.87 (2H, m), 7.94-7.99 (1H, m).

Reference Example 89 tert-butyl [(1S)-1-methyl-2-oxopropyl]carbamate

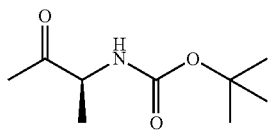

A solution of tert-butyl{(1S)-1-[methoxy(methyl)carbamoyl]ethyl}carbamate (5.26 g) in tetrahydrofuran (300 mL) was cooled with dry ice/acetone under a nitrogen atmosphere, and 1.6 mol/L-methyllithium/diethyl ether solution (38.8 mL) was added. After stirring at the same temperature for 1.5 hr, saturated aqueous ammonium chloride solution (100 mL) was added to the reaction solution, and the mixture was extracted with ethyl acetate. The obtained organic layer was washed with saturated brine, dried over anhydrous magnesium sulfate, and concentration under reduced pressure to give the title compound as a colorless oil (yield: 4.48 g).

$^1$H-NMR (CDCl$_3$) δ: 1.34 (3H, d, J=7.2 Hz), 1.44 (9H, s), 2.21 (3H, s), 4.23-4.40 (1H, m), 5.26 (1H, brs).

Reference Example 90

(4S,5S)-4-hydroxy-4,5-dimethylpyrrolidin-2-one

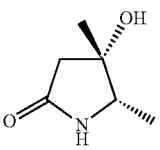

A solution of diisopropylamine (3.44 g) in tetrahydrofuran (50 mL) was ice-cooled under a nitrogen atmosphere and 1.6 mol/L n-butyllithium-hexane solution (20.8 mL) was added. The mixture was stirred at the same temperature for 20 min, and the reaction solution was cooled with dry ice/acetone. Ethyl acetate (3.28 mL) was added to the reaction solution, and the mixture was stirred at the same temperature for 30 min. A solution of tert-butyl [(1S)-1-methyl-2-oxopropyl]carbamate (4.48 g) in tetrahydrofuran (10 mL) was added. The mixture was stirred at the same temperature for 5 hr, saturated aqueous ammonium chloride solution (100 mL) was added, and the mixture was extracted with ethyl acetate. The obtained organic layer was washed with saturated brine, dried over anhydrous magnesium sulfate, and concentrated under reduced pressure. The residue was purified by silica gel column chromatography (eluent: ethyl acetate/hexane=0→30%), the obtained oil was dissolved in 4 mol/L hydrogen chloride-ethyl acetate solution (50 mL), and the mixture was stirred at room temperature for 2 hr. The reaction solution was concentrated under reduced pressure, the residue was dissolved in tetrahydrofuran (150 mL), and diisopropylethylamine (11.5 mL) was added. The reaction solution was refluxed under heating for 4 hr, and concentrated under reduced pressure. The residue was purified by silica gel column chromatography (eluent: methanol/ethyl acetate=0→10%), and the obtained solid was recrystallized from isopropanol/hexane to give the title compound as colorless crystals (yield: 1.51 g, 55%).
$^1$H-NMR (CDCl$_3$) δ: 1.00 (3H, d, J=6.4 Hz), 1.20 (3H, s), 2.06 (1H, d, J=6.2 Hz), 2.24 (1H, d, J=6.2 Hz), 3.33 (1H, q, J=6.4 Hz), 4.72 (1H, s), 7.48 (1H, brs).
mp: 168-171° C.

Reference Example 91 tert-butyl [(1S)-1-ethyl-2-oxopropyl]carbamate

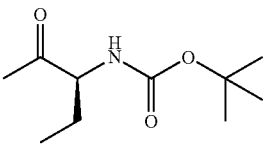

A solution of tert-butyl {(1S)-1-[methoxy(methyl)carbamoyl]propyl}carbamate (15.0 g) in tetrahydrofuran (150 mL) was cooled using dry ice/acetone under a nitrogen atmosphere, and 1.0 mol/L-methyllithium/diethyl ether solution (300 mL) was added. The mixture was stirred at the same temperature for 4 hr, saturated aqueous ammonium chloride solution (300 mL) was added to the reaction solution, and the mixture was extracted with ethyl acetate. The obtained organic layer was washed with saturated aqueous ammonium chloride solution and saturated brine, dried over anhydrous magnesium sulfate, and concentration under reduced pressure to give the title compound as a colorless oil (yield: 12.75 g).

$^1$H-NMR (CDCl$_3$) δ: 0.89 (3H, dd, J=7.6, 7.4 Hz), 1.44 (9H, s), 1.52-1.73 (1H, m), 1.86-2.03 (1H, m), 2.20 (3H, s), 4.21-4.38 (1H, m), 5.22 (1H, brs).

Reference Example 92

(4S,5S)-5-ethyl-4-hydroxy-4-methylpyrrolidin-2-one

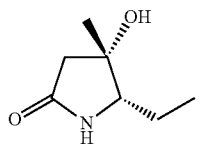

A solution of diisopropylamine (7.50 g) in tetrahydrofuran (110 mL) was ice-cooled under a nitrogen atmosphere, and 1.6 mol/L n-butyllithium-hexane solution (45.4 mL) was added. The mixture was stirred at the same temperature for 30 min, and the reaction solution was cooled with dry ice/acetone. Ethyl acetate (7.17 ml) was added to the reaction solution, and the mixture was stirred at the same temperature for 1 hr. A solution of tert-butyl [(1S)-1-ethyl-2-oxopropyl] carbamate (9.75 g) in tetrahydrofuran (60 mL) was added, and the mixture was stirred at the same temperature for 5.5 hr. A saturated aqueous ammonium chloride solution (200 mL) was added, and the mixture was extracted with ethyl acetate. The obtained organic layer was washed with saturated aqueous ammonium chloride solution and saturated brine, dried over anhydrous magnesium sulfate, and concentrated under reduced pressure. The residue was purified by silica gel column chromatography (eluent: ethyl acetate/hexane=10→30%) and the obtained oil was dissolved in 4 mol/L hydrogen chloride-ethyl acetate solution (80 mL), and the mixture was stirred at room temperature for 2 hr. The reaction solution was concentrated under reduced pressure, the residue was dissolved in tetrahydrofuran (285 mL), and diisopropylethylamine (22.2 mL) was added. The reaction solution was refluxed under heating for 4 hr, and concentrated under reduced pressure. The residue was purified by silica gel column chromatography (eluent: methanol/ethyl acetate=3→13%), and the obtained solid was recrystallized from ethyl acetate/hexane to give the title compound as colorless crystals (yield: 4.69 g, 68%).

$^1$H-NMR (CDCl$_3$) δ: 1.04 (3H, dd, J=7.5 Hz), 1.40 (3H, s), 1.44-1.62 (1H, m), 1.62-1.80 (1H, m), 2.46 (2H, d, J=1.5 Hz), 2.80 (1H, s), 3.32 (1H, dd, J=9.4, 4.2 Hz), 6.78 (1H, brs).

mp: 87-111° C.

Reference Example 93 tert-butyl [(1S)-2-cyclopropyl-1-methyl-2-oxoethyl]carbamate

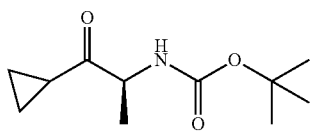

A solution of tert-butyl {(1S)-1-[methoxy(methyl)carbamoyl]ethyl}carbamate (10.0 g) in tetrahydrofuran (110 mL) was cooled using dry ice/acetone under a nitrogen atmosphere, and 1.0 mol/L-cyclopropylmagnesium bromide/tetrahydrofuran solution (100 mL) was added. The mixture was warmed to room temperature and stirred for 5 hr, saturated aqueous ammonium chloride solution (200 mL) was added to the reaction solution, and the mixture was extracted with ethyl acetate. The obtained organic layer was washed with water and saturated brine, dried over anhydrous magnesium sulfate, and concentrated under reduced pressure. The residue was purified by silica gel column chromatography (eluent: ethyl acetate/hexane=0→30%) to give the title compound as a yellow oil (yield: 3.65 g, 40%).

$^1$H-NMR (CDCl$_3$) δ: 0.88-1.01 (2H, m), 1.02-1.17 (2H, m), 1.42 (3H, d, J=7.4 Hz), 1.45 (9H, s), 1.95-2.06 (1H, m), 4.43-4.60 (1H, m), 5.35 (1H, brs).

Reference Example 94

(4R,5S)-4-cyclopropyl-4-hydroxy-5-methylpyrrolidin-2-one

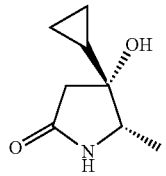

A solution of diisopropylamine (4.06 g) in tetrahydrofuran (40 mL) was ice-cooled under a nitrogen atmosphere, and 1.6 mol/L n-butyllithium-hexane solution (24.6 mL) was added. The mixture was stirred at the same temperature for 20 min, and the reaction solution was cooled with dry ice/acetone. Ethyl acetate (3.88 ml) was added to the reaction solution, the mixture was stirred at the same temperature for 30 min, and a solution of tert-butyl [(1S)-2-cyclopropyl-1-methyl-2-oxoethyl]carbamate (3.65 g) in tetrahydrofuran (10 mL) was added. The mixture was stirred at the same temperature for 7 hr, saturated aqueous ammonium chloride solution (100 mL) was added, and the mixture was extracted with ethyl acetate. The obtained organic layer was washed with water and saturated brine, dried over anhydrous magnesium sulfate, and concentrated under reduced pressure. The residue was purified by silica gel column chromatography (eluent: ethyl acetate/hexane=0→30%), the obtained oil was dissolved in 4 mol/L hydrogen chloride-ethyl acetate solution (30 mL), and the mixture was stirred at room temperature for 2 hr. The reaction solution was concentrated under reduced pressure, the residue was dissolved in tetrahydrofuran (80 mL), and diisopropylethylamine (8.09 mL) was added. The reaction solution was refluxed under heating for 4 hr, and concentrated under reduced pressure. The residue was purified by silica gel column chromatography (eluent: methanol/ethyl acetate=0→5%), and the obtained solid was recrystallized from ethyl acetate/hexane to give the title compound as colorless crystals (yield: 1.65 g, 71%).

$^1$H-NMR (CDCl$_3$) δ: 0.27-0.61 (4H, m), 0.93-1.06 (1H, m), 1.24 (3H, d, J=6.6 Hz), 2.04 (1H, s), 2.22 (1H, d, J=17.2 Hz), 2.38 (1H, d, J=17.2 Hz), 3.71 (1H, q, J=6.6 Hz), 5.90 (1H, brs).

mp: 133-140° C.

Reference Example 95 tert-butyl [(1S)-1-(cyclopropylcarbonyl)propyl]carbamate

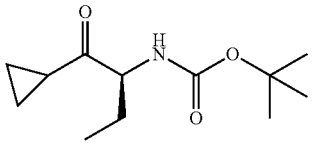 [SMILES: CC[C@H](NC(=O)OC(C)(C)C)C(=O)C1CC1]

A solution of tert-butyl {(1S)-1-[methoxy(methyl)carbamoyl]propyl}carbamate (14.3 g) in tetrahydrofuran (130 mL) was ice-cooled under a nitrogen atmosphere, and 1.0 mol/L-cyclopropylmagnesium bromide/tetrahydrofuran solution (300 mL) was added. The mixture was stirred at the same temperature for 4.5 hr, saturated aqueous ammonium chloride solution (300 mL) was added to the reaction solution, and the mixture was extracted with ethyl acetate. The obtained organic layer was washed with saturated aqueous ammonium chloride solution and saturated brine, dried over anhydrous magnesium sulfate, and concentrated under reduced pressure. The residue was purified by silica gel column chromatography (eluent: ethyl acetate/hexane=0→16%) to give the title compound as a colorless oil (yield: 10.7 g, 94%).

$^1$H-NMR (CDCl$_3$) δ: 0.90 (3H, dd, J=7.6, 7.4 Hz), 0.88-1.16 (4H, m), 1.44 (9H, s), 1.67-1.81 (1H, m), 1.92-2.11 (2H, m), 4.44-4.59 (1H, m), 5.32 (1H, brs).

Reference Example 96

(4R,5S)-4-cyclopropyl-5-ethyl-4-hydroxypyrrolidin-2-one

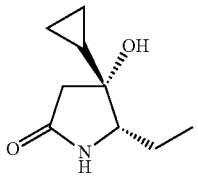

A solution of diisopropylamine (7.28 g) in tetrahydrofuran (110 mL) was ice-cooled under a nitrogen atmosphere, and 1.6 mol/L n-butyllithium-hexane solution (44.1 mL) was added. The mixture was stirred at the same temperature for 20 min, and the reaction solution was cooled with dry ice/acetone. Ethyl acetate (6.96 mL) was added to the reaction solution, the mixture was stirred at the same temperature for 1 hr, and a solution of tert-butyl [(1S)-1-s (cyclopropylcarbonyl)propyl]carbamate (10.7 g) in tetrahydrofuran (60 mL) was added. The mixture was stirred at the same temperature for 5 hr, saturated aqueous ammonium chloride solution (300 mL) was added, and the mixture was extracted with ethyl acetate. The obtained organic layer was washed with saturated aqueous ammonium chloride solution and saturated brine, dried over anhydrous magnesium sulfate, and concentrated under reduced pressure. The residue was purified by silica gel column chromatography (eluent: ethyl acetate/hexane=5→25%), the obtained oil was dissolved in 4 mol/L hydrogen chloride-ethyl acetate solution (100 mL), and the mixture was stirred at room temperature for 2 hr. The reaction solution was concentrated under reduced pressure, the residue was dissolved in tetrahydrofuran (300 mL), and diisopropylethylamine (22.7 mL) was added. The reaction solution was refluxed under heating for 4 hr, and concentrated under reduced pressure. The residue was purified by silica gel column chromatography (eluent: methanol/ethyl acetate=3→10%), and the obtained solid was recrystallized from ethyl acetate/diethyl ether/hexane to give the title compound as colorless crystals (yield: 2.80 g, 39%).

$^1$H-NMR (CDCl$_3$) δ: 0.29-0.55 (4H, m), 0.95-1.08 (1H, m), 1.04 (3H, dd, J=7.6, 7.4 Hz), 1.45-1.63 (1H, m), 1.65-1.82 (1H, m), 2.23 (1H, d, J=17.0 Hz), 2.37 (1H, d, J=17.0 Hz), 2.44 (1H, s), 3.45 (1H, dd, J=9.4, 4.0 Hz), 6.69 (1H, brs).

mp: 87-102° C.

Reference Example 97

(2S)-2-[(3-chlorophenyl)amino]propan-1-ol

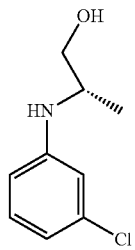

A solution of (2S)-2-aminopropan-1-ol (11.7 g), 1-chloro-3-iodobenzene (36.1 g), tripotassium phosphate (66.4 g), copper iodide (1.42 g), and ethylene glycol (16.7 mL) in propane-2-ol (155 mL) was stirred at 80° C. for 24 hr under an argon atmosphere. Water (500 mL) was added to the reaction solution, and the mixture was extracted with diethyl ether. The obtained organic layer was washed with saturated brine, dried over anhydrous magnesium sulfate, and concentrated under reduced pressure. The residue was purified by silica gel column chromatography (eluent: ethyl acetate/hexane=0→30%) to give the title compound as a colorless oil (yield: 26.9 g, 97%).

$^1$H-NMR (CDCl$_3$) δ: 1.21 (3H, d, J=6.0 Hz), 1.78 (1H, brs), 3.47-3.68 (3H, m), 3.72 (1H, brd, J=10.0 Hz), 6.51 (1H, ddd, J=8.1, 2.3, 0.8 Hz), 6.63 (1H, dd, J=2.3, 2.1 Hz), 6.68 (1H, ddd, J=7.9, 2.1, 0.8 Hz), 7.07 (1H, dd, J=8.1, 7.9 Hz).

Reference Example 98

N-[(1S)-2-(tert-butyldimethylsilyloxy)-1-methylethyl]-3-chloroaniline

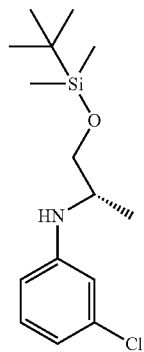 [SMILES: C[C@@H](CO[Si](C)(C)C(C)(C)C)Nc1cccc(Cl)c1]

To a solution of (2S)-2-[(3-chlorophenyl)amino]propane-1-ol (7.00 g) in N,N-dimethylformamide (19 mL) were added imidazole (2.82 g) and tert-butyl(chloro)dimethylsilane (6.38 g), and the mixture was stirred at 50° C. for 14 hr. Water (200 mL) was added to the reaction solution, and the mixture was extracted with diethyl ether. The obtained organic layer was dried over anhydrous magnesium sulfate, and concentrated under reduced pressure. The residue was purified by silica gel column chromatography (eluent: ethyl acetate/hexane=0→40%) to give the title compound as a colorless oil (yield: 7.40 g, 65%).

$^1$H-NMR (CDCl$_3$) δ: 0.04 (3H, s), 0.05 (3H, s), 0.90 (9H, s), 1.19 (3H, d, J=6.2 Hz), 3.46-3.57 (1H, m), 3.61 (2H, d, J=4.2 Hz), 3.90 (1H, d, J=7.4 Hz), 6.46 (1H, d, J=8.1 Hz), 6.58 (1H, s), 6.63 (1H, d, J=7.9 Hz), 7.05 (1H, dd, J=8.1, 7.9 Hz).

Reference Example 99 tert-butyl (3-chlorophenyl)[(1S)-2-hydroxy-1-methylethyl]carbamate

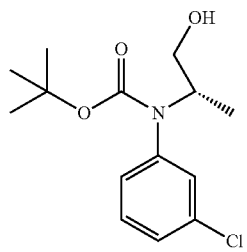 [SMILES: C[C@@H](CO)N(C(=O)OC(C)(C)C)c1cccc(Cl)c1]

A solution of N-[(1S)-2-(tert-butyldimethylsilyloxy)-1-methylethyl]-3-chloroaniline (2.66 g) in tetrahydrofuran (20 mL) was cooled using dry ice/acetone under a nitrogen atmosphere, and 1.6 mol/L n-butyllithium-hexane solution (6.65 mL) was added. The mixture was stirred at the same temperature for 30 min, a solution of di-tert-butyl-dicarbonate (2.52 g) in tetrahydrofuran (5 mL) was added. The reaction solution was warmed to room temperature and stirred for 4 hr, water (50 mL) was added, and the mixture was extracted with ethyl acetate. The obtained organic layer was dried over anhydrous magnesium sulfate, and concentrated under reduced pressure. The residue was purified by silica gel column chromatography (eluent: ethyl acetate/hexane=0→5%), the obtained oil was dissolved in tetrahydrofuran (25 mL). 1.0 mol/L Tetrabutylammonium fluoride/tetrahydrofuran solution (11.5 mL) was added to the reaction solution, and the mixture was stirred at room temperature for 4 hr. Water (50 mL) was added to the reaction solution, and the mixture was extracted with ethyl acetate. The obtained organic layer was washed with saturated brine, dried over anhydrous magnesium sulfate, and concentrated under reduced pressure. The residue was purified by silica gel column chromatography (eluent: ethyl acetate/hexane=0→40%) to give the title compound as a colorless oil (yield: 1.61 g, 64%).

$^1$H-NMR (CDCl$_3$) δ: 1.08 (3H, d, J=7.2 Hz), 1.37 (9H, s), 2.42 (1H, brs), 3.46-3.59 (1H, m), 3.62-3.74 (1H, m), 4.29-4.45 (1H, m), 7.04-7.08 (1H, m), 7.16-7.19 (1H, m), 7.26-7.30 (2H, m).

Reference Example 100 tert-butyl (3-chlorophenyl)[(1S)-1-methyl-2-oxoethyl]carbamate

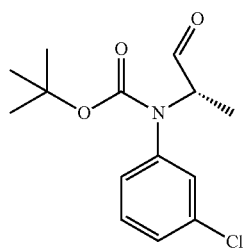 [SMILES: C[C@@H](C=O)N(C(=O)OC(C)(C)C)c1cccc(Cl)c1]

A solution of oxalyl chloride (318 mg) in methylene chloride (6 mL) was cooled using dry ice/acetone under a nitrogen atmosphere, and a solution of DMSO (258 mg) in methylene chloride (6 mL) was added. The mixture was stirred at the same temperature for 10 min, a solution of tert-butyl (3-chlorophenyl)[(1S)-2-hydroxy-1-methylethyl]carbamate (500 mg) in methylene chloride (8 mL) was added, and the mixture was stirred at the same temperature for 10 min. Triethylamine (0.925 mL) was added, and the mixture was stirred at the same temperature for 30 min. Water (30 mL) was added, and the mixture was extracted with ethyl acetate. The obtained organic layer was washed with saturated brine, dried over anhydrous magnesium sulfate, and concentration under reduced pressure to give the title compound as a colorless oil (yield: 480 mg, 96%).

$^1$H-NMR (CDCl$_3$) δ: 1.38-1.44 (3H, m), 1.42 (9H, s), 4.09-4.20 (1H, m), 7.09-7.16 (1H, m), 7.22-7.34 (3H, m), 9.75 (1H, s).

Reference Example 101

(4S,5S)-1-(3-chlorophenyl)-3,3-difluoro-4-hydroxy-5-methylpyrrolidin-2-one

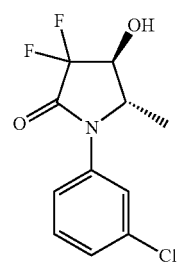

tert-Butyl (3-chlorophenyl)[(1S)-1-methyl-2-oxoethyl]carbamate (19.5 g) and ethyl bromodifluoroacetate (41.3 g) were dissolved in tetrahydrofuran (110 mL), and to a suspension of a zinc powder (13.6 g) in tetrahydrofuran (25 mL) was added dropwise the solution at room temperature. After heating under reflux for 1 hr, the mixture was cooled to room temperature, 1 mol/L aqueous potassium hydrogen sulfate solution (300 mL) was added, and the mixture was extracted with ethyl acetate. The extracted organic layer was washed with saturated brine, dried over anhydrous magnesium sulfate, and concentrated under reduced pressure. The residue was purified by silica gel column chromatography (eluent: ethyl acetate/hexane=0→10%), the obtained oil was dissolved in 4 mol/L hydrogen chloride/ethyl acetate solution (100 mL), and the mixture was stirred at room temperature for 2 hr. The reaction solution was concentrated under reduced pressure, tetrahydrofuran (275 mL) and diisopropylethylamine (21.3 mL, 119 mmol) were added, and the mixture was heated under reflux for 12 hr. The reaction solution was cooled to room temperature, water (200 mL) was added, and the mixture was extracted with ethyl acetate. The obtained organic layer was washed with saturated brine, dried over anhydrous magnesium sulfate, and concentrated under reduced pressure. The residue was purified by silica gel column chromatography (eluent: ethyl acetate/hexane=10→40%) to give the title compound as a yellow oil (yield: 3.76 g, 21%).

$^1$H-NMR (CDCl$_3$) δ: 1.37 (3H, dd, J=6.4, 1.3 Hz), 2.47 (1H, brs), 4.02-4.19 (2H, m), 7.26-7.31 (1H, m), 7.33-7.43 (2H, m), 7.47-7.53 (1H, m).

Reference Example 102 tert-butyl [(1S)-1-formylpropyl]carbamate

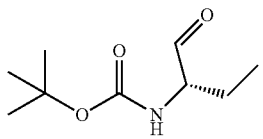

A solution of tert-butyl[(1S)-1-(hydroxymethyl)propyl]carbamate (30.0 g) in dimethyl sulfoxide (300 mL) was ice-cooled under a nitrogen atmosphere, and triethylamine (64.4 mL) and a solution of sulfur trioxide pyridine complex (80.7 g) in dimethyl sulfoxide (300 mL) were successively added. The mixture was stirred at the same temperature for 30 min and then at room temperature for 3 hr, 1 mol/L aqueous citric acid solution (500 mL) was added to the reaction solution, and the mixture was extracted with diethyl ether. The obtained organic layer was washed with water and saturated brine, dried over anhydrous magnesium sulfate, and concentrated under reduced pressure. The residue was purified by silica gel column chromatography (eluent: ethyl acetate/hexane=0→30%) to give the title compound as a white powder (yield: 24.3 g, 85%).

$^1$H-NMR (CDCl$_3$) δ: 0.97 (3H, dd, J=7.6, 7.4 Hz), 1.45 (9H, s), 1.54-1.77 (1H, m), 1.85-2.02 (1H, m), 4.14-4.29 (1H, m), 5.11 (1H, brs), 9.59 (1H, s).

mp: 39-43° C.

Reference Example 103

(4R,5S)-5-ethyl-3,3-difluoro-4-hydroxypyrrolidin-2-one

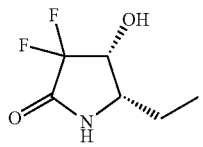

tert-Butyl [(1S)-1-formylpropyl]carbamate (24.00 g) and ethyl bromodifluoroacetate (77.0 g) were dissolved in tetrahydrofuran (220 mL), and to a suspension of a zinc powder (25.4 g) in tetrahydrofuran (50 mL) was added dropwise the solution at room temperature. After heating under reflux for 1 hr, the mixture was cooled to room temperature, 1 mol/L aqueous potassium hydrogen sulfate solution (400 mL) was added, and the mixture was extracted with ethyl acetate. The extracted organic layer was washed with water and saturated brine, dried over anhydrous magnesium sulfate, and concentrated under reduced pressure. The residue was purified by silica gel column chromatography (eluent: ethyl acetate/hexane=10→40%), the obtained oil was dissolved in 4 mol/L hydrogen chloride/ethyl acetate solution (150 mL), and the mixture was stirred at room temperature for 2 hr. The reaction solution was concentrated under reduced pressure, and the residue was dissolved in tetrahydrofuran (600 mL). Diisopropylethylamine (32.8 mL) was added, and the mixture was heated under reflux for 4 hr. The reaction solution was concentrated under reduced pressure, the residue was filtered through silica gel, and the filtrate was concentrated under reduced pressure. The obtained residue was recrystallized from ethyl acetate/hexane to give the title compound as a white powder (yield: 7.20 g, 54%).

$^1$H-NMR (CD$_3$SOCD$_3$) δ: 0.89 (3H, dd, J=7.5, 7.5 Hz), 1.18-1.38 (1H, m), 1.51-1.75 (1H, m), 3.47 (1H, dd, J=13.0, 6.6 Hz), 4.14-4.39 (1H, m), 6.12 (1H, brd, J=5.7 Hz), 8.99 (1H, brs).

mp: 118-121° C.

Reference Example 104

Benzyl [(1S)-1-formylpropyl]carbamate

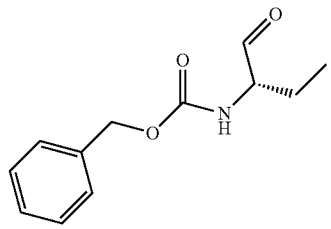 [SMILES: CC[C@@H](C=O)NC(=O)OCc1ccccc1]

A solution of benzyl [(1S)-1-(hydroxymethyl)propyl]carbamate (30.0 g) in dimethyl sulfoxide (260 mL) was ice-cooled under a nitrogen atmosphere, and triethylamine (56.9 mL) and a solution of sulfur trioxide pyridine complex (71.3 g) in dimethyl sulfoxide (260 mL) was successively added. The mixture was stirred at the same temperature for 1 hr, and at room temperature for 4 hr. A 1 mol/L aqueous citric acid solution (450 mL) was added to the reaction solution, and the mixture was extracted with diethyl ether. The obtained organic layer was washed with saturated brine, dried over anhydrous magnesium sulfate, and concentrated under reduced pressure. The residue was purified by silica gel column chromatography (eluent: ethyl acetate/hexane=0→30%) to give the title compound as a colorless oil (yield: 16.3 g, 55%).

$^1$H-NMR (CDCl$_3$) δ: 0.96 (3H, dd, J=7.5, 7.5 Hz), 1.63-1.81 (1H, m), 1.90-2.08 (1H, m), 4.24-4.39 (1H, m), 5.12 (2H, s), 5.37 (1H, brs), 7.31-7.42 (5H, m), 9.59 (1H, s).

Reference Example 105

N-(4-bromo-3-chloro-2-fluorophenyl)acetamide

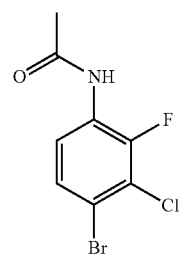

To a solution of 4-bromo-3-chloro-2-fluoroaniline (15.0 g) in ethyl acetate (200 mL) was added dropwise acetic anhydride (7.57 mL) at 0° C. Then, pyridine (10.8 mL) was added dropwise, and the mixture was stirred at room temperature overnight. The mixture was diluted with ethyl acetate, washed with water and saturated brine, and dried over magnesium sulfate. The solvent was evaporated under reduced pressure. The obtained solid was washed with hexane to give the title compound as a colorless solid (yield: 17.1 g, 96%).

$^1$H-NMR (DMSO-d$_6$) δ: 2.10 (3H, s), 7.58 (1H, dd, J=9.1, 1.9 Hz), 7.83-7.90 (1H, m), 9.98 (1H, s).

Reference Example 106

4-amino-2-chloro-3-fluorobenzonitrile

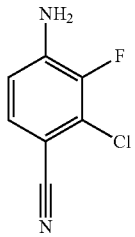

A mixture of N-(4-bromo-3-chloro-2-fluorophenyl)acetamide (17.0 g) and copper(I) cyanide (5.88 g) in N,N-dimethylformamide was stirred at 150° C. overnight. After warming to room temperature, water was added, and the mixture was extracted with methyl acetate. The organic layer was washed with saturated brine, and dried over magnesium sulfate, and the solvent was evaporated under reduced pressure to give N-(3-chloro-4-cyano-2-fluorophenyl)acetamide. Ethanol (250 mL)-concentrated hydrogen chloride (26.6 mL) was added to N-(3-chloro-4-cyano-2-fluorophenyl)acetamide, and the mixture was refluxed overnight. The mixture was ice-cooled, and neutralized with saturated aqueous sodium hydrogen carbonate solution, and the mixture was extracted with ethyl acetate. The organic layer was washed with saturated brine, and dried over magnesium sulfate, and the solvent was evaporated under reduced pressure. The obtained residue was purified by column, and the obtained solid was washed with hexane to give the title compound as a pale-yellow solid (yield: 7.0 g, 64%).

$^1$H-NMR (CDCl$_3$) δ: 4.35 (2H, br.s.), 6.63-6.71 (1H, m), 7.25 (1H, dd, J=8.5, 1.7 Hz).

Reference Example 107

2-chloro-3-fluoro-4-iodobenzonitrile

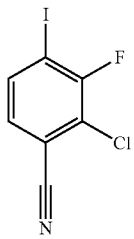

To a suspension of copper iodide (I) (9.24 g) in acetonitrile (100 mL) was added tert-butyl nitrite (90%, 6.95 g) at room temperature. Then, a solution of 4-amino-2-chloro-3-fluorobenzonitrile (6.9 g) in acetonitrile (100 mL) was added dropwise at 65° C. over 1 hr. The mixture was stirred for 2 hr, and allowed to room temperature, aqueous sodium thiosulfate solution was added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane→hexane/ethyl acetate=4:1). The obtained solid was washed with hexane to give the title compound as yellow crystals (yield: 7.1 g, 62%).

$^1$H-NMR (CDCl$_3$) δ: 7.22 (1H, dd, J=8.2, 1.4 Hz), 7.80 (1H, dd, J=8.2, 5.6 Hz).

Reference Example 108

N-(3-chloro-4-cyanophenyl)phenylalanine

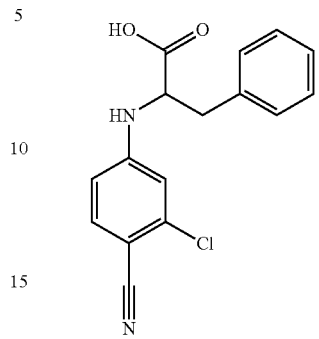

To a solution of 2-chloro-4-fluorobenzonitrile (5.0 g) in dimethyl sulfoxide (100 mL) were added phenylalanine (6.37 g) and cesium carbonate (13.6 g), and the mixture was stirred at 90° C. overnight. After allowing to room temperature, ethyl acetate was added, and the mixture was extracted 3 times with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 9.67 g, 100%).

$^1$H-NMR (CDCl$_3$) δ: 3.09-3.19 (1H, m), 3.24-3.32 (1H, m), 4.37-4.47 (1H, m), 4.67-4.76 (1H, m), 6.44 (1H, dd, J=8.6, 2.4 Hz), 6.59 (1H, d, J=2.3 Hz), 7.12-7.19 (2H, m), 7.27-7.35 (3H, m), 7.40 (1H, d, J=8.7 Hz).

Reference Example 109

4-(2-benzyl-3-hydroxy-5-oxo-2,5-dihydro-1H-pyrrol-1-yl)-2-chlorobenzonitrile

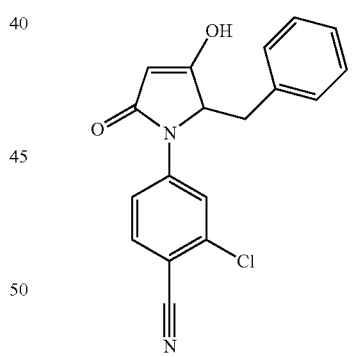

To a solution of N-(3-chloro-4-cyanophenyl)phenylalanine (2.0 g), Meldrum's acid (1.05 g) and 4-(N,N-dimethylamino)pyridine (1.22 g) in tetrahydrofuran (30 mL) was added N,N'-carbonyldiimidazole (1.29 g) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (30 mL), and the mixture was refluxed for 45 min. After allowing to room temperature, the mixture was extracted 3 times with saturated aqueous sodium hydrogen carbonate solution. The aqueous layers were combined, and acidified with citric acid, and the mixture was extracted with ethyl acetate. The organic layer was washed with saturated brine, and dried over magnesium sulfate. The solvent was evaporated under reduced pressure, and the obtained residue was recrystallized from tetrahydrofuran-hexane to give the title compound as pale-yellow crystals (yield: 1.41 g, 65%).

$^1$H-NMR (DMSO-$d_6$) δ: 3.01-3.21 (2H, m), 4.80 (1H, s), 5.25 (1H, t, J=3.9 Hz), 6.73-6.81 (2H, m), 7.13-7.18 (3H, m), 7.70 (1H, dd, J=8.8, 2.2 Hz), 7.96 (1H, d, J=8.7 Hz), 8.00 (1H, d, J=1.9 Hz), 12.50 (1H, br.s.).

mp: 188-189° C.

Reference Example 110

N-(3-chloro-4-cyanophenyl)norvaline

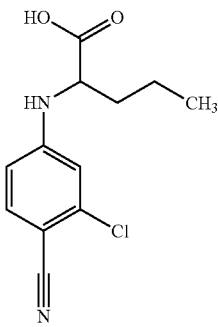 [SMILES: CCCC(Nc1ccc(C#N)c(Cl)c1)C(=O)O]

To a solution of 2-chloro-4-fluorobenzonitrile (5.0 g) in dimethyl sulfoxide (80 mL) were added L-norvaline (4.52 g) and cesium carbonate (13.6 g), and the mixture was stirred at 90° C. overnight. After allowing to room temperature, ethyl acetate was added, and the mixture was extracted twice with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 8.12 g, 100%).

$^1$H-NMR (CDCl$_3$) δ: 0.97 (3H, t, J=7.3 Hz), 1.40-1.54 (2H, m), 1.71-2.00 (2H, m), 4.08-4.16 (1H, m), 4.71 (1H, br.s.), 6.50 (1H, dd, J=8.7, 2.5 Hz), 6.64 (1H, d, J=2.5 Hz), 7.42 (1H, d, J=8.5 Hz).

Reference Example 111

2-chloro-4-(3-hydroxy-5-oxo-2-propyl-2,5-dihydro-1H-pyrrol-1-yl)benzonitrile

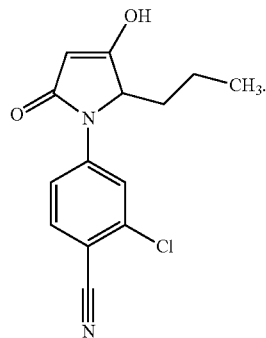 [SMILES: CCCC1C(O)=CC(=O)N1c1ccc(C#N)c(Cl)c1]

To a solution of N-(3-chloro-4-cyanophenyl)norvaline (4.0 g), Meldrum's acid (2.40 g) and 4-(N,N-dimethyl)aminopyridine (2.90 g) in tetrahydrofuran (60 mL) was added N,N'-carbonyldiimidazole (3.08 g) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (60 mL), and the mixture was refluxed for 45 min. After allowing to room temperature, the mixture was extracted twice with saturated aqueous sodium hydrogen carbonate solution. The aqueous layers were combined, and acidified with citric acid, and the mixture was extracted with ethyl acetate. The organic layer was washed with saturated brine, and dried over magnesium sulfate. The solvent was evaporated under reduced pressure, and the obtained residue was washed with ethyl acetate to give the title compound as colorless crystals (yield: 1.89 g, 43%).

$^1$H-NMR (DMSO-$d_6$) δ: 0.69-0.80 (3H, m), 0.90-1.14 (2H, m), 1.69-1.81 (2H, m), 5.00 (1H, t, J=4.0 Hz), 5.03 (1H, s), 7.66 (1H, dd, J=8.7, 2.1 Hz), 7.92 (1H, d, J=8.9 Hz), 8.05 (1H, d, J=1.9 Hz), 12.40 (1H, br.s.).

mp: 156-158° C.

Reference Example 112

N-(3-chloro-4-cyanophenyl)-4-fluorophenylalanine

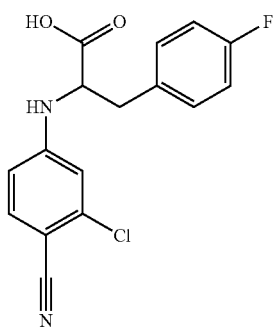 [SMILES: N#Cc1ccc(NC(Cc2ccc(F)cc2)C(=O)O)cc1Cl]

To a solution of 2-chloro-4-fluorobenzonitrile (1.8 g) in dimethyl sulfoxide (30 mL) were added 4-fluorophenylalanine (2.54 g) and cesium carbonate (4.90 g), and the mixture was stirred at 90° C. overnight. After allowing to room temperature, ethyl acetate was added, and the mixture was extracted twice with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 3.69 g, 100%).

$^1$H-NMR (CDCl$_3$) δ: 3.07-3.30 (2H, m), 4.40 (1H, q, J=5.9 Hz), 4.72 (1H, d, J=6.6 Hz), 6.46 (1H, dd, J=8.7, 2.3 Hz), 6.60 (1H, d, J=2.3 Hz), 6.94-7.05 (2H, m), 7.07-7.16 (2H, m), 7.41 (1H, d, J=8.7 Hz).

Reference Example 113

2-chloro-4-[2-(4-fluorobenzyl)-3-hydroxy-5-oxo-2,5-dihydro-1H-pyrrol-1-yl]benzonitrile

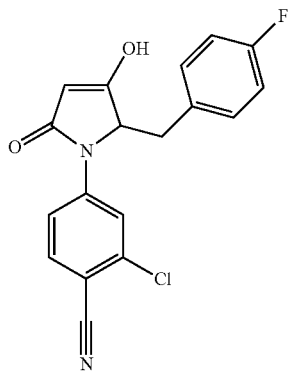 [SMILES: N#Cc1ccc(N2C(=O)C=C(O)C2Cc2ccc(F)cc2)cc1Cl]

To a solution of N-(3-chloro-4-cyanophenyl)-4-fluorophenylalanine (3.67 g), Meldrum's acid (1.74 g) and 4-(N,N-dimethylamino)pyridine (2.11 g) in tetrahydrofuran (50 mL) was added N,N'-carbonyldiimidazole (2.24 g, 13.8 mmol) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (50 mL), and the mixture was refluxed for 45 min. After allowing to room temperature, the organic layer was washed with water and saturated brine, and dried over magnesium sulfate. The solvent was evaporated under reduced pressure, and the obtained residue was washed with ethyl acetate-isopropyl ether to give the title compound as colorless crystals (yield: 2.54 g, 64%).

$^1$H-NMR (DMSO-$d_6$) δ: 2.99-3.20 (2H, m), 4.82 (1H, s), 5.24 (1H, t, J=3.8 Hz), 6.74-6.86 (2H, m), 6.94-7.06 (2H, m), 7.70 (1H, dd, J=8.8, 2.2 Hz), 7.95 (1H, d, J=8.7 Hz), 8.00 (1H, d, J=2.1 Hz), 12.52 (1H, br.s.).

mp: 192-194° C.

Reference Example 114

N-(3-chloro-4-cyanophenyl)valine

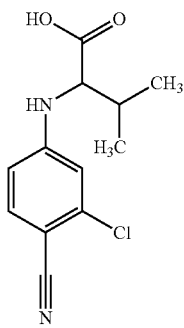

To a solution of 2-chloro-4-fluorobenzonitrile (3.50 g) in dimethyl sulfoxide (60 mL) were added L-valine (3.16 g) and cesium carbonate (9.53 g), and the mixture was stirred at 90° C. overnight. After allowing to room temperature, ethyl acetate was added, and the mixture was extracted twice with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 5.69 g, 100%).

$^1$H-NMR (CDCl$_3$) δ: 1.07 (6H, t, J=6.7 Hz), 2.16-2.31 (1H, m), 3.91-3.99 (1H, m), 4.71 (1H, d, J=8.9 Hz), 6.51 (1H, dd, J=8.7, 2.3 Hz), 6.67 (1H, d, J=2.5 Hz), 7.42 (1H, d, J=8.7 Hz).

Reference Example 115

2-chloro-4-[3-hydroxy-2-(1-methylethyl)-5-oxo-2,5-dihydro-1H-pyrrol-1-yl]benzonitrile

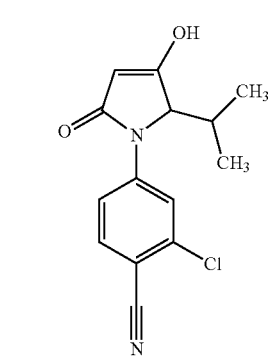 [SMILES: CC(C)C1C(O)=CC(=O)N1c1ccc(C#N)c(Cl)c1]

To a solution of N-(3-chloro-4-cyanophenyl)valine (5.66 g), Meldrum's acid (3.39 g) and 4-(N,N-dimethylamino)pyridine (4.11 g) in tetrahydrofuran (70 mL) was added N,N'-carbonyldiimidazole (4.36 g) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (70 mL), and the mixture was refluxed for 45 min. After allowing to room temperature, the organic layer was washed with water and saturated brine, and dried over magnesium sulfate. The solvent was evaporated under reduced pressure, and the obtained residue was washed with ethyl acetate-isopropyl ether to give the title compound as colorless crystals (yield: 653 mg, 11%).

$^1$H-NMR (DMSO-$d_6$) δ: 0.65 (3H, d, J=6.8 Hz), 1.12 (3H, d, J=7.0 Hz), 2.01-2.16 (1H, m), 4.90 (1H, d, J=2.6 Hz), 5.03 (1H, s), 7.61 (1H, dd, J=8.7, 1.9 Hz), 7.92 (1H, d, J=8.5 Hz), 8.02 (1H, d, J=2.1 Hz), 12.33 (1H, br.s.).

mp: 217-219° C.

Reference Example 116

N-(3-chloro-4-cyanophenyl)-4-cyanophenylalanine

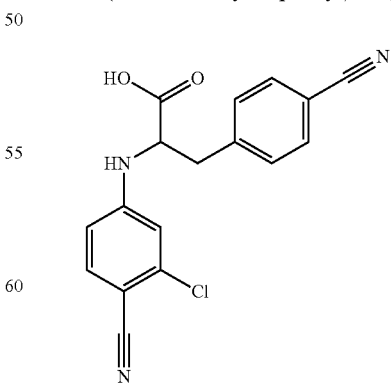

To a solution of 2-chloro-4-fluorobenzonitrile (0.90 g) in dimethyl sulfoxide (20 mL) were added 4-cyanophenylalanine (1.00 g) and cesium carbonate (2.23 g), and the mixture was stirred at 90° C. overnight. After warming to room temperature, ethyl acetate was added, and the mixture was extracted twice with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 1.57 g, 92%).

$^1$H-NMR (CDCl$_3$) δ: 3.17-3.38 (2H, m), 4.41-4.51 (1H, m), 4.78 (1H, d, J=7.7 Hz), 6.49 (1H, dd, J=8.6, 2.4 Hz), 6.63 (1H, d, J=2.5 Hz), 7.24-7.30 (2H, m), 7.44 (1H, d, J=8.5 Hz), 7.56-7.64 (2H, m).

Reference Example 117

2-chloro-4-[2-(4-cyanobenzyl)-3-hydroxy-5-oxo-2,5-dihydro-1H-pyrrol-1-yl]benzonitrile

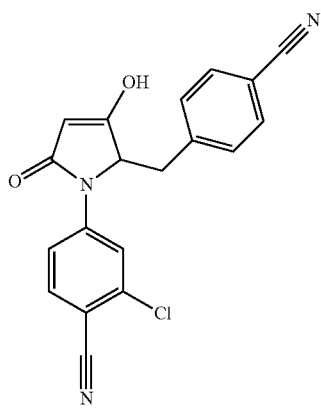 [SMILES: N#Cc1ccc(CC2C(O)=CC(=O)N2c2ccc(C#N)c(Cl)c2)cc1]

To a solution of N-(3-chloro-4-cyanophenyl)-4-cyanophenylalanine (1.57 g), Meldrum's acid (0.76 g) and 4-(N,N-dimethylamino)pyridine (0.88 g) in tetrahydrofuran (70 mL) was added N,N'-carbonyldiimidazole (0.94 g) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (30 mL), and the mixture was refluxed for 45 min. After allowing to room temperature, the organic layer was washed with water and saturated brine, and dried over magnesium sulfate. The solvent was evaporated under reduced pressure, and the obtained residue was washed with ethyl acetate-isopropyl ether to give the title compound as pale-yellow crystals (yield: 578 mg, 34%).

$^1$H-NMR (DMSO-d$_6$) δ: 3.08-3.30 (2H, m), 4.84 (1H, s), 5.33 (1H, t, J=4.0 Hz), 6.98 (2H, d, J=8.1 Hz), 7.63-7.73 (3H, m), 7.94-8.00 (2H, m), 12.60 (1H, br.s.).

mp: 190-192° C.

Reference Example 118

N-(3-chloro-4-cyanophenyl)-3-cyclopropylalanine

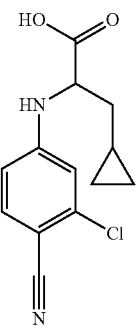 [SMILES: N#Cc1ccc(NC(CC2CC2)C(=O)O)cc1Cl]

To a solution of 2-chloro-4-fluorobenzonitrile (1.33 g) in dimethyl sulfoxide (20 mL) were added 3-cyclopropyl-L-alanine (1.00 g) and cesium carbonate (3.28 g), and the mixture was stirred at 90° C. overnight. After allowing to room temperature, ethyl acetate was added, and the mixture was extracted twice with saturated aqueous sodium hydrogen carbonate solution. The aqueous layers were combined, and acidified with citric acid, and the mixture was extracted twice with ethyl acetate. The organic layers were combined, washed with saturated brine, and dried over magnesium sulfate. The solvent was evaporated under reduced pressure to give the title compound as a brown oil (yield: 2.05 g, 100%).

$^1$H-NMR (CDCl$_3$) δ: 0.10-0.21 (2H, m), 0.47-0.58 (2H, m), 0.72-0.87 (1H, m), 1.71-1.92 (2H, m), 4.14-4.24 (1H, m), 4.95 (1H, d, J=7.9 Hz), 6.51 (1H, dd, J=8.7, 2.5 Hz), 6.66 (1H, d, J=2.3 Hz), 7.41 (1H, d, J=8.5 Hz).

Reference Example 119

2-chloro-4-[2-(cyclopropylmethyl)-3-hydroxy-5-oxo-2,5-dihydro-1H-pyrrol-1-yl]benzonitrile

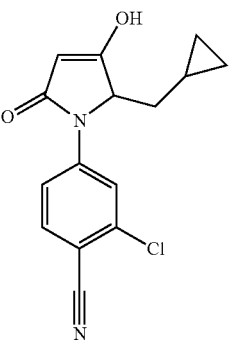 [SMILES: N#Cc1ccc(N2C(=O)C=C(O)C2CC2CC2)cc1Cl]

To a solution of N-(3-chloro-4-cyanophenyl)-3-cyclopropylalanine (2.05 g), Meldrum's acid (1.35 g) and 4-(N,N-dimethylamino)pyridine (1.56 g) in tetrahydrofuran (40 mL) was added N,N'-carbonyldiimidazole (1.66 g) at 0° C., and the mixture was stirred at room temperature overnight. A 5% aqueous potassium hydrogen sulfate solution was added to the reaction mixture, and the mixture was extracted with ethyl acetate. The organic layer was washed with 5% aqueous potassium hydrogen sulfate solution and saturated brine, and dried over magnesium sulfate. The solvent was evaporated under reduced pressure. The residue was dissolved in ethyl acetate (40 mL), and the mixture was refluxed for 45 min. After allowing to room temperature, the organic layer was washed with water and saturated brine, and dried over magnesium sulfate. The solvent was evaporated under reduced pressure, and the obtained residue was washed with ethyl acetate-isopropyl ether to give the title compound as pale-yellow crystals (yield: 844 mg, 34%).

$^1$H-NMR (DMSO-$d_6$) δ: −0.40 to −0.29 (1H, m), −0.10 to 0.02 (1H, m), 0.15-0.45 (3H, m), 1.64-1.81 (2H, m), 5.04 (1H, t, J=3.8 Hz), 5.08 (1H, s), 7.67 (1H, dd, J=8.7, 2.1 Hz), 7.91 (1H, d, J=8.7 Hz), 8.04 (1H, d, J=2.1 Hz), 12.39 (1H, s).

mp: 152-154° C.

Example 1

2-fluoro-4-[(2S,3S)-3-hydroxy-2-methyl-5-oxopyrrolidin-1-yl]-3-methylbenzonitrile

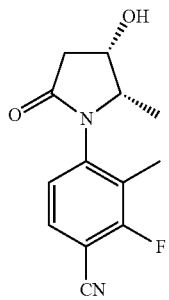 [SMILES: Cc1c(N2C(=O)C[C@H](O)[C@@H]2C)ccc(C#N)c1F]

To a solution of 4-[(2S,3S)-3-(tert-butyldimethylsilyloxy)-2-methyl-5-oxopyrrolidin-1-yl]-2-fluoro-3-methylbenzonitrile (330 mg) in THF (10 mL) was added tetrabutylammonium fluoride-THF solution (1.18 mL, 1 mol/L), and the mixture was stirred at room temperature for 5 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography, and recrystallized from hexane-ethyl acetate to give the title compound as a colorless solid (yield: 139 mg, 62%).

$^1$H-NMR (CDCl$_3$) δ: 1.13 (3H, d, J=6.4 Hz), 1.80 (1H, d, J=4.2 Hz), 2.20 (3H, d, J=2.7 Hz), 2.60 (1H, dd, J=17.4, 2.3 Hz), 2.87 (1H, dd, J=17.4, 5.7 Hz), 4.15-4.26 (1H, m), 4.54-4.61 (1H, m), 6.98 (1H, d, J=7.6 Hz), 7.45-7.55 (1H, m).

mp: 114-115° C.

Example 2 rac-2-chloro-4-[(2R,3R)-3-hydroxy-2,3,4,4-tetramethyl-5-oxopyrrolidin-1-yl]benzonitrile

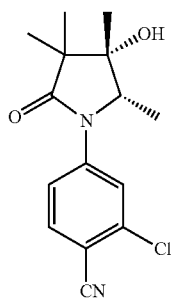 [SMILES: C[C@@H]1N(c2ccc(C#N)c(Cl)c2)C(=O)C(C)(C)[C@]1(C)O]

A solution of 2-chloro-4-(3,3,5-trimethyl-2,4-dioxopyrrolidin-1-yl)benzonitrile (90 mg) in THF (5 mL) was cooled to −78° C., methylmagnesium bromide-ether solution (0.22 mL, 3 mol/L) was added under a nitrogen atmosphere, and the reaction mixture was warmed to room temperature. The reaction mixture was again cooled to −78° C., a 3 mol/L methylmagnesium bromide-ether solution (0.89 mL) was added, and the reaction mixture was warmed to room temperature. The reaction mixture was added to saturated aqueous ammonium chloride solution, and the mixture was extracted with ethyl acetate. The extract was washed with saturated brine, dried over anhydrous magnesium sulfate, and concentrated under reduced pressure. The residue was purified by silica gel column chromatography, and recrystallized from hexane-ethyl acetate to give the title compound as a colorless solid (yield: 29 mg, 30%).

$^1$H-NMR (CDCl$_3$) δ: 1.12 (3H, s), 1.25 (3H, d, J=6.4 Hz), 1.25 (3H, s), 1.32 (3H, s), 1.41 (1H, s), 4.11 (1H, q, J=6.4 Hz), 7.36 (1H, dd, J=8.5, 2.1 Hz), 7.56 (1H, d, J=2.1 Hz), 7.67 (1H, d, J=8.5 Hz).

mp: 161-163° C.

Example 3 rac-4-[(2R,3R)-3-hydroxy-2,3,4,4-tetramethyl-5-oxopyrrolidin-1-yl]-2-methoxybenzonitrile

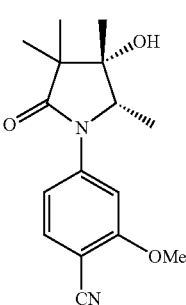 [SMILES: COc1cc(N2C(=O)C(C)(C)[C@](C)(O)[C@@H]2C)ccc1C#N]

Using 2-methoxy-4-(3,3,5-trimethyl-2,4-dioxopyrrolidin-1-yl)benzonitrile (100 mg) and methylmagnesium bromide-THF solution (3.67 mL, 1.0 mol/L), and in the same manner as in Example 2, the title compound was obtained as a colorless, solid (yield: 96 mg, 90%).

$^1$H-NMR (CDCl$_3$) δ: 1.13 (3H, s), 1.23-1.27 (6H, m), 1.32 (3H, s), 1.45 (1H, s), 3.94 (3H, s), 4.08-4.16 (1H, m), 6.75 (1H, dd, J=8.3, 1.9 Hz), 7.26 (1H, d, J=1.9 Hz), 7.54 (1H, d, J=8.3 Hz).

mp: 134-135° C.

Example 4 rac-4-[(2R,3R)-3-hydroxy-2,3,4,4-tetramethyl-5-oxopyrrolidin-1-yl]-2-(trifluoromethyl)benzonitrile

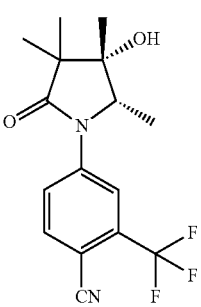 [SMILES: C[C@@H]1N(c2ccc(C#N)c(C(F)(F)F)c2)C(=O)C(C)(C)[C@]1(C)O]

Using 2-(trifluoromethyl)-4-(3,3,5-trimethyl-2,4-dioxopyrrolidin-1-yl)benzonitrile (100 mg) and methylmagnesium bromide-THF solution (3.22 mL, 1.0 mol/L), and in the same manner as in Example 2, the title compound was obtained as a colorless solid (yield: 77 mg, 73%).

¹H-NMR (CDCl₃) δ: 1.13 (3H, s), 1.26 (3H, d, J=6.2 Hz), 1.26 (3H, s), 1.34 (3H, s), 1.47 (1H, s), 4.18 (1H, q, J=6.4 Hz), 7.68 (1H, dd, J=8.5, 2.1 Hz), 7.79 (1H, d, J=2.1 Hz), 7.84 (1H, d, J=8.5 Hz).

mp: 197-199° C.

Example 5 rac-4-[(4R,5R)-4-hydroxy-3,3,5-trimethyl-2-oxopyrrolidin-1-yl]2-(trifluoromethyl)benzonitrile

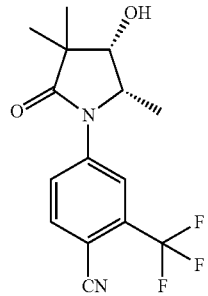 [SMILES: C[C@H]1[C@@H](O)C(C)(C)C(=O)N1c1ccc(C#N)c(C(F)(F)F)c1]

A solution of 2-(trifluoromethyl)-4-(3,3,5-trimethyl-2,4-dioxopyrrolidin-1-yl)benzonitrile (50 mg) in THF (5 mL) was cooled to −78° C., lithium tri(sec-butyl)borohydride-THF solution (0.242 mL, 1 mol/L) was added, and the mixture was stirred at −78° C. for 30 min. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography, and the obtained solid was recrystallized from hexane-ethyl acetate to give the title compound as a colorless solid (yield: 32.2 mg, 64%).

¹H-NMR (CDCl₃) δ: 1.24 (3H, s), 1.31-1.36 (6H, m), 1.80 (1H, d, J=5.1 Hz), 4.12 (1H, t, J=5.3 Hz), 4.42-4.53 (1H, m), 7.75 (1H, dd, J=8.7, 2.3 Hz), 7.85 (1H, d, J=8.7 Hz), 7.93 (1H, d, J=2.3 Hz).

mp: 120.5-121.5° C.

Example 6 rac-4-[(4R,5R)-4-hydroxy-3,3,5-trimethyl-2-oxopyrrolidin-1-yl]-2-methoxybenzonitrile

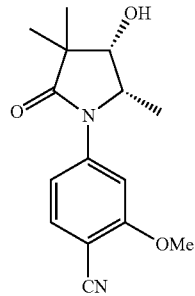 [SMILES: COc1cc(N2C(=O)C(C)(C)[C@H](O)[C@@H]2C)ccc1C#N]

Using 2-methoxy-4-(3,3,5-trimethyl-2,4-dioxopyrrolidin-1-yl)benzonitrile (100 mg) and lithium tri(sec-butyl)borohydride-THF solution (0.551 mL, 1 mol/L), and in the same manner as in Example 5, the title compound was obtained as a colorless solid (yield: 75 mg, 74%).

¹H-NMR (CDCl₃) δ: 1.23 (3H, s), 1.30-1.34 (6H, m), 1.78 (1H, d, J=5.3 Hz), 3.94 (3H, s), 4.10 (1H, t, J=5.4 Hz), 4.37-4.47 (1H, m), 6.80 (1H, dd, J=8.5, 1.9 Hz), 7.46 (1H, d, J=1.9 Hz), 7.55 (1H, d, J=8.5 Hz).

mp: 130-132° C.

Example 7 rac-2,6-difluoro-4-[(4R,5R)-4-hydroxy-3,3,5-trimethyl-2-oxopyrrolidin-1-yl]benzonitrile

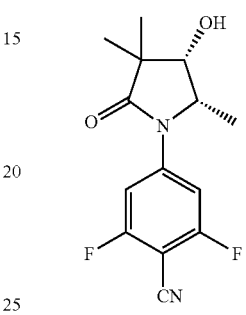

Using 2,6-difluoro-4-(3,3,5-trimethyl-2,4-dioxopyrrolidin-1-yl)benzonitrile (100 mg) and lithium tri(sec-butyl)borohydride-THF solution (0.539 mL, 1 mol/L), and in the same manner as in Example 5, the title compound was obtained as a colorless solid (yield: 67 mg, 67%).

¹H-NMR (CDCl₃) δ: 1.23 (3H, s), 1.30 (3H, s), 1.36 (3H, d, J=6.6 Hz), 1.83 (1H, d, J=5.1 Hz), 4.13 (1H, t, J=5.6 Hz), 4.31-4.41 (1H, m), 7.25-7.32 (2H, m).

mp: 139.5-140.5° C.

Example 8 rac-2-chloro-4-[(4R,5R)-4-hydroxy-3,3,5-trimethyl-2-oxopyrrolidin-1-yl]-3-methylbenzonitrile

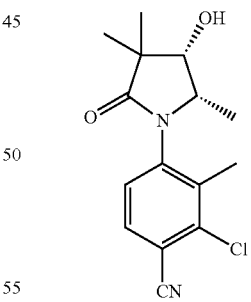

Using 2-chloro-3-methyl-4-(3,3,5-trimethyl-2,4-dioxopyrrolidin-1-yl)benzonitrile (23 mg) and lithium tri(sec-butyl)borohydride-THF solution (0.119 mL, 1 mol/L), and in the same manner as in Example 5, the title compound was obtained as a colorless solid (yield: 15 mg, 66%).

¹H-NMR (CDCl₃) δ: 1.10 (3H, d, J=6.6 Hz), 1.27 (3H, brs), 1.31 (3H, s), 1.75 (1H, d, J=4.3 Hz), 2.29 (3H, s), 4.05 (1H, t, J=4.3 Hz), 4.29 (1H, brs), 7.05 (1H, brs), 7.56 (1H, d, J=8.1 Hz).

mp: 219-221° C.

Example 9 rac-2-chloro-4-[(4R,5R)-5-ethyl-4-hydroxy-3,3-dimethyl-2-oxopyrrolidin-1-yl]benzonitrile

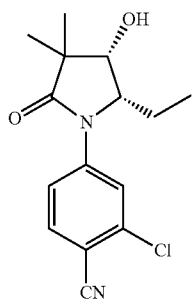 [SMILES: CC[C@H]1[C@@H](O)C(C)(C)C(=O)N1c1ccc(C#N)c(Cl)c1]

Using 2-chloro-4-(5-ethyl-3,3-dimethyl-2,4-dioxopyrrolidin-1-yl)benzonitrile (60 mg) and lithium tri(sec-butyl)borohydride THF solution (0.307 mL, 1 mol/L), and in the same manner as in Example 5, the title compound was obtained as a colorless solid (yield: 50 mg, 84%).

$^1$H-NMR (CDCl$_3$) δ: 1.03 (3H, t, J=7.5 Hz), 1.20 (3H, s), 1.32 (3H, s), 1.60-1.84 (3H, m), 4.04-4.15 (2H, m), 7.34 (1H, dd, J=8.5, 2.1 Hz), 7.56 (1H, d, J=2.1 Hz), 7.67 (1H, d, J=8.5 Hz).

mp: 166-168° C.

Example 10 rac-4-[(4R,5R)-5-ethyl-4-hydroxy-3,3-dimethyl-2-oxopyrrolidin-1-yl]-2-methoxybenzonitrile

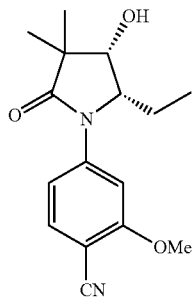 [SMILES: CC[C@H]1[C@@H](O)C(C)(C)C(=O)N1c1ccc(C#N)c(OC)c1]

Using 4-(5-ethyl-3,3-dimethyl-2,4-dioxopyrrolidin-1-yl)-2-methoxybenzonitrile (120 mg) and lithium tri(sec-butyl)borohydride-THF solution (0.629 mL, 1 mol/L), and in the same manner as in Example 5, the title compound was obtained as a colorless solid (yield: 93 mg, 77%).

$^1$H-NMR (CDCl$_3$) δ: 1.01 (3H, t, J=7.5 Hz), 1.21 (3H, s), 1.32 (3H, s), 1.48-1.88 (3H, m), 3.94 (3H, s), 4.11 (2H, dd, J=4.0, 1.9 Hz), 6.74 (1H, dd, J=8.3, 1.9 Hz), 7.26 (1H, d, J=1.9 Hz), 7.55 (1H, d, J=8.3 Hz).

mp: 143.4-145° C.

Example 11 rac-4-[(4R,5R)-5-ethyl-4-hydroxy-3,3-dimethyl-2-oxopyrrolidin-1-yl]-2-(trifluoromethyl)benzonitrile

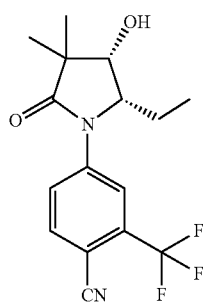 [SMILES: CC[C@H]1[C@@H](O)C(C)(C)C(=O)N1c1ccc(C#N)c(C(F)(F)F)c1]

Using 4-(5-ethyl-3,3-dimethyl-2,4-dioxopyrrolidin-1-yl)-2-(trifluoromethyl)benzonitrile (120 mg) and lithium tri(sec-butyl)borohydride-THF solution (0.555 mL, 1 mol/L), and in the same manner as in Example 5, the title compound was obtained as a colorless solid (yield: 76 mg, 63%).

$^1$H-NMR (CDCl$_3$) δ: 1.04 (3H, t, J=7.5 Hz), 1.22 (3H, s), 1.33 (3H, s), 1.64-1.83 (3H, m), 4.11-4.22 (2H, m), 7.65 (1H, dd, J=8.5, 2.1 Hz), 7.81 (1H, d, J=2.1 Hz), 7.84 (1H, d, J=8.5 Hz).

mp: 141.5-143° C.

Example 12 rac-2-chloro-4-[(2R,3R)-2-ethyl-3-hydroxy-3,4,4-trimethyl-5-oxopyrrolidin-1-yl]benzonitrile

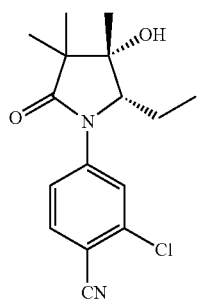 [SMILES: CC[C@@H]1N(c2ccc(C#N)c(Cl)c2)C(=O)C(C)(C)[C@]1(C)O]

Using 2-chloro-4-(5-ethyl-3,3-dimethyl-2,4-dioxopyrrolidin-1-yl)benzonitrile (48 mg) and methylmagnesium bromide-THF solution (1.65 mL, 1.0 mol/L), and in the same manner as in Example 2, the title compound was obtained as a colorless solid (yield: 27 mg, 53%).

$^1$H-NMR (CDCl$_3$) δ: 1.01 (3H, t, J=7.6 Hz), 1.11 (3H, s), 1.23 (3H, s), 1.39 (3H, s), 1.50 (1H, s), 1.63-1.77 (1H, m), 1.78-1.93 (1H, m), 3.89 (1H, dd, J=8.7, 3.0 Hz), 7.34 (1H, dd, J=8.5, 2.1 Hz), 7.55 (1H, d, J=2.1 Hz), 7.67 (1H, d, J=8.5 Hz).

mp: 197.1-198.5° C.

Example 13 rac-2-chloro-4-[(4R,5R)-5-ethyl-4-hydroxy-3,3-dimethyl-2-oxopyrrolidin-1-yl]-3-methylbenzonitrile

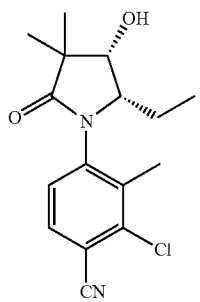 [SMILES: CC[C@H]1[C@@H](O)C(C)(C)C(=O)N1c1ccc(C#N)c(Cl)c1C]

Using 2-chloro-4-(5-ethyl-3,3-dimethyl-2,4-dioxopyrrolidin-1-yl)-3-methylbenzonitrile (310 mg) and lithium tri(sec-butyl)borohydride-THF solution (1.53 mL, 1 mol/L), and in the same manner as in Example 5, the title compound was obtained as a colorless solid (yield: 211 mg, 68%).

$^1$H-NMR (CDCl$_3$) δ: 0.92 (3H, t, J=7.5 Hz), 1.13-1.51 (8H, m), 1.72 (1H, d, J=4.2 Hz), 2.23-2.35 (3H, m), 3.88-4.13 (2H, m), 6.99-7.19 (1H, m), 7.55 (1H, d, J=8.1 Hz).

mp: 180.5-181.5° C.

Example 14 rac-2-chloro-4-[(2R,3R)-3-hydroxy-2,3,4,4-tetramethyl-5-oxopyrrolidin-1-yl]-3-methylbenzonitrile

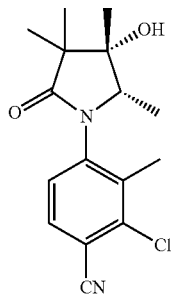 [SMILES: Cc1c(N2C(=O)C(C)(C)[C@](C)(O)[C@@H]2C)ccc(C#N)c1Cl]

Using 2-chloro-3-methyl-4-(3,3,5-trimethyl-2,4-dioxopyrrolidin-1-yl)benzonitrile (40 mg) and methylmagnesium bromide-THF solution (1.38 mL, 1.0 mol/L), and in the same manner as in Example 2, the title compound was obtained as a colorless solid (yield: 24 mg, 57%).

$^1$H-NMR (CDCl$_3$) δ: 0.95-1.12 (3H, m), 1.15-1.25 (6H, m), 1.30 (3H, s), 1.40-1.47 (1H, m), 2.24-2.34 (3H, m), 3.93-4.11 (1H, m), 6.98-7.23 (1H, m), 7.51-7.59 (1H, m).

mp: 174.5-175.5° C.

Example 15 rac-2-chloro-4-[(4R,5S)-4-hydroxy-3,3,5-trimethyl-2-oxopyrrolidin-1-yl]benzonitrile

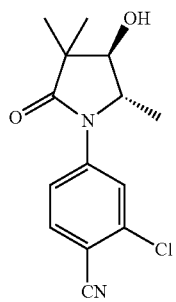 [SMILES: C[C@H]1[C@H](O)C(C)(C)C(=O)N1c1ccc(C#N)c(Cl)c1]

To a solution of rac-2-chloro-4-[(4R,5S)-4-(tert-butyldimethylsilyloxy)-3,3,5-trimethyl-2-oxopyrrolidin-1-yl]benzonitrile (121 mg) in THF (5.5 mL) was added tetrabutylammonium fluoride-THF solution (0.5 mL, 1 mol/L), and the mixture was stirred at room temperature for 7 hr. Water was added to the reaction mixture, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/2) to give the title compound as a colorless solid (yield: 47.2 mg, 55%).

$^1$H-NMR (CDCl$_3$) δ: 1.17 (3H, s), 1.31 (3H, s), 1.37 (3H, d, J=6.2 Hz), 1.91 (1H, d, J=5.7 Hz), 3.79 (1H, t, J=5.9 Hz), 3.90-4.03 (1H, m), 7.40 (1H, dd, J=8.4, 2.2 Hz), 7.61-7.73 (2H, m). mp: 163-164° C.

Example 16 rac-2-chloro-4-[(4R,5R)-4-hydroxy-3,3,5-trimethyl-2-oxopyrrolidin-1-yl]benzonitrile

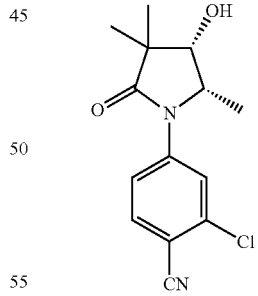

Using rac-2-chloro-4-[(4R,5R)-4-(tert-butyldimethylsilyloxy)-3,3,5-trimethyl-2-oxopyrrolidin-1-yl]benzonitrile (400 mg) and tetrabutylammonium fluoride-THF solution (3 mL, 1 mol/L), and in the same manner as in Example 15, the title compound was obtained as a colorless solid (yield: 204 mg, 72%).

$^1$H-NMR (CDCl$_3$) δ: 1.23 (3H, s), 1.31 (3H, s), 1.32 (3H, d, J=6.6 Hz), 1.81 (1H, brs), 4.06-4.16 (1H, m), 4.33-4.48 (1H, m), 7.39-7.50 (1H, m), 7.61-7.73 (2H, m).

mp: 143-144° C.

Example 17

2-chloro-4-[(4S,5S)-4-hydroxy-5-methyl-2-oxopyrrolidin-1-yl]benzonitrile

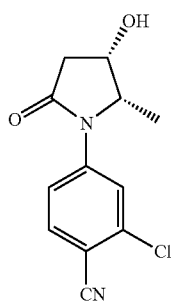 [SMILES: C[C@H]1[C@@H](O)CC(=O)N1c1ccc(C#N)c(Cl)c1]

Using 2-chloro-4-[(4S,5S)-4-(tert-butyldimethylsilyloxy)-5-methyl-2-oxopyrrolidin-1-yl]benzonitrile (1.2 g) and tetrabutylammonium fluoride-THF solution (4 mL, 1 mol/L), and in the same manner as in Example 15, the title compound was obtained as a colorless solid (yield: 690 mg, 62%).

$^1$H-NMR (CDCl$_3$) δ: 1.32 (3H, d, J=6.3 Hz), 2.00 (1H, d, J=4.5 Hz), 2.68 (1H, dd, J=17.4, 5.4 Hz), 2.85 (1H, dd, J=17.4, 6.6 Hz), 4.30-4.42 (1H, m), 4.56-4.65 (1H, m), 7.48 (1H, dd, J=8.7, 1.8 Hz), 7.66 (1H, d, J=8.7 Hz), 7.73 (1H, d, J=1.8 Hz). mp: 161-162° C.

Example 18

2-chloro-4-[(4S,5S)-4-hydroxy-5-methyl-2-oxopyrrolidin-1-yl]-3-methylbenzonitrile

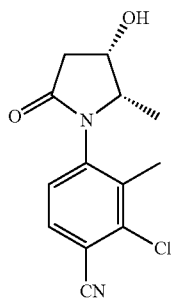 [SMILES: Cc1c(N2C(=O)C[C@H](O)[C@@H]2C)ccc(C#N)c1Cl]

Using 2-chloro-4-[(4S,5S)-4-(tert-butyldimethylsilyloxy)-5-methyl-2-oxopyrrolidin-1-yl]-3-methylbenzonitrile (500 mg) and tetrabutylammonium fluoride-THF solution (1.4 mL, 1 mol/L), and in the same manner as in Example 15, the title compound was obtained as a colorless solid (yield: 210 mg, 44%).

$^1$H-NMR (CDCl$_3$) δ: 1.12 (3H, d, J=6.6 Hz), 1.90 (1H, d, J=4.2 Hz), 2.32 (3H, s), 2.59 (1H, dd, J=17.4, 2.1 Hz), 2.87 (1H, dd, J=17.4, 5.7 Hz), 4.10-4.30 (1H, br), 4.50-4.60 (1H, m), 7.00-7.20 (1H, m), 7.56 (1H, d, J=8.1 Hz).

mp: 172-173° C.

Example 19

2-chloro-4-[(4R,5S)-3,3-difluoro-4-hydroxy-5-methyl-2-oxopyrrolidin-1-yl]benzonitrile

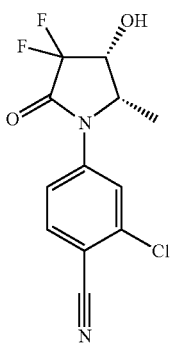 [SMILES: C[C@H]1[C@@H](O)C(F)(F)C(=O)N1c1ccc(C#N)c(Cl)c1]

Using 4-bromo-2-chlorobenzonitrile (556 mg), (4R,5S)-3,3-difluoro-4-hydroxy-5-methylpyrrolidin-2-one (448 mg), 4,5-bis(diphenylphosphino)-9,9-dimethylxanthene (219 mg), tris(dibenzylideneacetone)dipalladium(0) (113 mg) and cesium carbonate (1.18 g), and in the same manner as in Reference Example 3, the title compound was obtained as a white powder (yield: 34.2 mg, 5%).

$^1$H-NMR (DMSO-d$_6$) δ: 1.38 (3H, d, J=5.3 Hz), 2.79 (1H, brs), 4.36-4.72 (2H, m), 7.60 (1H, dd, J=8.7, 1.7 Hz), 7.74 (1H, d, J=8.7 Hz), 7.85 (1H, d, J=1.7 Hz).

IR(KBr): 3427, 2233, 1730, 1598 cm$^{-1}$.

mp: 126-127° C.

Example 20 rac-2-chloro-4-[(4R,5R)-4-hydroxy-5-isopropyl-3,3-dimethyl-2-oxopyrrolidin-1-yl]benzonitrile

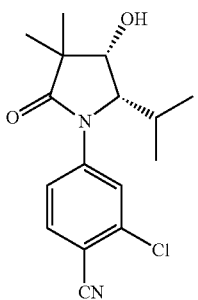 [SMILES: CC(C)[C@H]1[C@@H](O)C(C)(C)C(=O)N1c1ccc(C#N)c(Cl)c1]

Using 2-chloro-4-(5-isopropyl-3,3-dimethyl-2,4-dioxopyrrolidin-1-yl)benzonitrile (300 mg) and lithium tri(sec-butyl)borohydride-THF solution (1.48 mL, 1 mol/L), and in the same manner as in Example 5, the title compound was obtained as a colorless solid (yield: 209 mg, 69%).

$^1$H-NMR (CDCl$_3$) δ: 0.90 (3H, d, J=7.0 Hz), 1.06 (3H, d, J=7.0 Hz), 1.19 (3H, s), 1.29 (3H, s), 1.63 (1H, d, J=5.3 Hz), 2.24-2.46 (1H, m), 4.07-4.26 (2H, m), 7.36 (1H, dd, J=8.5, 2.1 Hz), 7.55 (1H, d, J=2.1 Hz), 7.67 (1H, d, J=8.5 Hz).

mp: 119-121° C.

Example 21 rac-2-chloro-4-[(4R,5R)-4-hydroxy-5-isobutyl-3,3-dimethyl-2-oxopyrrolidin-1-yl]benzonitrile

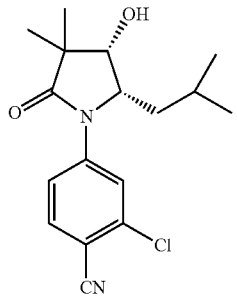 [SMILES: CC(C)C[C@H]1[C@@H](O)C(C)(C)C(=O)N1c1ccc(C#N)c(Cl)c1]

Using 2-chloro-4-(5-isobutyl-3,3-dimethyl-2,4-dioxopyrrolidin-1-yl)benzonitrile (620 mg) and lithium tri(sec-butyl)borohydride-THF solution (2.92 mL, 1 mol/L), and in the same manner as in Example 5, the title compound was obtained as a colorless solid (yield: 363 mg, 58%).

$^1$H-NMR (CDCl$_3$) δ: 0.95 (3H, d, J=6.6 Hz), 1.03 (3H, d, J=6.4 Hz), 1.20 (3H, s), 1.31 (3H, s), 1.35-1.47 (1H, m), 1.64-1.90 (3H, m), 4.09 (1H, t, J=4.8 Hz), 4.21-4.33 (1H, m), 7.31 (1H, d, J=8.5 Hz), 7.55 (1H, s), 7.67 (1H, d, J=8.5 Hz).

mp: 224-226° C.

Example 22 rac-2-chloro-4-[(4R,5R)-3,3-diethyl-4-hydroxy-5-methyl-2-oxopyrrolidin-1-yl]benzonitrile

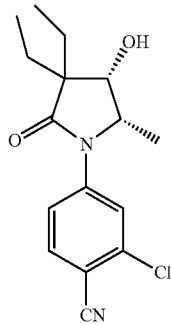 [SMILES: CCC1(CC)C(=O)N(c2ccc(C#N)c(Cl)c2)[C@@H](C)[C@H]1O]

Using 2-chloro-4-(3,3-diethyl-5-methyl-2,4-dioxopyrrolidin-1-yl)benzonitrile (67 mg) and lithium tri(sec-butyl)borohydride-THF solution (0.33 mL, 1 mol/L), and in the same manner as in Example 5, the title compound was obtained as colorless crystals (yield: 34.5 mg, 51%).

$^1$H-NMR (CDCl$_3$) δ: 0.92 (3H, t, J=7.6 Hz), 1.02 (3H, t, J=7.6 Hz), 1.30 (3H, d, J=6.4 Hz), 1.57-1.95 (5H, m), 4.16 (1H, t, J=5.3 Hz), 4.34-4.45 (1H, m), 7.41 (1H, dd, J=8.6, 2.0 Hz), 7.63-7.69 (2H, m).

mp: 166-168° C.

Example 23 rac-2-chloro-4-[(4R,5R)-4-hydroxy-5-(hydroxymethyl)-3,3-dimethyl-2-oxopyrrolidin-1-yl]benzonitrile

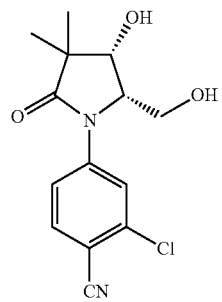 [SMILES: CC1(C)C(=O)N(c2ccc(C#N)c(Cl)c2)[C@@H](CO)[C@H]1O]

Using 2-chloro-4-[5-(hydroxymethyl)-3,3-dimethyl-2,4-dioxopyrrolidin-1-yl]benzonitrile (80 mg) and lithium tri(sec-butyl)borohydride-THF solution (0.82 mL, 1 mol/L), and in the same manner as in Example 5, the title compound was obtained as colorless crystals (yield: 45.4 mg, 56%).

$^1$H-NMR (CDCl$_3$) δ: 1.24 (3H, s), 1.32 (3H, s), 2.40 (1H, t, J=5.9 Hz), 2.66 (1H, d, J=4.7 Hz), 3.90-4.07 (2H, m), 4.33-4.45 (2H, m), 7.48 (1H, dd, J=8.5, 2.0 Hz), 7.68 (1H, d, J=8.5 Hz), 7.72 (1H, d, J=2.0 Hz).

mp: 142-143° C.

Example 24 rac-2-fluoro-4-[(4R,5R)-4-hydroxy-3,3,5-trimethyl-2-oxopyrrolidin-1-yl]-3-methylbenzonitrile

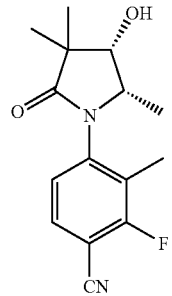 [SMILES: Cc1c(N2C(=O)C(C)(C)[C@H](O)[C@@H]2C)ccc(C#N)c1F]

Using 2-fluoro-3-methyl-4-(3,3,5-trimethyl-2,4-dioxopyrrolidin-1-yl)benzonitrile (60 mg) and lithium tri(sec-butyl)borohydride-THF solution (0.33 mL, 1 mol/L), and in the same manner as in Example 5, the title compound was obtained as colorless crystals (yield: 41.4 mg, 69%).

$^1$H-NMR (CDCl$_3$) δ: 1.11 (3H, d, J=6.6 Hz), 1.27 (3H, s), 1.31 (3H, s), 1.78 (1H, d, J=4.3 Hz), 2.16 (3H, d, J=2.5 Hz), 4.05 (1H, t, J=4.4 Hz), 4.23-4.34 (1H, m), 6.97 (1H, d, J=8.5 Hz), 7.45-7.52 (1H, m).

mp: 177-178° C.

Example 25 rac-2-fluoro-4-[(2R,3R)-3-hydroxy-2,3,4,4-tetramethyl-5-oxopyrrolidin-1-yl]-3-methylbenzonitrile

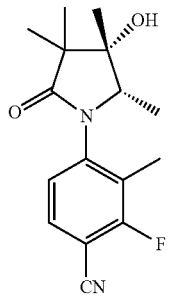 [SMILES: Cc1c(N2C(=O)C(C)(C)[C@](C)(O)[C@@H]2C)ccc(C#N)c1F]

Using 2-fluoro-3-methyl-4-(3,3,5-trimethyl-2,4-dioxopyrrolidin-1-yl)benzonitrile (60 mg) and methylmagnesium bromide-THF solution (2.19 mL, 1.0 mol/L), and in the same manner as in Example 2, the title compound was obtained as colorless crystals (yield: 40 mg, 63%).

$^1$H-NMR (CDCl$_3$) δ: 1.02 (3H, d, J=6.4 Hz), 1.18 (3H, brs), 1.22 (3H, s), 1.30 (3H, s), 1.43 (1H, brs), 2.18 (3H, brs), 4.04 (1H, brs), 6.83-7.15 (1H, m), 7.47 (1H, t, J=7.6 Hz).

mp: 174.5-175.5° C.

Example 26 rac-2-chloro-4-[(4R,5R)-4-hydroxy-5-(methoxymethyl)-3,3-dimethyl-2-oxopyrrolidin-1-yl]benzonitrile

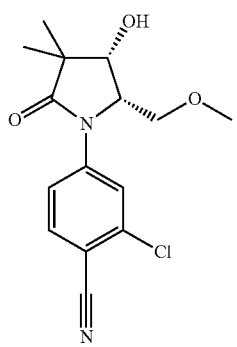 [SMILES: COC[C@H]1[C@@H](O)C(C)(C)C(=O)N1c1ccc(C#N)c(Cl)c1]

Using 2-chloro-4-[5-(methoxymethyl)-3,3-dimethyl-2,4-dioxopyrrolidin-1-yl]benzonitrile (170 mg) and lithium tri(sec-butyl)borohydride-THF solution (0.83 mL, 1 mol/L), and in the same manner as in Example 5, the title compound was obtained as colorless crystals (yield: 142 mg, 83%).

$^1$H-NMR (CDCl$_3$) δ: 1.23 (3H, s), 1.29 (3H, s), 2.84 (1H, d, J=6.2 Hz), 3.31 (3H, s), 3.62-3.75 (2H, m), 4.27 (1H, t, J=6.1 Hz), 4.39-4.48 (1H, m), 7.47 (1H, dd, J=8.5, 2.0 Hz), 7.67 (1H, d, J=8.5 Hz), 7.73 (1H, d, J=2.0 Hz).

mp: 130.5-131.5° C.

Example 27

2-methoxy-4-[(4R,5S)-3,3-difluoro-4-hydroxy-5-methyl-2-oxopyrrolidin-1-yl]benzonitrile

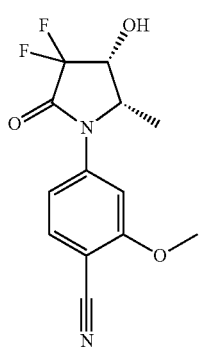 [SMILES: COc1cc(N2C(=O)C(F)(F)[C@H](O)[C@@H]2C)ccc1C#N]

Using 4-bromo-2-methoxybenzonitrile (2.34 g), (4R,5S)-3,3-difluoro-4-hydroxy-5-methylpyrrolidin-2-one (2.00 g), 4,5-bis(diphenylphosphino)-9,9-dimethylxanthene (976 mg), tris(dibenzylideneacetone)dipalladium(0) (504 mg) and cesium carbonate (5.30 g), and in the same manner as in Reference Example 18, the title compound was obtained as a colorless solid (yield: 201 mg, 7%).

$^1$H-NMR (DMSO-d$_6$) δ: 1.16 (3H, d, J=6.4 Hz), 3.94 (3H, s), 4.50-4.81 (2H, m), 7.36 (1H, dd, J=8.5, 1.9 Hz), 7.57 (1H, dd, J=1.9 Hz), 7.82 (1H, d, J=8.5 hz).

Example 28

2-trifluoromethyl-4-[(4R,5S)-3,3-difluoro-4-hydroxy-5-methyl-2-oxopyrrolidin-1-yl]benzonitrile

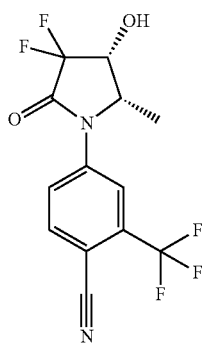 [SMILES: C[C@H]1[C@@H](O)C(F)(F)C(=O)N1c1ccc(C#N)c(C(F)(F)F)c1]

Using 2-trifluoromethyl-4-iodobenzonitrile (1.64 g), (4R,5S)-3,3-difluoro-4-hydroxy-5-methylpyrrolidin-2-one (1.00 g), 4,5-bis(diphenylphosphino)-9,9-dimethylxanthene (488 mg), tris(dibenzylideneacetone)dipalladium(0) (303 mg) and cesium carbonate (2.54 g), and in the same manner as in Reference Example 18, the title compound was obtained as a colorless solid (yield: 84.7 mg, 5%).

$^1$H-NMR (CDCl$_3$) δ: 1.35-1.46 (3H, m), 2.77 (1H, brs), 4.47-4.73 (2H, m), 7.93 (2H, s), 8.05 (1H, s).

mp: 128-131° C.

Example 29

2-chloro-4-[(2S,3S)-3-hydroxy-2,3-dimethyl-5-oxopyrrolidin-1-yl]benzonitrile

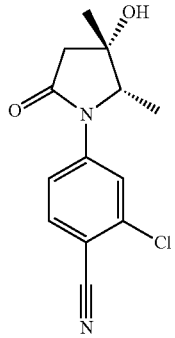 [SMILES: C[C@@H]1N(c2ccc(C#N)c(Cl)c2)C(=O)C[C@]1(C)O]

Using 4-bromo-2-chlorobenzonitrile (615 mg), (4S,5S)-4-hydroxy-4,5-dimethylpyrrolidin-2-one (423 mg), 4,5-bis(diphenylphosphino)-9,9-dimethylxanthene (241 mg), tris(dibenzylideneacetone)dipalladium(0) (125 mg) and cesium carbonate (1.31 g), and in the same manner as in Reference Example 18, the title compound was obtained as a colorless solid (yield: 431 mg, 60%).

$^1$H-NMR (CDCl$_3$) δ: 1.28 (3H, d, J=6.4 Hz), 1.52 (3H, s), 2.01 (1H, s), 2.63 (1H, d, J=17.0 Hz), 2.79 (1H, d, J=17.0 Hz), 4.07 (1H, q, J=6.4 Hz), 7.46 (1H, d, J=8.7 Hz), 7.67 (1H, d, J=8.7 Hz), 7.70 (1H, s).

mp: 93-99° C.

Example 30 rac-2-chloro-4-[(4R,5S)-4-hydroxy-3,3,5-trimethyl-2-oxopyrrolidin-1-yl]-3-methylbenzonitrile

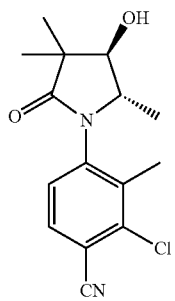 [SMILES: Cc1c(N2C(=O)C(C)(C)[C@@H](O)[C@@H]2C)ccc(C#N)c1Cl]

To a solution of rac-4-[(4R,5S)-4-(tert-butyldimethylsilyloxy)-3,3,5-trimethyl-2-oxopyrrolidin-1-yl]-2-chloro-3-methylbenzonitrile (103 mg) in THF (5 mL) was added tetrabutylammonium fluoride-THF solution (1.00 mL, 1 mol/L), and the mixture was stirred at room temperature for 17 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/3), and recrystallized from hexane-ethyl acetate to give the title compound as a colorless solid (yield: 41.4 mg, 28.4%).

$^1$H-NMR (CDCl$_3$) δ: 1.11-1.25 (3H, m), 1.14 (3H, d, J=6.0 Hz), 1.31 (3H, s), 1.93 (1H, d, J=5.9 Hz), 2.27 (3H, s), 3.73-3.91 (2H, m), 7.03-7.18 (1H, m), 7.57 (1H, d, J=8.3 Hz).

mp: 148-149° C.

Example 31

2-chloro-4-[(2S,3S,4S)-3-hydroxy-2,4-dimethyl-5-oxopyrrolidin-1-yl]benzonitrile

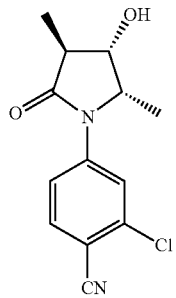 [SMILES: C[C@@H]1C(=O)N(c2ccc(C#N)c(Cl)c2)[C@@H](C)[C@H]1O]

A solution of diisopropylamine (0.150 mL) in THF (7 mL) was cooled to −78° C., and n-butyllithium-hexane solution (0.648 mL, 1.6 mol/L) was added dropwise. After the completion of the dropwise addition, the mixture was stirred at −78° C. for 1 hr. Subsequently, a solution of 2-chloro-4-[(2S,3S)-3-hydroxy-2-methyl-5-oxopyrrolidin-1-yl]benzonitrile (100 mg) in THF (2.5 mL) was added dropwise, and the mixture was further stirred at −78° C. for 30 min. Methyl iodide (0.124 mL) was added dropwise at −78° C., and the mixture was further stirred at −10° C. to −78° C. for 30 min. Acetic acid (1.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/3) to give the title compound as a colorless solid (yield: 44.4 mg, 42.0%).

$^1$H-NMR (CDCl$_3$) δ: 1.30-1.36 (6H, m), 1.92 (1H, brs), 2.63-2.76 (1H, m), 4.11-4.25 (1H, m), 4.29-4.43 (1H, m), 7.61-7.67 (2H, m), 7.95 (1H, t, J=1.2 Hz).

mp: 149-151° C.

Example 32

2-chloro-4-[(2S,3S,4R)-3-hydroxy-4-(1-hydroxy-1-methylethyl)-2-methyl-5-oxopyrrolidin-1-yl]benzonitrile

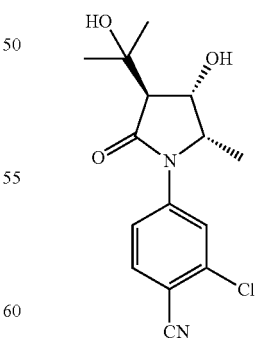

A solution of diisopropylamine (0.150 mL) in THF (7 mL) was cooled to −78° C., and n-butyllithium-hexane solution (0.648 mL, 1.6 mol/L) was added dropwise. After the completion of the dropwise addition, the mixture was stirred at −78° C. for 1 hr. Subsequently, a solution of 2-chloro-4-[(2S,3S)-

3-hydroxy-2-methyl-5-oxopyrrolidin-1-yl]benzonitrile (100 mg) in THF (1.5 mL) was added dropwise, and the mixture was further stirred at −78° C. for 30 min. Acetone (0.124 mL) was added dropwise at −78° C., and the mixture was further stirred at −20° C. to −78° C. for 40 min. Acetic acid (1.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/3) to give the title compound as a colorless solid (yield: 30.1 mg, 24.5%).

$^1$H-NMR (CDCl$_3$) δ: 1.32 (3H, d, J=6.4 Hz), 1.37 (3H, s), 1.49 (3H, s), 2.72 (1H, d, J=3.4 Hz), 2.81 (1H, d, J=9.6 Hz), 2.91 (1H, brs), 4.33-4.49 (1H, m), 4.48-4.62 (1H, m), 7.56-7.70 (2H, m), 7.98 (1H, d, J=2.1 Hz).

mp: 131-132° C.

Example 33

2-chloro-4-[(3S,4S,5S)-3-ethyl-4-hydroxy-5-methyl-2-oxopyrrolidin-1-yl]benzonitrile

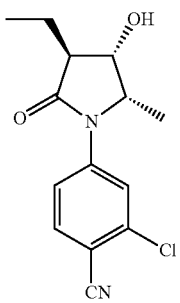 [SMILES: CC[C@@H]1C(=O)N(c2ccc(C#N)c(Cl)c2)[C@@H](C)[C@H]1O]

A solution of diisopropylamine (0.150 mL) in THF (8 mL) was cooled to −78° C., and n-butyllithium-hexane solution (0.650 mL, 1.6 mol/L) was added dropwise. After the completion of the dropwise addition, the mixture was stirred at −78° C. for 1 hr. Subsequently, a solution of 2-chloro-4-[(2S,3S)-3-hydroxy-2-methyl-5-oxopyrrolidin-1-yl]benzonitrile (100 mg) in THF (2.0 mL) was added dropwise, and the mixture was further stirred at −78° C. for 1 hr. Iodoethane (0.150 mL) was added dropwise at −78° C., and the mixture was further stirred at −78° C. to −30° C. for 1 hr. Acetic acid (1.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=20/1→1/4) to give the title compound as a colorless solid (yield: 6.7 mg, 6.0%).

$^1$H-NMR (CDCl$_3$) δ: 1.10 (3H, t, J=7.5 Hz), 1.32 (3H, d, J=6.0 Hz), 1.61-1.80 (1H, m), 1.81-1.98 (2H, m), 2.53-2.66 (1H, m), 4.26-4.42 (2H, m), 7.56-7.70 (2H, m), 7.93 (1H, d, J=1.5 Hz).

mp: 109-110° C.

Example 34

4-[(3S,4S,5S)-3-benzyl-4-hydroxy-5-methyl-2-oxopyrrolidin-1-yl]-2-chlorobenzonitrile

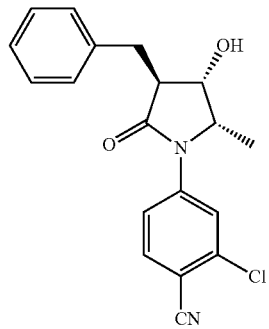 [SMILES: C[C@H]1[C@@H](O)[C@H](Cc2ccccc2)C(=O)N1c1ccc(C#N)c(Cl)c1]

A solution of diisopropylamine (0.150 mL) in THF (8 mL) was cooled to −78° C., and n-butyllithium-hexane solution (0.648 mL, 1.6 mol/L) was added dropwise. After the completion of the dropwise addition, the mixture was stirred at −78° C. for 1 hr. Subsequently, a solution of 2-chloro-4-[(2S,3S)-3-hydroxy-2-methyl-5-oxopyrrolidin-1-yl]benzonitrile (100 mg) in THF (2.5 mL) was added dropwise, and the mixture was further stirred at −78° C. for 30 min. A solution of benzyl bromide (0.16 mL) in THF (1.5 mL) was added dropwise at −78° C., and the mixture was further stirred at −78° C. to −30° C. for 1 hr. Acetic acid (1.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=50/1→1/2) to give the title compound as a colorless solid (yield: 40.8 mg, 30.0%).

$^1$H-NMR (CDCl$_3$) δ: 1.25 (3H, d, J=6.6 Hz), 1.48 (1H, d, J=4.2 Hz), 2.58-3.04 (2H, m), 3.25-3.36 (1H, m), 4.11-4.24 (1H, m), 4.25-4.36 (1H, m), 7.21-7.40 (5H, m), 7.51-7.61 (1H, m), 7.61-7.68 (1H, m), 7.88 (1H, d, J=2.1 Hz).

mp: 99-101° C.

Example 35

2-chloro-4-[(2S,3S,4S)-3-hydroxy-2-methyl-4-(2-methylprop-2-en-1-yl)-5-oxopyrrolidin-1-yl]benzonitrile

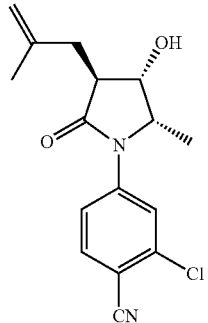 [SMILES: C=C(C)C[C@@H]1C(=O)N(c2ccc(C#N)c(Cl)c2)[C@@H](C)[C@H]1O]

A solution of diisopropylamine (0.300 mL) in THF (15 mL) was cooled to −78° C., and n-butyllithium-hexane solution (1.26 mL, 1.6 mol/L) was added dropwise. After the completion of the dropwise addition, the mixture was stirred at −78° C. for 1 hr. Subsequently, a solution of 2-chloro-4-[(2S,3S)-3-hydroxy-2-methyl-5-oxopyrrolidin-1-yl]benzonitrile (200 mg) in THF (4.0 mL) was added dropwise, and the mixture was further stirred at −78° C. for 1 hr. 3-Bromo- 2-methylpropene (0.10 mL) was added dropwise at −78° C., and the mixture was further stirred at −78° C. to −10° C. for 1 hr. Acetic acid (1.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/2) to give the title compound as a colorless solid (yield: 111.8 mg, 46.1%).

¹H-NMR (CDCl₃) δ: 1.32 (3H, d, J=6.4 Hz), 1.84 (3H, s), 2.10 (1H, d, J=3.6 Hz), 2.22 (1H, dd, J=14.0, 10.4 Hz), 2.68-2.80 (1H, m), 2.86 (1H, ddd, J=10.4, 8.3, 4.2 Hz), 4.26-4.46 (2H, m), 4.88-4.96 (2H, m), 7.59-7.69 (2H, m), 7.95 (1H, d, J=0.9 Hz).

mp: 110-112° C.

Example 36

2-chloro-4-[(2S,3S,4S)-3-hydroxy-4-isobutyl-2-methyl-5-oxopyrrolidin-1-yl]benzonitrile

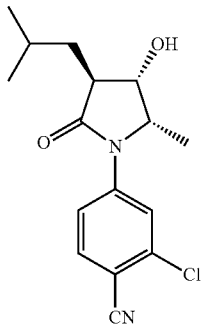 [SMILES: CC(C)C[C@@H]1C(=O)N(c2ccc(C#N)c(Cl)c2)[C@@H](C)[C@H]1O]

To a solution of 2-chloro-4-[(2S,3S,4S)-3-hydroxy-2-methyl-4-(2-methylprop-2-en-1-yl)-5-oxopyrrolidin-1-yl]benzonitrile (22.3 mg) in methanol (3.0 mL) was added palladium/fibroin (12.0 mg), and the mixture was stirred for 48 hr under a hydrogen atmosphere. The reaction mixture was filtered, and the filtrate was concentrated under reduced pressure. The obtained residue was purified by silica gel column chromatography (eluent: hexane/ethyl acetate=50/1→1/1) to give the title compound as a pale-yellow oil (yield: 4.3 mg, 19.1%).

¹H-NMR (CDCl₃) δ: 0.97-1.02 (6H, m), 1.32 (3H, d, J=6.4 Hz), 1.35-1.53 (1H, m), 1.67-1.83 (1H, m), 1.90-2.16 (2H, m), 2.69 (1H, dt, J=7.8, 6.0 Hz), 4.19-4.43 (2H, m), 7.54-7.72 (2H, m), 7.90 (1H, d, J=1.9 Hz).

Example 37 rac-2-chloro-4-[(6R,7R)-7-hydroxy-6-methyl-4-oxo-5-azaspiro[2.4]hept-5-yl]benzonitrile

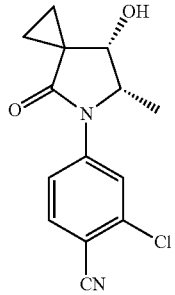 [SMILES: C[C@H]1[C@@H](O)C2(CC2)C(=O)N1c1ccc(C#N)c(Cl)c1]

To a solution of rac-4-((6R,7R)-7-(tert-butyldimethylsilyloxy)-6-methyl-4-oxo-5-azaspiro[2.4]hept-5-yl)-2-chlorobenzonitrile (140 mg) in THF (5 mL) was added tetrabutylammonium fluoride-THF solution (2.00 mL, 1 mol/L), and the mixture was stirred at room temperature for 18 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=1/0→3/1) to give the title compound as a colorless solid (yield: 32.3 mg, 32.5%).

¹H-NMR (CDCl₃) δ: 0.93-1.08 (1H, m), 1.17-1.37 (3H, m), 1.37 (3H, d, J=6.4 Hz), 1.61-1.72 (1H, m), 4.34 (1H, t, J=6.0 Hz), 4.39-4.45 (1H, m), 7.51 (1H, dd, J=8.6, 2.1 Hz), 7.66 (1H, d, J=8.6 Hz), 7.76 (1H, d, J=2.1 Hz).

mp: 134-136° C.

Example 38

4-[(4S,5S)-4-hydroxy-3,3,5-trimethyl-2-oxopyrrolidin-1-yl]-2-(trifluoromethyl)benzonitrile

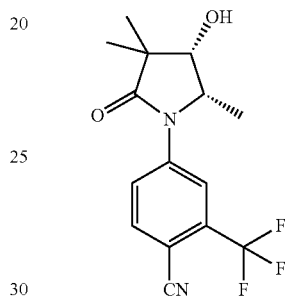

To a solution of 4-((4S,5S)-4-(tert-butyldimethylsilyloxy)-3,3,5-trimethyl-2-oxopyrrolidin-1-yl)-2-(trifluoromethyl)benzonitrile (232.2 mg) in THF (6 mL) was added tetrabutylammonium fluoride-THF solution (2.0 mL, 1 mol/L), and the mixture was stirred at room temperature for 1 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/3), and recrystallized from hexane-ethyl acetate to give the title compound as a colorless solid (yield: 38.9 mg, 22.9%).

¹H-NMR (CDCl₃) δ: 1.24 (3H, s), 1.31-1.36 (6H, m), 1.80 (1H, d, J=5.1 Hz), 4.12 (1H, t, J=5.3 Hz), 4.42-4.53 (1H, m), 7.75 (1H, dd, J=8.7, 2.3 Hz), 7.85 (1H, d, J=8.7 Hz), 7.93 (1H, d, J=2.3 Hz).

mp: 120-121° C.

Example 39

4-[(4R,5S)-4-hydroxy-3,3,5-trimethyl-2-oxopyrrolidin-1-yl]-2-(trifluoromethyl)benzonitrile

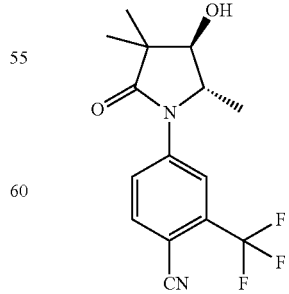

To a mixed solution of 4-[(4R,5S)-4-(tert-butyldimethylsilyloxy)-3,3,5-trimethyl-2-oxopyrrolidin-1-yl)]-2-(trifluoromethyl)benzonitrile (391.7 mg) in THF (12 mL) and methanol (12 mL) was added 6 mol/L hydrochloric acid (12.0 mL), and the mixture was stirred at room temperature for 4 hr. The reaction mixture was added to saturated aqueous sodium hydrogen carbonate, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/3) to give the title compound as a colorless oil (yield: 203.6 mg, 66%).

$^1$H-NMR (CDCl$_3$) δ: 1.18 (3H, s), 1.33 (3H, s), 1.39 (3H, d, J=6.2 Hz), 1.98 (1H, d, J=5.8 Hz), 3.82 (1H, t, J=5.8 Hz), 3.96-4.09 (1H, m), 7.11 (1H, dd, J=8.5, 2.1 Hz), 7.85 (1H, d, J=8.5 Hz), 7.91 (1H, d, J=2.1 Hz).

Example 40

4-[(2S,3S)-3-hydroxy-2-methyl-5-oxopyrrolidin-1-yl]-2-(trifluoromethyl)benzonitrile

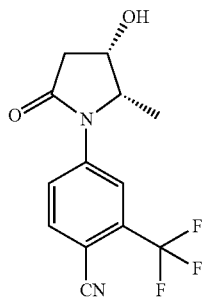 [SMILES: C[C@H]1[C@@H](O)CC(=O)N1c1ccc(C#N)c(C(F)(F)F)c1]

To a solution of 4-[(2S,3S)-3-(tert-butyldimethylsilyloxy)-2-methyl-5-oxopyrrolidin-1-yl]-2-(trifluoromethyl)benzonitrile (5.61 g) in THF (50 mL) was added tetrabutylammonium fluoride-THF solution (20.0 mL, 1 mol/L), and the mixture was stirred at room temperature for 24 hr. The reaction mixture was added to water, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=30/1→1/3) to give the title compound as a colorless oil (yield: 1.42 g, 35%).

$^1$H-NMR (CDCl$_3$) δ: 1.34 (3H, d, J=6.6 Hz), 1.84 (1H, d, J=4.7 Hz), 2.71 (1H, dd, J=17.4, 5.4 Hz), 2.88 (1H, dd, J=17.4, 6.8 Hz), 4.37-4.50 (1H, m), 4.57-4.70 (1H, m), 7.77-7.89 (2H, m), 7.92-7.88 (1H, m).

Example 41

4-[(2S,3S,4S)-3-hydroxy-2,4-dimethyl-5-oxopyrrolidin-1-yl]-2-(trifluoromethyl)benzonitrile

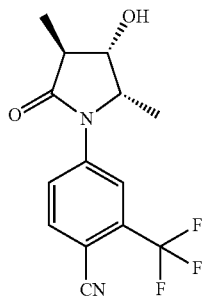 [SMILES: C[C@@H]1C(=O)N(c2ccc(C#N)c(C(F)(F)F)c2)[C@@H](C)[C@H]1O]

A solution of diisopropylamine (0.860 mL) in THF (30 mL) was cooled to −78° C., and n-butyllithium-hexane solution (3.64 mL, 1.6 mol/L) was added dropwise. After the completion of the dropwise addition, the mixture was stirred at −78° C. for 1 hr. Subsequently, a solution of 4-[(2S,3S)-3-hydroxy-2-methyl-5-oxopyrrolidin-1-yl]-2-(trifluoromethyl)benzonitrile (661 mg) in THF (5.0 mL) was added dropwise, and the mixture was further stirred at −78° C. for 1 hr. Iodomethane (0.75 mL) was added dropwise at −78° C., and the mixture was further stirred at −78° C. for 1 hr. Acetic acid (3.0 mL) was added to the reaction mixture, and the mixture was warmed to room temperature. Water was added, and the mixture was extracted with ethyl acetate. The extract was washed with saturated brine, dried over anhydrous magnesium sulfate, and concentrated under reduced pressure. The residue was purified by silica gel column chromatography (eluent: hexane/ethyl acetate=10/1→1/3) to give the title compound as a colorless solid (yield: 442.9 mg, 63.7%).

$^1$H-NMR (CDCl$_3$) δ: 1.34 (3H, d, J=6.9 Hz), 1.35 (3H, d, J=6.4 Hz), 1.95-2.06 (1H, m), 2.64-2.81 (1H, m), 4.21 (1H, ddd, J=9.2, 7.2, 5.4 Hz), 4.35-4.51 (1H, m), 7.77-7.87 (1H, m), 7.90-8.00 (1H, m), 8.20 (1H, d, J=2.3 Hz).

mp: 82-85° C.

Example 42

2-chloro-4-[(6S,7S)-7-hydroxy-6-methyl-4-oxo-5-azaspiro[2.4]hept-5-yl]benzonitrile

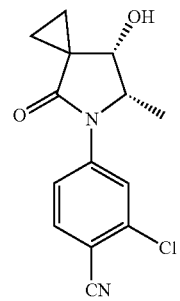 [SMILES: C[C@H]1[C@@H](O)C2(CC2)C(=O)N1c1ccc(C#N)c(Cl)c1]

To a solution of 4-[(6S,7S)-7-(tert-butyldimethylsilyloxy)-6-methyl-4-oxo-5-azaspiro[2.4]hept-5-yl]-2-chlorobenzonitrile (89.0 mg) in a mixed solvent of THF (6 mL) and methanol (6 mL) was added 6 mol/L hydrochloric acid (4.0 mL), and the mixture was stirred at room temperature for 18 hr. The reaction mixture was added to saturated aqueous sodium hydrogen carbonate, and the mixture was extracted with ethyl acetate. The extract was washed with saturated brine, dried over anhydrous magnesium sulfate, and concentrated under reduced pressure. The residue was purified by silica gel column chromatography, and recrystallized from hexane-ethyl acetate to give the title compound as a colorless solid (yield: 48.7 mg, 66%).

$^1$H-NMR (CDCl$_3$) δ: 0.93-1.08 (1H, m), 1.17-1.37 (3H, m), 1.37 (3H, d, J=6.4 Hz), 1.61-1.72 (1H, m), 4.34 (1H, t, J=6.0 Hz), 4.39-4.45 (1H, m), 7.51 (1H, dd, J=8.6, 2.1 Hz), 7.66 (1H, d, J=8.6 Hz), 7.76 (1H, d, J=2.1 Hz).

mp: 164-166° C.

Example 43

2-chloro-4-[(6S,7R)-7-hydroxy-6-methyl-4-oxo-5-azaspiro[2.4]hept-5-yl]benzonitrile

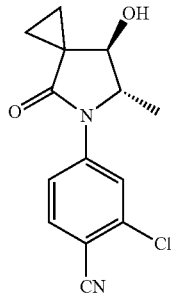 [SMILES: C[C@H]1[C@H](O)C2(CC2)C(=O)N1c1ccc(C#N)c(Cl)c1]

To a solution of 4-[(6S,7R)-7-(tert-butyldimethylsilyloxy)-6-methyl-4-oxo-5-azaspiro[2.4]hept-5-yl]-2-chlorobenzonitrile (65.7 mg) in a mixed solvent of THF (6 mL) and methanol (6 mL) was added 6 mol/L hydrochloric acid (4.0 mL), and the mixture was stirred at room temperature for 1 hr. The reaction mixture was added to saturated aqueous sodium hydrogen carbonate, and the mixture was extracted with ethyl acetate.

The extract was washed with saturated brine, dried over anhydrous magnesium sulfate, and concentrated under reduced pressure. The residue was purified by silica gel column chromatography, and recrystallized from hexane-ethyl acetate to give the title compound as a colorless solid (yield: 42.0 mg, 90%).

$^1$H-NMR (CDCl$_3$) δ: 1.07-1.47 (4H, m), 1.39 (3H, d, J=6.6 Hz), 1.85-1.95 (1H, m), 3.77 (1H, d, J=3.8 Hz), 4.33 (1H, q, J=6.6 Hz), 7.59-7.71 (2H, m), 7.99-8.01 (1H, m).

mp: 169-172° C.

Example 44

2-chloro-4-[(6S,7S)-7-hydroxy-6,7-dimethyl-4-oxo-5-azaspiro[2.4]hept-5-yl]benzonitrile

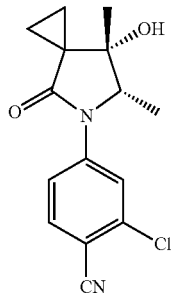

To a solution of 2-chloro-4-[(6S)-6-methyl-4,7-dioxo-5-azaspiro[2.4]hept-5-yl]benzonitrile (35 mg) in tetrahydrofuran (6.0 mL) was added dropwise 1 mol/L-methylmagnesium bromide/tetrahydrofuran solution (1.3 mL) under ice-cooling, and the mixture was stirred at the same temperature for 1 hr. Brine was added to the reaction mixture, and the mixture was extracted with ethyl acetate.

The extract was dried over anhydrous magnesium sulfate and concentrated under reduced pressure. The residue was purified by silica gel column chromatography (eluent: hexane/ethyl acetate=10/1→1/3) to give the title compound as a colorless solid (yield: 27.5 mg, 74%).

$^1$H-NMR (CDCl$_3$) δ: 0.92-1.05 (1H, m), 1.07-1.32 (3H, m), 1.29 (3H, s), 1.35 (3H, d, J=6.4 Hz), 1.44 (1H, s), 4.14 (1H, q, J=6.4 Hz), 7.51 (1H, dd, J=8.5, 2.1 Hz), 7.66 (1H, d, J=8.5 Hz), 7.75 (1H, d, J=2.1 Hz).

mp: 150-152° C.

Example 45

4-[(6S,7R)-7-hydroxy-6-methyl-4-oxo-5-azaspiro[2.4]hept-5-yl]-2-(trifluoromethyl)benzonitrile

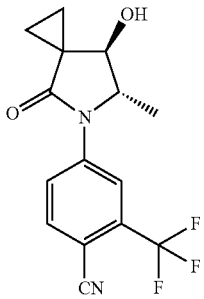 [SMILES: C[C@H]1[C@H](O)C2(CC2)C(=O)N1c1ccc(C#N)c(C(F)(F)F)c1]

To a solution of 4-[(6S,7R)-7-(tert-butyldimethylsilyloxy)-6-methyl-4-oxo-5-azaspiro[2.4]hept-5-yl]-2-(trifluoromethyl)benzonitrile (670 mg) in tetrahydrofuran (12 mL)-methanol (6 mL) was added 6 mol/L hydrochloric acid (5 mL), and the mixture was stirred at room temperature for 2 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/3) to give the title compound as a colorless solid (yield: 381.9 mg, 78%).

$^1$H-NMR (CDCl$_3$) δ: 1.08-1.24 (2H, m), 1.41 (3H, d, J=6.6 Hz), 1.31-1.45 (2H, m), 1.91 (1H, d, J=1.7 Hz), 3.80 (1H, d, J=4.7 Hz), 4.39 (1H, q, J=6.7 Hz), 7.81 (1H, d, J=8.5 Hz), 7.96 (1H, d, J=8.5 Hz), 8.27 (1H, s).

mp: 109-110° C.

Example 46

4-[(6S,7S)-7-hydroxy-6-methyl-4-oxo-5-azaspiro[2.4]hept-5-yl]-2-(trifluoromethyl)benzonitrile

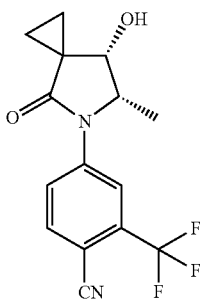 [SMILES: C[C@H]1[C@@H](O)C2(CC2)C(=O)N1c1ccc(C#N)c(C(F)(F)F)c1]

To a solution of 4-[(6S,7S)-7-(tert-butyldimethylsilyloxy)-6-methyl-4-oxo-5-azaspiro[2.4]hept-5-yl]-2-(trifluoromethyl)benzonitrile (309.4 mg) in tetrahydrofuran (3 mL)-methanol (3 mL) was added 6 mol/L hydrochloric acid (3 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/3) to give the title compound as a colorless solid (yield: 152.3 mg, 67%).

¹H-NMR (CDCl₃) δ: 0.97-1.10 (1H, m), 1.20-1.36 (3H, m), 1.37 (3H, d, J=6.4 Hz), 1.66 (1H, d, J=6.4 Hz), 4.36 (1H, t, J=6.2 Hz), 4.48-4.61 (1H, m), 7.76-7.88 (2H, m), 8.02 (1H, d, J=2.1 Hz).

mp: 155-156° C.

Example 47

4-[(6S,7R)-7-hydroxy-6-methyl-4-oxo-5-azaspiro[2.4]hept-5-yl]-2-methoxybenzonitrile

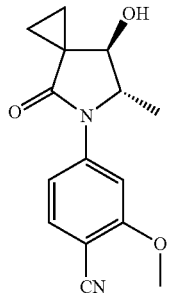 [SMILES: COc1cc(N2C(=O)C3(CC3)[C@@H](O)[C@@H]2C)ccc1C#N]

To a solution of 4-[(6S,7R)-7-(tert-butyldimethylsilyloxy)-6-methyl-4-oxo-5-azaspiro[2.4]hept-5-yl]-2-methoxybenzonitrile (320 mg) in tetrahydrofuran (8 mL)-methanol (8 mL) was added 6 mol/L hydrochloric acid (6 mL), and the mixture was stirred at room temperature for 2 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/3) to give the title compound as a colorless solid (yield: 49.7 mg, 22%).

¹H-NMR (CDCl₃) δ: 1.10-1.21 (2H, m), 1.30-1.42 (2H, m), 1.39 (3H, d, J=6.6 Hz), 1.78 (1H, d, J=5.1 Hz), 3.77 (1H, d, J=5.1 Hz), 3.93 (3H, s), 4.31-4.41 (1H, m), 6.90 (1H, dd, J=8.5, 2.1 Hz), 7.54 (1H, d, J=8.5 Hz), 7.97 (1H, d, J=2.1 Hz).

mp: 167-169° C.

Example 48

4-[(6S,7R)-6-ethyl-7-hydroxy-4-oxo-5-azaspiro[2.4]hept-5-yl]-2-(trifluoromethyl)benzonitrile

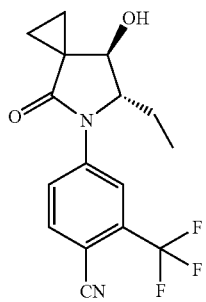 [SMILES: CC[C@H]1[C@H](O)C2(CC2)C(=O)N1c1ccc(C#N)c(C(F)(F)F)c1]

To a solution of 4-[(6S,7R)-7-(tert-butyldimethylsilyloxy)-6-ethyl-4-oxo-5-azaspiro[2.4]hept-5-yl]-2-(trifluoromethyl)benzonitrile (433.7 mg) in tetrahydrofuran (6 mL)-methanol (12 mL) was added 6 mol/L hydrochloric acid (5 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/2) to give the title compound as a colorless solid (yield: 266.1 mg, 83%).

¹H-NMR (CDCl₃) δ: 1.01 (3H, t, J=7.5 Hz), 1.15-1.24 (2H, m), 1.35-1.45 (2H, m), 1.59-1.72 (1H, m), 1.74-1.89 (2H, m), 3.89 (1H, d, J=4.9 Hz), 4.25 (1H, dd, J=8.9, 2.8 Hz), 7.82 (1H, d, J=8.7 Hz), 7.92 (1H, dd, J=8.7, 2.1 Hz), 8.25 (1H, d, J=2.1 Hz).

mp: 106-110° C.

Example 49

2-chloro-4-[(4S,5S)-3,3-difluoro-4-hydroxy-5-methyl-2-oxopyrrolidin-1-yl]benzonitrile

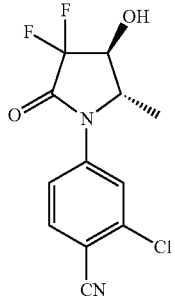 [SMILES: C[C@H]1[C@H](O)C(F)(F)C(=O)N1c1ccc(C#N)c(Cl)c1]

To a solution of (4S,5S)-1-(3-chloro-4-iodophenyl)-3,3-difluoro-4-hydroxy-5-methylpyrrolidin-2-one (113 mg) in DMF (3.5 mL) were added zinc cyanide (12 mg) and tetrakis(triphenylphosphine)palladium(0) (34 mg), and the mixture was stirred at 100° C. for 4 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/2) to give the title compound as a colorless solid (yield: 75 mg, 90%).

¹H-NMR (CDCl₃) δ: 1.44 (3H, dd, J=6.6, 1.5 Hz), 2.38-2.46 (1H, m), 4.15-4.23 (1H, m), 4.23-4.30 (1H, m), 7.62 (1H, dd, J=8.7, 2.1 Hz), 7.74 (1H, d, J=8.7 Hz), 7.86 (1H, d, J=2.1 Hz).

mp: 133-139° C.

Example 50

4-[(4R,5S)-4-hydroxy-3,3,5-trimethyl-2-oxopyrrolidin-1-yl]-2-(trifluoromethyl)benzonitrile

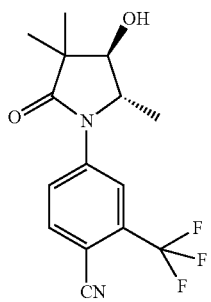 [SMILES: C[C@H]1[C@H](O)C(C)(C)C(=O)N1c1ccc(C#N)c(C(F)(F)F)c1]

To a solution of 4-[(4R,5S)-4-(tert-butyldimethylsilyloxy)-3,3,5-trimethyl-2-oxopyrrolidin-1-yl]-2-(trifluoromethyl)benzonitrile (391.7 mg) in tetrahydrofuran (12 mL)-methanol (12 mL) was added 6 mol/L hydrochloric acid (12 mL), and the mixture was stirred at room temperature for 4 hr. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=10/1→1/3) to give the title compound as a colorless oil (yield: 203.6 mg, 71%).

¹H-NMR (CDCl₃) δ: 1.18 (3H, s), 1.33 (3H, s), 1.39 (3H, d, J=6.2 Hz), 1.98 (1H, d, J=5.8 Hz), 3.82 (1H, t, J=5.8 Hz), 3.96-4.09 (1H, m), 7.11 (1H, dd, J=8.5, 2.1 Hz), 7.85 (1H, d, J=8.5 Hz), 7.91 (1H, d, J=2.1 Hz).

Example 51

2-chloro-4-[(2S,3R)-2-ethyl-3-hydroxy-5-oxopyrrolidin-1-yl]benzonitrile

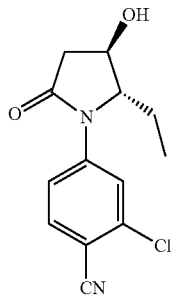 [SMILES: CC[C@H]1[C@H](O)CC(=O)N1c1ccc(C#N)c(Cl)c1]

To a solution of 4-[(2S,3R)-3-(tert-butyldimethylsilyloxy)-2-ethyl-5-oxopyrrolidin-1-yl]-2-chlorobenzonitrile (366 mg) in tetrahydrofuran (5 mL)-methanol (5 mL) was added 6 mol/L hydrochloric acid (5 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=10/1→1/3) to give the title compound as a colorless solid (yield: 221.2 mg, 87%).

¹H-NMR (CDCl₃) δ: 1.00 (3H, t, J=7.5 Hz), 1.41-1.59 (1H, m), 1.69-1.85 (1H, m), 1.97 (1H, brs), 2.55 (1H, dd, J=18.0, 1.2 Hz), 3.01 (1H, dd, J=18.0, 5.9 Hz), 4.08 (1H, dd, J=9.3, 3.0 Hz), 4.32-4.40 (1H, m), 7.59 (1H, dd, J=8.7, 2.1 Hz), 7.66 (1H, d, J=8.7 Hz), 7.91 (1H, d, J=2.1 Hz).

mp: 118-120° C.

Example 52

2-chloro-4-[(2S,3R,4R)-2-ethyl-3-hydroxy-4-methyl-5-oxopyrrolidin-1-yl]benzonitrile

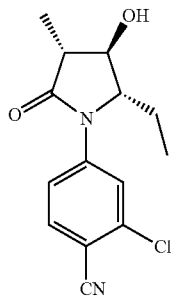 [SMILES: CC[C@H]1[C@H](O)[C@@H](C)C(=O)N1c1ccc(C#N)c(Cl)c1]

A solution of diisopropylamine (0.208 mL) in tetrahydrofuran (8 mL) was cooled to −78° C., n-butyllithium-hexane solution (0.885 mL, 1.6 mol/L) was added dropwise, and the mixture was stirred for 1 hr. A solution of 2-chloro-4-[(2S, 3R)-2-ethyl-3-hydroxy-5-oxopyrrolidin-1-yl]benzonitrile (145.5 mg) in tetrahydrofuran (2 mL) was added dropwise and the mixture was stirred at −78° C. for 1 hr. A solution of iodomethane (0.176 mL) in tetrahydrofuran (2 mL) was added dropwise at −78° C., and the mixture was stirred at −78° C. for 30 min and at 0° C. for 30 min. Water was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/3) to give the title compound as a colorless solid (yield: 57.0 mg, 37%).

¹H-NMR (CDCl₃) δ: 0.90 (3H, t, J=7.5 Hz), 1.39 (3H, d, J=7.4 Hz), 1.48-1.65 (1H, m), 1.80-1.95 (1H, m), 2.25 (1H, d, J=4.5 Hz), 2.55-2.67 (1H, m), 3.89-3.99 (2H, m), 7.42 (1H, dd, J=8.5, 2.0 Hz), 7.67 (1H, d, J=8.5 Hz), 7.69 (1H, d, J=2.0 Hz).

mp: 120-123° C.

Example 53

2-chloro-4-[(2S,3S)-2-ethyl-3-hydroxy-5-oxopyrrolidin-1-yl]benzonitrile

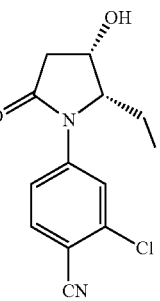

To a solution of 4-[(2S,3S)-3-(tert-butyldimethylsilyloxy)-2-ethyl-5-oxopyrrolidin-1-yl]-2-chlorobenzonitrile (550 mg) in tetrahydrofuran (3 mL)-methanol (3 mL) was added 6 mol/L hydrochloric acid (4 mL), and the mixture was stirred at room temperature for 72 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=10/1→1/3) to give the title compound as a colorless solid (yield: 93.3 mg, 24%).

¹H-NMR (CDCl₃) δ: 1.02 (3H, t, J=7.3 Hz), 1.69-1.82 (3H, m), 2.67 (1H, dd, J=16.8, 3.9 Hz), 2.85 (1H, dd, J=16.8, 6.9 Hz), 4.06-4.18 (1H, m), 4.62-4.73 (1H, m), 7.40 (1H, d, J=8.5 Hz), 7.59-7.72 (2H, m).

mp: 138-140° C.

Example 54

2-chloro-4-[(2S,3R)-2-ethyl-3-hydroxy-5-oxopyrrolidin-1-yl]-3-methylbenzonitrile

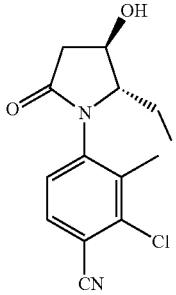 [SMILES: CC[C@H]1[C@H](O)CC(=O)N1c1ccc(C#N)c(Cl)c1C]

To a solution of 4-[(2S,3R)-3-(tert-butyldimethylsilyloxy)-2-ethyl-5-oxopyrrolidin-1-yl]-2-chloro-3-methylbenzonitrile (650 mg) in tetrahydrofuran (20 mL)-methanol (10 mL) was added 6 mol/L hydrochloric acid (10 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=10/1→1/9) to give the title compound as a colorless solid (yield: 227.1 mg, 49%).

$^1$H-NMR (CDCl$_3$) δ: 0.91 (3H, t, J=7.4 Hz), 1.33-1.50 (1H, m), 1.51-1.68 (1H, m), 2.31 (3H, s), 2.44-2.55 (1H, m), 2.50 (1H, dd, J=17.6, 2.4 Hz), 2.94 (1H, dd, J=17.6, 6.2 Hz), 3.69-3.82 (1H, m), 4.31-4.41 (1H, m), 7.18 (1H, d, J=8.3 Hz), 7.56 (1H, d, J=8.3 Hz).

mp: 153-155° C.

Example 55

2-chloro-4-[(2S,3S,4S)-2-ethyl-3-hydroxy-4-methyl-5-oxopyrrolidin-1-yl]benzonitrile

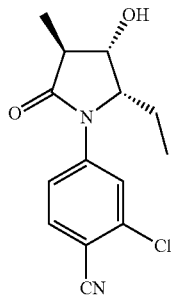 [SMILES: CC[C@H]1[C@@H](O)[C@H](C)C(=O)N1c1ccc(C#N)c(Cl)c1]

To a solution of diisopropylamine (0.111 mL) in tetrahydrofuran (5 mL) was added dropwise n-butyllithium-hexane solution (0.472 mL, 1.6 mol/L) at −78° C., the mixture was stirred for 1 hr, and a solution of 2-chloro-4-[(2S,3S)-2-ethyl-3-hydroxy-5-oxopyrrolidin-1-yl]benzonitrile (80 mg) in tetrahydrofuran (3 mL) was added dropwise. The mixture was stirred at −78° C. for 30 min, iodomethane (0.100 mL) was added dropwise at −78° C., and the mixture was stirred at 0° C. for 2 hr. Acetic acid (0.500 mL) was added dropwise to the reaction mixture, water was added, and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/3) to give the title compound as a colorless solid (yield: 10.8 mg, 13%).

$^1$H-NMR (CDCl$_3$) δ: 1.00 (3H, t, J=7.5 Hz), 1.30 (3H, d, J=7.2 Hz), 1.60-1.80 (1H, m), 1.80-1.99 (1H, m), 2.34 (1H, brs), 2.65-2.81 (1H, m), 4.08-4.31 (2H, m), 7.54 (1H, d, J=8.5 Hz), 7.65 (1H, d, J=8.5 Hz), 7.86 (1H, s).

mp: 121-125° C.

Example 56

4-[(2S,3R)-2-ethyl-3-hydroxy-5-oxopyrrolidin-1-yl]-2-(trifluoromethyl)benzonitrile

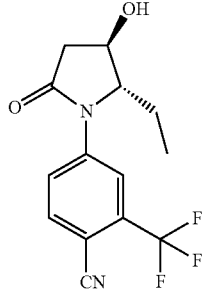 [SMILES: CC[C@H]1[C@H](O)CC(=O)N1c1ccc(C#N)c(C(F)(F)F)c1]

To a solution of 4-[(2S,3R)-3-(tert-butyldimethylsilyloxy)-2-ethyl-5-oxopyrrolidin-1-yl]-2-(trifluoromethyl)benzonitrile (1.32 g) in tetrahydrofuran (30 mL)-ethanol (15 mL) was added 6 mol/L hydrochloric acid (15 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=6/1→1/9) to give the title compound as a colorless solid (yield: 507.3 mg, 53%).

$^1$H-NMR (CDCl$_3$) δ: 1.00 (3H, t, J=7.5 Hz), 1.41-1.59 (1H, m), 1.69-1.85 (1H, m), 1.97 (1H, brs), 2.55 (1H, dd, J=18.0, 1.2 Hz), 3.01 (1H, dd, J=18.0, 5.9 Hz), 4.08 (1H, dd, J=9.3, 3.0 Hz), 4.32-4.40 (1H, m), 7.59 (1H, dd, J=8.7, 2.1 Hz), 7.66 (1H, d, J=8.7 Hz), 7.91 (1H, d, J=2.1 Hz).

mp: 116-118° C.

Example 57

4-[(2S,3R)-2-ethyl-3-hydroxy-5-oxopyrrolidin-1-yl]-2-methoxybenzonitrile

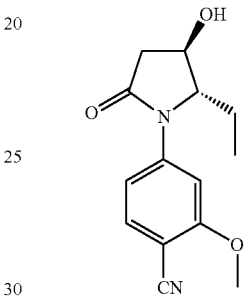

To a solution of 4-[(2S,3R)-3-(tert-butyldimethylsilyloxy)-2-ethyl-5-oxopyrrolidin-1-yl]-2-methoxybenzonitrile (1.04 g) in tetrahydrofuran (30 mL)-ethanol (15 mL) was added 6 mol/L hydrochloric acid (15 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=5/1→0/1) to give the title compound as a colorless solid (yield: 528.3 mg, 73%).

$^1$H-NMR (CDCl$_3$) δ: 0.99 (3H, t, J=7.6 Hz), 1.40-1.61 (1H, m), 1.70-1.87 (1H, m), 2.01 (1H, d, J=4.2 Hz), 2.55 (1H, dd, J=18.0, 1.3 Hz), 3.01 (1H, dd, J=18.0, 6.0 Hz), 3.94 (3H, s), 4.08 (1H, dd, J=9.3, 2.8 Hz), 4.30-4.39 (1H, m), 6.87 (1H, dd, J=8.5, 2.1 Hz), 7.53 (1H, d, J=8.5 Hz), 7.76 (1H, d, J=2.1 Hz)

mp: 138-141° C.

Example 58

2-chloro-4-[(2S,3S)-2-ethyl-3-hydroxy-5-oxopyrrolidin-1-yl]-3-methylbenzonitrile

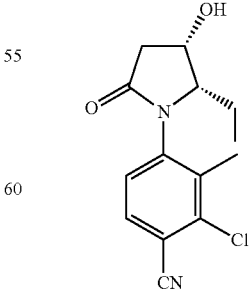

To a solution of 4-[(2S,3S)-3-(tert-butyldimethylsilyloxy)-2-ethyl-5-oxopyrrolidin-1-yl]-2-chloro-3-methylbenzonitrile (134.5 mg) in tetrahydrofuran (10 mL)-methanol (5 mL)

was added 6 mol/L hydrochloric acid (5 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=10/1→1/4) to give the title compound as a colorless solid (yield: 66.2 mg, 69%).

$^1$H-NMR (CDCl$_3$) δ: 0.94 (3H, t, J=7.4 Hz), 1.29-1.50 (1H, m), 1.55-1.77 (1H, m), 1.72 (1H, brs), 2.32 (3H, brs), 2.58 (1H, d, J=17.4 Hz), 2.85 (1H, dd, J=17.4, 5.3 Hz), 3.84-4.05 (1H, m), 4.57-4.68 (1H, m), 6.99-7.17 (1H, m), 7.56 (1H, d, J=8.3 Hz).

mp: 142-146° C.

Example 59

4-[(2S,3S)-2-ethyl-3-hydroxy-5-oxopyrrolidin-1-yl]-2-(trifluoromethyl)benzonitrile

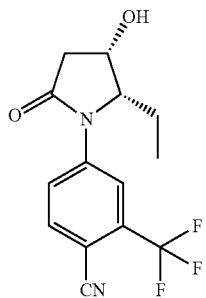 [SMILES: CC[C@H]1[C@@H](O)CC(=O)N1c1ccc(C#N)c(C(F)(F)F)c1]

To a solution of 4-[((2S,3S)-3-(tert-butyldimethylsilyloxy)-2-ethyl-5-oxopyrrolidin-1-yl]-2-(trifluoromethyl)benzonitrile (7.76 g) in tetrahydrofuran (60 mL)-ethanol (30 mL) was added 6 mol/L hydrochloric acid (60 mL), and the mixture was stirred at room temperature for 18 hr. Saturated aqueous sodium hydrogen carbonate was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=50/1→1/4), and the obtained solid was recrystallized from ethyl acetate/hexane to give the title compound as a colorless solid (yield: 2.36 g, 42%).

$^1$H-NMR (CDCl$_3$) δ: 1.03 (3H, t, J=7.5 Hz), 1.70-1.86 (3H, m), 2.70 (1H, dd, J=17.4, 4.0 Hz), 2.87 (1H, dd, J=17.4, 6.6 Hz), 4.15-4.24 (1H, m), 4.66-4.75 (1H, m), 7.73 (1H, dd, J=8.5, 2.1 Hz), 7.85 (1H, d, J=8.5 Hz), 7.86 (1H, d, J=2.1 Hz).

mp: 111-112° C.

Example 60

4-[(2S,3S,4S)-2-ethyl-3-hydroxy-4-methyl-5-oxopyrrolidin-1-yl]-2-(trifluoromethyl)benzonitrile

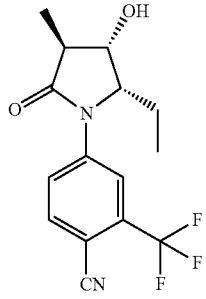 [SMILES: CC[C@H]1[C@@H](O)[C@H](C)C(=O)N1c1ccc(C#N)c(C(F)(F)F)c1]

To a solution of diisopropylamine (0.603 mL) in tetrahydrofuran (8 mL) was added dropwise n-butyllithium-hexane solution (2.56 mL, 1.6 mol/L) at −78° C., the mixture was stirred for 1 hr, and a solution of 4-[(2S,3S)-2-ethyl-3-hydroxy-5-oxopyrrolidin-1-yl]-2-(trifluoromethyl)benzonitrile (490 mg) in tetrahydrofuran (6 mL) was added dropwise. The mixture was stirred at −78° C. for 30 min, iodomethane (0.510 mL) was added dropwise at −78° C., and the mixture was stirred at 0° C. for 1 hr. Aqueous ammonium chloride solution was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/4) and further purified by basic silica gel chromatography (eluent: hexane/ethyl acetate=30/1→1/4) to give the title compound as a colorless solid (yield: 66.5 mg, 13%).

$^1$H-NMR (CDCl$_3$) δ: 1.01 (3H, t, J=7.5 Hz), 1.32 (3H, d, J=7.2 Hz), 1.64-1.81 (1H, m), 1.83-2.00 (2H, m), 2.62-2.82 (1H, m), 4.19-4.37 (2H, m), 7.82 (1H, d, J=8.5 Hz), 7.89 (1H, dd, J=8.5, 2.1 Hz), 8.09 (1H, d, J=2.1 Hz).

mp: 113-119° C.

Example 61

4-[(2S,3S,4S)-2-ethyl-3-hydroxy-4-methyl-5-oxopyrrolidin-1-yl]-2-methoxybenzonitrile

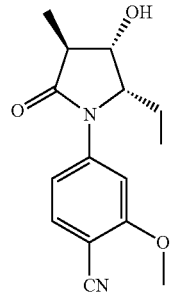 [SMILES: CC[C@H]1[C@@H](O)[C@H](C)C(=O)N1c1ccc(C#N)c(OC)c1]

To a solution of diisopropylamine (0.291 mL) in tetrahydrofuran (8 mL) was added dropwise n-butyllithium-hexane solution (1.24 mL, 1.6 mol/L) at −78° C., the mixture was stirred for 1 hr, and a solution of 4-[(2S,3S)-2-ethyl-3-hydroxy-5-oxopyrrolidin-1-yl]-2-methoxybenzonitrile (206.5 mg) in tetrahydrofuran (6 mL) was added dropwise. The mixture was stirred at −78° C. for 30 min, iodomethane (0.247 mL) was added dropwise at −78° C., and the mixture was stirred at 0° C. for 1 hr. Aqueous ammonium chloride solution was added to the reaction mixture, and the mixture was extracted with ethyl acetate. The extract was dried over anhydrous magnesium sulfate and concentrated under reduced pressure. The residue was purified by silica gel column chromatography (eluent: hexane/ethyl acetate=30/1→1/4) to give the title compound as a colorless solid (yield: 108.8 mg, 50%).

$^1$H-NMR (CDCl$_3$) δ: 1.00 (3H, t, J=7.5 Hz), 1.31 (3H, d, J=7.2 Hz), 1.62-1.82 (1H, m), 1.81-2.00 (1H, m), 1.91 (1H, d, J=5.1 Hz), 2.65-2.79 (1H, m), 3.93 (3H, s), 4.15-4.33 (2H, m), 6.84 (1H, dd, J=8.5, 1.9 Hz), 7.53 (1H, d, J=8.5 Hz), 7.72 (1H, d, J=1.9 Hz).

mp: 78-81° C.

Example 62

2-chloro-4-[(2S,3S)-3-hydroxy-2,3-dimethyl-5-oxopyrrolidin-1-yl]-3-methylbenzonitrile

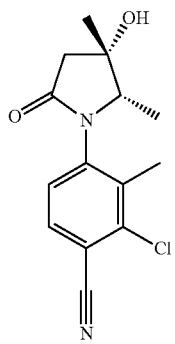 [SMILES: Cc1c(N2C(=O)C[C@](C)(O)[C@@H]2C)ccc(C#N)c1Cl]

A solution of 2-chloro-4-iodo-3-methylbenzonitrile (1.29 g), (4S,5S)-4-hydroxy-4,5-dimethylpyrrolidin-2-one (500 mg), 4,5-bis(diphenylphosphino)-9,9-dimethylxanthene (343 mg), tris(dibenzylideneacetone)dipalladium(0) (177 mg) and cesium carbonate (1.86 g) in 1,4-dioxane (4 mL) was tightly sealed, and the mixture was stirred at 120° C. for 3 hr using microwave reactor. The reaction mixture was filtered through silica gel, and the filtrate was concentrated under reduced pressure. The residue was purified by silica gel column chromatography (eluent: ethyl acetate/hexane=30→70%, basic silica gel eluent: ethyl acetate/hexane=30→80%), and the obtained solid was recrystallized from ethyl acetate/hexane to give the title compound as colorless crystals (yield: 603 mg, 56%).

$^1$H-NMR (CDCl$_3$) δ: 1.05 (3H, d, J=6.6 Hz), 1.52 (3H, s), 1.68 (1H, brs), 2.33 (3H, s), 2.67 (2H, s), 3.98 (1H, brs), 7.00-7.18 (1H, m), 7.57 (1H, d, J=8.3 Hz).

mp: 164-171° C.

Example 63

4-[(2S,3S)-3-hydroxy-2,3-dimethyl-5-oxopyrrolidin-1-yl]-2-(trifluoromethyl)benzonitrile

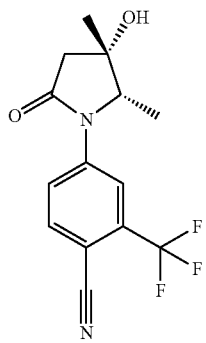 [SMILES: C[C@@H]1N(c2ccc(C#N)c(C(F)(F)F)c2)C(=O)C[C@]1(C)O]

Using 4-iodo-2-(trifluoromethyl)benzonitrile (958 mg), (4S,5S)-4-hydroxy-4,5-dimethylpyrrolidin-2-one (500 mg), 4,5-bis(diphenylphosphino)-9,9-dimethylxanthene (286 mg), tris(dibenzylideneacetone)dipalladium(0) (148 mg) and cesium carbonate (1.55 g), and in the same manner as in Example 62, the title compound was obtained as colorless crystals (yield: 508 mg, 52%).

$^1$H-NMR (CDCl$_3$) δ: 1.30 (3H, d, J=6.6 Hz), 1.54 (3H, s), 1.93 (1H, s), 2.65 (1H, d, J=17.2 Hz), 2.82 (1H, d, J=17.2 Hz), 4.14 (1H, q, J=6.6 Hz), 7.78 (1H, dd, J=8.7, 1.9 Hz), 7.85 (1H, d, J=8.7 Hz), 7.92 (1H, d, J=1.9 Hz).

mp: 134-137° C. (ethyl acetate/hexane).

Example 64

4-[(2S,3S)-3-hydroxy-2,3-dimethyl-5-oxopyrrolidin-1-yl]-2-methoxybenzonitrile

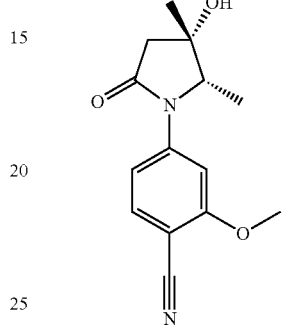

Using 4-bromo-2-methoxybenzonitrile (684 mg), (4S,5S)-4-hydroxy-4,5-dimethylpyrrolidin-2-one (500 mg), 4,5-bis(diphenylphosphino)-9,9-dimethylxanthene (286 mg), tris(dibenzylideneacetone)dipalladium(0) (148 mg) and cesium carbonate (1.55 g), and in the same manner as in Example 62, the title compound was obtained as a colorless amorphous solid (yield: 410 mg, 48%).

$^1$H-NMR (CDCl$_3$) δ: 1.27 (3H, d, J=6.4 Hz), 1.52 (3H, s), 1.97 (1H, s), 2.63 (1H, d, J=17.0 Hz), 2.79 (1H, d, J=17.0 Hz), 3.93 (3H, s), 4.08 (1H, q, J=6.4 Hz), 6.82 (1H, dd, J=8.5, 1.9 Hz), 7.42 (1H, d, J=1.9 Hz), 7.54 (1H, d, J=8.5 Hz).

LCMS (m/z): 261 (M+H)$^{30}$.

Example 65

2-fluoro-4-[(2S,3S)-3-hydroxy-2,3-dimethyl-5-oxopyrrolidin-1-yl]-3-methylbenzonitrile

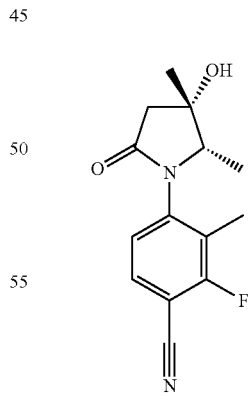

Using 4-bromo-2-fluoro-3-methylbenzonitrile (484 mg), (4S,5S)-4-hydroxy-4,5-dimethylpyrrolidin-2-one (350 mg), 4,5-bis(diphenylphosphino)-9,9-dimethylxanthene (200 mg), tris(dibenzylideneacetone)dipalladium(0) (103 mg) and cesium carbonate (1.08 g), and in the same manner as in Example 62, the title compound was obtained as colorless crystals (yield: 376 mg, 63%).

¹H-NMR (CDCl₃) δ: 1.05 (3H, d, J=6.6 Hz), 1.51 (3H, s), 1.81 (1H, s), 2.20 (3H, d, J=2.5 Hz), 2.66-2.66 (2H, m), 3.99 (1H, q, J=6.6 Hz), 6.98 (1H, d, J=8.1 Hz), 7.48 (1H, dd, J=8.1, 7.0 Hz).

mp: 138-141° C. (ethyl acetate/hexane).

Example 66

2-chloro-4-[(2S,3S)-2-ethyl-3-hydroxy-3-methyl-5-oxopyrrolidin-1-yl]benzonitrile

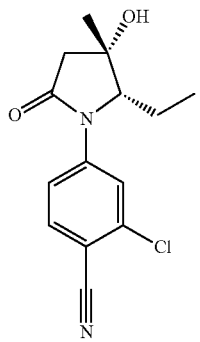 [SMILES: CC[C@@H]1N(c2ccc(C#N)c(Cl)c2)C(=O)C[C@]1(C)O]

Using 4-bromo-2-chlorobenzonitrile (459 mg), (4S,5S)-5-ethyl-4-hydroxy-4-methylpyrrolidin-2-one (350 mg), 4,5-bis(diphenylphosphino)-9,9-dimethylxanthene (180 mg), tris(dibenzylideneacetone)dipalladium(0) (93 mg) and cesium carbonate (929 mg), and in the same manner as in Example 62, the title compound was obtained as colorless crystals (yield: 318 mg, 56%).

¹H-NMR (CD₃SOCD₃) δ: 0.86 (3H, dd, J=7.6, 7.4 Hz), 1.38 (3H, s), 1.44-1.64 (1H, m), 1.66-1.84 (1H, m), 2.49 (1H, d, J=17.0 Hz), 2.69 (1H, d, J=17.0 Hz), 4.11 (1H, dd, J=7.7, 3.4 Hz), 5.30 (1H, s), 7.65 (1H, dd, J=8.7, 1.9 Hz), 7.97 (1H, d, J=8.7 Hz), 8.00 (1H, d, J=1.9 Hz).

mp: 144-146° C. (ethyl acetate/hexane).

Example 67

2-chloro-4-[(2S,3S)-2-ethyl-3-hydroxy-3-methyl-5-oxopyrrolidin-1-yl]-3-methylbenzonitrile

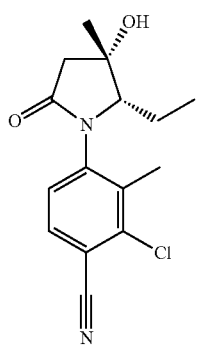 [SMILES: CC[C@@H]1N(c2ccc(C#N)c(Cl)c2C)C(=O)C[C@]1(C)O]

Using 2-chloro-4-iodo-3-methylbenzonitrile (565 mg), (4S,5S)-5-ethyl-4-hydroxy-4-methylpyrrolidin-2-one (350 mg), 4,5-bis(diphenylphosphino)-9,9-dimethylxanthene (180 mg), tris(dibenzylideneacetone)dipalladium(0) (93 mg) and cesium carbonate (929 mg), and in the same manner as in Example 62, the title compound was obtained as colorless crystals (yield: 132 mg, 22%).

¹H-NMR (CDCl₃) δ: 0.87 (3H, dd, J=7.6 Hz), 1.31-1.51 (1H, m), 1.59 (3H, s), 1.63-1.84 (1H, m), 1.68 (1H, s), 2.32 (3H, s), 2.67 (2H, s), 3.77 (1H, s), 7.12 (1H, d, J=8.3 Hz), 7.57 (1H, d, J=8.3 Hz).

mp: 156-158° C. (ethyl acetate/hexane).

Example 68

4-[(2S,3S)-2-ethyl-3-hydroxy-3-methyl-5-oxopyrrolidin-1-yl]-2-(trifluoromethyl)benzonitrile

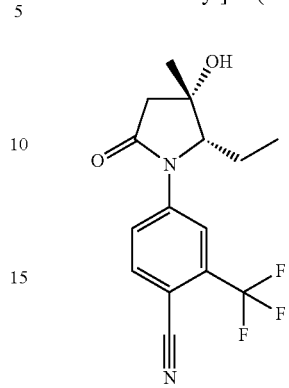

Using 4-iodo-2-(trifluoromethyl)benzonitrile (605 mg), (4S,5S)-5-ethyl-4-hydroxy-4-methylpyrrolidin-2-one (350 mg), 4,5-bis(diphenylphosphino)-9,9-dimethylxanthene (180 mg), tris(dibenzylideneacetone)dipalladium(0) (93 mg) and cesium carbonate (929 mg), and in the same manner as in Example 62, the title compound was obtained as a white powder (yield: 422 mg, 66%).

¹H-NMR (CDCl₃) δ: 1.00 (3H, dd, J=7.6, 7.4 Hz), 1.59 (3H, s), 1.71 (1H, dddd, J=14.7, 7.6, 7.4, 3.2 Hz), 1.78 (1H, s), 1.91 (1H, dddd, J=15.0, 14.7, 7.6, 7.4 Hz), 2.63 (1H, d, J=17.2 Hz), 2.89 (1H, d, J=17.2 Hz), 3.96 (1H, dd, J=7.7, 3.4 Hz), 7.75-7.91 (2H, m), 7.99 (1H, s).

mp: 137-139° C. (ethyl acetate/hexane).

Example 69

2-chloro-4-[(2S,3R)-3-cyclopropyl-3-hydroxy-2-methyl-5-oxopyrrolidin-1-yl]benzonitrile

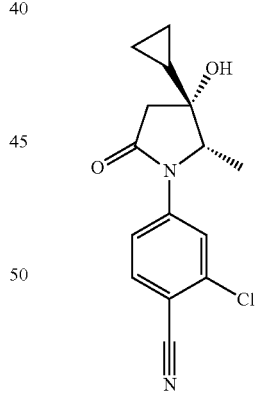

Using 4-bromo-2-chlorobenzonitrile (424 mg), (4R,5S)-4-cyclopropyl-4-hydroxy-5-methylpyrrolidin-2-one (350 mg), 4,5-bis(diphenylphosphino)-9,9-dimethylxanthene (166 mg), tris(dibenzylideneacetone)dipalladium(0) (86 mg) and cesium carbonate (902 mg), and in the same manner as in Example 62, the title compound was obtained as a white powder (yield: 58 mg, 11%).

¹H-NMR (DMSO-d₆) δ: 0.29-0.53 (4H, m), 0.97-1.20 (1H, m), 1.12 (3H, d, J=6.2 Hz), 2.37-2.65 (2H, m), 4.33 (1H, q, J=6.2 Hz), 4.97 (1H, s), 7.61 (1H, dd, J=8.7, 1.7 Hz), 7.90 (1H, d, J=1.7 Hz), 7.97 (1H, d, J=8.7 Hz).

mp: 93-100° C. (ethyl acetate/hexane).

Example 70

2-chloro-4-[(2S,3R)-3-cyclopropyl-3-hydroxy-2-methyl-5-oxopyrrolidin-1-yl]-3-methylbenzonitrile

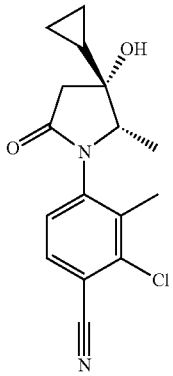 [SMILES: Cc1c(N2C(=O)C[C@@](O)(C3CC3)[C@@H]2C)ccc(C#N)c1Cl]

Using 2-chloro-4-iodo-3-methylbenzonitrile (522 mg), (4R,5S)-4-cyclopropyl-4-hydroxy-5-methylpyrrolidin-2-one (350 mg), 4,5-bis(diphenylphosphino)-9,9-dimethylxanthene (166 mg), tris(dibenzylideneacetone)dipalladium(0) (86 mg) and cesium carbonate (902 mg), and in the same manner as in Example 62, the title compound was obtained as a white powder (yield: 308 mg, 54%).

$^1$H-NMR (CDCl$_3$) δ: 0.36-0.53 (2H, m), 0.53-0.66 (2H, m), 0.97-1.21 (1H, m), 1.08 (3H, d, J=6.4 Hz), 1.69 (1H, brs), 2.33 (3H, s), 2.38 (1H, d, J=17.0 Hz), 2.53 (1H, d, J=17.0 Hz), 4.13 (1H, brs), 7.06-7.19 (1H, m), 7.57 (1H, d, J=8.3 Hz).

mp: 231-236° C. (ethyl acetate/hexane).

Example 71

4-[(2S,3R)-3-cyclopropyl-3-hydroxy-2-methyl-5-oxopyrrolidin-1-yl]-2-(trifluoromethyl)benzonitrile

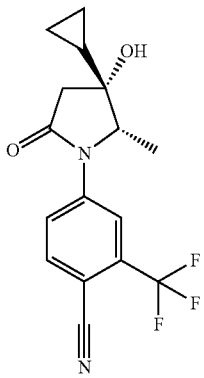 [SMILES: C[C@@H]1N(c2ccc(C#N)c(C(F)(F)F)c2)C(=O)C[C@@]1(O)C1CC1]

Using 4-iodo-2-(trifluoromethyl)benzonitrile (558 mg), (4R,5S)-4-cyclopropyl-4-hydroxy-5-methylpyrrolidin-2-one (350 mg), 4,5-bis(diphenylphosphino)-9,9-dimethylxanthene (166 mg), tris(dibenzylideneacetone)dipalladium(0) (86 mg) and cesium carbonate (902 mg), and in the same manner as in Example 62, the title compound was obtained as a yellow powder (yield: 123 mg, 20%).

$^1$H-NMR (CDCl$_3$) δ: 0.38-0.69 (4H, m), 1.09-1.25 (1H, m), 1.32 (3H, d, J=6.4 Hz), 1.70 (1H, s), 2.53 (1H, d, J=17.2 Hz), 2.62 (1H, d, J=17.2 Hz), 4.26 (1H, q, J=6.4 Hz), 7.78 (1H, d, J=8.5 Hz), 7.85 (1H, d, J=8.5 Hz), 7.92 (1H, s).

mp: 84-90° C.

Example 72

2-chloro-4-[(2S,3R)-3-cyclopropyl-2-ethyl-3-hydroxy-5-oxopyrrolidin-1-yl]benzonitrile

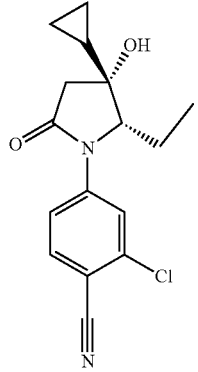 [SMILES: CC[C@@H]1N(c2ccc(C#N)c(Cl)c2)C(=O)C[C@@]1(O)C1CC1]

Using 4-bromo-2-chlorobenzonitrile (389 mg), (4R,5S)-4-cyclopropyl-5-ethyl-4-hydroxypyrrolidin-2-one (350 mg), 4,5-bis(diphenylphosphino)-9,9-dimethylxanthene (153 mg), tris(dibenzylideneacetone)dipalladium(0) (79 mg) and cesium carbonate (786 mg), and in the same manner as in Example 62, the title compound was obtained as pale-yellow crystals (yield: 104 mg, 20%).

$^1$H-NMR (CDCl$_3$) δ: 0.38-0.53 (2H, m), 0.53-0.69 (2H, m), 0.99 (3H, dd, J=7.5, 7.4 Hz), 1.12-1.33 (1H, m), 1.62-1.78 (1H, m), 1.65 (1H, s), 1.80-2.01 (1H, m), 2.50 (1H, d, J=17.2 Hz), 2.74 (1H, d, J=17.2 Hz), 4.00 (1H, dd, J=7.6, 3.1 Hz), 7.54 (1H, dd, J=8.7, 2.1 Hz), 7.66 (1H, d, J=8.7 Hz), 7.81 (1H, d, J=2.1 Hz).

mp: 128-132° C. (ethyl acetate/n-heptane).

Example 73

2-chloro-4-[(2S,3R)-3-cyclopropyl-2-ethyl-3-hydroxy-5-oxopyrrolidin-1-yl]-3-methylbenzonitrile

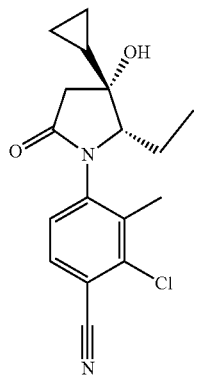 [SMILES: CC[C@@H]1N(c2ccc(C#N)c(Cl)c2C)C(=O)C[C@@]1(O)C1CC1]

Using 2-chloro-4-iodo-3-methylbenzonitrile (478 mg), (4R,5S)-4-cyclopropyl-5-ethyl-4-hydroxypyrrolidin-2-one (350 mg), 4,5-bis(diphenylphosphino)-9,9-dimethylxanthene (153 mg), tris(dibenzylideneacetone)dipalladium(0) (79 mg) and cesium carbonate (786 mg), and in the same manner as in Example 62, the title compound was obtained as colorless crystals (yield: 78 mg, 14%).

$^1$H-NMR (DMSO-d$_6$) δ: 0.39-0.53 (4H, m), 0.76 (3H, dd, J=6.8, 6.6 Hz), 1.08-1.27 (2H, m), 1.60-1.75 (1H, m), 2.24

(3H, s), 2.29 (1H, d, J=6.2 Hz), 2.49-2.62 (1H, m), 4.05 (1H, brs), 4.95 (1H, brs), 7.45-7.49 (1H, m), 7.90 (1H, d, J=8.3 Hz).
mp: 177-179° C. (ethyl acetate/n-heptane).

Example 74

2-chloro-4-[(4R,5S)-5-ethyl-3,3-difluoro-4-hydroxy-2-oxopyrrolidin-1-yl]benzonitrile

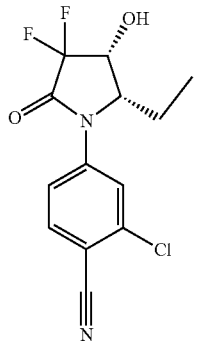 [SMILES: CC[C@H]1[C@@H](O)C(F)(F)C(=O)N1c1ccc(C#N)c(Cl)c1]

Using 4-bromo-2-chlorobenzonitrile (2.28 g), (4R,5S)-5-ethyl-3,3-difluoro-4-hydroxypyrrolidin-2-one (2.00 g), 4,5-bis(diphenylphosphino)-9,9-dimethylxanthene (954 mg), tris(dibenzylideneacetone)dipalladium(0) (554 mg) and cesium carbonate (4.84 g), and in the same manner as in Example 62, the title compound was obtained as pale-yellow crystals (yield: 153 mg, 10%).
$^1$H-NMR (CD$_3$SOCD$_3$) δ: 0.83 (3H, dd, J=7.4, 7.4 Hz), 1.30-1.79 (2H, m), 4.45-4.78 (2H, m), 6.54 (1H, d, J=4.2 Hz), 7.76 (1H, d, J=8.7 Hz), 8.06 (1H, s), 8.08 (1H, d, J=8.7 Hz).
mp: 137-140° C. (ethyl acetate/hexane).

Example 75

4-[(4R,5S)-5-ethyl-3,3-difluoro-4-hydroxy-2-oxopyrrolidin-1-yl]-2-methoxybenzonitrile

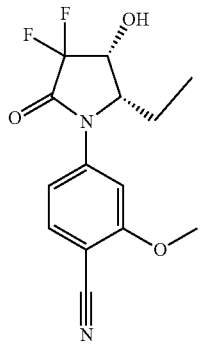 [SMILES: CC[C@H]1[C@@H](O)C(F)(F)C(=O)N1c1ccc(C#N)c(OC)c1]

Using 4-bromo-2-methoxybenzonitrile (2.14 g), (4R,5S)-5-ethyl-3,3-difluoro-4-hydroxypyrrolidin-2-one (2.00 g), 4,5-bis(diphenylphosphino)-9,9-dimethylxanthene (954 mg), tris(dibenzylideneacetone)dipalladium(0) (554 mg) and cesium carbonate (4.84 g), and in the same manner as in Example 62, the title compound was obtained as a white powder (yield: 895 mg, 30%).
$^1$H-NMR (CD$_3$SOCD$_3$) δ: 0.83 (3H, dd, J=7.3 Hz), 1.35-1.79 (2H, m), 3.93 (3H, s), 4.45-4.74 (2H, m), 6.53 (1H, s), 7.26 (1H, d, J=8.5 Hz), 7.47 (1H, s), 7.82 (1H, d, J=8.5 Hz).
mp: 161-164° C. (ethyl acetate/hexane).

Example 76

4-[(4R,5S)-5-ethyl-3,3-difluoro-4-hydroxy-2-oxopyrrolidin-1-yl]-2-fluoro-3-methylbenzonitrile

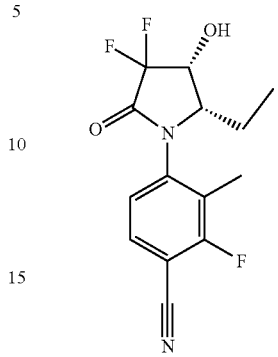

A solution of benzyl [(1S)-1-formylpropyl]carbamate (3.00% g) and ethyl bromodifluoroacetate (4.21 g) in acetonitrile (110 mL) was ice-cooled under a nitrogen atmosphere, and tris(triphenylphosphonium)rhodium (I) chloride (126 mg) was added. The mixture was stirred at the same temperature for 30 min, 1.0 mol/L-diethylzinc/hexane solution (20.3 mL) was added, and the mixture was stirred at the same temperature for 4 hr and at room temperature for 14 hr. Water (100 mL) was added to the reaction mixture, and the mixture was extracted with ethyl acetate. The obtained organic layer was washed with saturated brine, dried over anhydrous magnesium sulfate, and concentrated under reduced pressure. The residue was purified by silica gel column chromatography (eluent: ethyl acetate/hexane=0→30%). The obtained oil was dissolved in methanol (10 mL), and the solution was ice-cooled. 1 mol/L aqueous sodium hydroxide solution (7.2 mL) was added, and the mixture was stirred at room temperature for 2 hr. The reaction solution was concentrated under reduced pressure, and ethyl acetate and water were added to the obtained residue. The aqueous layer was separated, 6 mol/L hydrochloric acid was added, and the mixture was extracted with ethyl acetate. The obtained organic layer was concentrated under reduced pressure, the obtained residue was dissolved in methanol (10 mL), and 1 mol/L aqueous sodium hydroxide solution (4.37 mL) and 10% palladium carbon (containing 50% water, 146 mg) were added. The reaction solution was stirred for 20 hr under a hydrogen atmosphere, and filtered through celite. The filtrate was concentrated under reduced pressure, and the obtained residue was dissolved in dimethyl sulfoxide (10 mL). 2,4-Difluoro-3-methylbenzonitrile (982 mg) and diisopropylethylamine (2.47 mL) were added, and the mixture was stirred at 100° C. for 12 hr. The reaction solution was cooled to room temperature, 1 mol/L aqueous hydrochloric acid solution (30 mL) was added, and the mixture was extracted with ethyl acetate. The obtained organic layer was concentrated under reduced pressure, acetic acid (5 mL) was added to the residue, and the mixture was stirred at 100° C. for 18 hr. The reaction solution was cooled to room temperature, saturated aqueous sodium hydrogen carbonate solution (50 mL) was added, and the mixture was extracted with ethyl acetate. The obtained organic layer was washed with saturated brine, dried over anhydrous magnesium sulfate, and concentrated under reduced pressure. The residue was purified by silica gel column chromatography (eluent: ethyl acetate/hexane=20→50%, basic silica gel eluent: ethyl acetate/hexane=60→100%), and the obtained solid was recrystallized from ethyl acetate/diethyl ether/hexane to give the title compound as colorless crystals (yield: 91 mg, 2%).
$^1$H-NMR (DMSO-d$_6$) δ: 0.79 (3H, dd, J=7.2, 7.0 Hz), 1.17-1.39 (1H, m), 1.46-1.69 (1H, m), 2.08 (3H, s), 4.26 (1H, brs), 4.57-4.70 (1H, m), 6.57 (1H, brs), 7.47 (1H, brd, J=7.6 Hz), 7.91 (1H, dd, J=7.6 Hz).

mp: 176-180° C. (ethyl acetate/diethyl ether/hexane).

Example 77

4-[(2S,3S)-2-ethyl-3-hydroxy-5-oxopyrrolidin-1-yl]-2-methoxybenzonitrile

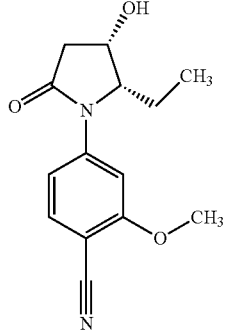 [SMILES: CC[C@H]1[C@@H](O)CC(=O)N1c1ccc(C#N)c(OC)c1]

A solution of (4S,5S)-4-(tert-butyldimethylsilyloxy)-5-ethylpyrrolidin-2-one (340 m), 4-iodo-2-methoxybenzonitrile (434 mg), cesium carbonate (683 mg), tris(dibenzylideneacetone)dipalladium(0) (64.0 mg) and 4,5-bis(diphenylphosphino)-9,9-dimethylxanthene (121 mg) in dioxane (10 mL) was stirred at 80° C. for 6.5 hr under an argon atmosphere. After allowing to room temperature, water was added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (eluent: hexane-ethyl acetate=99:1→1:1). The obtained residue was dissolved in ethanol (10 mL)-tetrahydrofuran (10 mL), 6 mol/L hydrochloric acid (4.66 mL) was added, and the mixture was stirred overnight at room temperature. The mixture was neutralized with saturated aqueous sodium hydrogen carbonate solution under ice-cooling, and extracted with ethyl acetate. The organic layer was washed with saturated brine, and dried over magnesium sulfate, and the solvent was evaporated under reduced pressure. The obtained residue was purified by silica gel column chromatography (eluent: hexane:ethyl acetate=9:1→1:9), and recrystallized from tetrahydrofuran-hexane to give the title compound as colorless crystals (yield: 115 mg, 32%).

$^1$H-NMR (CDCl$_3$) δ: 1.01 (3H, t, J=7.5 Hz), 1.68-1.82 (3H, m), 2.62-2.70 (1H, m), 2.81-2.90 (1H, m), 3.94 (3H, s), 4.08-4.17 (1H, m), 4.62-4.72 (1H, m), 6.80 (1H, dd, J=8.3, 1.9 Hz), 7.31 (1H, d, J=1.7 Hz), 7.55 (1H, d, J=8.3 Hz).

mp: 158-160° C.

Example 78

2-chloro-4-[(2S,3S)-2-ethyl-3-hydroxy-5-oxopyrrolidin-1-yl]-3-fluorobenzonitrile

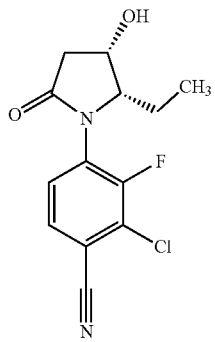 [SMILES: CC[C@H]1[C@@H](O)CC(=O)N1c1ccc(C#N)c(Cl)c1F]

A solution of (4S,5S)-4-(tert-butyldimethylsilyloxy)-5-ethylpyrrolidin-2-one (300 mg), 2-chloro-3-fluoro-4-iodobenzonitrile (416 mg), cesium carbonate (602 mg), tris(dibenzylideneacetone)dipalladium(0) (56.4 mg) and 4,5-bis(diphenylphosphino)-9,9-dimethylxanthene (107 mg) in dioxane (10 mL) was stirred at 80° C. overnight under an argon atmosphere. After allowing to room temperature, water was added to the reaction mixture, and the mixture was extracted with ethyl acetate. The extract was washed with saturated brine, dried over anhydrous magnesium sulfate, and concentrated under reduced pressure. The residue was purified by basic silica gel column chromatography (eluent: hexane→hexane-ethyl acetate=2:1). The obtained residue was dissolved in ethanol (10 mL)-tetrahydrofuran (10 mL), concentrated hydrochloric acid (2.06 mL) was added, and the mixture was stirred overnight at room temperature. The mixture was neutralized with saturated aqueous sodium hydrogen carbonate solution under ice-cooling, and extracted with ethyl acetate. The organic layer was washed with saturated brine, and dried over magnesium sulfate, and the solvent was evaporated under reduced pressure. The obtained residue was purified by silica gel column chromatography (eluent: hexane→ethyl acetate), and recrystallized from hexane-ethyl acetate to give the title compound as colorless crystals (yield: 86 mg, 25%).

$^1$H-NMR (CDCl$_3$) δ: 0.99 (3H, t, J=7.4 Hz), 1.40-1.74 (3H, m), 2.61 (1H, dd, J=17.6, 1.5 Hz), 2.86 (1H, dd, J=17.4, 5.7 Hz), 4.06-4.16 (1H, m), 4.59-4.68 (1H, m), 7.38-7.45 (1H, m), 7.50-7.55 (1H, m).

mp: 142-144° C.

Example 79 rac-4-[(2S,3S)-2-benzyl-3-hydroxy-5-oxopyrrolidin-1-yl]-2-chlorobenzonitrile

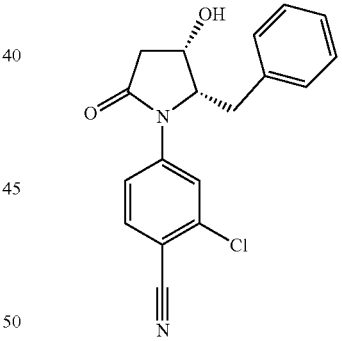

To a mixture of 4-(2-benzyl-3-hydroxy-5-oxo-2,5-dihydro-1H-pyrrol-1-yl)-2-chlorobenzonitrile (400 mg) and acetic acid (0.60 mL) in acetonitrile (20 mL) was added sodium borohydride (86 mg) at 0° C. in small portions. The mixture was warmed to room temperature, and stirred for 3 hr. Water was added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1→ethyl acetate), and recrystallized from tetrahydrofuran-hexane to give the title compound as colorless crystals (yield: 310 mg, 77%).

$^1$H-NMR (DMSO-d$_6$) δ: 2.38 (1H, dd, J=16.8, 5.7 Hz), 2.65 (1H, dd, J=16.8, 6.8 Hz), 2.82 (1H, dd, J=13.6, 5.3 Hz), 3.01 (1H, dd, J=13.6, 7.7 Hz), 4.34 (1H, br.s.), 4.65-4.74 (1H,

Example 80

2-chloro-4-[(2S,3S)-3-hydroxy-5-oxo-2-propylpyrrolidin-1-yl]benzonitrile

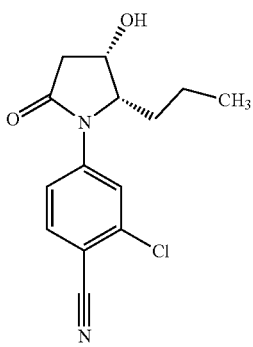 [SMILES: CCC[C@H]1[C@@H](O)CC(=O)N1c1ccc(C#N)c(Cl)c1]

To a mixture of 2-chloro-4-(3-hydroxy-5-oxo-2-propyl-2,5-dihydro-1H-pyrrol-1-yl)benzonitrile (800 mg) and acetic acid (1.82 mL) in acetonitrile (25 mL) was added sodium borohydride (273 mg) at 0° C. in small portions. The mixture was warmed to room temperature and stirred for 1 hr. Water and saturated brine were added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1-Methyl acetate), and recrystallized from tetrahydrofuran-hexane to give the title compound as colorless crystals (yield: 578 mg, 72%).

$^1$H-NMR (CDCl$_3$) δ: 0.96 (3H, t, J=7.2 Hz), 1.28-1.81 (4H, m), 1.90 (1H, d, J=4.9 Hz), 2.61-2.88 (2H, m), 4.14-4.24 (1H, m), 4.59-4.69 (1H, m), 7.38 (1H, dd, J=8.5, 2.1 Hz), 7.64 (1H, d, J=1.9 Hz), 7.68 (1H, d, J=8.5 Hz).

mp: 143-146° C.

Example 81 rac-2-chloro-4-[(2S,3S)-2-(4-fluorobenzyl)-3-hydroxy-5-oxopyrrolidin-1-yl]benzonitrile

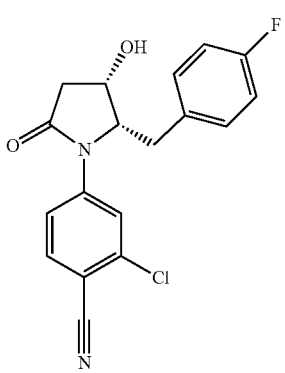 [SMILES: N#Cc1ccc(N2C(=O)C[C@H](O)[C@@H]2Cc2ccc(F)cc2)cc1Cl]

To a mixture of 2-chloro-4-[2-(4-fluorobenzyl)-3-hydroxy-5-oxo-2,5-dihydro-1H-pyrrol-1-yl]benzonitrile (1.00 g) and acetic acid (1.84 mL) in acetonitrile (10 mL) was added sodium borohydride (276 mg) at 0° C. in small portions. The mixture was warmed to room temperature and stirred for 1 hr. Water and saturated brine were added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1→ethyl acetate), and recrystallized from tetrahydrofuran-hexane to give the title compound as colorless crystals (yield: 717 mg, 71%).

$^1$H-NMR (CDCl$_3$) δ: 1.89 (1H, d, J=4.3 Hz), 2.47-2.58 (1H, m), 2.70-2.82 (1H, m), 2.93-3.12 (2H, m), 4.44-4.58 (2H, m), 6.94-7.04 (2H, m), 7.13-7.23 (2H, m), 7.47 (1H, dd, J=8.7, 1.9 Hz), 7.65-7.71 (2H, m).

mp: 154-156° C.

Example 82

2-chloro-4-[(2S,3S)-3-hydroxy-2-(1-methylethyl)-5-oxopyrrolidin-1-yl]benzonitrile

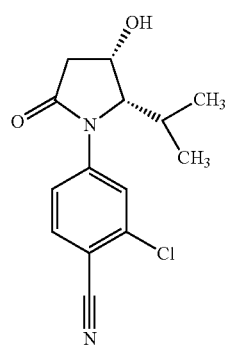 [SMILES: CC(C)[C@H]1[C@@H](O)CC(=O)N1c1ccc(C#N)c(Cl)c1]

To a mixture of 2-chloro-4-[3-hydroxy-2-(1-methylethyl)-5-oxo-2,5-dihydro-1H-pyrrol-1-yl]benzonitrile (300 mg) and acetic acid (0.68 mL) in acetonitrile (10 mL) was added sodium borohydride (103 mg) at 0° C. in small portions. The mixture was warmed to room temperature and stirred for 1 hr. Water was added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1→-ethyl acetate), and recrystallized from hexane-ethyl acetate to give the title compound as colorless crystals (yield: 76 mg, 25%).

$^1$H-NMR (CDCl$_3$) δ: 0.93 (3H, d, J=7.2 Hz), 1.08 (3H, d, J=7.2 Hz), 1.90 (1H, d, J=4.9 Hz), 2.19-2.38 (1H, m), 2.65-2.89 (2H, m), 4.22-4.28 (1H, m), 4.79-4.90 (1H, m), 7.45 (1H, dd, J=8.5, 2.1 Hz), 7.67 (1H, d, J=8.5 Hz), 7.70 (1H, d, J=1.9 Hz).

mp: 100-102° C.

Example 83 rac-2-chloro-4-[(2S,3S)-2-(4-cyanobenzyl)-3-hydroxy-5-oxopyrrolidin-1-yl]benzonitrile

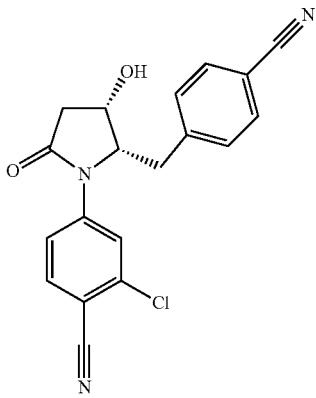 [SMILES: N#Cc1ccc(C[C@H]2[C@@H](O)CC(=O)N2c2ccc(C#N)c(Cl)c2)cc1]

To a mixture of 2-chloro-4-[2-(4-cyanobenzyl)-3-hydroxy-5-oxo-2,5-dihydro-1H-pyrrol-1-yl]benzonitrile (300 mg) and acetic acid (0.54 mL) in acetonitrile (10 mL) was added sodium borohydride (81 mg) at 0° C. in small portions. The mixture was warmed to room temperature and stirred for 1 hr. Water was added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1→ethyl acetate), and recrystallized from tetrahydrofuran-hexane to give the title compound as colorless crystals (yield: 162 mg, 54%).

$^1$H-NMR (CDCl$_3$) δ: 1.97 (1H, d, J=4.5 Hz), 2.52 (1H, dd, J=17.3, 4.2 Hz), 2.72-2.85 (1H, m), 3.01-3.24 (2H, m), 4.47-4.58 (2H, m), 7.37 (2H, d, J=8.5 Hz), 7.48 (1H, dd, J=8.6, 2.2 Hz), 7.60 (2H, d, J=8.5 Hz), 7.67 (1H, d, J=1.9 Hz), 7.70 (1H, d, J=8.5 Hz).

mp: 176-178° C.

Example 84

2-chloro-4-[(2S,3S)-2-(cyclopropylmethyl)-3-hydroxy-5-oxopyrrolidin-1-yl]benzonitrile

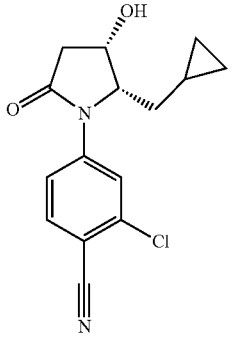 [SMILES: N#Cc1ccc(N2C(=O)C[C@H](O)[C@@H]2CC2CC2)cc1Cl]

To a mixture of 2-chloro-4-[2-(cyclopropylmethyl)-3-hydroxy-5-oxo-2,5-dihydro-1H-pyrrol-1-yl]benzonitrile (400 mg) and acetic acid (0.87 mL) in acetonitrile (10 mL) was added sodium borohydride (131 mg) at 0° C. in small portions. The mixture was warmed to room temperature and stirred for 1 hr. Water was added, and the mixture was extracted with ethyl acetate. The organic layer was washed with saturated brine, and dried over magnesium sulfate, and the solvent was evaporated under reduced pressure. The obtained residue was purified by basic silica gel column chromatography (eluent: hexane:ethyl acetate=4:1-3 ethyl acetate), and recrystallized from tetrahydrofuran-hexane to give the title compound as colorless crystals (yield: 310 mg, 77%).

$^1$H-NMR (CDCl$_3$) δ: 0.06-0.16 (2H, m), 0.46-0.56 (2H, m), 0.66-0.79 (1H, m), 1.41-1.52 (1H, m), 1.74-1.87 (1H, m), 1.96 (1H, d, J=4.7 Hz), 2.68-2.91 (2H, m), 4.31-4.39 (1H, m), 4.71-4.80 (1H, m), 7.45 (1H, dd, J=8.7, 2.1 Hz), 7.63-7.69 (2H, m).

mp: 137-139° C.

Experimental Example 1

AR Binding Inhibitory Test

To a solution containing a wild-type androgen receptor (AR) were added radiolabel mibolerone (3 nM) and a compound (100 nM), and the mixture was incubated at 4° C. for 3 hr. B (Bound)/F (Free) were separated by the dextran/charcoal method. The label count of B was measured, and the inhibitory rate of the compound was calculated. The results are shown in Table 1.

TABLE 1

| Compound Example No. | Inhibitory rate (%) at 100 nM |
|---|---|
| 8 | 90 |
| 17 | 90 |
| 40 | 90 |
| 41 | 96 |
| 55 | 99 |
| 59 | 94 |
| 74 | 97 |
| 75 | 95 |

Experimental Example 2

Compound Evaluation in Reporter Assay System Using Cos-7 Cell

Cos-7 (5,000,000 cells) were sown in a 150 cm$^2$ flask, and cultured in a culture medium (DMEM medium containing 10% Dextran Charcoal (DCC)-Fetal Bovine Serum (FBS), 2 mM glutamine) for 24 hr. Vector DNA containing AR gene, and vector DNA containing luciferase gene bound at the downstream of an androgen responsive promoter derived from MMTV (Mouse Mammary Tumor Virus) were co-transfected by a liposome method. After culturing for 4 hr, the cells were harvested, and 10,000 cells were plated in a 96 well plate and cultured for 2 hr. 5α-Dihydrotestosterone (1 μM) or a compound (100 nM) was added, and the cells were further cultured for 24 hr, after which the luciferase activity was measured. The induction rate by the compound was calculated with the luciferase activity induced by the addition of 5α-dihydrotestosterone (1 μM) as 100. The results are shown in Table 2.

TABLE 2

| Compound Example No. | Induction rate (%) at 100 nM |
|---|---|
| 8 | 106 |
| 17 | 23 |
| 40 | 40 |
| 41 | 81 |
| 55 | 80 |
| 59 | 67 |
| 74 | 79 |
| 75 | 69 |

Formulation Example 1

Injection Containing Compound of Example 1

| (1) compound of Example 1 | 5.0 mg |
|---|---|
| (2) sodium chloride | 20.0 mg |
| (3) distilled water | amount to make total 2 ml |

The compound (5.0 mg) of Example 1 and sodium chloride (20.0 mg) were dissolved in distilled water, and water was added to the total amount of 2.0 ml. The solution was filtered, and aseptically filled in an ampule (2 ml). The ampule is sterilized and tightly sealed to give a solution for injection.

INDUSTRIAL APPLICABILITY

The compound of the present invention has a superior action as an androgen receptor modulator (particularly agonist), and is useful for the prophylaxis or treatment of hypogonadism, male climacteric disorder, frailty, cachexia, osteoporosis and the like, for which administration of androgen receptor modulator (particularly agonist) is effective.

This application is based on patent application Nos. 2007-205966 and 2007-299658 filed in Japan, the contents of which are incorporated in full herein by this reference.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A compound represented by the formula (I'):

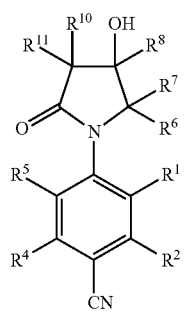

(I')

wherein $R^1$ is a hydrogen atom, a halogen atom or a lower alkyl group;

$R^2$ is a halogen atom, a lower alkyl group optionally having halogen atom(s) or a lower alkoxy group optionally having halogen atom(s);

$R^4$ is a hydrogen atom or a halogen atom;

$R^5$ and $R^6$ are each a hydrogen atom;

$R^7$ is a lower alkyl group optionally having substituent(s) selected from a hydroxy group, a lower alkoxy group and a $C_{3-6}$ cycloalkyl group, or an aralkyl group optionally having substituent(s) selected from a halogen atom and a cyano group;

$R^8$ is a hydrogen atom, a lower alkyl group or a $C_{3-6}$ cycloalkyl group; and $R^{10}$ and $R^{11}$ are the same or different and each is a hydrogen atom, a halogen atom, a lower alkyl group, a lower alkenyl group, an aralkyl group, or a lower alkyl group substituted by a hydroxyl group (in this case, $R^{10}$ and $R^{11}$ optionally form cyclopropane together with the adjacent carbon atom).

2. A pharmaceutical composition comprising the compound of claim 1 and a pharmaceutically acceptable carrier.

3. The pharmaceutical composition of claim 2, which is an androgen receptor modulator.

4. The pharmaceutical composition of claim 2, which is an androgen receptor agonist.

5. The pharmaceutical composition of claim 2, which is a tissue-selective androgen receptor modulator.

6. The pharmaceutical composition of claim 2, which is an agent for the prophylaxis or treatment of hypogonadism, male climacteric disorder, frailty, cachexia or osteoporosis.

7. The pharmaceutical composition of claim 2, which is a frailty suppressant, a muscle strength enhancer, a muscle increasing agent, a cachexia suppressant, a body weight decrease suppressant, an agent for the prophylaxis or treatment of prostate hypertrophy, amyotrophy or muscle loss caused by a disease or an agent for reducing the prostate weight.

8. A method for the prophylaxis or treatment of hypogonadism, male climacteric disorder, frailty, cachexia or osteoporosis in a mammal, which comprises administering an effective amount of the compound of claim 1.

* * * * *